US012410454B2

(12) United States Patent
Jennewein et al.

(10) Patent No.: US 12,410,454 B2
(45) **Date of Patent: *Sep. 9, 2025**

(54) PRODUCTION OF HUMAN MILK OLIGOSACCHARIDES IN MICROBIAL HOSTS WITH ENGINEERED IMPORT / EXPORT

(71) Applicant: Chr. Hansen A/S, Hoersholm (DK)

(72) Inventors: Stefan Jennewein, Bad Honnef (DE); Dirk Wartenberg, Bonn (DE)

(73) Assignee: Chr. Hansen A/S, Hoersholm (DK)

( * ) Notice: Subject to any disclaimer, the term of this patent is extended or adjusted under 35 U.S.C. 154(b) by 351 days.

This patent is subject to a terminal disclaimer.

(21) Appl. No.: 17/323,769

(22) Filed: May 18, 2021

(65) Prior Publication Data

US 2021/0277436 A1 Sep. 9, 2021

Related U.S. Application Data

(63) Continuation of application No. 15/758,653, filed as application No. PCT/EP2016/071420 on Sep. 12, 2016, now Pat. No. 11,046,985.

(30) Foreign Application Priority Data

Sep. 12, 2015 (EP) .................................... 15184968

(51) Int. Cl.
*C12P 19/18* (2006.01)
*C12N 9/10* (2006.01)
*C12N 15/70* (2006.01)

(52) U.S. Cl.
CPC ............ *C12P 19/18* (2013.01); *C12N 9/1051* (2013.01); *C12N 15/70* (2013.01); *C12Y 204/01146* (2013.01)

(58) Field of Classification Search
CPC ....... C12P 19/18; C12N 9/1051; C12N 15/70; C12Y 204/01146
See application file for complete search history.

(56) References Cited

U.S. PATENT DOCUMENTS

| | | | | |
|---|---|---|---|---|
| 8,652,808 | B2 * | 2/2014 | Jennewein | C12N 15/70 435/72 |
| 9,512,433 | B2 | 12/2016 | Jennewein et al. | |
| 11,046,985 | B2 * | 6/2021 | Jennewein | C12N 9/1051 |
| 2011/0236934 | A1 | 9/2011 | Samain et al. | |
| 2012/0135467 | A1 | 5/2012 | Jennewein et al. | |
| 2014/0120611 | A1 | 5/2014 | Jennewein et al. | |

FOREIGN PATENT DOCUMENTS

| | | | | |
|---|---|---|---|---|
| CN | 103060252 | * | 4/2013 | |
| EP | 2722394 | A1 | 4/2014 | |
| JP | 2003504072 | A | 2/2003 | |
| JP | 2007525186 | A | 9/2007 | |
| JP | 2012529274 | A | 11/2012 | |
| RU | 2473695 | C2 | 1/2013 | |
| WO | 2007101862 | A1 | 9/2007 | |
| WO | WO-2010142305 | A1 * | 12/2010 | C12N 15/70 |
| WO | 2014122328 | A1 | 8/2014 | |
| WO | 2015032413 | A1 | 3/2015 | |
| WO | 2015106943 | A1 | 7/2015 | |
| WO | 2015117812 | A1 | 8/2015 | |
| WO | 2015150328 | A1 | 10/2015 | |

OTHER PUBLICATIONS

Koita, Dissertation, University of Illinois at Urbana Champaign, 2012, pp. 1-121 (Year: 2012).*
Baumgartner, et al. ChemBioChem 2014, 15, pp. 1896-1900 (Year: 2014).*
Pao, et al. Microbiology and Molecular Biology Reviews (1998) pp. 1-34 (Year: 1998).*
Han, et al. Biotechnology Advances 30 (2012) pp. 1268-1278 (Year: 2012).*
Vincent, et al. JBC, vol. 280, Issue 20, 2005, pp. 19649-19655 (Year: 2005).*
Baumgartner, et al Enzyme and Microbial Technology 75-76 (2015) pp. 37-43 (Year: 2015).*
Smilovitz et al.; Breast milk oligosaccharides: structure-function relationships in the neonate; Annu. Rev. Nutr. (2014) 34:143-169.
PCT International Search Report for PCT/EP2016/071420, mailed Oct. 28, 2016.
Weichert, et al., "Bioengineered 2'-fucosyllactose and 3-fucosyllactose inhibit the adhesion of *Pseudomonas aeruginosa* and enteric pathogens to human intestinal and respiratory cell lines," Nutrition Research, (2013), vol. 33: 831-838.
Jennewein: "Abschlussbericht zum Forderprojekt Entwicklung eines innovativen Produktionsverfahrens fur Fucosyllctosen Mit dem," Jennewein Biotechnologie GmbH, Project Report, 2012, pp. 1-31.
Khushnuma Koita, "Optimizing Pentose Sugar Utilization in *Escherichia coli* for the Production of Biofuels," University of Illinois at Urbana-Champaign Dissertation, 2012.
Koita, et al., "Identification and Analysis of the Putative Pentose Sugar Efflux Transporters in *Escherichia coli*," PLOS One, (2012), vol. 7, No. 8: pp. 1-10.
Baumgärtner, et al., "Construction of *Escherichia coli* strains with chromosomally integrated expression cassettes for the synthesis of 2'-fucosyllactose," Microbial Cell Factories, (2013), vol. 12: 1-13.
Petschacher, et al., "Biotechnological production of fucosylated human milk oligosaccharides: Prokaryotic fucosyltransferases and their use in biocatalytic cascades or whole cell conversion systems," Journal of Biotechnology, (2016), vol. 235: 61-83.

(Continued)

*Primary Examiner* — Melenie L Gordon
*Assistant Examiner* — Jessica Faye Edwards
(74) *Attorney, Agent, or Firm* — Kelly K. Reynolds

(57) ABSTRACT

The present invention relates to methods for the production of oligosaccharides in genetically modified bacterial host cells, as well as to the genetically modified host cells used in the methods. The genetically modified host cell comprises at least one recombinant glycosyltransferase, and at least one nucleic acid sequence coding for a protein enabling the export of the oligosaccharide.

19 Claims, 6 Drawing Sheets

Specification includes a Sequence Listing.

(56) References Cited

OTHER PUBLICATIONS

Baumgärtner, et al., "Synthesis of fucosylated lacto-N-tetraose using whole-cell biotransformation," Bioorganic & Medicinal Chemistry, (2015), vol. 23: 6799-6806.
Saumonneau et al.,"Design of an alpha-L-transfucosidase for the synthesis of fucosylated HMOs," Glycobiology, (2016), vol. 26, No. 3: 261-269.
Bernard Priem, et al., "A new fermentation process allows large-scale production of human milk oligosaccharides by metabolically engineered bacteria," Glycobiology, (2002), vol. 12, No. 4: 235-240.
Florian Baumgartner, "Synthesis of the Human Milk Oligosaccaride Lacto-N-Tetraose in Metabolically Engineered, Plasmid-Free *E. coli*," ChemBioChem Communications, (201), vol. 15, 1896-1900.

* cited by examiner

Lactose
Lactose
Lacto-N-triose II (LNT-II)
Lacto-N-triose II (LNT-II)
Lacto-*N*-tetraose (LNT)
Lacto-*N*-tetraose (LNT)

PRODUCTION OF HUMAN MILK OLIGOSACCHARIDES IN MICROBIAL HOSTS WITH ENGINEERED IMPORT / EXPORT

CROSS-REFERENCE TO RELATED APPLICATIONS

This application is a Continuation of U.S. application Ser. No. 15/758,653, filed on Mar. 8, 2018, which is a National Stage entry of International Application No. PCT/EP2016/071420, filed Sep. 12, 2016, which claims priority to European Patent Application No. 15184968.4, filed Sep. 12, 2015. The disclosure of the priority applications are incorporated in their entirety herein by reference.

REFERENCE TO SEQUENCE LISTING SUBMITTED AS A COMPLIANT ASCII TEXT FILE (.txt)

Pursuant to the EFS-Web legal framework and 37 CFR §§ 1.821-825 (see MPEP § 2442.03(a)), a Sequence Listing in the form of an ASCII-compliant text file (entitled "3000045-002001_Sequence_Listing_ST25.txt" created on 12 Jan. 2021, and 291,414 bytes in size) is submitted concurrently with the instant application, and the entire contents of the Sequence Listing are incorporated herein by reference.

BACKGROUND

Human milk is regarded as the best diet for the development of infants. It is composed of fats, proteins, vitamins, minerals, trace elements and a complex carbohydrate mixture which comprises lactose and approximately 150 structurally diverse oligosaccharides (Human milk oligosaccharides, HMO).

DESCRIPTION OF RELATED ART

Efforts to produce HMO chemically or by biotechnological approaches mainly attracted common attention due to their beneficial impact on the development of the gastrointestinal flora of infants, thus, advocating their use as nutritional additives. Besides these prebiotic properties, many other positive effects of HMO could be observed so far, expanding their field of application.

However, extensive scientific studies demand pure single compounds which are hardly achievable. This is especially true for complex free neutral and acidic oligosaccharides for which competitive large-scale production processes are still lacking. (e.g. lacto-N-tetraose (Gal(β1-3)GlcNAc(β1-3)Gal(β1-4)Gluc), lacto-N-neotetraose (Gal(β1-4)GlcNAc(β1-3)Gal(β1-4)Gluc), lacto-N-fucopentaose I (Fuc(α1-2) Gal(β1-3)GlcNAc(β1-3)Gal(β1-4)Gluc) lacto-N-neofucopenaose I (Fuc(α1-2) Gal(β1-4)GlcNAc(β1-3)Gal(β1-4)Gluc) (Lacto-N-sialylpentaose a (LST-a; Neu5Ac(α2-3)Gal(β1-3)GlcNAc(β1-3)Gal(β1-4)Gluc)) The metabolic engineering of a microorganism to produce these compounds represents the most promising approach since chemical methods are rather inefficient to produce these molecules at multi-ton scale.

Several fermentative approaches were already developed for the structural simpler HMOs such as 2'-fucosyllactose, 3-fucosyllactose or 3'-sialyllactose, using mainly metabolically engineered *Escherichia coli* strains.

However, large-scale quantities are only achievable through boosting the oligosaccharide export out of the bacterial cell, thus, (i) enhancing the productivity and (ii) allowing the recovering of the desired oligosaccharide from the culture broth. The need for solving the export problem seems to enlarge with the size of the produced sugar. Also, with the currently available fermentation processes, upon production of more complex oligosaccharides, the problem of an unwanted export of oligosaccharide precursors from the producing cell occurs, leading to an undesirable mix of product and precursor oligosaccharides in the fermentation medium. Whereas multiple transporter proteins are known to transfer mono- or disaccharides across the membrane, hardly any knowledge exists on the transport of larger oligosaccharides (e.g., trisaccharides and larger oligosaccharides).

For example, the genome of the often used fermentation model organism *E. coli* encodes more than 500 distinct transporter proteins (Busch and Saier, Crit Rev Biochem Mol Biol. 2002; 37(5):287-337). The classification of those membrane transport proteins is quite diverse and subgroups may vary in translocation mechanisms, protein structures or evolutionary origins.

Classically energy-driven active transporters perform substrate movement against its concentration or electrochemical gradient, while kinetics and direction of the substrate flow through channels primarily follows such gradients. Depending on the source of energy used for the translocation, pumps can be principally divided into primary active and secondary active transporters, exploiting metabolic energy like ATP or the electrochemical potential, respectively (Davidson and Maloney, Trends Microbiol. 2007 October; 15(10):448-55; Forrest et al, Biochim Biophys Acta. 2011 February; 1807(2):167-88). Although in-depth knowledge was achieved for several membrane proteins permitting energy generation, the import of carbohydrates and the efflux of proteins and antibacterial substances, however, keen insights into mechanistic processes or information on natural or probable substrates were gained only for a minor portion of annotated bacterial transporters so far.

The *E. coli* lactose permease LacY probably represents the most intensively characterized solute transporter (Guan and Kaback, Annu Rev Biophys Biomol Struct. 2006; 35:67-91) and is a member of the large and exceptionally diverse major facilitator superfamily (MFS)—that belongs to the secondary active transporter class—transporting sugars, drugs, hydrophobic molecules, peptides, organic ions, etc. by uniport, symport or antiport (Saier et al., J Mol Microbiol Biotechnol. 1999 November; 1(2):257-79). Apart from a few exceptions a common structural feature of MFS transporters are two six-helical subdomains that transverse the cytoplasmic membrane. The existence of functionally homologous amino acid positions between related $H^+$-coupled MFS symporters further suggests a similar kinetic mechanism as determined for the lactose permease (Madej and Kaback, Proc Natl Acad Sci USA. 2013 Dec. 10; 110(50):E4831-8).

Since decades, enormous knowledge about the import of carbohydrates into bacteria could be acquired. But regarding the export of carbohydrates, especially about molecules that are non-surface-associated, only little information is available. This is not unexpected since sugars actually depict a favourable carbon- and energy source, thus, once in the cell they shouldn't be released to a competitive environment.

However, the natural function of sugar exporters probably involve the reduction of osmotic or sugar-phosphate stress which might point to a flexible substrate spectrum. Interestingly, the export of a variety of galactosides like IPTG, TMG and lactose was shown for members of the so called sugar efflux transporter family (SET), which belong to the group of MFS transporters (Liu et al., J Biol Chem. 1999 Aug. 13; 274(33):22977-84; Liu et al., Mol Microbiol. 1999 March; 31(6):1845-51).

The *E. coli* transport protein SetA was even described to transfer the human milk oligosaccharide 3-fucosyllactose resulting in an improved production of said compound during fermentation of a recombinant *E. coli* strain overexpressing setA (see applicant's international patent application WO 2010/142305). Similarly, the expression of a sugar efflux transporter from *Yersinia* was shown to enable the export of the human milk oligosaccharide 2'-fucosyllactose out of an engineered *E. coli* production strain.

Apart from this, from a mechanistic and energetic point of view, only the ion-gradient-driven transport systems have the potential to translocate solutes in both directions across the membrane. This is exemplarily true for the above mentioned LacY, a galactoside/$H^+$ symporter, which is part of the bacterial lac operon that allows the metabolism of lactose in *E. coli*. This permease primarily imports lactose into the cell but it is also capable to transfer its substrate in the opposite direction.

Besides the major facilitator superfamily, which represents the largest group of transporters, bacteria possess further mechanisms to excrete solutes—often summarized in the classes of multidrug efflux pumps. Alike for the MFS, the activities of the small multidrug resistance superfamily (SMR), the multidrug and toxic compound extrusion superfamily (MATE) and the resistance-nodulation-cell division superfamily (RND) rely on the electrochemical gradient. The fifth class is the adenosine triphosphate (ATP)-binding cassette superfamily (ABC) which uses ATP as energy source to drive molecules from the cell. As for the MFS, members of SMR, MATE, RND and ABC transport structurally diverse molecules. Further, most of their so far identified substrates are not naturally occurring, and, thus, their preferences are hardly predictable.

Although chemical synthesizing processes are known for human milk oligosaccharides, these processes are very cost-intensive and do not lead to satisfying amounts. On the other hand, fermentation processes using genetically modified microorganisms still have the drawback that the export of larger oligosaccharides (tetra-, penta-, hexasaccharides) represents a major limitation for the establishment of cost effective production processes. As a consequence, there still is the need for improved processes for the production of large-scale human oligosaccharides.

SUMMARY

According to the invention, this and other objects are solved by the methods and microbial host cell(s) as claimed in the attached claims.

With the methods and host cells according to the invention it is possible to produce a desired oligosaccharide, preferably an oligosaccharide that is not produced in an unmodified host cell, and also preferably an oligosaccharide belonging to the human milk oligosaccharides, in large amounts obtainable from the medium. As such, the oligosaccharide is, so to say, obtainable in free from in the medium; it is not bound to a surface protein or membrane protein or other protein of the surface of the host cell.

According to the invention, a method for the production of a desired oligosaccharide by a genetically modified microbial host cell, comprising the steps of a) providing a genetically modified microbial host cell that comprises at least one recombinant glycosyltransferase, and that has the expression or activity of at least one endogenous sugar export protein modified such, that the expression or activity of the sugar export protein is either (i) increased or (ii) decreased or inactivated as compared to an genetically unmodified host cell, so that (i) the export of a oligosaccharide into the medium is either decreased or abolished, or (ii) the transport of a desired oligosaccharide is increased, respectively, as compared to an genetically unmodified host cell, b) cultivating the host cell in a medium under conditions permissive for the production of the desired oligosaccharide, whereby the desired oligosaccharide is transported into the medium. The method may further comprise the step of c) obtaining the desired oligosaccharide from the medium.

DETAILED DESCRIPTION OF A PREFERRED EMBODIMENT

Figure 1:
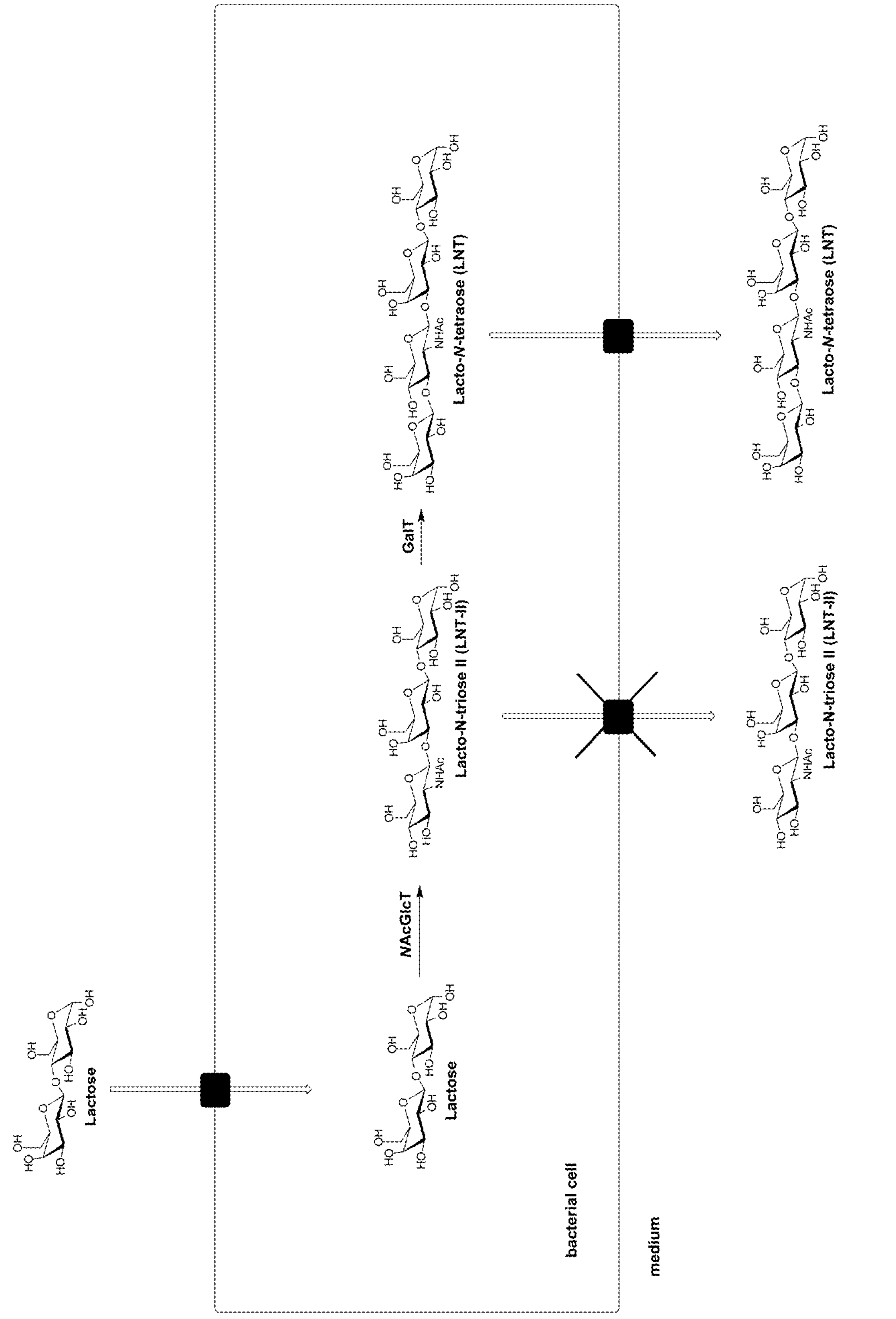
FIG. 1 shows a schematic illustration for the production of either lac-to-N-triose II or lacto-N-tetraose in a host cell cultivated in a medium.

In the method according to the invention, it is preferred if the desired oligosaccharide is a human milk oligosaccharide comprising a lacto-N-triose II (LNT-II; GlcNAc(β1-3)Gal (β1-4)Gluc) as a core trisaccharide. In this connection, an oligosaccharide having a "core trisaccharide" is meant to comprise the specific trisaccharide representing the reducing end of a desired oligosaccharide, and comprising, as the case may be, additional saccharide moieties, with the specific trisaccharide representing the major moiety.

Accordingly, in an embodiment of the method and the host cell according to the invention, the desired oligosaccharide is selected from the group consisting of: lacto-N-triose II, lacto-N-tetraose, lacto-N-neotetraose, lacto-N-fucopentaose I, lacto-N-fucopentaose II, lacto-N-fucopentaose Ill, lacto-N-fucopentaose V, lacto-N-difucosylhexose I, lacto-N-difucosylhexaose II, lacto-N-sialylpentaose LSTa, LSTb, LSTc, disialyllacto-N-tetraose, disialyllacto-N-neotetraose.

In order to overcome the above mentioned drawbacks of limited oligosaccharide export the object is further solved by a method according to the invention, wherein the host cell comprises: at least one homologous or heterologous nucleic acid sequence coding for a protein enabling the export of a desired oligosaccharide into the culture medium, wherein said host cell has been modified such, that the expression of the homologous or heterologous nucleic acid sequence is overexpressed or under control of a promoter enabling the overexpression of the nucleic acid sequence; and/or the deletion, disruption, diminishment or inactivation of at least one endogenous nucleic acid sequence coding for an exporter protein that exports precursors of the desired oligosaccharide outside the host cell; and/or at least one homologous or heterologous nuclei acid sequence coding for a protein mediating the import of a precursor of a desired oligosaccharide into said host cell, wherein preferably the nucleic acid sequence is overexpressed, and wherein preferably the precursor is larger than a disaccharide.

The genetically modified microbial host cell comprising the characteristics as set forth herein are cultured in the presence of glucose, sucrose, glycerin or a combination thereof—using these substrates as carbon- and energy sources—as well as in the presence of lactose or oligosaccharides larger than disaccharides, e.g., LNT-II.

In a preferred embodiment of this method and host cell, said protein enabling the export of a desired oligosaccharide belongs to the class of secondary active transporters, and more preferably effects the export of an oligosaccharide comprising at least three moieties.

According to preferred embodiments, for the export of desired oligosaccharides a suitable exporter is expressed in addition to the genes that are responsible for intracellular oligosaccharide biosynthesis.

According to one aspect of the method and host cell of the invention, the at least one nucleic acid sequence coding for a protein enabling the export of a desired oligosaccharide is an endogenous or a recombinant nucleic acid.

In a preferred embodiment of the method and the host cell of the invention, the nucleic acid sequence coding for a protein enabling the export of a desired oligosaccharide is of bacterial, archeal, plant, yeast or animal origin; preferably, the at least one nucleic acid sequence coding for a protein enabling the export of a desired oligosaccharide is a gene selected from the group consisting of yebQ and yjhB from *Escherichia coli*, proP from *Mannheimia succiniciproducens* and setA from *Cedecea neteri* or functional fragments thereof.

Preferably, the oligosaccharide exporter is a protein selected from at least one of the following: SetA, SetB, SetC, YdeA, Cmr, YnfM, MdtD, YfcJ, YhhS, EmrD, YdhC, YbdA, YdeE, MhpT, YebQ, YjhB, Bcr and YdeA of *E. coli*, or ProP from *Mannheimia succiniciproducens* and SetA from *Cedecea neteri* or variants or homologs thereof.

In yet another preferred embodiment, the recombinant glycosyltransferase is selected from at least one of the following: a galactosyltransferase, a sialyltransferase, an N-acetylglucosaminyltransferase and a fucosyltransferase, and is preferably selected from at least one of the following: β-1,3-N-acetylglucosaminyltransferase, β-1,3-galactosyltransferase, β-1,4-galactosyltransferase, β-1,6-galactosyltransferase, α-2,3-sialyltransferase, α-2,6-sialyltansferase, α-1,2-fucosyltransferase, or α-1,3-fucosyltransferase.

A preferred embodiment of the method and the host cell of the invention, concerns the a host cell or its provision, wherein the host cell comprises (i) a β-1,3-N-acetylglucosaminyltransferase, and (ii) a β-1,3-galactosyltransferase or a β-1,4-galactosyltransferase as glycosyltransferases. In this connection it is preferred, if said β-1,3-N-acetylglucosaminyltransferase has the activity of ligating N-acetylglucosamine to lactose generating lacto-N-triose II, and if said β-1,3-galactosyltransferase or said β-1,4-galactosyltransferase, respectively, have the activity to galactosylate lacto-N-triose II thus generating lacto-N-tetraose or lacto-N-neotetraose, respectively. The here developed system is easily adaptable to even more complex oligosaccharides by the expression of further glycosyltransferases.

With the microbial cell and the method according to the invention, it is possible to ferment a desired oligosaccharide in large quantities, especially an oligosaccharide comprising LNT-II as core structure, and to recover it from the culture broth.

In a preferred embodiment, said β-1,3-N-acetylglucosaminyltransferase belongs to the class of lgtA of *Neisseria meningitides* or PmnagT of *Pasteurella multocida*, or variants thereof.

Preferably, the glycosyltransferase is selected from a galactosyltransferase, a sialyltransferase, an N-acetylglucosaminyltransferase and a fucosyltransferase.

In yet another preferred embodiment, the lacto-N-tetraose generating β-1,3-galactosyltransferase is WbdO or a functional variant thereof. According to an aspect of the invention, the β-1,3-galactosyltransferase is a β-1,3-galactosyltransferase derived from *Salmonella enterica* (wbdO, acc. no. AY730594), and is preferably encoded by a gene selected from the group consisting of wbgO from *Escherichia coli* O55:H7 or furA from *Lutiella nitroferrum*, or a functional fragments thereof.

The invention also concerns a genetically modified microbial host cell, preferably a bacterial host cell, as described above in which the endogenous β-galactosidase gene is inactivated or deleted and in which a functional lactose permease gene is present.

Accordingly, in a preferred embodiment of the method and the host cell of the invention, a genetically modified host cell is provided, in which, where applicable, an endogenous β-galactosidase gene and a glucosamine-6-phosphate deaminase gene are inactivated or deleted, and wherein said genetically modified host cell comprises a nucleic acid sequence coding for a functional lactose permease protein, preferably LacY.

In a preferred embodiment, the genetically modified host cell comprises an increased UDP-N-acetylglucosamine and UDP-galactose, GDP-fucose or CMP-N-acetylneuraminic acid production capability as compared to a genetically unmodified host cell.

In a refinement of this embodiment of the method of and of the host cell of the invention, said increased UDP-N-acetylglucosamine and UDP-galactose production capability comprises the overexpression of one or more genes encoding for proteins comprising the following activities for a: L-glutamine: D-fructose-6-phosphate aminotransferase, N-acetyl glucosamine-1-phosphate uridyltransferase/glucosamine-1-phosphate acetyl transferase, phosphoglucosamine mutase, UDP-galactose-4-epimerase, phosphoglucomutase, glucose-1-phosphate uridylyltransferase.

For the synthesis of, e.g. LNT, UDP-galactose and UDP-N-acetylglucosamine are required. UDP-galactose can be obtained by feeding galactose to the HMO producing bacterial host cell via the fermentation medium. The galactose is then taken up by the cell, phosphorylated to galactose-1-phosphate and then converted to UDP-galactose. Genes encoding these enzymatic activities are well known in the literature (Grossiord et al., J. Bacteriol 2003 185(3) 870-878). The supply for UDP-galactose can be also obtained from the cells own metabolism, and the metabolism can be improved by further genetic modification, such as the overexpression of the UDP-galactose-4'-epimerase, or the UDP-galactose-4'-epimerase in combination with the glucose-1-phosphate-1-uridinyltransferase. UDP-N-acetlyglucosamine can be also obtained from the bacterial host cell's own UDP-N-acetylglucosamine metabolism. The provision of UDP-N-acetylglucosamine for the synthesis of N-aectylglucosamine containing oligosaccharides can be improved by the inactivation of the N-acetylglucosamine catabolism within the producing cell.

According to one aspect of the invention, the genetically modified host cell is cultivated in the presence of glucose, sucrose, glycerol or a combination thereof, but neither by addition or in the presence of N-acetylglucosamine or galactose nor in a combination thereof.

In a preferred embodiment of the method and of the host cell of the invention, the desired oligosaccharide is lacto-N-triose II, which is produced by total fermentation from a simple carbon source in the host cell by the action of the heterologous expressed glycosyltransferases β-1,4-galactosyltransferase and β-1,3-N-acetylglucosaminyltransferase.

The present invention, as already mentioned above, also concerns a genetically modified host cell for the production of a desired oligosaccharide, the oligosaccharide comprising a lacto-N-triose II (LNT-II; GlcNAc(β1-3)Gal(β1-4)Gluc) as a core trisaccharid, wherein the host cell comprises at least one recombinant glycosyltransferase, the glycosyltransferase being preferably selected from a galactosyltransferase, a sialyltransferase, and an N-acetylglucosaminyltransferase, and has the expression or activity of at least endogenous sugar transport protein modified such, that the expression or activity of the endogenous sugar transport protein is functionally inactivated for the export of a precursor of the desired oligosaccharide.

A preferred embodiment concerns a host cell as described above, comprising (i) a heterologous expressed β-1,3-N-acetylglucosaminyltransferase, and (ii) a heterologous expressed β-1,3-galactosyltransferase or a heterologous expressed β-1,4-galactosyltransferase as glycosyltransferases, wherein the host cell further preferably comprises at least one homologous or heterologous nucleic acid sequence coding for a protein enabling the export of the oligosaccharide into a culture medium the host cell is cultivated in, wherein said protein enabling the export of the desired oligosaccharide belongs to the class of secondary active transporters, wherein said host cell has been modified such, that the expression of the homologous or heterologous nucleic acid sequence is overexpressed or under control of a promoter enabling the overexpression of the nucleic acid sequence. In preferred embodiments of the host cell, said at least one nucleic acid sequence coding for a protein enabling the export of the desired oligosaccharide is an endogenous or a recombinant nucleic acid sequence.

As already outlined for the method according to the invention, it is also preferred in the host cell of the invention, if said nucleic acid sequence coding for a protein enabling the export of a desired oligosaccharide is of bacterial, archeal, plant, yeast or animal origin.

According to another aspect of the invention, the host cell as described above further comprises: the deletion, disruption, diminishment or inactivation of at least one endogenous nucleic acid sequence coding for an exporter protein that exports precursors of the desired oligosaccharide outside the host cell; and/or at least one homologous or heterologous nucleic acid sequence coding for a protein enabling the import of a precursor of a desired oligosaccharide into said host cell, wherein preferably the nucleic acid sequence is overexpressed, and wherein preferably the precursor is larger than a disaccharide.

With the overexpression of at least one homologous or heterologous nucleic acid sequence coding for a protein enabling the import of a precursor of a desired oligosaccharide into said host cell, it is possible to feed precursors of a desired oligosaccharide to the culture medium, which get imported into the host cell, such as, e.g., LNT-II.

According to one aspect of the invention, in the host cell said at least one nucleic acid sequence coding for a protein enabling the export of a desired oligosaccharide is a gene selected from the group consisting of yebQ and yjhB from *Escherichia coli*, proP from *Mannheimia succiniciproducens* and setA from *Cedecea neteri* or functional fragments thereof.

According to yet another preferred embodiment, the desired oligosaccharide is lacto-N-triose II, and the protein enabling the export of the oligosaccharide into a culture medium the host cell is cultivated in, is YjhB from *Escherichia coli*, ProP from *Mannheimia succiniciproducens* and SetA from *Cedecea neteri* or functional fragments thereof.

According to a preferred embodiment, the microbial host according to the invention is further modified not to express proteins exporting precursors of a desired oligosaccharide.

In a preferred embodiment of the host cell, the desired oligosaccharide is lacto-N-tetraose, the precursor is lacto-N-triose II, and the host cell has deleted, disrupted or inactivated at least one nucleic acid sequence coding for an exporter protein that is able to export lacto-N-triose II outside the host cell.

In this connection it is preferred, if the protein enabling the export of lacto-N-tetraose is selected from YebQ from *Escherichia coli* BL21(DE3), SpoVB of *Bacillus amyloliquefaciens*, YabM of *Erwinia pyrilfolia*, Bcr of *E. coli* MG1655, YdeA of *E. coli* MG1655, ProP2 of *Haemophilus parainfluenzae*, SetA of *Pectobacterium carotovorum*, FucP of *E. coli* MG1655, MdeA of *Staphylococcus aureus* Bmb9393, ImrA of *Lactococcus lactis*, SetA of *Pseudomonas* sp. MT-1 and SetA of *Beauveria bassiana* D1-5.

Preferably, the oligosaccharide exporter is a protein selected from at least one of the following: SetA, SetB, SetC, YdeA, Cmr, YnfM, MdtD, YfcJ, YhhS, EmrD, YdhC, YbdA, YdeE, MhpT, YebQ, YjhB, Bcr and YdeA of *E. coli*, or ProP from *Mannheimia succiniciproducens* and SetA from *Cedecea neteri* or variants or homologs thereof.

Presently, the term "nucleic acid" refers to a single- or double-stranded deoxyribonucleotide or ribonucleotide macromolecule and encompasses known analogues or natural or synthetically produced nucleotides that hybridize with the desired nucleic acid and that encode a certain polypeptide.

The term "recombinant" or "genetically modified", as used herein with reference to a microbial host cell indicates that the microbial host cell replicates a heterologous nucleic acid, or expresses a peptide or protein encoded by a heterologous nucleic acid (i.e., a sequence "foreign to said cell"). Recombinant cells can contain genes that are not found within the native (non-recombinant) form of the cell. Recombinant cells can also contain genes found in the native form of the cell wherein the genes are modified and re-introduced into the cell by artificial means. The term also encompasses cells that contain a nucleic acid endogenous to the cell that has been modified without removing the nucleic acid from the cell; such modifications include those obtained by gene replacement, site-specific mutation, and related techniques. Accordingly, a "recombinant polypeptide" is one which has been produced by a recombinant cell. A "heterologous sequence" or a "heterologous nucleic acid", as used herein, is one that originates from a source foreign to the particular host cell (e.g. from a different species), or, if from the same source, is modified from its original form. Thus, a heterologous nucleic acid operably linked to a promoter is from a source different from that from which the promoter was derived, or, if from the same source, is modified from its original form. The heterologous sequence may be stably introduced, e.g. by transfection, transformation, conjugation or transduction, into the genome of the host microbial host cell, thus representing a genetically modified host cell. Techniques may be applied which will depend on the host cell the sequence is to be introduced. Various techniques are known to a person skilled in the art and are, e.g., disclosed in Sambrook et al., Molecular Cloning: A Laboratory Manual, 2nd Ed., Cold Spring Harbor Laboratory Press, Cold Spring Harbor, N.Y. (1989).

Accordingly, a "microbial host cell" is presently understood as a microbial, preferably bacterial, cell which has been transformed or transfected, or is capable of transformation or transfection by an exogenous polynucleotide sequence.

Thus, the nucleic acid sequences as used in the present invention, may, e.g., be comprised in a vector which is to be stably transformed/transfected or otherwise introduced into host microorganism cells.

Presently, the term "operably linked" as used herein, shall mean a functional linkage between a nucleic acid expression control sequence (such as a promoter, signal sequence, or array of transcription factor binding sites) and a second nucleic acid sequence, wherein the expression control sequence affects transcription and/or translation of the nucleic acid corresponding to the second sequence. Accordingly, the term "Promoter" designates DNA sequences which usually "precede" a gene in a DNA polymer and provide a site for initiation of the transcription into mRNA. "Regulator" DNA sequences, also usually "upstream" of (i.e., preceding) a gene in a given DNA polymer, bind proteins that determine the frequency (or rate) of transcriptional initiation. Collectively referred to as "promoter/regulator" or "control" DNA sequence, these sequences which precede a selected gene (or series of genes) in a functional DNA polymer cooperate to determine whether the transcription (and eventual expression) of a gene will occur. DNA sequences which "follow" a gene in a DNA polymer and provide a signal for termination of the transcription into mRNA are referred to as transcription "terminator" sequences.

A great variety of expression systems can be used to produce the polypeptides of the invention. Such vectors include, among others, chromosomal, episomal and virus-derived vectors, e.g., vectors derived from bacterial plasmids, from bacteriophage, from transposons, from yeast episomes, from insertion elements, from yeast chromosomal elements, from viruses, and vectors derived from combinations thereof, such as those derived from plasmid and bacteriophage genetic elements, such as cosmids and phagemids. The expression system constructs may contain control regions that regulate as well as engender expression. Generally, any system or vector suitable to maintain, propagate or express polynucleotides and to synthesize a polypeptide in a host may be used for expression in this regard. The appropriate DNA sequence may be inserted into the expression system by any of a variety of well-known and routine techniques, such as, for example, those set forth in Sambrook et al., supra.

The art is rich in patent and literature publications relating to "recombinant DNA" methodologies for the isolation, synthesis, purification and amplification of genetic materials for use in the transformation of selected host organisms. Thus, it is common knowledge to transform host organisms with "hybrid" viral or circular plasmid DNA which includes selected exogenous (i.e. foreign or "heterologous") DNA sequences. The procedures known in the art first involve generation of a transformation vector by enzymatically cleaving circular viral or plasmid DNA to form linear DNA strands. Selected foreign DNA strands usually including sequences coding for desired protein product are prepared in linear form through use of the same/similar enzymes. The linear viral or plasmid DNA is incubated with the foreign DNA in the presence of ligating enzymes capable of effecting a restoration process and "hybrid" vectors are formed which include the selected exogenous DNA segment "spliced" into the viral or circular DNA plasmid.

As used herein, the term "cultivating" means growing a bacterial cell in a medium and under conditions permissive and suitable for the production of the desired oligosaccharide(s). A couple of suitable bacterial host cells as well as mediums and conditions for their cultivation will be readily available for one skilled in the art upon reading the disclosure of this invention in connection with the skilled person's technical and expert background.

As used herein, the term "recovering" or "obtaining" means isolating, harvesting, purifying, collecting or otherwise separating from the host cell culture the oligosaccharide produced by the host cell according to the invention.

A "microbial" host cell according to the invention, and as generally understood, means any microorganism, including bacteria, fungi and archaea, which is generally suitable for cultivation in large amounts, and which can be genetically modified according to the invention in order to produce a desired oligosaccharide. Preferred microorganisms are bacteria, e.g. *Escherichia coli, Corynebacterium glutamicum* and the yeast *Saccharomyces* sp., which have the advantage that these microorganisms can be grown easily and inexpensively in laboratory settings, and the bacteria and yeast have been intensively investigated for over many years Generally, and throughout the present invention, the term "glycosyltransferase activity" or "glycosyltransferase" designates and encompasses enzymes that are responsible for the biosynthesis of disaccharides, oligosaccharides and polysaccharides, and they catalyze the transfer of monosaccharide moieties from an activated nucleotide monosaccharide/sugar (the "glycosyl donor") to a glycosyl acceptor molecule.

Generally, and throughout the present invention, the terms "exporter" or "exporter protein" or "protein enabling the export of a desired oligosaccharide", which terms are presently being used synonymously, designates one or more polypeptides that solely or as part of a multi-protein complex transfers an oligosaccharide from the intracellular milieu of a bacterial cell into the periplasm of said cell or the culture supernatant, thus, enabling the oligosaccharide to pass the cellular membrane and/or the cell wall of said cell.

Within the scope of the present invention, also nucleic acid/polynucleotide and polypeptide polymorphic variants, alleles, mutants, and interspecies homologs are comprised by those terms, that have an amino acid sequence that has greater than about 60% amino acid sequence identity, 65%, 70%, 75%, 80%, 85%, 90%, preferably 91%, 92%, 93%, 94%, 95%, 96%, 97%, 98% or 99% or greater amino acid sequence identity, preferably over a region of at least about 25, 50, 100, 200, 500, 1000, or more amino acids, to a polypeptide encoded by a wild type glycosyltransferase activity or oligosaccharide export displaying protein.

"Variant(s)" as the term is used herein, is a polynucleotide or polypeptide that differs from a reference polynucleotide or polypeptide, respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques, by direct synthesis, and by other recombinant methods known to the persons skilled in the art.

Accordingly, a "functional fragment" of any of the genes/proteins disclosed therein, is meant to designate sequence variants of the genes/proteins still retaining the same or somewhat lesser activity of the gene or protein the respective fragment is derived from.

In this connection, the term "nucleic acid sequence encoding . . . " generally refers to any polyribonucleotide or polydeoxyribonucleotide, which may be unmodified RNA or DNA or modified RNA or DNA, and generally represents a gene which encodes a certain polypeptide or protein.

In this context, the term "polypeptide(s)" refers to any peptide or protein comprising two or more amino acids joined to each other by peptide bonds or modified peptide bonds. "Polypeptide(s)" refers to both short chains, commonly referred to as peptides, oligopeptides and oligomers and to longer chains generally referred to as "proteins". Polypeptides may contain amino acids other than the 20 gene encoded amino acids. "Polypeptide(s)" include those modified either by natural processes, such as processing and other post-translational modifications, but also by chemical modification techniques. It will be appreciated that the same type of modification may be present in the same or varying degree at several sites in a given polypeptide, without essentially altering the activity of the polypeptide. Also, a given polypeptide may contain many types of modifications. Modifications can occur anywhere in a polypeptide, including the peptide backbone, the amino acid side-chains, and the amino or carboxyl termini.

Further, with the expression "precursor" compounds are encompassed which are involved in the biosynthetic pathway of the oligosaccharide according to the invention or which are produced and naturally present in the host cell.

A "precursor that is larger than a disaccharide" is presently understood as a sugar moiety that comprises more than two monosaccharide residues.

The term "desired oligosaccharide" refers to a sugar polymer consisting of at least three moieties, thus, comprising trisaccharides, tetrasaccharides, pentasaccharides etc., preferably an oligosaccharide selected from at least one of the following: lacto-N-triose II, lacto-N-tetraose, lacto-N-neotetraose, lacto-N-fucopentaose I, lacto-N-fucopentaose II, lacto-N-fucopentaose III, lacto-N-fucopentaose V, lacto-N-difucosylhexose I, lacto-N-difucosylhexaose II, lacto-N-sialylpentaose LSTa, LSTb, LSTc, disialyllacto-N-tetraose, disialyllacto-N-neotetraose.

Presently, and as generally understood in the relevant field, the expression "homologous" refers to a nucleic acid sequence that encodes for a specific product or products and is derived from the same species, in which said nucleic acid sequence is inserted. Accordingly, the term "heterologous" refers to a nucleic acid sequence encoding for a specific product or products and being derived from a species other than those in which said nucleic acid sequence is inserted.

The term "endogenous" herein and generally within the field means that the nucleic acid encoding for an enzyme of interest is originating from the bacterial host cell and has not been introduced into said host cell, whereas a "recombinant" nucleic acid has been introduced into said host cell and does not originates from said host cell.

The expression "overexpressed", or "overexpressing" or "under control of a promoter sequence enabling the overexpression of said nucleic acid sequence" presently, and generally in the art, means the expression of a gene in greater-than-normal amounts, i.e. in increased quantity thus leading to an increased amount of the protein the nucleic acid sequence is coding for.

In some embodiments, the nucleic acid sequence is placed under the control of an inducible promoter, which is a promoter that directs expression of a gene where the level of expression is alterable by environmental or developmental factors such as, for example, temperature, pH, anaerobic or aerobic conditions, light, transcription factors and chemicals. Such promoters are referred to herein as "inducible" promoters, which allow one to control the timing of expression of the proteins used in the present invention. For *E. coli*, and other microbial host cells, inducible promoters are known to those of skill in the art.

Further advantages are evident from the description and the drawings.

It is understood that the features mentioned above and those yet to be explained below can be used not only in the respective combinations indicated, but also in other combinations or in isolation, without leaving the context of the present invention.

Figure 2:
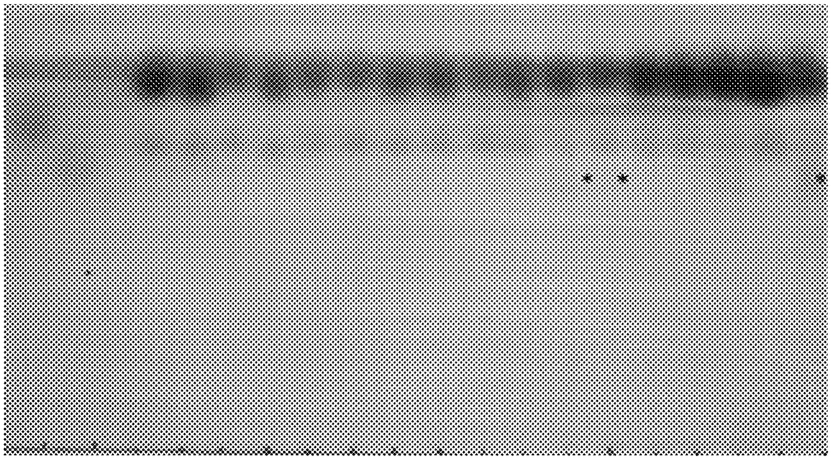
FIG. 2 shows the results of the TLC analysis of culture extracts of lacto-N-triose II (LNT II) producing *E. coli* BL21(DE3) strains overexpressing the β-1,3-N-acetyl glucosaminyltransferase gene PmnagT(13, 14)

The invention will be described in more detail in the examples and the attached figures, in which FIG. 1 shows a schematic illustration for the production of either lacto-N-triose II or lacto-N-tetraose in a host cell cultivated in a medium;

FIG. 2 shows the results of the TLC analysis of culture extracts of lacto-N-triose II (LNT II) producing *E. coli*

Figure 3:
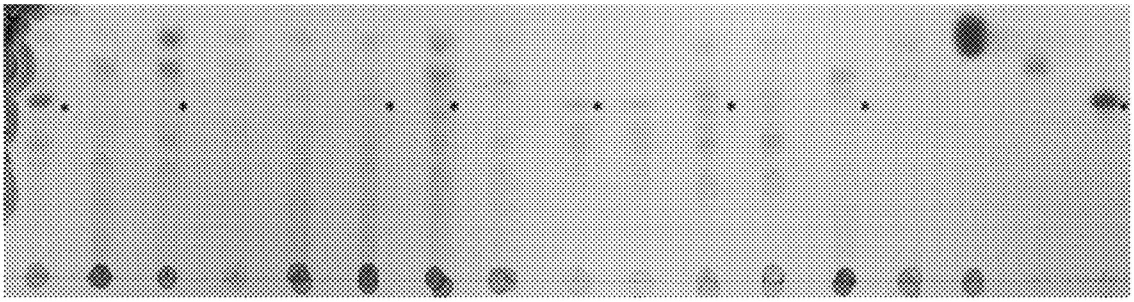
FIG. 3 shows the results of the TLC analysis of culture extracts of lacto-N-tetraose (LNT) producing *E. coli* BL21 (DE3) strains overexpressing the β-1,4-galactosyltransferase encoding genes BfgalT2 (1), PmgalT7 (3), MsgalT8 (6), gatD (7), lex1 (9), IgtB (11) or IsgD (13)
Figure 4:
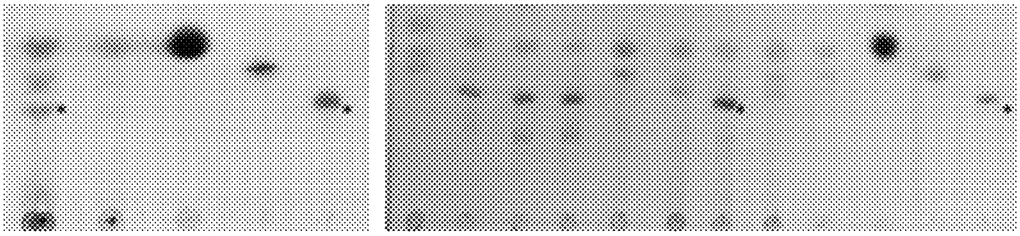
FIG. 4 shows the results of the TLC analysis of culture extracts of lacto-N-tetraose (LNT) producing *E. coli* BL21 (DE3) strains overexpressing the β-1,4-galactosyltransferase encoding genes KdgalT10 (1), cpsI14J (7), cpslaJ (8, 9), HpgalT (12)
Figure 5:
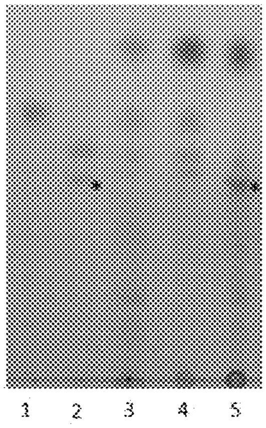
FIG. 5 shows the results of the TLC analysis of culture extracts of lacto-N-tetraose producing *E. coli* BL21(DE3) strains overexpressing the β-1,4-galactosyltransferase encoding gene waaX (5)
Figure 6:
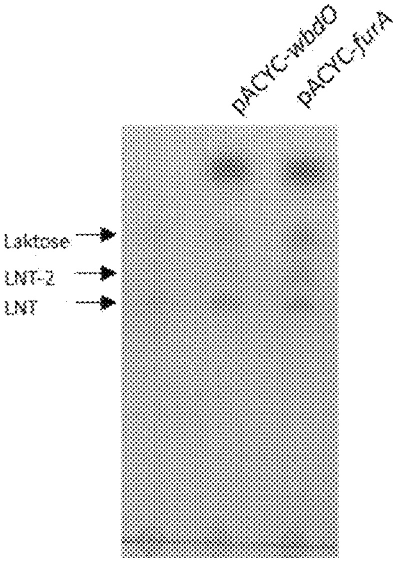
FIG. 6 shows the results of the TLC analysis of culture extracts of lacto-N-tetraose producing *E. coli* BL21(DE3) strains overexpressing the β-1,3-galactosyltransferase encoding genes wbdO or furA.
Figure 7:
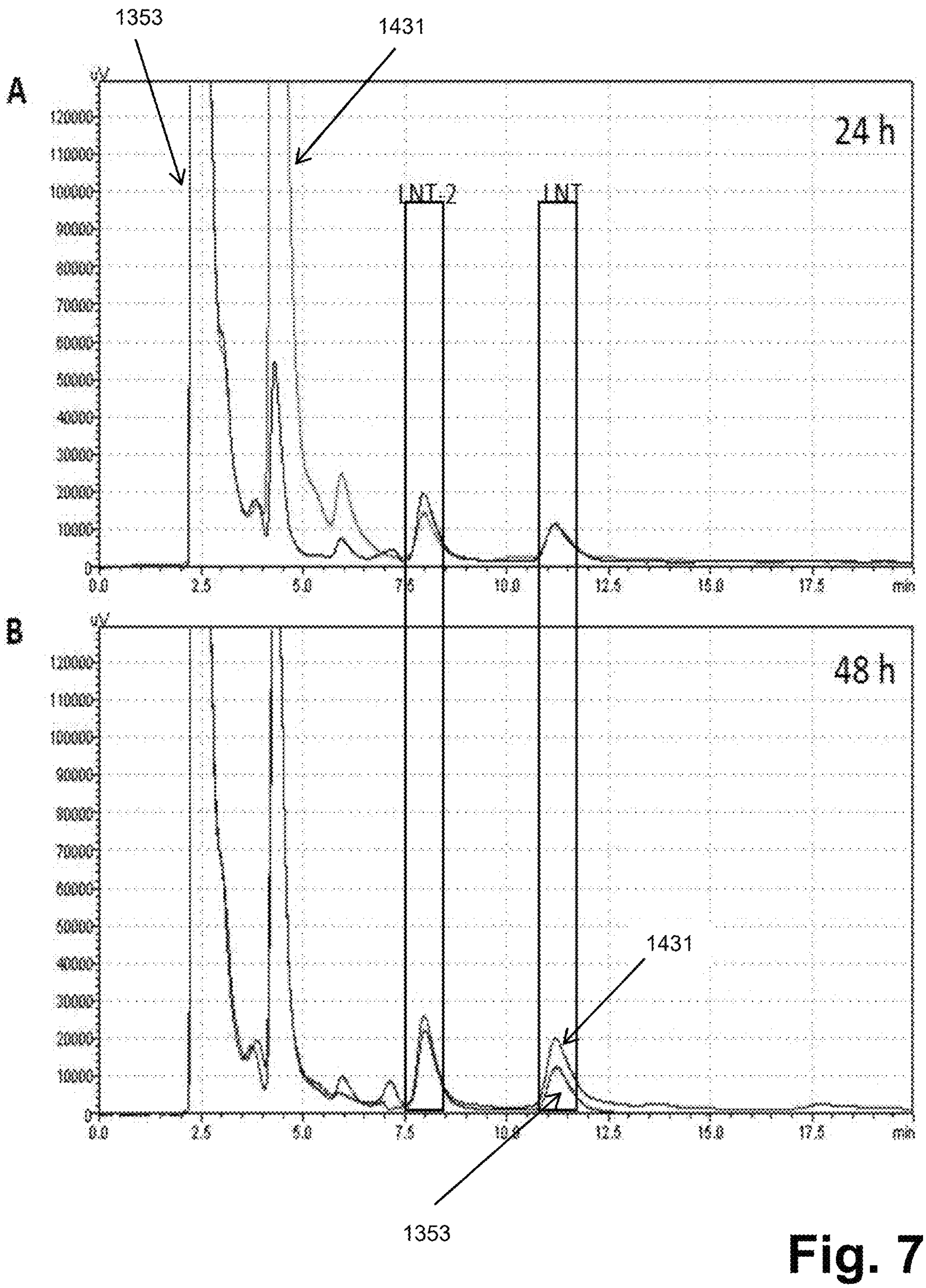
FIG. 7 shows the results of HPLC analyses of the culture superna-tant of lacto-N-tetraose producing *E. coli* BL21 (DE3) strain. (A) Supernatant of *E. coli* BL21(DE3) 1353 and 1431 grown in the presence of glucose and lactose after 24 h of incubation. (B) Supernatant of *E. coli* BL21(DE3) 1353 and 1431 grown in the presence of glucose and lactose after 48 h of incubation.
Figure 8:
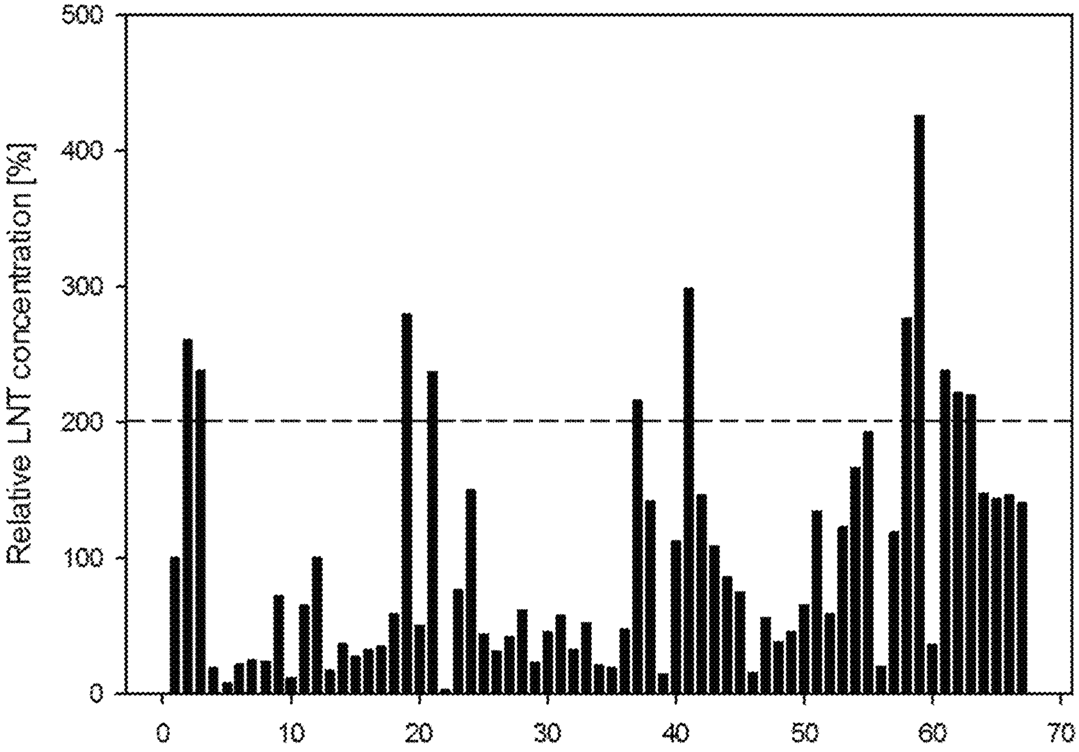
FIG. 8 shows a diagram depicting the relative concentration of lacto-N-tetraose in the supernatant of *E. coli* BL21 (DE3) strains overexpressing sugar efflux transporters compared to the control strain 1353.
Figure 9:
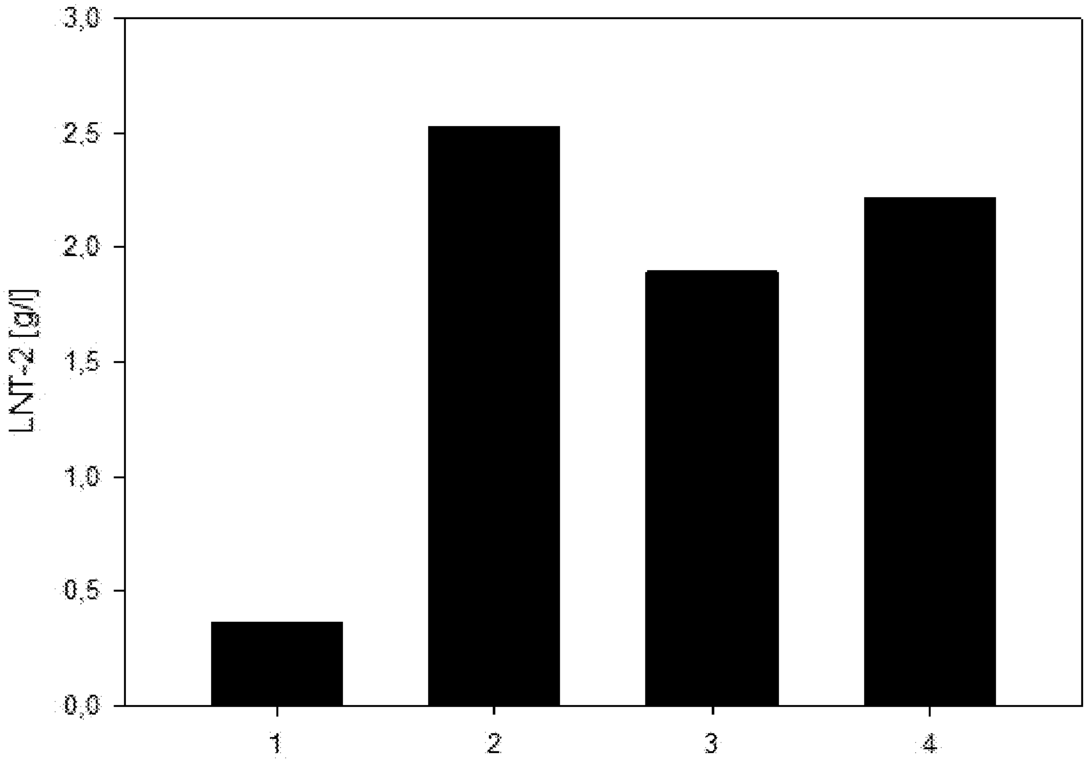
FIG. 9 shows a diagram depicting concentrations of lacto-N-triose II in the supernatant of *E. coli* BL21 (DE3) strains overexpressing the sugar efflux transport-ers TP11 (2), YjhB (3) or TP70 (4).

BL21(DE3) strains overexpressing the β-1,3-N-acetyl glucosaminyltransferase gene PmnagT(13, 14);

FIG. 3 shows the results of the TLC analysis of culture extracts of lacto-N-tetraose (LNT) producing *E. coli* BL21 (DE3) strains overexpressing the β-1,4-galactosyltransferase encoding genes BfgalT2 (1), PmgalT7 (3), MsgalT8 (6), gatD (7), lex1 (9), IgtB (11) or IsgD (13);

FIG. 4 shows the results of the TLC analysis of culture extracts of lacto-N-tetraose (LNT) producing *E. coli* BL21 (DE3) strains overexpressing the β-1,4-galactosyltransferase encoding genes KdgalT10 (1), cpsI14J (7), cpslaJ (8, 9), HpgalT (12);

FIG. 5 shows the results of the TLC analysis of culture extracts of lacto-N-tetraose producing *E. coli* BL21(DE3) strains overexpressing the β-1,4-galactosyltransferase encoding gene waaX (5);

FIG. 6 shows the results of the TLC analysis of culture extracts of lacto-N-tetraose producing *E. coli* BL21(DE3) strains overexpressing the β-1,3-galactosyltransferase encoding genes wbdO or furA;

FIG. 7 shows the results of HPLC analyses of the culture supernatant of lacto-N-tetraose producing *E. coli* BL21 (DE3) strain. (A) Supernatant of *E. coli* BL21(DE3) 1353 and 1431 grown in the presence of glucose and lactose after 24 h of incubation. (B) Supernatant of *E. coli* BL21(DE3) 1353 and 1431 grown in the presence of glucose and lactose after 48 h of incubation;

FIG. 8 shows a diagram depicting the relative concentration of lacto-N-tetraose in the supernatant of *E. coli* BL21 (DE3) strains overexpressing sugar efflux transporters compared to the control strain 1353; and FIG. 9 shows a diagram depicting concentrations of lacto-N-triose II in the supernatant of *E. coli* BL21 (DE3) strains overexpressing the sugar efflux transporters TP11 (2), YjhB (3) or TP70 (4).

EXAMPLES

FIG. 1 shows a schematic drawing of an exemplary host cell 10 according to the invention, importing lactose and synthesizing lacto-N-triose II (LNT 11) and lacto-N-tetraose (LNT). Lactose is imported from the medium the host cell is cultivated in into the cell via transporter 1. The enzyme N-acetylglucosaminyltransferase NacGlcT ligates N-acetylglucosamine to the acceptor substrate lactose, thus generating LNT-II. LNT-II is exported from the cell via exporter protein 20. Since LNT-II is a precursor of LNT or LNnT, the exporter exporting LNT-II represents an exporter protein exporting precursors of the latter oligosaccharides. As can further be seen from FIG. 1, the cell comprises a protein having β-1,3-galactosyltransferase activity enabling the galactosylation of LNT-II to intracellularly generate LNT; the cell may also and/or alternatively comprise or β-1,4-galactosyltransferase activity enabling the galactosylation of LNT-II to intracellularly generate lacto-N-neotetraose LNnt. LNT—or as the case may be LNnt—is then exported, via a oligosaccharide exporter from the cell into the culture medium the cell is cultivated in.

The exporters are membrane-bound, and their expression can be either overexpressed, which—in case of overexpression of the LNT-II exporter leads to an increased LNT-II export and to a decreased LNT export, whereas when the LNT-II exporting exporter protein is deleted or otherwise inactivated, this leads to an improved LNT-export. The LNT-II exporter preferably is an endogenous exporter protein, whereas the LNT-exporter protein preferably is a heterologous exporter protein.

Example 1

Development of an *E. coli* Lacto-N-Triose II Production Strain

*Escherichia coli* BL21(DE3) was used to construct a lacto-N-triose II (LNT-2) producing strain. Metabolic engineering included mutagenesis and deletions of specific genes, respectively, and genomic integrations of heterologous genes. The genes lacZ and araA were inactivated by mutagenesis using mismatch-oligonucleotides as described by Ellis et al., “High efficiency mutagenesis, repair, and engineering of chromosomal DNA using single-stranded oligonucleotides”, Proc. Natl. Acad. Sci. USA 98: 6742-6746 (2001).

Genomic deletions were performed according to the method of Datsenko and Warner (Proc. Natl. Acad. Sci. USA 97:6640-6645 (2000)). To prevent intracellular degradation of N-acetylglucosamine, genes encoding N-acetylglucosamine-6-phosphate deacetylase (nagA) and glucosamine-6-phosphate deaminase (nagB) were deleted from the genome of the *E. coli* strain BL21 (DE3) strain. Also genes wzxC-wcaJ were deleted. WcaJ encodes an UDP-glucose:undecaprenyl phosphate glucose-1-phosphate transferase catalysing the first step in colanic acid synthesis (Stevenson et al., J. Bacteriol. 1996, 178:4885-4893). In addition the genes fucI and fucK, coding for L-fucose isomerase and L-fuculose kinase, respectively, were removed.

Genomic integration of heterologous genes was performed by transposition. Either the EZ-Tn5™ transposase (Epicentre, USA) was used to integrate linear DNA-fragments or the hyperactive C9-mutant of the mariner transposase Himarl (Lampe et al., Proc. Natl. Acad. Sci. 1999, USA 96:11428-11433) was employed for transposition. To produce EZ-Tn5 transposomes the gene of interest together with a FRT-site flanked antibiotic resistance marker was amplified with primer 1119 and 1120 (all primer used are listed in table 3 below); the resulting PCR-product carried on both sites the 19-bp Mosaic End recognition sites for the EZ-Tn5 transposase. For integration using Himarl transposase expression constructs (operons) of interest were similarly cloned together with a FRT-site flanked antibiotic resistance marker into the pEcomar vector. The pEcomar vector encodes the hyperactive C9-mutant of the mariner transposase Himarl under the control of the arabinose inducible promoter $P_{araB}$. The expression fragment <$P_{tet}$-lacY-FRT-aadA-FRT> (SeqID1) was integrated by using the EZ-Tn5 transposase. After successful integration of the gene for the lactose importer LacY from *E. coli* K12 TG1 (acc. no. ABN72583) the resistance gene was eliminated from streptomycin resistant clones by the FLP recombinase encoded on plasmid pCP20 (Datsenko and Warner, Proc. Natl. Acad. Sci. 2000, USA 97:6640-6645). The N-acetylglucosaminyltransferase gene lgtA from *Neisseria meningitidis* MC58 (acc. no. NP_274923) was codon-optimized for expression in *E. coli* and prepared synthetically by gene synthesis. Together with the gene galT, encoding a galactose-1-phosphate uridylyltransferase from *E. coli* K-12 substr. MG1655 (acc. no. NP_415279) that was similarly obtained by gene synthesis, lgtA was inserted by transposition (SeqID2) using plasmid pEcomar-lgtA-galT. To enhance de novo synthesis of UDP-N-acetylglucosamine, genes encoding L-glutamine:D-fuctose-6-phosphate aminotransferase (glmS), phosphoglucosamine mutase from *E. coli* K-12 substr. MG1655

(glmM) and N-acetylglucosamine-1-phosphate uridyltransferase/glucosamine-1-phosphate acetyltransferase (glmU) from *E. coli* K-12 substr. MG1655 (acc. no. NP_418185, NP_417643, NP_418186, respectively) were codon-optimized and obtained by gene synthesis. The operon glmUM was cloned under the control of constitutive tetracyclin promoter $P_{tet}$ while glmS was cloned under the constitutive $P_{T5}$ promoter. The transposon cassette <$P_{tet}$-glmUM-$P_{T5}$-glmS-FRT-dhfr-FRT> (SeqID3), flanked by the inverted terminal repeats specifically recognized by the mariner-like element Himarl transposase was inserted from pEcomar-glmUM-glmS revealing a lacto-N-triose II production strain. Additionally, the expression fragment <$P_{tet}$-lacY(6H/S)-FRT-aadA-FRT> (SeqID4) was integrated by using the EZ-Tn5 transposase.

The gal-operon (galETKM) was amplified from *E. coli* K12 TG1 (SeqID6) using primer 605 and 606 and inserted into the galM ybhJ locus of *E. coli* BL21 (DE3) strain by homologous recombination facilitated by using the red recombinase helper plasmid pKD46 (Datsenko and Warner, Proc. Natl. Acad. Sci. 2000, USA 97:6640-6645). Sequences of the heterologous genes and gene clusters are deposit in appendix 1.

Example 2

Batch Fermentation of *E. coli* BL21 (DE3) 707 screening various β-1,3-N-acetyl-glycosaminyltransferases The gene for the β-1,3-N-acetyl-glucosaminyltransferase PmnagT from *Pasteurella multocida* subsp. *multocida* str. HN06 (acc. no. PMCN06_0022) was codon-optimized and synthetically synthesized by GenScript Cooperation (Piscataway, USA). Cloning of the gene occurred by sequence and ligation-independent cloning into the plasmid pET-DUET (Merck KGaA, Darmstadt, Germany). All primer used for cloning are listed in table 3 below.

*E. coli* BL21(DE3) 707 (table 2 below) harbouring plamid pET-PmnagT coding for a β-1,3-N-acetyl glucosaminyltransferase was grown at 30° C. in mineral salts medium (Samain et al., J. Biotech. 1999, 72:33-47) supplemented with 2% (wt/vol) glucose and ampicillin 100 μg $ml^{-1}$. When the cultures reached an OD660 nm of 0.1, gene expression was induced by addition of 0.3 mM IPTG. After four hours of incubation 1.5 mM lactose was added. After an additional incubation for 24 hours at 30° C. in shaking flasks cells were harvested. LNT-2 was detected by thin layer chromatography. Therefore, cells were mechanically disrupted in a defined volume using glass beads. Subsequently, samples were applied on TLC Silica Gel 60 $F_{254}$ (Merck KGaA, Darmstadt, Germany). The mobile phase was composed of acetone:butanol:acetic acid:water (35:35:7:23).

The result of the TLC analysis is shown in FIG. 2. The formation of a compound showing the same migration rate as the trisaccharide standard LNT-II could be observed when the gene PmnagT was overexpressed. The LNT-II production strain 724 served as a control (19). Standards for lactose (1) and LNT-II (2) are depicted. LNT-II product formation in the samples is marked by asterisks.

Example 3

Generation of an *E. coli* Lacto-N-Triose II Production Strain Overexpressing a Homologous Sugar Efflux Transporter The export of oligosaccharides produced in *E. coli* was proven to be a limiting factor during the fermentation process. However, trisaccharides like 2'-fucosyllactose and LNT-2 are translocated into the culture supernatant to some extent, thus probably encoding a working sugar efflux transporter. In order to improve the efflux of lacto-N-triose II (LNT-II; GluNAc(β1-3)Gal(β1-4)Glc), the *E. coli* BL21 (DE3) strain 1326 (table 2 below) was used for the screening of a library of sugar efflux transporters (SET). Putative SET proteins from *E. coli* were amplified from genomic DNA of *E. coli* BL21 (DE3) and integrated into vector pINT by sequence and ligation-independent cloning. Using the example of the gene yjhB, the primer 2567, 2568, 2526 and 2443 were used, generating the plasmid pINT-yjhB.

The primer sequences used for cloning are listed in table 3 below. *E. coli* BL21(DE3) 1326 harbouring plasmids encoding for 20 different *E. coli* transporters were grown at 30° C. in mineral salts medium (Samain et al., J. Biotech. 1999, 72:33-47) supplemented with 2% (wt/vol) glucose, ampicillin 100 μg $ml^{-1}$ and zeocin 40 μg $ml^{-1}$. When the cultures reached an OD660 nm of 0.1, gene expression of the genes was induced by addition of 200 ng/ml anhydrotetracycline. After four hours of incubation 2.5 mM lactose was added. After an additional incubation for 24 and 48 hours at 30'C in shaking flasks the LNT-II concentration in the supernatant was determined by LC-MS.

Mass analysis was performed by characteristic fragment ion detection using an LC Triple-Quadrupole MS detection system. Precursor ions are selected and analyzed in quadrupole 1, fragmentation takes place in the collision cell using nitrogen as CID gas, selection of fragment ions is performed in quadrupole 3.

Lacto-N-tetraose (LNT (Gal(β1-3)GlcNAc(β1-3)Gal(β1-4)Glc)), LNT-II and Maltotriose (internal standard for quantification) were analyzed in ESI positive ionization mode. LNT forms an ion of m/z 708.3 $[M+H^+]$, LNT-II an ion of m/z 546.1 $[M+H^+]$ and Maltotriose an ion of m/z 522.0 $[M+NH_4^+]$. Adduct formation of this carbohydrate [m/z 504.0] takes place with an ammonium ion ($NH4^+$), resulting in mass shift of +18. Thus for Maltotriose a precursor ion of m/z 522.0 was selected. The precursor ion was further fragmented in the collision cell into the characteristic fragment ions m/z 487.1, m/z 325.0 and m/z 163.2. The molecular ion of LNT (m/z 708.3) was fragmented into m/z 546.3, m/z 528.3, m/z 366.2 and m/z 204.0. LNT-II (m/z 546.1) was fragmented into m/z 204.2, 186.0, 138.0 and 126.0 (see method description).

Chromatographic separation of LNT and LNT-II was performed on a Luna $NH_2$ HPLC column (Phenomenex, Aschaffenburg, Germany). This was necessary due to partial fragmentation of LNT during ionization resulting in LNT-II signals affecting quantification results of the individual carbohydrates.

Only for the strain expressing the gene yjhB, an increased amount of LNT-2 in the culture supernatant was observed (see table 1 below).

Table 1: Calculated concentrations of LNT-II in the culture supernatant of an *E. coli* BL21 (DE3) strain overexpressing yjhB and the reference strain.

| Sample | Calc. conc. after 24 h of incubation [μM] | Calc. conc. after 48 h of incubation [μM] | Analyte RT |
|---|---|---|---|
| 1326 | 751 | 1265 | 0.616 |
| 1326 pINT-yjhB | 413 | 1975 | 0.609 |

Example 4

Batch Fermentations of *E. coli* BL21(DE3) 724 Screening Various β-1,4-Galactosyltransferases The genes for the β-1,4-galactosyltransferases lex1 from Aggregatibacter aphrophilus NJ8700 (acc. no. YP_003008647), PmgalT7 from *Pasteurella multocida* subsp. *multocida* str. HN06 (acc. No. PMCN06_0021), MsgalT8 from *Myxococcus stipitatus* DSM14675 (acc. no. MYSTI_04346), KdgalT10 from *Kingella denitrificans* ATCC 33394 (acc. no. HMPREF9098_2407), gatD from *Pasteurella multocida* M1404 (acc. no. GQ444331), BfgalT2 from *Bacterioidis fragilis* NCTC9343 (acc. no. BF9343 0585), IsgD from *Haemophilus* influenza (acc. no. AAA24981) and HpgalT from *Helicobacter pylori* (acc. no. AB035971) were codon-optimized and synthetically synthesized by GenScript Cooperation (Piscataway, USA). Cloning of the genes occurred by sequence and ligation-independent cloning (Li and Elledge, Nat Methods. 2007 March; 4(3):251-6.). Therefore, the plasmid pINT, harbouring the malE gene under control of an anhydrotetracyline-inducible promoter, was used, enabling the generation of a N-terminal fusion of the β-1,4-galactosyltransferase genes with ma/E. Solely, the β-1,4-galactosyltransferase encoding gene waaX from *Pectobacterium atrosepticum* JG10-08 (acc. no. ECA0154) was cloned into plasmid pACYC-Duet (Merck KGaA, Darmstadt, Germany). All primer used for cloning are listed in table 3 below.

*E. coli* BL21(DE3) 724 (table 2 below) harbouring plamid pCDF-galE and a plasmid coding for the gene fusion of malE with a β-1,4-galactosyltransferase was grown at 30° C. in mineral salts medium (Samain et al., J. Biotech. 1999, 72:33-47) supplemented with 2% (wt/vol) glucose, ampicillin 100 μg $ml^{-1}$ and zeocin 40 μg $ml^{-1}$. When the cultures reached an OD660 nm of 0.1, gene expression of the galE gene and the β-1,4-galactosyltransferase was induced by addition of 0.3 mM IPTG and 200 ng/ml anhydrotetracycline. *E. coli* BL21(DE3) 534 (table 2 below) harbouring plamids pET-lgtA, pCOLA-glmUM-glmS, pCDF-galT-galE and pACYC-waaX was grown at 30° C. in mineral salts medium supplemented with 2% (wt/vol) glucose, ampicillin 100 μg $ml^{-1}$, chloramphenicol 34 μg $ml^{-1}$, streptomycin 50 μg $ml^{-1}$ and kanamycin 30 μg $ml^{-1}$. When the cultures reached an OD660 nm of 0.1, gene expression was induced by addition of 0.3 mM IPTG. Four hours after induction of gene expression 2 mM lactose were added. After an additional incubation for 48 hours at 30° C. in shaking flasks, cells were harvested and mechanically disrupted. Lacto-N-neotetraose (LNnT (Gal(β1-4)GlcNAc(β1-3)Gal(β1-4) Glc)) was detected by thin layer chromatography. Therefore, cells were mechanically disrupted using glass beads. Subsequently, samples were applied on TLC Silica Gel 60 $F_{254}$ (Merck KGaA, Darmstadt, Germany). The mobile phase was composed of acetone:butanol:acetic acid:water (35:35:7:23).

The results of the TLC analyses are shown in FIGS. 3-5. FIG. 3 shows the TLC analysis of culture extracts of lacto-N-tetraose (LNT) producing *E. coli* BL21(DE3) strains overexpressing the β-1,4-galactosyltransferase encoding genes BfgalT2 (1), PmgalT7 (3), MsgalT8 (6), gatD (7), lex1 (9), IgtB (11) or IsgD (13). Standards for lactose (15), LNT-II (16) and LNnT (17) are depicted. LNnT product formation in the samples is marked by asterisks.

FIG. 4 shows the TLC analysis of culture extracts of lacto-N-tetraose (LNT) producing *E. coli* BL21(DE3) strains overexpressing the β-1,4-galactosyltransferase encoding genes KdgalT10 (1), cpsI14J (7), cpslaJ (8, 9), HpgalT (12). Standards for lactose (3, 15), LNT-II (4, 16) and LNnT (5, 17) are depicted. LNnT product formation in the samples is marked by asterisks.

FIG. 5 shows the TLC analysis of culture extracts of lacto-N-tetraose producing *E. coli* BL21(DE3) strains overexpressing the β-1,4-galactosyltransferase encoding gene waaX (5). Standards for lactose (1), LNT-II and LNnT (2) are depicted. Again, LNnT product formation in the samples is marked by asterisks.

The formation of a compound showing the same migration rate as the tetrasaccharide standard LNnT could be observed when the following genes were overexpressed: lex1, PmgalT7, MsgalT8, BfgalT2, gatD, IsgD, KdgalT10, HpgalT, wax.

The β-1,4-galactosyltransferases cpsIaJ and cpsI14J, known from literature to produce LNnT (Watanabe et al., J Biochem. 2002 February; 131(2):183-91; Kolkman et al., J Bacteriol. 1996 July; 178(13):3736-41), were also included in the activity screening and served as positive control. Using the described expression system, the formation of LNnT could be observed by CpsIaJ and CpsI14J (FIG. 3). In total, 11 out of 30 tested genes were observed to produce LNnT from LNT-II and UDP-galactose.

Example 5

Batch Fermentations of *E. coli* BL21(DE3) 534 Screening Different β-1,3-Galactosyltransferases Using genomic DNA of *E. coli* K12 DH5a as template, galE was amplified using primer 1163 and 1162. The PCR product was purified, restricted with restriction endonucleases NdeI and XhoI and ligated into the second multiple cloning site of vector pCDFDuet (Merck KGaA, Darmstadt, Germany), which was cut with the same enzymes. GalE is expressed from the IPTG inducible T7 promoter. The *E. coli* K12 gene galT was amplified from genomic DNA and integrated into plasmid pCDF-galE by sequence and ligation-independent cloning using primer 991-994, producing the plasmid pCDF-galT-galE.

Using the codon-optimized gene of lgtA as template, amplification occurred using primer 688 and 689. The PCR product was purified, restricted with restriction endonucleases NdeI and AatII and ligated into the multiple cloning site of vector pETDuet (Merck KGaA, Darmstadt, Germany), which was cut with the same enzymes, producing the plasmid pET-lgtA.

Cloning of the codon-optimized gene construct of glmUM occurred by sequence and ligation-independent cloning into the plasmid pCOLA-Duet (Merck KGaA, Darmstadt, Germany) using primer 848-851. The codon-optimized form of glmS was amplified using primer 852 and 853. The PCR product was purified, restricted with restriction endonucleases NdeI and AatII and ligated into the second multiple cloning site of vector pCOLA-glmUM, which was cut with the same enzymes, producing the plasmid pCOLA-glmUM-glmS.

The genes for the β-1,3-galactosyltransferases wbdO from *Salmonella enterica* subsp. *salamae* serovar Greenside (acc. no. AY730594) and furA from *Lutiella nitroferrum* 2002 (FuraDRAFT_0419) were also codon-optimized and synthetically synthesized by GenScript Cooperation (Piscataway, USA). Cloning of the genes occurred by sequence and ligation-independent cloning into the plasmid pACYC-Duet (Merck KGaA, Darmstadt, Germany). All primer used for cloning are listed in table 3 below.

*E. coli* BL21(DE3) 534 harbouring plasmids pET-lgtA, pCOLA-glmUM-glmS, pCDF-galT-galE and a plasmid coding for a β-1,3-galactosyltransferase pACYC-furA or pACYC-wbdO was grown at 30° C. in mineral salts medium (Samain et al., J. Biotech. 1999, 72:33-47) supplemented with 2% (w/v) glucose, ampicillin 100 μg $ml^{-1}$, chloramphenicol 34 μg $ml^{-1}$, streptomycin 50 μg $ml^{-1}$ and kanamycin 30 μg $ml^{-1}$. When the cultures reached an OD660 nm of 0.1, gene expression was induced by addition of 0.3 mM IPTG. After four hours of incubation 2 mM lactose was added. After an additional incubation for 48 hours at 30° C. in shaking flasks, cells were harvested. LNT was detected by thin layer chromatography. Therefore, cells were mechanically disrupted using glass beads. Subsequently, samples were applied on TLC Silica Gel 60 $F_{254}$ (Merck KGaA, Darmstadt, Germany). The mobile phase was composed of acetone:butanol:acetic acid:water (35:35:7:23).

The results of the TLC analyses are shown in FIG. 6, showing TLC analysis of culture extracts of lacto-N-tetraose producing *E. coli* BL21(DE3) strains overexpressing the β-1,3-galactosyltransferase encoding genes wbdO or furA. LNT product formation in the samples is marked. Out of 12 tested putative β-1,3-galactosyltransferases, the formation of a compound showing the same migration rate as the tetrasaccharide standard LNT could only be observed when genes wbdO and furA were overexpressed.

Example 6

Development of an Improved Plasmid-Free *E. coli* Lacto-N-Tetraose Production Strain

*Escherichia coli* BL21(DE3) strain 724 was used to construct a lacto-N-tetraose (LNT) producing strain. Metabolic engineering included the genomic integration of the transposon cassettes <$P_{tet}$-wbdO-$P_{T5}$-galE-FRT-cat-FRT> (SeqID5), flanked by the inverted terminal repeats specifically recognized by the mariner-like element Himarl transposase, which was inserted from pEcomar-wbdO-galE. The resulting strain 1353 was further metabolically engineered to exhibit an increased intracellular LNT-II pool resulting in the elevated production of LNT. Therefore, the mayor facilitator superfamily transporter yjhB (acc. no. YP_003001824) was deleted from the genome of the *E. coli* strain, generating strain 1431 (table 2 below).

Batch fermentation of the *E. coli* BL21(DE3) strains 1353 and 1431 was conducted for 48 hours at 30° C. in mineral salts medium (Samain et al., J. Biotech. 1999, 72:33-47) containing 2% (wt/vol) glucose as sole carbon and energy source. When the cultures reached an OD660 nm of 0.5, 2.5 mM lactose was added. The presence of LNT-II and LNT in the culture supernatant was detected by high performance liquid chromatography (HPLC).

Analysis by HPLC was performed using a refractive index detector (RID-10A) (Shimadzu, Duisburg, Germany) and a ReproSil Carbohydrate, 5 μm (250 mm×4.6 mm) (Dr. Maisch GmbH, Germany) connected to an HPLC system (Shimadzu, Duisburg, Germany). Elution was performed isocratically with acetonitril:$H_2O$ (68/32 (v/v)) as eluent at 35° C. and a flow rate of 1.4 ml/min. 40 μl of the sample were applied to the column. Samples were filtered (0.22 μm pore size) and cleared by solid phase extraction on an ion exchange matrix (Strata ABW, Phenomenex, Aschaffenburg, Germany).

The results of the HPLC analyses are shown in FIG. 7, showing HPLC analyses of the culture supernatant of lacto-N-tetraose producing *E. coli* BL21 (DE3) strain. (A) Supernatant of *E. coli* BL21(DE3) 1353 (black graph) and 1431 (pink graph) grown in the presence of glucose and lactose after 24 h of incubation. (B) Supernatant of *E. coli* BL21

(DE3) 1353 (blue graph) and 1431 (brown graph) grown in the presence of glucose and lactose after 48 h of incubation. As can be seen from the HPLC analyses, the deletion of yjhB in a LNT producing strain resulted in an elevated accumulation of LNT in the culture supernatant.

Example 7

Generation of an *E. coli* Lacto-N-Tetraose Production Strain Overexpressing a Sugar Efflux Transporter Since an export of lacto-N-tetraose into the medium is only moderate for production strains, a screening of a sugar efflux transporter library was conducted. In accordance to example 3 putative SET proteins were either amplified from *E. coli* genomic DNA or were codon-optimized and synthetically synthesized by GenScript Cooperation (Piscataway, USA). Following amplification genes were integrated into vector pINT by sequence and ligation-independent cloning. The primer design for the cloning of *E. coli* genes was in accordance to example 3. Synthetic genes were synthesized with standardized nucleotide overhangs and likewise integrated into the expression vector using the primer 2527, 2444, 2526 and 2443. The primer sequences used for cloning are listed in table 3 below.

*E. coli* BL21(DE3) 1353 (table 2 below) harbouring plasmids encoding for 66 different transporters were grown at 30° C. in mineral salts medium (Samain et al., J. Biotech. 1999, 72:33-47) supplemented with 3% (w/v) glucose, 5 g $l^{-1}$ $NH_4Cl_2$, ampicillin 100 μg $ml^{-1}$ and kanamycin 15 μg $ml^{-1}$. Precultivation appeared in 96-well plates harbouring a total volume of 200 μl. After 24 h of incubation at 30° C. by continuous shaking, 50 μl per well was transferred into 96-well deep well plates harbouring a total volume of 400 μl mineral salts medium additionally supplemented with 200 ng $ml^{-1}$ anhydrotetracycline and 10 mM lactose. After a sustained incubation for 24 to 48 hours the LNT concentrations in the supernatant were determined by LC-MS. Mass analysis was performed as described in example 3.

FIG. 8 shows the relative concentration of lacto-N-tetraose in the supernatant of *E. coli* BL21 (DE3) strains overexpressing sugar efflux transporters compared to the control strain 1353. The LNT titer of strain 1353 was set to 100%. As shown in FIG. 8, the overexpression of 11 out of 66 genes resulted in a doubled LNT production. Among these, also a protein encoded in the genome of *E. coli* BL21 (DE3) proved to enhance the LNT export (TP37, yebQ, acc. no. NC_012971). YebQ is a predicted MFS transporter, putatively involved in multi drug efflux, which might represent a responsible transporter protein that realizes the observed basal efflux of LNT during fermentation of strain 1353.

Furthermore, the exporters encoded by the genes spoVB of *Bacillus amyloliquefaciens* (TP1, acc. no. AFJ60154), yabMof *Erwinia pyrilfoliae* (TP2, acc. no. CAY73138), bcr of *E. coli* MG1655 (TP18, acc. no. AAC75243), ydeA of *E. coli* MG1655 (TP20, acc. no. AAC74601), proP2 of *Haemophilus parainfluenzae* (TP54, acc. no. EGC72107), setA of *Pectobacterium carotovorum* (TP55, acc. no. ZP_03829909), fucP of *E. coli* MG1655 (TP59, acc. no. AIZ90162), mdeA of *Staphylococcus aureus* Bmb9393 (TP61, acc. no. SABB_01261), lmrA of *Lactococcus lactis* (TP62, acc. no. L116532), setA of *Pseudomonas* sp. MT-1 (TP72, acc. no. BAP78849) and setA of *Beauveria bassiana* D1-5 (TP73, acc. no. KGQ13398) resulted in an increased LNT production when overexpressed in the *E. coli* production strain 1353.

Example 8

Generation of an *E. coli* Lacto-N-Triose II Production Strain by Overexpression of Heterologous Sugar Efflux Transporters The LNT exporter screening described in example 6 interestingly disclosed two proteins—TP11 from *Mannheimia succiniciproducens* MBEL55E (proP, acc. no. AAU37785) and TP70 from *Cedecea neteri* M006 (setA, acc. no. WP_039290253)—whose overexpression resulted in a significantly increased production of LNT-II and consequently in a decreased LNT production (data not shown). This observation was confirmed in an experimental setup as described in example 3. The overexpression of the sugar efflux transporter YjhB served as a positive control. The overexpression of TP11 as well as TP70 resulted in an approximately 4-fold increase in LNT-II production which was even slightly more than for YjhB: FIG. 9 shows a diagram displaying the concentrations of lacto-N-triose II in the supernatant of *E. coli* BL21 (DE3) strains overexpressing the sugar efflux transporters TP11 (2), YjhB (3) or TP70 (4). Strain 1326 harbouring an empty control plasmid served as a control (1). Thus, 3 sugar efflux transporters were identified which target LNT-II for export and whose overexpression might be useful to engineer a LNT-II production strain.

TABLE 2

Strains and plasmids

| Strain | Genotype | Ref. |
|---|---|---|
| *E. coli* BL21(DE3) | F-ompT hsdSB(rB-, mB-) gal dcm (DE3) | Merck KGaA, Darmstadt, Germany |
| *E. coli* BL21(DE3) 534 | *E. coli* BL21(DE3) ΔlacZ Δara ΔwcaJ ΔfuclK ΔnagAB harbouring genomic integrations of: galETKM, lacy | This study |
| *E. coli* BL21(DE3) 724 | *E. coli* BL21(DE3) ΔlacZ Δara ΔwcaJ ΔfuclK ΔnagAB harbouring genomic integrations of: galETKM, lacY, lgtA-galT-kanR, glmUM-glmS-dhfr | This study |
| *E. coli* BL21(DE3) 1326 | *E. coli* BL21(DE3) ΔlacZ Δara ΔwcaJ ΔfuclK ΔnagAB harbouring genomic integrations of: galETKM, lacY, lgtA-galT-kanR, glmUM-glmS-dhfr, lacy(6HIS)-aadA | This study |
| *E. coli* BL21(DE3) 707 | *E. coli* BL21(DE3) ΔlacZ Δara ΔwcaJ ΔfuclK ΔnagAB harbouring genomic integrations of: galETKM, lacY, glmUM-glmS-dhfr | This study |
| *E. coli* BL21(DE3) 1353 | *E. coli* BL21(DE3) ΔlacZ Δara ΔwcaJ ΔfuclK ΔnagAB harbouring genomic integrations of: galETKM, lacY, lgtA-galT-kanR, glmUM-glmS-dhfr, wbdO-galE-cat | This study |
| *E. coli* BL21(DE3) 1431 | *E. coli* BL21(DE3) ΔlacZ Δara ΔwcaJ ΔfuclK ΔnagAB harbouring genomic integrations of: galETKM, lacY, lgtA-galT-kanR, glmUM-glmS-dhfr, wbdO-galE-cat, ΔyjhB-aacC1 | This study |
| pCDF-galE | galE of *E. coli* K12 integrated into vector pCDFDuet | EP 14 162 869.3 |
| pET-lgtA (SeqID7) | lgtA of *Neisseria meningitidis* integrated into vector pETDuet | This study |
| pCDF-galT-galE (SeqID8) | galT and galE of *Escherichia coli* K12 integrated into vector pCDFDuet | This study |
| pCOLA-glmUM-glmS (SeqID9) | glmU, glmM and glmS of *Escherichia coli* K12 integrated into vector pCOLADuet | This study |
| pINT-malE-lex1 | Gene fusion of malE with lex-1 of *Aggregatibacter aphrophilus* NJ8700 integrated into vector pINT | EP 14 162 869.3 |
| pINT-malE-PmgalT7 (SeqID10) | Gene fusion of PmgalT7 of *Pasteurella multocida* subsp. *multocida* str. HN06 integrated into vector pINT | This study |
| pINT-malE-MsgalT8 (SeqID11) | Gene fusion of MsgalT8 of *Myxococcus stipitatus* DSM14675 integrated into vector pINT | This study |
| pINT-malE-KdgalT10 (SeqID12) | Gene fusion of KdgalT10 of *Kingella denitrificans* ATCC 33394 integrated into vector pINT | This study |
| pINT-malE-gatD (SeqID13) | Gene fusion of gatD of *Pasteurella multocida* M1404 integrated into vector pINT | This study |
| pINT-malE-BFgalT2 (SeqID14) | Gene fusion of BfgalT2 of *Bacterioidis fragilis* NCTC9343 integrated into vector pINT | This study |
| pINT-malE-IsgD (SeqID15) | Gene fusion of IsgD of *Haemophilus influenza* integrated into vector pINT | This study |
| pINT-malE-HPgalT (SeqID16) | Gene fusion of HpgalT of *Helicobacter pylori* integrated into vector pINT | This study |
| pACYC-waaX (SeqID17) | waaX of *Pectobacterium atrosepticum* JG10-08 integrated into vector pACYCDuet | This study |

TABLE 2-continued

| Strains and plasmids | | |
|---|---|---|
| Strain | Genotype | Ref. |
| pACYC-wbdO (SeqID18) | wbdO of *Salmonella enterica* subsp. *salamae serovar* Greenside integrated into vector pACYCDuet | This study |
| pACYC-furA (SeqID19) | furA of *Lutiella nitroferrum* 2002 integrated into vector pACYCDuet | This study |
| pET-PmnagT (SeqID20) | PmnagT of *Pasteurella multocida* subsp. *multocida* str. HN06 integrated into vector pETDuet | This study |
| PINT-yjhB (SeqID21) | yjhB of *E. coli* BL21 DE3 integrated into vector pINT | This study |
| pINT-yebQ (SeqID22) | yebQ of *E. coli* BL21 DE3 integrated into vector pINT | This study |
| pINT-proP (SeqID23) | proP of *Mannheimia succiniciproducens* MBEL55E integrated into vector pINT | This study |
| pINT-Cn-setA (SeqID24) | setA of *Cedecea neteri* M006 integrated into vector pINT | This study |
| pINT-spoVB (SeqID25) | spoVB of *Bacillus amyloliquefaciens* integrated into vector pINT | This study |
| pINT-yabM (SeqID26) | yabM of *Erwinia pyrifoliae* integrated into vector pINT | This study |
| pINT-ydeA (SeqID27) | ydeA of *E. coli* MG1655 integrated into vector pINT | This study |
| pINT-proP2 (SeqID28) | proP2 of *Haemophilus parainfluenzae* integrated into vector pINT | This study |
| pINT-Pc-setA (SeqID29) | setA of *Pectobacterium carotovorum* integrated into vector pINT | This study |
| pINT-fucP (SeqID30) | fucP of *Escherichia coli* BL21 (DE3) integrated into vector pINT | This study |
| pINT-mdeA (SeqID31) | mdeA of *Staphylococcus aureus* Bmb9393 integrated into vector pINT | This study |
| pINT-lmrA (SeqID32) | lmrA of *Lactococcus lactis* integrated into vector pINT | This study |
| pINT-Ps-setA (SeqID33) | setA of *Pseudomonas* sp. MT-1 integrated into vector pINT | This study |
| pINT-Bb-setA (SeqID34) | setA of *Beauveria bassiana* D1-5 integrated into vector pINT | This study |

TABLE 3

| Oligonucleotides used for PCR | |
|---|---|
| Primer | Sequence 5'-3' |
| 605 KI gal fwd | TTACTCAGCAATAAACTGATATTCCGTCAGGCTGG (SeqID35) |
| 606 KI gal rev | TTGTAATCTCGCGCTCTTCACATCAGACTTTCCATATAGAGCGTAATTTC CGTTAACGTCGGTAGTGCTGACCTTGCCGGAGG (SeqID36) |
| 1119 ME-for | CTGTCTCTTATCACATCTCCTGAAATGGCCAGATGTAATTCCTAATTTTT GTTG (SeqID37) |
| 1120 ME rev | CTGTCTCTTATCACATCTCACATTACATCTGAGCGATTGTTAGG (SeqID38) |
| 1163 galE_NdeI-for | GATCACATATGAGAGTTCTGGTTACCGGTG (SeqID39) |
| 1164 galE_XhoI-rev | GATCACTCGAGTCATTAATCGGGATATCCCTGTGGATGGC (SeqID40) |
| 5176 lex1 pINT-f | GTCGATGAAGCCCTGAAAGACGCGCAGACTATGCACTTCATTGAAAAC AAAAACTTCGTC (SeqID41) |
| 5177 lex1 pINT-r | GATGGCCTTTTTGCGTGTCGACGCGGCCGCCTAGATAAACAGGATGAT ATTTTTGCCTIG (SeqID42) |
| 5178 pINT lexl-f | CAAGGCAAAAATATCATCCTGTTTATCTAGGCGGCCGCGTCGACACGC AAAAAGGCCATC (SeqID43) |
| 5179 pINT lexl-r | GACGAAGTTTTTGTTTTCAATGAAGTGCATAGTCTGCGCGTCTTTCAGG GCTTCATCGAC (SeqID44) |
| 5192 waaX pINT for | GTCGATGAAGCCCTGAAAGACGCGCAGACTATGATTGATAACCTGATTA AGCGTACCCCG (SeqID45) |

TABLE 3-continued

| Oligonucleotides used for PCR | |
|---|---|
| Primer | Sequence 5'-3' |
| 5193 waaX pINT rev | ATGGCCTTTTTGCGTGTCGACGCGGCCGCTTAATTCGAGCGGGTAAAG ATCTTCATCAGG (SeqID46) |
| 5194 pINT waaX for | CTGATGAAGATCTTTACCCGCTCGAATTAAGCGGCCGCGTCGACACGC AAAAAGGCCATC (SeqID47) |
| 5195 pINT waaX rev | CGGGGTACGCTTAATCAGGTTATCAATCATAGTCTGCGCGTCTTTCAGG GCTTCATCGAC (SeqID48) |
| 5164 PmgalT7 pINT for | GTCGATGAAGCCCTGAAAGACGCGCAGACTATGAGCGGTGAACACTAT GTCATTAGCCTG (SeqID49) |
| 5165 PmgalT7 pINT rev | GATGGCCTTTTTGCGTGTCGACGCGGCCGCTCATTTAAATTCGATGATC ATCTTGTCGTT (SeqID50) |
| 5166 pINT PmgalT7 for | AACGACAAGATGATCATCGAATTTAAATGAGCGGCCGCGTCGACACGC AAAAAGGCCATC (SeqID51) |
| 5167 pINT PmgalT7 rev | CAGGCTAATGACATAGTGTTCACCGCTCATAGTCTGCGCGTCTTTCAGG GCTTCATCGAC (SeqID52) |
| 5168 MsgalT8 pINT for | GTCGATGAAGCCCTGAAAGACGCGCAGACTATGGATGAAATCAAACTG TCGGTGGTTATG (SeqID53) |
| 5169 MsgalT8 pINT rev | GATGGCCTTTTTGCGTGTCGACGCGGCCGCTCATTGGCGACGCCAATC GAACGCAACGCG (SeqID54) |
| 5170 pINT MsgalT8 for | CGCGTTGCGTTCGATTGGCGTCGCCAATGAGCGGCCGCGTCGACACG CAAAAAGGCCATC (SeqID55) |
| 5171 pINT MsgalT8 rev | CATAACCACCGACAGTTTGATTTCATCCATAGTCTGCGCGTCTTTCAGG GCTTCATCGAC (SeqID56) |
| 5561 KdgalT10 pINT for | GTCGATGAAGCCCTGAAAGACGCGCAGACTATGGAAAACTATGTCGTC TCTATCCGCACC (SeqID57) |
| 5562 KdgalT10 pINT-rev | GATGGCCTTTTTGCGTGTCGACGCGGCCGCTCATTTGAACGGAACAAT CTTTTTGTCATC (SeqID58) |
| 5563 pINT-KdgalT10 for | GATGACAAAAAGATTGTTCCGTTCAAATGAGCGGCCGCGTCGACACGC AAAAAGGCCATC (SeqID59) |
| 5564 pINT-KdgalT10 rev | GGTGCGGATAGAGACGACATAGTTTTCCATAGTCTGCGCGTCTTTCAG GGCTTCATCGAC (SeqID60) |
| 5172 gatD pINT for | GTCGATGAAGCCCTGAAAGACGCGCAGACTATGTCCTCAGCTTTCCATT ACGTCATTAGC (SeqID61) |
| 5173 gatD pINT rev | GATGGCCTTTTTGCGTGTCGACGCGGCCGCTCATTCAAATTCGATAATC ATGGTGATTTT (SeqID62) |
| 5174 pINT gatD for | AAAATCACCATGATTATCGAATTTGAATGAGCGGCCGCGTCGACACGCA AAAAGGCCATC (SeqID63) |
| 5175 pINT gatD rev | GCTAATGACGTAATGGAAAGCTGAGGACATAGTCTGCGCGTCTTTCAG GGCTTCATCGAC (SeqID64) |
| 5160 BfglaT2 pINT for | GTCGATGAAGCCCTGAAAGACGCGCAGACTATGAACGTGAATAAGCCG ACCACCGAAAAG (SeqID65) |
| 5161 BfgalT2 pINT rev | GATGGCCTTTTTGCGTGTCGACGCGGCCGCTCAGTATTCTTCAATTTTG TCCAGTTGATA (SeqID66) |
| 5162 pINT BfgalT2 for | TATCAACTGGACAAAATTGAAGAATACTGAGCGGCCGCGTCGACACGC AAAAAGGCCATC (SeqID67) |
| 5163 pINT BfgalT2 rev | CTTTTCGGTGGTCGGCTTATTCACGTTCATAGTCTGCGCGTCTTTCAGG GCTTCATCGAC (SeqID68) |
| 5746 | GTGATCAACGCCGCCAGCGGTCGTCAGACTGTCGATGAAGCCCTGAAA GACGCGCAGACT (SeqID69) |

TABLE 3-continued

| Oligonucleotides used for PCR | |
|---|---|
| Primer | Sequence 5'-3' |
| 5747 | GCGGCCGCGTCGACACGCAAAAAGGCCATCCATCCGTCAGGATGGCC TTCTGCTTAATTT (SeqID70) |
| 5748 | AAATTAAGCAGAAGGCCATCCTGACGGATGGATGGCCTTTTTGCGTGT CGACGCGGCCGC (SeqID71) |
| 5749 | AGTCTGCGCGTCTTTCAGGGCTTCATCGACAGTCTGACGACCGCTGGC GGCGTTGATCAC (SeqID72) |
| 1886 SLIC wbdO pACYC for | GTTTAACTTTAATAAGGAGATATACCATGCTGACGGAAGTGCGCCCGGT CTCTACGACGAAACCGC (SeqID73) |
| 1887 SLIC wbdO pACYC rev | CGACCTGCAGGCGCGCCGAGCTCGAATTCATTTGATGTATTTGCAATA GAACACAGAAAAGACCGT (SeqID74) |
| 1888 SLIC pACYC wbdo rev | GTGTTCTATTGCAAATACATCAAATGAATTCGAGCTCGGCGCGCCTGCA GGTCGACAAGCTTGCGG (SeqID75) |
| 1889 SLIC pACYC Wbd0 For | GAGACCGGGCGCACTTCCGTCAGCATGGTATATCTCCTTATTAAAGTTA AACAAAATTATTTCTACAGG (SeqID76) |
| 1890 SLIC pACYC furA rev | GTATGGTGACCCTGTGGCGCAAATGAGAATTCGAGCTCGGCGCGCCTG CAGGTCGACAAGCT (SeqID77) |
| 1891 SLIC pACYC furA for | GCGCTGCCCTGTTTGATTTTATCCATGGTATATCTCCTTATTAAAGTTAA ACAAAATTATTTCT (SeqID78) |
| 1892 SLIC furA pACYC rev | CCTGCAGGCGCGCCGAGCTCGAATTCTCATTTGCGCCACAGGGTCACC ATACGTGCCGGCAGG (SeqID79) |
| 1893 SLIC furA pACYC for | GITTAACTTTAATAAGGAGATATACCATGGATAAAATCAAACAGGGCAG CGCCTCTCTGGTTGTCG (SeqID80) |
| 3055 SLIC PmnagT pET rev | CAGACTCGAGGGTACCGACGTCCTAATAAGTAGATGAATATTTATCAGG ACGAAGAT (SeqID81) |
| 3056 SLIC pET PmnagT for | AACTAAAGGTTTATTTTCCATATGTATATCTCCTTCTTATACTTAACTAAT ATAC (SeqID82) |
| 3057 SLIC pET PmnagT rev | TAAATATTCATCTACTTATTAGGACGTCGGTACCCTCGAGTCTGGTAAA GAAACCGCTGCTGCG (SeqID83) |
| 3058 SLIC PmnagT pET for | GTATAAGAAGGAGATATACATATGGAAAATAAACCTTTAGTTTCAGTTTT GATTTGTGC (SeqID84) |
| 2567_SLIC_yjhB-for | TAACTTTAAGAAGGAGATATACAAGAGCTCGAGTCGAAGGAGATAGAAC CATGGCAACAGCATGGTATAAACAAG (SeqID85) |
| 2568_SLIC_yjhB-rev | GCGTGTCGACGCGTTTAGAGGCCCCAAGGGGTTATGCTAGTATCGATT TATCATTTAGCCACGGATAGTTTATAAATTTTAC (SeqID86) |
| 2526_SLIC_pINT_TP-rev | GGTTCTATCTCCTTCGACTCGAGCTCTTGTATATCTCCTTCTTAAAGTTA AACAAAATTATTTCTAGATTTTTGTCGAAC (SeqID87) |
| 2443_SLIC_pINT_TP-forw | TAAATCGATACTAGCATAACCCCTTGGGGCCTCTAAACGCGTCGACAC GCAAAAAGGCCATCC (SeqID88) |
| 2527_SLIC_TP_pINT-forw | GTTCGACAAAAATCTAGAAATAATTTTGTTTAACTTTAAGAAGGAGATAT ACAAGAGCTCGAGTCGAAGGAGATAGAACC (SeqID89) |
| 2444_SLIC_TP_pINT-rev | GGATGGCCTTTTTGCGTGTCGACGCGTTTAGAGGCCCCAAGGGGTTAT GCTAGTATCGATTTA (SeqID90) |
| 688 IgtA AatII rev | ATATGACGTCTCATTAGCGGTTTTTCAGGAGACG (SeqID91) |
| 689 IgtA NdeI for | ATATCATATGCCGTCCGAAGCATTCCGTCGTCACC (SeqID92) |
| 991 galT-pCDF for | TAACTTTAATAAGGAGATATACCATGACGCAATTTAATCCCGTTGATCAT CCACATCGCCGC (SeqID93) |
| 992 pCDF-galT for | ATTTTCGCGAATCCGGAGTGTAAAAGCTTGCGGCCGCATAATGCTTAAG TCGAACAGAAAGTAATCG (SeqID94) |
| 993 galT-pCDF rev | AAGCATTATGCGGCCGCAAGCTTTTACACTCCGGATTCGCGAAAATGG ATATCGCTGACTGCGCGCAAACGC (SeqID95) |

TABLE 3-continued

| Oligonucleotides used for PCR | |
|---|---|
| Primer | Sequence 5'-3' |
| 994 pCDF-galT rev | TCAACGGGATTAAATTGCGTCATGGTATATCTCCTTATTAAAGTTAAACA AAATTATTTCTACAGGGG (SeqID96) |
| 848 gImM pCOLA SLIC rev | ATGGTGATGGCTGCTGCCCATTTAAACCGCTTTGACTGCGTCGGCAATA CGGTGCGC (SeqID97) |
| 849 glmU pCOLA SLIC for | GTTTAACTTTAATAAGGAGATATACCATGCTGAACAACGCGATGTCTGTT GTTATCCTGG (SeqID98) |
| 850 pCOLA glmM SLIC rev | CGCAGTCAAAGCGGTTTAAATGGGCAGCAGCCATCACCATCATCACCA CAGCC (SeqID99) |
| 851 pCOLA glmU SLIC for | TCGCGTTGTTCAGCATGGTATATCTCCTTATTAAAGTTAAACAAAATTAT TTCTACAGG (SeqID100) |
| 852 glmSco pCOLA for Ndel | ATATATCATATGTGCGGTATCGTTGGTGCTATCGC (SeqID101) |
| 853 glmSco pCOLA rev AatII | ATATATGACGTCTTATTCCACGGTCACGGATTTCGC (SeqID102) |

The invention claimed is:

1. A method for production of an oligosaccharide by a genetically modified microbial host cell, wherein the oligosaccharide is a lacto-N-tetraose comprising a lacto-N-triose II (LNT-II; GlcNAc(b1-3)Gal(b1-4)Gluc) as a core trisaccharide, the method comprising:

providing a genetically modified microbial host cell that comprises:

at least one recombinant glycosyltransferase selected from the group consisting of a β-1,3-N-acetylglucosaminyltransferase and a β-1,3-galactosyltransferase;

increased expression or activity of at least one homologous or heterologous sugar export protein capable of exporting the oligosaccharide; and decreased expression or inactivation of at least one export protein that exports LNT-II from the host cell;

cultivating the host cell in a medium under conditions permissive for the production of the oligosaccharide, whereby the oligosaccharide is exported into the medium at an increased level compared to an unmodified host cell, and obtaining the oligosaccharide from the medium.

2. The method of claim 1, wherein the host cell further comprises:

overexpression of at least one homologous or heterologous nucleic acid sequence coding for the sugar export protein capable of exporting the oligosaccharide into the culture medium; and/or deletion, disruption, diminishment or inactivation of at least one endogenous nucleic acid sequence coding for an export protein that exports precursors of the oligosaccharide outside the host cell; and/or overexpression of at least one homologous or heterologous sequence coding for a protein mediating import of a precursor of the oligosaccharide into said host cell, wherein the precursor is larger than a disaccharide.

3. The method of claim 2, wherein said sugar export protein capable of exporting the oligosaccharide belongs to the class of secondary active transporters.

4. The method of claim 2, wherein the nucleic acid sequence coding for the homologous or heterologous sugar export protein capable of exporting the oligosaccharide is of bacterial, archeal, plant, yeast or animal origin.

5. The method of claim 2, wherein said at least one nucleic acid sequence coding for the sugar export protein that exports precursors of the oligosaccharide outside the host cell is a gene selected from the group consisting of yebQ from *Escherichia coli*, yjhB from *Escherichia coli*, proP from *Mannheimia succiniciproducens*, and setA from *Cedecea neteri*.

6. The method of claim 1, wherein said β-1,3-N-acetylglucosaminyltransferase belongs to the class of lgtA of *Neisseria meningitides* or PmnagT of *Pasteurella multocida*.

7. The method of claim 1, wherein the β-1,3-galactosyltransferase is encoded by a WbdO gene.

8. The method of claim 1, wherein-ii the genetically modified microbial host cell further comprises an endogenous β-galactosidase gene and glucosamine-6-phosphate deaminase gene that are inactivated or deleted, and wherein said genetically modified microbial host cell further comprises a nucleic acid sequence coding for a functional lactose permease protein.

9. The method of claim 1, wherein the genetically modified microbial host cell further comprises an increased UDP-N-acetylglucosamine and a UDP-galactose, or GDP-fucose, or CMP-N-acetylneuraminic acid production, as compared to a genetically unmodified host cell, wherein optionally said increased UDP-N-acetylglucosamine and UDP-galactose production capability is by an overexpression of one or more genes encoding a protein selected from the group consisting of L-glutamine:D-fructose-6-phosphate aminotransferase, N-acetyl glucosamine-1-phosphate uridyltransferase/glucosamine-1-phosphate acetyl transferase, phosphoglucosamine mutase, UDP-galactose-4-epimerase, phosphoglucomutase, and glucose-1-phosphate uridylyltransferase.

10. The method of claim 8, wherein said genetically modified microbial host cell is cultivated in the presence of glucose, sucrose, glycerol or a combination thereof.

11. The method of claim 10, wherein the microbial host cell is cultured in the absence of N-acetylglucosamine and galactose.

12. A genetically modified microbial host cell for the production of lacto-N-tetraose comprising a lacto-N-triose II (LNT-II; GlcNAc(β1-3)Gal(β1-4)Gluc) as a core trisaccharide, wherein the host cell comprises at least one recombinant glycosyltransferase, selected from the group consisting of a β-1,3-N-acetylglucosaminyltransferase and a β-1,3-galactosyltransferase;

at least one homologous or heterologous nucleic acid sequence coding for a sugar export protein capable exporting of the acto-N-tetraose into a culture medium the host cell is cultivated in wherein said sugar export protein capable of exporting the lacto-N-tetraose belongs to the class of secondary active transporters, and wherein said homologous or heterologous nucleic acid sequence coding for the sugar export protein capable of exporting the lacto-N-tetraose is overexpressed or under control of a promoter sequence enabling the overexpression of said nucleic acid sequence; and inactivated expression or activity of at least one endogenous sugar export protein that exports LNT-II from the host cell.

13. The microbial host cell of claim 12, further comprising an overexpression of at least one homologous or heterologous nucleic acid sequence coding for a protein mediating the import of a precursor of the acto-N-tetraose into said host cell through genetic modification of the microbial host cell, wherein the precursor is larger than a disaccharide.

14. The microbial host cell of claim 12, wherein said nucleic acid sequence coding for the sugar export protein capable of exporting the acto-N-tetraose is of bacterial, archeal, plant, yeast or animal origin.

15. The microbial host cell of claim 12, wherein said at least one nucleic acid sequence coding for the export protein that exports LNT-II from the host cell is a gene selected from the group consisting of yebQ from *Escherichia coli*, yjhB from *Escherichia coli*, proP from *Mannheimia succiniciproducens*, and setA from *Cedecea neteri*.

16. The microbial host cell of claim 14, wherein the sugar export protein capable of exporting the lacto-N-tetraose is selected from the group consisting of YebQ from *Escherichia coli* BL21(DE3), SpoVB of *Bacillus amyloliquefaciens*, YabM of *Erwinia pyrilfolia*, Bcr of *E. coli* MG1655, YdeA of *E. coli* MG1655, ProP2 of *Haemophilus parainfluenzae*, SetA of *Pectobacterium carotovorum*, FucP of *E. coli* MG1655, MdeA of *Staphylococcus aureus* Bmb9393, ImrA of *Lactococcus lactis*, SetA of *Pseudomonas* sp. MT-1 and SetA of *Beauveria bassiana* Dl-5.

17. The method of claim 1, wherein the sugar export protein capable of exporting the lacto-N-tetraose is selected from the group consisting of YebQ from *Escherichia coli* BL21(DE3), SpoVB of *Bacillus amyloliquefaciens*, YabM of *Erwinia pyrilfolia*, Bcr of *E. coli* MG1655, YdeA of *E. coli* MG1655, ProP2 of *Haemophilus parainfluenzae*, SetA of *Pectobacterium carotovorum*, FucP of *E. coli* MG1655, MdeA of *Staphylococcus aureus* Bmb9393, ImrA of *Lactococcus lactis*, SetA of *Pseudomonas* sp. MT-1 and SetA of *Beauveria bassiana* D1-5.

18. The method of claim 1, wherein the microbial host cell is an *Escherichia coli* cell, a *Corynebacterium glutamicum* cell or a *Saccharomyces* sp. cell.

19. The microbial host cell of claim 12, wherein the microbial host cell is an *Escherichia coli* cell, a *Corynebacterium glutamicum* cell or a *Saccharomyces* sp. cell.

* * * * *

SEQUENCE LISTING

<160> NUMBER OF SEQ ID NOS: 102

<210> SEQ ID NO 1
<211> LENGTH: 2851
<212> TYPE: DNA
<213> ORGANISM: Artificial Sequence
<220> FEATURE:
<223> OTHER INFORMATION: construct Ptet-lacY-FRT-add1-FRT

<400> SEQUENCE: 1
tggccagatg attaattcct aatttttgtt gacactctat cattgataga gttattttac 60
cactccctat cagtgataga gaaaagtgaa atgaatagtt cgacaaaaat ctagaaataa 120
ttttgtttaa ctttaagaag gagatataca aatgtactat ttaaaaaaca caaacttttg 180
gatgttcggt ttattctttt tcttttactt ttttatcatg ggagcctact tcccgttttt 240
cccgatttgg ctacatgaca tcaaccatat cagcaaaagt gatacgggta ttatttttgc 300
cgctatttct ctgttctcgc tattattcca accgctgttt ggtctgcttt ctgacaaact 360
cgggctgcgc aaatacctgc tgtggattat taccggcatg ttagtgatgt ttgcgccgtt 420
ctttattttt atcttcgggc cactgttaca atacaacatt ttagtaggat cgattgttgg 480
tggtatttat ctaggctttt gttttaacgc cggtgcgcca gcagtagagg catttattga 540
gaaagtcagc cgtcgcagta atttcgaatt tggtcgcgcg cggatgtttg gctgtgttgg 600
ctgggcgctg tgtgcctcga ttgtcggcat catgttcacc atcaataatc agtttgtttt 660
ctggctgggc tctggctgtg cactcatcct cgccgtttta ctctttttcg ccaaaacgga 720
tgcgccctct tctgccacgg ttgccaatgc ggtaggtgcc aaccattcgg catttagcct 780
taagctggca ctggaactgt tcagacagcc aaaactgtgg tttttgtcac tgtatgttat 840
tggcgtttcc tgcacctacg atgtttttga ccaacagttt gctaatttct ttacttcgtt 900
ctttgctacc ggtgaacagg gtacgcgggt atttggctac gtaacgacaa tgggcgaatt 960
acttaacgcc tcgattatgt tctttgcgcc actgatcatt aatcgcatcg gtgggaaaaa 1020
cgccctgctg ctggctggca ctattatgtc tgtacgtatt attggctcat cgttcgccac 1080
ctcagcgctg gaagtggtta ttctgaaaac gctgcatatg tttgaagtac cgttcctgct 1140
ggtgggctgc tttaaatata ttaccagcca gtttgaagtg cgtttttcag cgacgattta 1200
tctggtctgt ttctgcttct ttaagcaact ggcgatgatt tttatgtctg tactggcggg 1260
caatatgtat gaaagcatcg gtttccaggg cgcttatctg gtgctgggtc tggtggcgct 1320
gggcttcacc ttaatttccg tgttcacgct tagcggcccc ggcccgcttt ccctgctgcg 1380
tcgtcaggtg aatgaagtcg ctgggagcta agcggccgcg tcgacacgca aaaaggccat 1440
ccgtcaggat ggccttctgc ttaatttgat gcctggcagt ttatggcggg cgtcctgccc 1500
gccaccctcc gggccgttgc ttcgcaacgt tcaaatccgc tcccggcgga tttgtcctac 1560
tcaggagagc gttcaccgac aaacaacaga taaaacgaaa ggcccagtct ttcgactgag 1620
cctttcgttt tatttgatgc ctggcagttc cctactctcg catggggaga ccccacacta 1680
ccatcatgta tgaatatcct ccttagttcc tattccgaag ttcctattct ctagaaagta 1740
taggaacttc ggcgcgtcct acctgtgaca cgcgtgccgc agtctcacgc ccggagcgta 1800
gcgaccgagt gagctagcta tttgtttatt tttctaaata cattcaaata tgtatccgct 1860
catgagacaa taaccctgat aaatgcttca ataatattga aaaaggaaga gtatgaggga 1920
agcggtgatc gccgaagtat cgactcaact atcagaggta gttggcgtca tcgagcgcca 1980
tctcgaaccg acgttgctgg ccgtacattt gtacggctcc gcagtggatg gcggcctgaa 2040
gccacacagt gatattgatt tgctggttac ggtgaccgta aggcttgatg aaacaacgcg 2100
gcgagctttg atcaacgacc ttttggaaac ttcggcttcc cctggagaga gcgagattct 2160
ccgcgctgta gaagtcacca ttgttgtgca cgacgacatc attccgtggc gttatccagc 2220
taagcgcgaa ctgcaatttg gagaatggca gcgcaatgac attcttgcag gtatcttcga 2280
gccagccacg atcgacattg atctggctat cttgctgaca aaagcaagag aacatagcgt 2340
tgccttggta ggtccagcgg cggaggaact ctttgatccg gttcctgaac aggatctatt 2400
tgaggcgcta aatgaaacct taacgctatg gaactcgccg cccgactggg ctggcgatga 2460
gcgaaatgta gtgcttacgt tgtcccgcat ttggtacagc gcagtaaccg gcaaaatcgc 2520
gccgaaggat gtcgctgccg actgggcaat ggagcgcctg ccggcccagt atcagcccgt 2580
catacttgaa gctagacagg cttatcttgg acaagaagaa gatcgcttgg cctcgcgcgc 2640
agatcagttg gaagaatttg tccactacgt gaaaggcgag atcaccaagg tagtcggcaa 2700
ataatgtcta acaattcgtt caagccgagg ggccgcaaga tccggccacg atgacccggt 2760
cgtcgggtac cggcagggcg gggcgtaagg cgcgccattt aaatgaagtt cctattccga 2820
agttcctatt ctctagaaag tataggaact t 2851

<210> SEQ ID NO 2
<211> LENGTH: 4568
<212> TYPE: DNA
<213> ORGANISM: Artificial Sequence
<220> FEATURE:
<223> OTHER INFORMATION: construct Ptet-lgtA-PT5-galT-FRT-kanR-FRT

<400> SEQUENCE: 2
acaggttggc tgataagtcc ccggtctagc ttgcatgcag attgcagcat tacacgtctt 60
gagcgattgt gtaggctgga gctgcttcga agttcctata ctttctagag aataggaact 120
tcggaatagg aacttcattt aaatggcgcg ccttacgccc cgccctgccg gtaccgagag 180
cgcttttgaa gctggggtgg gcgaagaact ccagcatgag atccccgcgc tggaggatca 240
tccagccggc gtcccggaaa acgattccga agcccaacct ttcatagaag gcggcggtgg 300

-continued

```
aatcgaaatc tcgtgatggc aggttgggcg tcgcttggtc ggtcatttcg aaccccagag    360
tcccgctcag aagaactcgt caagaaggcg atagaaggcg atgcgctgcg aatcgggagc    420
ggcgataccg taaagcacga ggaagcggtc agcccattcg ccgccaagct cttcagcaat    480
atcacgggta gccaacgcta tgtcctgata gcggtccgcc acacccagcc ggccacagtc    540
gatgaatcca gaaaagcggc cattttccac catgatattc ggcaagcagg catcgccatg    600
ggtcacgacg agatcctcgc cgtcgggcat gcgcgccttg agcctggcga acagttcggc    660
tggcgcgagc ccctgatgct cttcgtccag atcatcctga tcgacaagac cggcttccat    720
ccgagtacgt gctcgctcga tgcgatgttt cgcttggtgg tcgaatgggc aggtagccgg    780
atcaagcgta tgcagccgcc gcattgcatc agccatgatg gatactttct cggcaggagc    840
aaggtgagat gacaggagat cctgccccgg cacttcgccc aatagcagcc agtcccttcc    900
cgcttcagtg acaacgtcga gcacagctgc gcaaggaacg cccgtcgtgg ccagccacga    960
tagccgcgct gcctcgtcct gcagttcatt cagggcaccg gacaggtcgg tcttgacaaa   1020
aagaaccggg cgcccctgcg ctgacagccg gaacacggcg gcatcagagc agccgattgt   1080
ctgttgtgcc cagtcatagc cgaatagcct ctccacccaa gcggccggag aacctgcgtg   1140
caatccatct tgttcaatca tgcgaaacga tcctcatcct gtctcttgat cagatcttga   1200
tcccctgcgc catcagatcc ttggcggcaa gaaagccatc cagtttactt tgcagggctt   1260
cccaacctta ccagagggcg ccccagctgg caattccggt tcgcttgctg tccataaaac   1320
cgcccagtct agctatcgcc atgtaagccc actgcaagct acctgctttc tctttgcgct   1380
tgcgttttcc cttgtccaga tagcccagta gctgacattc atccggggtc agcaccgttt   1440
ctgcggactg gctttctacg tgttccgctt cctttagcag cccttgcgcc ctgagtgctt   1500
gcggcagcgt gaggggatct tgacgcgtgt cacaggtagg acgcgccgaa gttcctatac   1560
tttctagaga ataggaactt cggaatagga actaaggagg atattcatac atgatggtag   1620
tgttcgaaat taatacgact cactataggg gaattgattc tggtaccaaa tgagtcgacc   1680
ggccagatga ttaattccta atttttgttg acactctatc attgatagag ttattttacc   1740
actccctatc agtgatagag aaaagtgaaa tgaatagttc gacaaaaatc tagaaataat   1800
tttgtttaac tttaagaagg agatatacaa atgccgtccg aagcattccg tcgtcaccgt   1860
gcttatcgcg aaaacaaact gcagccactg gtctctgtcc tgatctgcgc atacaacgtt   1920
gagaaatact tcgcacagtc tctggcagct gtagttaacc agacctggcg taacctggat   1980
atcctgatcg tagatgacgg ctctacggat ggtacgctgg cgatcgcaca gcgtttccag   2040
gaacaggacg gtcgtatccg cattctcgct cagccgcgta actctggtct gatcccgtct   2100
ctgaacatcg gtctggacga actggccaaa tctggtggtg gtggcgaata catcgcccgt   2160
actgacgccg acgacattgc ggccccggat tggatcgaaa aaatcgtagg tgaaatggag   2220
aaagaccgct ctatcatcgc gatgggtgct tggctggaag ttctgtccga agagaaagac   2280
ggtaaccgtc tggcccgtca ccatgaacac ggcaaaatct ggaaaaaacc gacccgtcac   2340
gaagatatcg cggacttctt cccgttcggt aacccgatcc ataacaacac catgatcatg   2400
cgtcgtagcg taatcgacgg tggtctgcgt tacaacaccg aacgtgattg ggcagaagac   2460
taccagtttt ggtatgacgt gtctaaactg ggtcgtctgg cttactaccc agaagcgctg   2520
gttaaatacc gtctgcacgc caaccaggtt agctccaaat actccatccg tcagcacgaa   2580
atcgcacagg gtatccagaa aacggctcgt aacgacttcc tgcagtccat gggtttcaaa   2640
acccgtttcg actctctgga gtaccgtcag atcaaagcgg ttgcgtatga gctgctggag   2700
```

-continued

```
aaacacctgc cggaagagga ctttgaacgt gcgcgtcgtt tcctgtacca gtgcttcaaa   2760

cgtaccgaca ctctgccggc gggtgcatgg ctcgactttg cagcggatgg tcgtatgcgt   2820

cgtctgttta ccctgcgtca gtacttcggt atcctgcatc gtctcctgaa aaaccgctaa   2880

tgatttcgtc gacacacagg aaacatatta aaaattaaaa cctgcaggag tttaaacgcg   2940

gccgcgatat cgttgtaaaa cgacggccag tgcaagaatc ataaaaaatt tatttgcttt   3000

caggaaaatt tttctgtata atagattcat aaatttgaga gaggagtttt tgtgagcgga   3060

taacaattcc ccatcttagt atattagtta agtataaata cacaaggaga tataccatga   3120

cgcaatttaa tcccgttgat catccacatc gccgctacaa cccgctcacc gggcaatgga   3180

ttctggtttc accgcaccgc gctaagcgcc cctggcaggg ggcgcaggaa acgccagcca   3240

aacaggtgtt acctgcgcac gatccagatt gcttcctctg cgcaggtaat gtgcgggtga   3300

caggcgataa aaaccccgat tacaccggga cttacgtttt cactaatgac tttgcggctt   3360

tgatgtctga cacgccagat gcgccagaaa gtcacgatcc gctgatgcgt tgccagagcg   3420

cgcgcggcac cagccgggtg atctgctttt caccggatca cagtaaaacg ctgccagagc   3480

tcagcgttgc agcattgacg gaaatcgtca aaacctggca ggagcaaacc gcagaactgg   3540

ggaaaacgta cccatgggtg caggtttttg aaaacaaagg cgcggcgatg ggctgctcta   3600

acccgcatcc gcacggtcag atttgggcaa atagcttcct gcctaacgaa gctgagcgcg   3660

aagaccgcct gcaaaaagaa tattttgccg aacagaaatc accaatgctg gtggattatg   3720

ttcagcgcga gctggcagac ggtagccgta ccgttgtcga aaccgaacac tggttagccg   3780

tcgtgcctta ctgggctgcc tggccgttcg aaacgctact gctgcccaaa gcccacgttt   3840

tacggatcac cgatttgacc gacgcccagc gcagcgatct ggcgctggcg ttgaaaaagc   3900

tgaccagtcg ttatgacaac ctcttccagt gctccttccc ctactctatg ggctggcacg   3960

gcgcgccatt taatggcgaa gagaatcaac actggcagct gcacgcgcac ttttatccgc   4020

ctctgctgcg ctccgccacc gtacgtaaat ttatggttgg ttatgaaatg ctggcagaga   4080

cccagcgaga cctgaccgca gaacaggcag cagagcgttt gcgcgcagtc agcgatatcc   4140

attttcgcga atccggagtg taacgcggag gcgcgccatt taaatcaacc tcagcggtca   4200

tagctgtttc ctgtgactga gcaataacta gcataacccc ttggggcctc taaacgggtc   4260

ttgaggggtt ttttgctgaa accaatttgc ctggcggcag tagcgcggtg gtcccacctg   4320

accccatgcc gaactcagaa gtgaaacgcc gtagcgccga tggtagtgtg gggtctcccc   4380

atgcgagagt agggaactgc caggcatcaa ataaaacgaa aggctcagtc gaaagactgg   4440

gcctttcggg atccaggccg gcctgttaac gaattaatct tccgcggcaa caaaaattag   4500

gaattaatca tctggccaat ttcaggtggc acttttcggg cagaccgggg acttatcagc   4560

caacctgt                                                           4568
```

<210> SEQ ID NO 3
<211> LENGTH: 6521
<212> TYPE: DNA
<213> ORGANISM: Artificial Sequence
<220> FEATURE:
<223> OTHER INFORMATION: construct Ptet-glmUM-PT5-glmS-FRT-dhfr-FRT

<400> SEQUENCE: 3

```
acaggttggc tgataagtcc ccggtctagc ttgcatgcag attgcagcat tacacgtctt     60

gagcgattgt gtaggctgga gctgcttcga aattaatacg actcactata ggggaattga    120
```

-continued

```
ttctggtacc aaatgagtcg accggccaga tgattaattc ctaatttttg ttgacactct    180

atcattgata gagttatttt accactccct atcagtgata gagaaaagtg aaatgaatag    240

ttcgacaaaa atctagaaat aattttgttt aactttaaga aggagatata caaatgctga    300

acaacgcgat gtctgttgtt atcctggcgg cgggtaaagg tacccgtatg tactctgacc    360

tgccgaaagt tctgcacacc ctggcgggta aagcgatggt tcagcacgtt atcgacgcgg    420

cgaacgaact gggtgcggcg cacgttcacc tggtttacgg tcacggtggt gacctgctga    480

aacaggcgct gaaagacgac aacctgaact gggttctgca ggcggaacag ctgggtaccg    540

gtcacgcgat gcagcaggcg gcgccgttct tcgcggacga cgaagacatc ctgatgctgt    600

acggtgacgt tccgctgatc tctgttgaaa ccctgcagcg tctgcgtgac gcgaaaccgc    660

agggtggtat cggtctgctg accgttaaac tggacgaccc gaccggttac ggtcgtatca    720

cccgtgaaaa cggtaaagta accggtatcg ttgaacacaa agacgcgacc gacgaacagc    780

gtcagatcca ggagatcaac accggtatcc tgatcgcgaa cggtgcagac atgaaacgtt    840

ggctggcgaa actgaccaac aacaacgcgc agggtgaata ctacatcacc gacatcatcg    900

cgctggcgta ccaggaaggt cgtgaaatcg ttgcggttca cccgcagcgt ctgtctgaag    960

ttgaaggtgt taacaaccgt ctgcagctgt ctcgtctgga acgtgtttac cagtctgaac   1020

aggcggaaaa actgctgctg gcgggtgtta tgctgcgtga cccggcgcgt ttcgacctgc   1080

gtggtaccct gacccacggt cgtgacgttg aaatcgacac caacgttatc atcgaaggta   1140

acgttaccct gggtcaccgt gtaaaaatcg gcaccggttg cgttatcaaa aactctgtta   1200

tcggtgacga ctgcgaaatc tctccgtaca ccgttgttga agacgcgaac ctggcggcgg   1260

cgtgcaccat cggtccgttc gcgcgtctgc gtccgggtgc ggaactgctg gaaggtgcgc   1320

acgttggtaa cttcgttgaa atgaaaaaag cgcgtctggg taaaggttct aaagcgggtc   1380

acctgaccta cctgggtgac gcggaaatcg gtgacaacgt taacatcggt gcgggtacca   1440

tcacctgcaa ctacgacggt gcgaacaaat tcaaaaccat catcggtgac gacgttttcg   1500

ttggttctga cacccagctg gttgcgccgg ttaccgttgg taaaggtgcg accatcgcgg   1560

cgggtaccac cgttacccgt aacgttggtg aaaacgcgct ggcgatctct cgtgttccgc   1620

agacccagaa agaaggttgg cgtcgtccgg ttaaaaaaaa ataacgaagg agatagaacc   1680

atgtccaacc gtaaatactt cggtacggac ggtatccgtg gtcgtgtagg tgatgctccg   1740

attacgccgg atttcgtcct gaaactcggt tgggcagcgg gtaaagttct cgcacgtcac   1800

ggctctcgta aaatcatcat cggtaaagac acccgtatct ctggttacat gctcgaatct   1860

gcactggaag cgggtctggc tgcagctggt ctgtctgcac tgttcacggg tccgatgcca   1920

accccagctg tagcgtacct gactcgcact ttccgtgcag aagcaggtat cgtgatctct   1980

gcctctcaca acccgttcta cgacaacggt atcaaattct tcagcatcga tggtaccaaa   2040

ctcccagacg cggttgaaga ggctatcgaa gcggaaatgg agaaagaaat ctcttgtgta   2100

gactctgccg aactcggtaa agcgtctcgt atcgttgatg cagcgggtcg ttacatcgag   2160

ttctgcaaag ccacctttcc gaacgaactg agcctgtctg agctgaaaat cgtcgtagac   2220

tgtgccaacg gtgcgactta ccacattgcc ccaaacgtac tgcgtgagct gggtgctaac   2280

gtcatcgcga tcggttgtga accgaacggt gtcaacatca acgcggaagt aggtgcgacc   2340

gatgttcgtg cactgcaggc tcgtgtactc gcggagaaag cggatctcgg tatcgccttt   2400

gacggtgatg gtgaccgtgt tatcatggtt gaccacgaag gtaacaaagt ggatggtgac   2460

cagatcatgt acatcattgc ccgtgaaggt ctgcgtcagg gtcagctgcg tggtggtgca   2520
```

-continued

```
gtaggtaccc tcatgagcaa catgggtctg gaactggccc tgaaacagct gggtatccca   2580
ttcgctcgtg ctaaagtagg cgaccgttac gttctggaga aaatgcagga gaaaggttgg   2640
cgtatcggtg ccgaaaactc tggtcacgtc atcctgctgg acaaaaccac taccggtgac   2700
ggtatcgtag caggtctgca ggtactcgcc gctatggccc gtaaccacat gtccctccat   2760
gacctctgct ctggtatgaa aatgttcccg cagatcctgg ttaacgttcg ttacaccgca   2820
ggttctggtg atccgctgga acacgagtct gtgaaagccg ttaccgcaga agtggaagcg   2880
gccctgggta accgtggtcg tgtactgctg cgtaaatccg gtactgagcc actgatccgt   2940
gttatggttg agggcgaaga tgaagcccag gtcaccgaat ttgcgcaccg tattgccgac   3000
gcagtcaaag cggtttaatt tcgtcgacac acaggaaaca tattaaaaat taaaacctgc   3060
aggagtttaa acgcggccgc gatatcgttg taaaacgacg gccagtgcaa gaatcataaa   3120
aaatttattt gctttcagga aaatttttct gtataataga ttcataaatt tgagagagga   3180
gtttttgtga gcggataaca attccccatc ttagtatatt agttaagtat aaatacacaa   3240
ggagatatac atatgtgcgg tatcgttggt gctatcgcac agcgtgatgt agcggagatc   3300
ctcctggaag gtctgcgtcg tctcgaatac cgtggttacg actctgccgg tctggcagta   3360
gtggatgcag aaggtcacat gactcgtctg cgtcgtctgg gtaaagtgca gatgctcgcg   3420
caggcggcgg aagaacaccc actccacggt ggtacgggta tcgcacacac tcgttgggca   3480
acccacggtg aaccgtctga ggtcaacgca cacccgcatg ttagcgagca catcgtagtc   3540
gttcacaacg gtatcatcga gaaccacgaa ccactccgtg aggaactcaa agcccgtggt   3600
tacaccttcg taagcgaaac cgacacggaa gttatcgccc acctcgttaa ctgggaactc   3660
aaacagggtg gtactctgcg tgaagcagtt ctgcgtgcca ttccacagct gcgtggtgca   3720
tacggtaccg tgatcatgga ctctcgtcat ccggataccc tgctcgccgc acgttctggt   3780
tctccactcg ttatcggtct gggtatgggt gagaacttca tcgcctctga tcagctggcc   3840
ctgctcccag ttacccgtcg cttcatcttc ctggaagagg gtgacatcgc cgaaatcacc   3900
cgtcgttccg ttaacatctt cgacaaaacg ggtgcggaag ttaaacgtca ggacatcgag   3960
tctaacctgc agtatgacgc tggtgacaaa ggcatctacc gtcactacat gcagaaagag   4020
atctacgaac agccgaacgc gatcaaaaac accctgaccg gtcgtatctc tcacggtcag   4080
gttgacctgt ctgagctggg tccaaacgcg gacgaactcc tgtccaaagt cgagcacatc   4140
cagatcctgg cttgtggtac ctcttacaac tccggtatgg tttctcgtta ctggttcgaa   4200
tctctggcag gtatcccatg cgacgttgaa atcgcctccg aattccgtta tcgtaaatct   4260
gcggtacgtc gtaactccct catgatcacc ctgtctcagt ctggtgaaac cgctgatact   4320
ctggcaggtc tgcgtctcag caaagaactg ggttacctgg gttctctggc catctgcaac   4380
gttccgggtt ctagcctggt tcgtgagtct gacctggctc tgatgaccaa cgcgggtacg   4440
gagatcggtg ttgcctctac caaagcgttc actacccagc tcactgtcct gctgatgctg   4500
gttgccaaac tgtctcgtct caaaggcctc gacgctagca tcgaacacga catcgtacac   4560
ggtctgcagg ccctcccatc tcgtatcgag cagatgctgt ctcaggacaa acgtatcgaa   4620
gcactggcag aagacttcag cgacaaacac cacgcgctgt ttctgggtcg tggtgaccag   4680
tacccaattg cgctggaagg tgccctgaaa ctgaaagaga tcagctacat ccatgcagag   4740
gcatacgcag cgggtgagct gaaacatggt ccactggccc tgatcgacgc agatatgccg   4800
gttattgtgg ttgctccgaa caacgaactg ctggagaaac tgaaatccaa catcgaggaa   4860
```

-continued

```
gtacgtgcgc gtggtggtca gctgtacgtg tttgctgacc aggacgcggg tttcgtttcc   4920

agcgacaaca tgcacatcat cgaaatgccg catgttgaag aggtaatcgc gccaatcttc   4980

tacaccgtac cgctgcagct gctggcgtac catgtagccc tgatcaaagg tacggacgtt   5040

gaccagccgc gtaacctggc gaaatccgtg accgtggaat aacgcggagg cgcgccattt   5100

aaatcaacct cagcggtcat agctgtttcc tgtgactgag caataactag cataacccct   5160

tggggcctct aaacgggtct tgaggggttt tttgctgaaa ccaatttgcc tggcggcagt   5220

agcgcggtgg tcccacctga ccccatgccg aactcagaag tgaaacgccg tagcgccgat   5280

ggtagtgtgg ggtctcccca tgcgagagta gggaactgcc aggcatcaaa taaaacgaaa   5340

ggctcagtcg aaagactggg cctttcggga tccaggccgg cctgttaacg aattaatctt   5400

ccgcggcggt atcgataagc ttgatatcga attccgaagt tcctattctc tagaaagtat   5460

aggaacttca ggtctgaaga ggagtttacg tccagccaag ctagcttggc tgcaggtcgt   5520

cgaaattcta ccgggtaggg gaggcgcttt tcccaaggca gtctggagca tgcgctttag   5580

cagccccgct gggcacttgg cgctacacaa gtggcctctg gcctcgcaca cattccacat   5640

ccaccggtag gcgccaaccg gctccgttct ttggtggccc cttcgcgcca ccttctactc   5700

ctcccctagt caggaagttc ccccccgccc cgcagctcgc gtcgtgcagg acgtgacaaa   5760

tggaagtagc acgtctcact agtctcgtgc agatggacag caccgctgag caatggaagc   5820

gggtaggcct ttggggcagc ggccaatagc agctttgctc cttcgctttc tgggctcaga   5880

ggctgggaag gggtgggtcc gggggcgggc tcaggggcgg gctcaggggc ggggcgggcg   5940

cccgaaggtc ctccggaggc ccggcattct gcacgcttca aaagcgcacg tctgccgcgc   6000

tgttctcctc ttcctcatct ccgggccttt cgacctgcag cctgttgaca attaatcatc   6060

ggcatagtat atcggcatag tataatacga caaggtgagg aactaaacca tgggtcaaag   6120

tagcgatgaa gccaacgctc ccgttgcagg gcagtttgcg cttcccctga gtgccacctt   6180

tggcttaggg gatcgcgtac gcaagaaatc tggtgccgct tggcagggtc aagtcgtcgg   6240

ttggtattgc acaaaactca ctcctgaagg ctatgcggtc gagtccgaat cccacccagg   6300

ctcagtgcaa atttatcctg tggctgcact tgaacgtgtg gcctaatgag gggatcaatt   6360

ctctagagct cgctgatcag aagttcctat tctctagaaa gtataggaac ttcgatggcg   6420

cctcatccct gaagccaata caacaaaaat taggaattaa tcatctggcc aatttcaggt   6480

ggcactttc gggcagaccg ggacttatc agccaacctg t                        6521
```

<210> SEQ ID NO 4
<211> LENGTH: 2937
<212> TYPE: DNA
<213> ORGANISM: Artificial Sequence
<220> FEATURE:
<223> OTHER INFORMATION: construct <Ptet-lacY(6HIS)-FRT-aadA-FRT>

<400> SEQUENCE: 4

```
ggccagatga ttaattccta atttttgttg acactctatc attgatagag ttattttacc     60

actccctatc agtgatagag aaaagtgaaa tgaatagttc gacaaaaatc tagaaataat    120

tttgtttaac tttaagaagg agatatacaa atggctact atttaaaaaa cacaaacttt    180

tggatgttcg gtttattctt tttcttttac ttttttatca tgggagccta cttcccgttt    240

ttcccgattt ggctacatga catcaaccat atcagcaaaa gtgatacggg tattattttt    300

gccgctattt ctctgttctc gctattattc caaccgctgt ttggtctgct ttctgacaaa    360

ctcgggctgc gcaaatacct gctgtggatt attaccggca tgttagtgat gtttgcgccg    420
```

-continued

```
ttctttattt ttatcttcgg gccactgtta caatacaaca ttttagtagg atcgattgtt    480
ggtggtattt atctaggctt ttgttttaac gccggtgcgc cagcagtaga ggcatttatt    540
gagaaagtca gccgtcgcag taatttcgaa tttggtcgcg cgcggatgtt tggctgtgtt    600
ggctgggcgc tgtgtgcctc gattgtcggc atcatgttca ccatcaataa tcagtttgtt    660
ttctggctgg gctctggctg tgcactcatc ctcgccgttt tactcttttt cgccaaaacg    720
gatgcgccct cttctcatca ccatcaccat cacgccacgg ttgccaatgc ggtaggtgcc    780
aaccattcgg catttagcct taagctggca ctggaactgt tcagacagcc aaaactgtgg    840
tttttgtcac tgtatgttat tggcgtttcc tgcacctacg atgtttttga ccaacagttt    900
gctaatttct ttacttcgtt ctttgctacc ggtgaacagg gtacgcgggt atttggctac    960
gtaacgacaa tgggcgaatt acttaacgcc tcgattatgt tctttgcgcc actgatcatt   1020
aatcgcatcg gtgggaaaaa cgccctgctg ctggctggca ctattatgtc tgtacgtatt   1080
attggctcat cgttcgccac ctcagcgctg gaagtggtta ttctgaaaac gctgcatatg   1140
tttgaagtac cgttcctgct ggtgggctgc tttaaatata ttaccagcca gtttgaagtg   1200
cgtttttcag cgacgattta tctggtctgt ttctgcttct ttaagcaact ggcgatgatt   1260
tttatgtctg tactggcggg caatatgtat gaaagcatcg gtttccaggg cgcttatctg   1320
gtgctgggtc tggtggcgct gggcttcacc ttaatttccg tgttcacgct tagcggcccc   1380
ggcccgcttt ccctgctgcg tcgtcaggtg aatgaagtcg cttaagcggc cgcgtcgaca   1440
cgcaaaaagg ccatccgtca ggatggcctt ctgcttaatt tgatgcctgg cagtttatgg   1500
cgggcgtcct gcccgccacc ctccgggccg ttgcttcgca acgttcaaat ccgctcccgg   1560
cggatttgtc ctactcagga gagcgttcac cgacaaacaa cagataaaac gaaaggccca   1620
gtctttcgac tgagcctttc gttttatttg atgcctggca gttccctact ctcgcatggg   1680
gagaccccac actaccatca tgtatgaata tcctccttag ttcctattcc gaagttccta   1740
ttctctagaa agtataggaa cttcggcgcg tcctacctgt gacacgcgtg ccgcagtctc   1800
acgcccggag cgtagcgacc gagtgagcta gctatttgtt tatttttcta aatacattca   1860
aatatgtatc cgctcatgag acaataaccc tgataaatgc ttcaataata ttgaaaaagg   1920
aagagtatga gggaagcggt gatcgccgaa gtatcgactc aactatcaga ggtagttggc   1980
gtcatcgagc gccatctcga accgacgttg ctggccgtac atttgtacgg ctccgcagtg   2040
gatggcggcc tgaagccaca cagtgatatt gatttgctgg ttacggtgac cgtaaggctt   2100
gatgaaacaa cgcggcgagc tttgatcaac gaccttttgg aaacttcggc ttcccctgga   2160
gagagcgaga ttctccgcgc tgtagaagtc accattgttg tgcacgacga catcattccg   2220
tggcgttatc cagctaagcg cgaactgcaa tttggagaat ggcagcgcaa tgacattctt   2280
gcaggtatct tcgagccagc cacgatcgac attgatctgg ctatcttgct gacaaaagca   2340
agagaacata gcgttgcctt ggtaggtcca gcggcggagg aactctttga tccggttcct   2400
gaacaggatc tatttgaggc gctaaatgaa accttaacgc tatggaactc gccgcccgac   2460
tgggctggcg atgagcgaaa tgtagtgctt acgttgtccc gcatttggta cagcgcagta   2520
accggcaaaa tcgcgccgaa ggatgtcgct gccgactggg caatggagcg cctgccggcc   2580
cagtatcagc ccgtcatact tgaagctaga caggcttatc ttggacaaga agaagatcgc   2640
ttggcctcgc gcgcagatca gttggaagaa tttgtccact acgtgaaagg cgagatcacc   2700
aaggtagtcg gcaaataatg tctaacaatt cgttcaagcc gaggggccgc aagatccggc   2760
```

-continued

```
cacgatgacc cggtcgtcgg gtaccggcag ggcggggcgt aaggcgcgcc atttaaatga   2820

agttcctatt ccgaagttcc tattctctag aaagtatagg aacttcgaag cagctccagc   2880

ctacacaatc gctcaagacg tgtaatgctg caatctgcat gcaagcttgg cactggc      2937
```

<210> SEQ ID NO 5
<211> LENGTH: 3856
<212> TYPE: DNA
<213> ORGANISM: Artificial Sequence
<220> FEATURE:
<223> OTHER INFORMATION: construct <Ptet-wbdO-PT5-galE-FRT-cat-FRT>

<400> SEQUENCE: 5

```
acaggttggc tgataagtcc ccggtctgcc cgaaaagtgc cacctgaaat tggccagatg     60

attaattcct aatttttgtt gattctggta ccaaatgagt cgaccggcca gatgattaat    120

tcctaatttt tgttgacact ctatcattga tagagttatt ttaccactcc ctatcagtga    180

tagagaaaag tgaaatgaat agttcgacaa aaatctagaa ataattttgt ttaactttaa    240

gaaggagata tacaaatgct gacggaagtg cgcccggtct ctacgacgaa accgctggtg    300

tctgtgattc tgccggtgaa caaattcaac ccgtatctgg atcgtgcaat tcattcaatc    360

ctgagtcagt cctatccgtc gattgaactg attatcattg caaacaattg caccaatgac    420

tttttcgatg ctctgaaaaa acgtgaatgt gaaaccatta aagtgctgcg cacgaacatc    480

gcgtatctgc cgtactgcct gaataaaggc ctggatctgt gtaacggtga ctttgttgcc    540

cgcatggatt cagatgacat ttcgcacccg gaacgtatcg atcgccaggt cgacttcctg    600

attaacaatc cggacatcga tgtggttggc accaatgcag tctatattga tgaagatgac    660

atcgaactgg aaaaaagcaa cctgccggtg aacaataacg ctattcgtaa aatgctgccg    720

tataaatgct gtctggtgca tccgtctgtt atgtttcgca aaaatgtcgt gatcaccagc    780

ggcggttaca tgttcgcgaa ttattctgaa gattacgaac tgtggaaccg tctggccgtt    840

gaaggccgca atttttataa cctgagcgaa tacctgctgt attaccgtct gcacaataac    900

caatcaacgt cgaaaaataa cctgtttatg gtgatggcga acgatgtcgc cattaaagtg    960

aaatatttcc tgctgaccaa gaaaattagc tacctgctgg gtatcattcg cacggtcttt   1020

tctgtgttct attgcaaata catcaaatga tttcgtcgac acacaggaaa catattaaaa   1080

attaaaacct gcaggagttt aaacgcggcc gcgatatcgt tgtaaaacga cggccagtgc   1140

aagaatcata aaaaatttat ttgctttcag gaaaattttt ctgtataata gattcataaa   1200

tttgagagag gagtttttgt gagcggataa caattcccca tcttagtata ttagttaagt   1260

ataaatacac cgcggaggcg tcgaaggaga tacaaccatg agagttctgg ttaccggtgg   1320

tagcggttac attggaagtc atacctgtgt gcaattactg caaaacggtc atgatgtcat   1380

cattcttgat aacctctgta acagtaagcg cagcgtactg cctgttatcg agcgtttagg   1440

cggcaaacat ccaacgtttg ttgaaggcga tattcgtaac gaagcgttga tgaccgagat   1500

cctgcacgat cacgctatcg acaccgtgat ccacttcgcc gggctgaaag ccgtgggcga   1560

atcggtacaa aaaccgctgg aatattacga caacaatgtc aacggcactc tgcgcctgat   1620

tagcgccatg cgcgccgcta acgtcaaaaa ctttattttt agctcctccg ccaccgttta   1680

tggcgatcag cccaaaattc catacgttga aagcttcccg accggcacac cgcaaagccc   1740

ttacggcaaa agcaagctga tggtggaaca gatcctcacc gatctgcaaa aagcccagcc   1800

ggactggagc attgccctgc tgcgctactt caacccggtt ggcgcgcatc cgtcgggcga   1860

tatgggcgaa gatccgcaag gcattccgaa taacctgatg ccatacatcg cccaggttgc   1920
```

-continued

```
tgtaggccgt cgcgactcgc tggcgatttt tggtaacgat tatccgaccg aagatggtac   1980
tggcgtacgc gattacatcc acgtaatgga tctggcggac ggtcacgtcg tggcgatgga   2040
aaaactggcg aacaagccag gcgtacacat ctacaacctc ggcgctggcg taggcaacag   2100
cgtgctggac gtggttaatg ccttcagcaa agcctgcggc aaaccggtta attatcattt   2160
tgcaccgcgt cgcgagggcg accttccggc ctactgggcg gacgccagca aagccgaccg   2220
tgaactgaac tggcgcgtaa cgcgcacact cgatgaaatg gcgcaggaca cctggcactg   2280
gcagtcacgc catccacagg gatatcccga ttaacgccat ttaaatcaac ctcagcggtc   2340
atagctgttt cctgtgactg agcaataact agcataaccc cttggggcct ctaaacgggt   2400
cttgaggggt tttttgctga aaccaatttg cctggcggca gtagcgcggt ggtcccacct   2460
gaccccatgc cgaactcaga agtgaaacgc cgtagcgccg atggtagtgt ggggtctccc   2520
catgcgagag tagggaactg ccaggcatca aataaaacga aaggctcagt cgaaagactg   2580
ggcctttcgg gatccaggcc ggcctgttaa cgaattaatc ttccgcggcg gtatcgataa   2640
gcttgatatc gaggctgaca tgggaattag ccatggtcca tatgaatatc ctccttagtt   2700
cctattccga agttcctatt ctctagaaag tataggaact tcggcgcgcc tacctgtgac   2760
ggaagatcac ttcgcagaat aaataaatcc tggtgtccct gttgataccg ggaagccctg   2820
ggccaacttt tggcgaaaat gagacgttga tcggcacgta agaggttcca actttcacca   2880
taatgaaata agatcactac cgggcgtatt ttttgagttg tcgagatttt caggagctaa   2940
ggaagctaaa atggagaaaa aaatcactgg atataccacc gttgatatat cccaatggca   3000
tcgtaaagaa cattttgagg catttcagtc agttgctcaa tgtacctata accagaccgt   3060
tcagctggat attacggcct ttttaaagac cgtaaagaaa aataagcaca agttttatcc   3120
ggcctttatt cacattcttg cccgcctgat gaatgctcat ccggaattac gtatggcaat   3180
gaaagacggt gagctggtga tatgggatag tgttcaccct tgttacaccg ttttccatga   3240
gcaaactgaa acgttttcat cgctctggag tgaataccac gacgatttcc ggcagtttct   3300
acacatatat tcgcaagatg tggcgtgtta cggtgaaaac ctggcctatt tccctaaagg   3360
gtttattgag aatatgtttt tcgtctcagc caatccctgg gtgagtttca ccagttttga   3420
tttaaacgtg gccaatatgg acaacttctt cgcccccgtt ttcaccatgg gcaaatatta   3480
tacgcaaggc gacaaggtgc tgatgccgct ggcgattcag gttcatcatg ccgtttgtga   3540
tggcttccat gtcggcagat gcttaatgaa tacaacagta ctgcgatgag tggcagggcg   3600
gggcgtaagg cgcgccattt aaatgaagtt cctattccga agttcctatt ctctagaaag   3660
tataggaact tcgaagcagc tccagcctac acaatcgctc aagacgtgta atgctgcaat   3720
ctgcatgcaa gcttggcact ggcgatggcg cctcatccct gaagccaata agcagctcca   3780
gcctacacaa tcgctcaaga cgtgtaatgc tgcaatctgc atgcaagcta gaccggggac   3840
ttatcagcca acctgt                                                    3856
```

<210> SEQ ID NO 6
<211> LENGTH: 4259
<212> TYPE: DNA
<213> ORGANISM: Artificial Sequence
<220> FEATURE:
<223> OTHER INFORMATION: construct galMKTE

<400> SEQUENCE: 6

```
ttactcagca ataaactgat attccgtcag gctggaatac tcttcgccag gacgcaggaa     60
```

-continued

```
gcagtccggt tgcggccatt cagggtggtt cgggctgtcc ggtagaaact cgctttccag    120
agccagccct tgccagtcgg cgtaaggttc ggttccccgc gacggtgtgc cgccgaggaa    180
gttgccggag tagaattgca gagccggagc ggtggtgtag accttcagct gcaatttttc    240
atctgctgac cagacatgcg ccgccacttt cttgccatcg cctttggcct gtaacaagaa    300
tgcgtgatcg taacctttca ctttgcgctg atcgtcgtcg gcaagaaact cactggcgat    360
gattttggcg ctgcggaaat caaaagacgt tccggcgaca gatttcaggc cgtcgtgcgg    420
aatgccgcct tcatcaaccg gcagatattc gtccgccaga atctgcaact tgtgattgcg    480
cacgtcagac tgctcgccgt caagattgaa atagacgtga ttagtcatat tcaccgggca    540
aggtttatca actgtggcgc gataagtaat ggagatacgg ttatcgtcgg tcagacgata    600
ttgcaccgtc gcgccgagat tacccgggaa gccctgatca ccatcatctg aactcagggc    660
aaacagcacc tgacgatcgt tctggttcac aatctgccag cgacgtttgt cgaacccttc    720
cggcccgccg tgcagctggt taacgccctg acttggcgaa agcgtcacgg tttcaccgtc    780
aaaggtataa cggctattgg cgatacggtt ggcataacga ccaatagagg cccccagaaa    840
cgcggcctga tcctgatagc attccgggct ggcacagccg agcagcgcct cgcggacgct    900
gccatcggaa agcggaatac gggcggaaag taaagtcgca ccccagtcca tcagcgtgac    960
taccatccct gcgttgttac gcaaagttaa cagtcggtac ggctgaccat cgggtgccag   1020
tgcgggagtt tcgttcagca ctgtcctgct ccttgtgatg gtttacaaac gtaaaaagtc   1080
tctttaatac ctgtttttgc ttcatattgt tcagcgacag cttgctgtac ggcaggcacc   1140
agctcttccg ggatcagcgc gacgatacag ccgccaaatc cgccgccggt catgcgtacg   1200
ccacctttgt cgccaatcac agctttgacg atttctacca gagtgtcaat ttgcggcacg   1260
gtgatttcga aatcatcgcg catagaggca tgagactccg ccatcaactc gcccatacgt   1320
ttcaggtcgc cttgctccag cgcgctggca gcttcaacgg tgcgggcgtt ttcagtcagt   1380
atatgacgca cgcgttttgc cacgatcggg tccagttcat gcgcaacagc gttgaactct   1440
tcaatggtga catcacgcag ggctggctgc tggaagaaac gcgcaccggt ttcgcactgt   1500
tcacgacggg tgttgtattc gctgccaacc agggtacgtt tgaagttact gttgatgatg   1560
acgacagcca cacctttggg catggaaact gctttggtcc ccagtgagcg gcaatcgatc   1620
agcaaggcat gatctttctt gccgagcgcg gaaattagct gatccatgat cccgcagtta   1680
cagcctacaa actggttttc tgcttcctga ccgttaagcg cgatttgtgc gccgtccagc   1740
ggcagatgat aaagctgctg caatacggtt ccgaccgcga cttccagtga agcggaagaa   1800
cttaacccgg caccctgcgg cacattgccg ctgatcacca tgtccacgcc gccgaagctg   1860
ttgttacgca gttgcagatg tttcaccacg ccacgaacgt agttagccca ttgatagttt   1920
tcatgtgcga caatgggcgc atcgagggaa aactcgtcga gctgattttc ataatcggct   1980
gccatcacgc gaactttacg gtcatcgcgt ggtgcacaac tgatcacggt ttgataatca   2040
atcgcgcagg gcagaacgaa accgtcgttg tagtcggtgt gttcaccaat caaattcacg   2100
cggccaggcg cctgaatggt gtgagtggca gggtagccaa atgcgttggc aaacagagat   2160
tgtgtttttt ctttcagact catttcttac actccggatt cgcgaaaatg gatatcgctg   2220
actgcgcgca aacgctctgc tgcctgttct gcggtcaggt ctcgctgggt ctctgccagc   2280
atttcataac caaccataaa tttacgtacg gtggcggagc gcagcagagg cggataaaag   2340
tgcgcgtgca gctgccagtg ttgattctct tcgccattaa atggcgcgcc gtgccagccc   2400
atagagtagg ggaaggagca ctggaagagg ttgtcataac gactggtcag ctttttcaac   2460
```

-continued gccagcgcca gatcgctgcg ctgggcgtcg gtcaaatcgg tgatccgtaa aacgtgggct 2520
ttgggcagca gtagcgtttc gaacggccag gcagcccagt aaggcacgac ggctaaccag 2580
tgttcggttt cgacaacggt acggctaccg tctgccagct cgcgctgaac ataatccacc 2640
agcattggtg atttctgttc ggcaaaatat tctttttgca ggcggtcttc gcgctcagct 2700
tcgttaggca ggaagctatt tgcccaaatc tgaccgtgcg gatgcgggtt agagcagccc 2760
atcgccgcgc ctttgttttc aaaaacctgc acccatgggt acgttttccc cagttctgcg 2820
gtttgctcct gccaggtttt gacgatttcc gtcaatgctg caacgctgag ctctggcagc 2880
gttttactgt gatccggtga aaagcagatc acccggctgg tgccgcgcgc gctctggcaa 2940
cgcatcagcg gatcgtgact ttctggcgca tctggcgtgt cagacatcaa agccgcaaag 3000
tcattagtga aaacgtaagt cccggtgtaa tcggggtttt tatcgcctgt cacccgcaca 3060
ttacctgcgc agaggaagca atctggatcg tgcgcaggta acacctgttt ggctggcgtt 3120
tcctgcgccc cctgccaggg gcgcttagcg cggtgcggtg aaaccagaat ccattgcccg 3180
gtgagcgggt tgtagcggcg atgtggatga tcaacgggat taaattgcgt catggtcgtt 3240
ccttaatcgg gatatccctg tggatggcgt gactgccagt gccaggtgtc ctgcgccatt 3300
tcatcgagtg tgcgcgttac gcgccagttc agttcacggt cggctttgct ggcgtccgcc 3360
cagtaggccg gaaggtcgcc ctcgcgacgc ggtgcaaaat gataattaac cggtttgccg 3420
caggctttgc tgaaggcatt aaccacgtcc agcacgctgt tgcctacgcc agcgccgagg 3480
ttgtagatgt gtacgcctgg cttgttcgcc agtttttcca tcgccacgac gtgaccgtcc 3540
gccagatcca ttacgtggat gtaatcgcgt acgccagtac catcttcggt cggataatcg 3600
ttaccaaaaa tcgccagcga gtcgcgacgg cctacagcaa cctgggcgat gtatggcatc 3660
aggttattcg gaatgccttg cggatcttcg cccatatcgc ccgacggatg cgcgccaacc 3720
gggttgaagt agcgcagcag ggcaatgctc cagtccggct gggctttttg cagatcggtg 3780
aggatctgtt ccaccatcag cttgcttttg ccgtaagggc tttgcggtgt gccggtcggg 3840
aagctttcaa cgtatggaat tttgggctga tcgccataaa cggtggcgga ggagctaaaa 3900
ataaagtttt tgacgttagc ggcgcgcatg gcgctaatca ggcgcagagt gccgttgaca 3960
ttgttgtcgt aatattccag cggtttttgt accgattcgc ccacggcttt cagcccggcg 4020
aagtggatca cggtgtcgat agcgtgatcg tgcaggatct cggtcatcaa cgcttcgtta 4080
cgaatatcgc cttcaacaaa cgttggatgt ttgccgccta aacgctcgat aacaggcagt 4140
acgctgcgct tactgttaca gaggttatca agaatgatga catcatgacc gttttgcagt 4200
aattgcacac aggtatgact tccaatgtaa ccgctaccac cggtaaccag aactctcat 4259

<210> SEQ ID NO 7
<211> LENGTH: 6431
<212> TYPE: DNA
<213> ORGANISM: Artificial Sequence
<220> FEATURE:
<223> OTHER INFORMATION: construct pET-lgtA

<400> SEQUENCE: 7
ggggaattgt gagcggataa caattcccct ctagaaataa ttttgtttaa ctttaagaag 60
gagatatacc atgggcagca gccatcacca tcatcaccac agccaggatc cgaattcgag 120
ctcggcgcgc ctgcaggtcg acaagcttgc ggccgcataa tgcttaagtc gaacagaaag 180
taatcgtatt gtacacggcc gcataatcga aattaatacg actcactata ggggaattgt 240

-continued

```
gagcggataa caattcccca tcttagtata ttagttaagt ataagaagga gatatacata    300
tgccgtccga agcattccgt cgtcaccgtg cttatcgcga aaacaaactg cagccactgg    360
tctctgtcct gatctgcgca tacaacgttg agaaatactt cgcacagtct ctggcagctg    420
tagttaacca gacctggcgt aacctggata tcctgatcgt agatgacggc tctacggatg    480
gtacgctggc gatcgcacag cgtttccagg aacaggacgg tcgtatccgc attctcgctc    540
agccgcgtaa ctctggtctg atcccgtctc tgaacatcgg tctggacgaa ctggccaaat    600
ctggtggtgg tggcgaatac atcgcccgta ctgacgccga cgacattgcg gccccggatt    660
ggatcgaaaa aatcgtaggt gaaatggaga aagaccgctc tatcatcgcg atgggtgctt    720
ggctggaagt tctgtccgaa gagaaagacg gtaaccgtct ggcccgtcac catgaacacg    780
gcaaaatctg gaaaaaaccg acccgtcacg aagatatcgc ggacttcttc ccgttcggta    840
acccgatcca taacaacacc atgatcatgc gtcgtagcgt aatcgacggt ggtctgcgtt    900
acaacaccga acgtgattgg gcagaagact accagttttg gtatgacgtg tctaaactgg    960
gtcgtctggc ttactaccca gaagcgctgg ttaaataccg tctgcacgcc aaccaggtta   1020
gctccaaata ctccatccgt cagcacgaaa tcgcacaggg tatccagaaa acggctcgta   1080
acgacttcct gcagtccatg ggtttcaaaa cccgtttcga ctctctggag taccgtcaga   1140
tcaaagcggt tgcgtatgag ctgctggaga aacacctgcc ggaagaggac tttgaacgtg   1200
cgcgtcgttt cctgtaccag tgcttcaaac gtaccgacac tctgccggcg ggtgcatggc   1260
tcgactttgc agcggatggt cgtatgcgtc gtctgtttac cctgcgtcag tacttcggta   1320
tcctgcatcg tctcctgaaa aaccgctaat gagacgtcgg taccctcgag tctggtaaag   1380
aaaccgctgc tgcgaaattt gaacgccagc acatggactc gtctactagc gcagcttaat   1440
taacctaggc tgctgccacc gctgagcaat aactagcata accccttggg gcctctaaac   1500
gggtcttgag gggttttttg ctgaaaggag gaactatatc cggattggcg aatgggacgc   1560
gccctgtagc ggcgcattaa gcgcggcggg tgtggtggtt acgcgcagcg tgaccgctac   1620
acttgccagc gccctagcgc ccgctccttt cgctttcttc ccttcctttc tcgccacgtt   1680
cgccggcttt ccccgtcaag ctctaaatcg ggggctccct ttagggttcc gatttagtgc   1740
tttacggcac ctcgacccca aaaaacttga ttagggtgat ggttcacgta gtgggccatc   1800
gccctgatag acggtttttc gccctttgac gttggagtcc acgttcttta atagtggact   1860
cttgttccaa actggaacaa cactcaaccc tatctcggtc tattcttttg atttataagg   1920
gattttgccg atttcggcct attggttaaa aaatgagctg atttaacaaa aatttaacgc   1980
gaattttaac aaaatattaa cgtttacaat ttctggcggc acgatggcat gagattatca   2040
aaaaggatct tcacctagat ccttttaaat taaaaatgaa gttttaaatc aatctaaagt   2100
atatatgagt aaacttggtc tgacagttac caatgcttaa tcagtgaggc acctatctca   2160
gcgatctgtc tatttcgttc atccatagtt gcctgactcc ccgtcgtgta gataactacg   2220
atacgggagg gcttaccatc tggccccagt gctgcaatga taccgcgaga cccacgctca   2280
ccggctccag atttatcagc aataaaccag ccagccggaa gggccgagcg cagaagtggt   2340
cctgcaactt tatccgcctc catccagtct attaattgtt gccgggaagc tagagtaagt   2400
agttcgccag ttaatagttt gcgcaacgtt gttgccattg ctacaggcat cgtggtgtca   2460
cgctcgtcgt ttggtatggc ttcattcagc tccggttccc aacgatcaag gcgagttaca   2520
tgatccccca tgttgtgcaa aaaagcggtt agctccttcg gtcctccgat cgttgtcaga   2580
agtaagttgg ccgcagtgtt atcactcatg gttatggcag cactgcataa ttctcttact   2640
```

-continued

```
gtcatgccat ccgtaagatg cttttctgtg actggtgagt actcaaccaa gtcattctga   2700
gaatagtgta tgcggcgacc gagttgctct tgcccggcgt caatacggga taataccgcg   2760
ccacatagca gaactttaaa agtgctcatc attggaaaac gttcttcggg gcgaaaactc   2820
tcaaggatct taccgctgtt gagatccagt tcgatgtaac ccactcgtgc acccaactga   2880
tcttcagcat cttttacttt caccagcgtt tctgggtgag caaaaacagg aaggcaaaat   2940
gccgcaaaaa agggaataag ggcgacacgg aaatgttgaa tactcatact cttccttttt   3000
caatcatgat tgaagcattt atcagggtta ttgtctcatg agcggataca tatttgaatg   3060
tatttagaaa aataaacaaa taggtcatga ccaaaatccc ttaacgtgag ttttcgttcc   3120
actgagcgtc agaccccgta gaaaagatca aaggatcttc ttgagatcct ttttttctgc   3180
gcgtaatctg ctgcttgcaa acaaaaaaac caccgctacc agcggtggtt tgtttgccgg   3240
atcaagagct accaactctt tttccgaagg taactggctt cagcagagcg cagataccaa   3300
atactgtcct tctagtgtag ccgtagttag gccaccactt caagaactct gtagcaccgc   3360
ctacatacct cgctctgcta atcctgttac cagtggctgc tgccagtggc gataagtcgt   3420
gtcttaccgg gttggactca agacgatagt taccggataa ggcgcagcgg tcgggctgaa   3480
cggggggttc gtgcacacag cccagcttgg agcgaacgac ctacaccgaa ctgagatacc   3540
tacagcgtga gctatgagaa agcgccacgc ttcccgaagg gagaaaggcg gacaggtatc   3600
cggtaagcgg cagggtcgga acaggagagc gcacgaggga gcttccaggg ggaaacgcct   3660
ggtatcttta tagtcctgtc gggtttcgcc acctctgact tgagcgtcga tttttgtgat   3720
gctcgtcagg ggggcggagc ctatggaaaa acgccagcaa cgcggccttt ttacggttcc   3780
tggccttttg ctggcctttt gctcacatgt tctttcctgc gttatcccct gattctgtgg   3840
ataaccgtat taccgccttt gagtgagctg ataccgctcg ccgcagccga acgaccgagc   3900
gcagcgagtc agtgagcgag gaagcggaag agcgcctgat gcggtatttt ctccttacgc   3960
atctgtgcgg tatttcacac cgcatatatg gtgcactctc agtacaatct gctctgatgc   4020
cgcatagtta agccagtata cactccgcta tcgctacgtg actgggtcat ggctgcgccc   4080
cgacacccgc caacacccgc tgacgcgccc tgacgggctt gtctgctccc ggcatccgct   4140
tacagacaag ctgtgaccgt ctccgggagc tgcatgtgtc agaggttttc accgtcatca   4200
ccgaaacgcg cgaggcagct gcggtaaagc tcatcagcgt ggtcgtgaag cgattcacag   4260
atgtctgcct gttcatccgc gtccagctcg ttgagtttct ccagaagcgt taatgtctgg   4320
cttctgataa agcgggccat gttaagggcg gttttttcct gtttggtcac tgatgcctcc   4380
gtgtaagggg gatttctgtt catgggggta atgataccga tgaaacgaga gaggatgctc   4440
acgatacggg ttactgatga tgaacatgcc cggttactgg aacgttgtga gggtaaacaa   4500
ctggcggtat ggatgcggcg ggaccagaga aaaatcactc agggtcaatg ccagcgcttc   4560
gttaatacag atgtaggtgt tccacagggt agccagcagc atcctgcgat gcagatccgg   4620
aacataatgg tgcagggcgc tgacttccgc gtttccagac tttacgaaac acggaaaccg   4680
aagaccattc atgttgttgc tcaggtcgca gacgttttgc agcagcagtc gcttcacgtt   4740
cgctcgcgta tcggtgattc attctgctaa ccagtaaggc aaccccgcca gcctagccgg   4800
gtcctcaacg acaggagcac gatcatgcta gtcatgcccc gcgcccaccg gaaggagctg   4860
actgggttga aggctctcaa gggcatcggt cgagatcccg gtgcctaatg agtgagctaa   4920
cttacattaa ttgcgttgcg ctcactgccc gctttccagt cgggaaacct gtcgtgccag   4980
```

-continued

```
ctgcattaat gaatcggcca acgcgcgggg agaggcggtt tgcgtattgg gcgccagggt   5040

ggtttttctt ttcaccagtg agacgggcaa cagctgattg cccttcaccg cctggccctg   5100

agagagttgc agcaagcggt ccacgctggt ttgccccagc aggcgaaaat cctgtttgat   5160

ggtggttaac ggcgggatat aacatgagct gtcttcggta tcgtcgtatc ccactaccga   5220

gatgtccgca ccaacgcgca gcccggactc ggtaatggcg cgcattgcgc ccagcgccat   5280

ctgatcgttg gcaaccagca tcgcagtggg aacgatgccc tcattcagca tttgcatggt   5340

ttgttgaaaa ccggacatgg cactccagtc gccttcccgt tccgctatcg gctgaatttg   5400

attgcgagtg agatatttat gccagccagc cagacgcaga cgcgccgaga cagaacttaa   5460

tgggcccgct aacagcgcga tttgctggtg acccaatgcg accagatgct ccacgcccag   5520

tcgcgtaccg tcttcatggg agaaaataat actgttgatg ggtgtctggt cagagacatc   5580

aagaaataac gccggaacat tagtgcaggc agcttccaca gcaatggcat cctggtcatc   5640

cagcggatag ttaatgatca gcccactgac gcgttgcgcg agaagattgt gcaccgccgc   5700

tttacaggct tcgacgccgc ttcgttctac catcgacacc accacgctgg cacccagttg   5760

atcggcgcga gatttaatcg ccgcgacaat ttgcgacggc gcgtgcaggg ccagactgga   5820

ggtggcaacg ccaatcagca acgactgttt gcccgccagt tgttgtgcca cgcggttggg   5880

aatgtaattc agctccgcca tcgccgcttc cactttttcc cgcgttttcg cagaaacgtg   5940

gctggcctgg ttcaccacgc gggaaacggt ctgataagag acaccggcat actctgcgac   6000

atcgtataac gttactggtt tcacattcac caccctgaat tgactctctt ccgggcgcta   6060

tcatgccata ccgcgaaagg ttttgcgcca ttcgatggtg tccgggatct cgacgctctc   6120

ccttatgcga ctcctgcatt aggaagcagc ccagtagtag gttgaggccg ttgagcaccg   6180

ccgccgcaag gaatggtgca tgcaaggaga tggcgcccaa cagtcccccg gccacggggc   6240

ctgccaccat acccacgccg aaacaagcgc tcatgagccc gaagtggcga gcccgatctt   6300

ccccatcggt gatgtcggcg atataggcgc cagcaaccgc acctgtggcg ccggtgatgc   6360

cggccacgat gcgtccggcg tagaggatcg agatcgatct cgatcccgcg aaattaatac   6420

gactcactat a                                                        6431
```

<210> SEQ ID NO 8
<211> LENGTH: 5739
<212> TYPE: DNA
<213> ORGANISM: Artificial Sequence
<220> FEATURE:
<223> OTHER INFORMATION: construct pCDF-galT-galE

<400> SEQUENCE: 8

```
ggggaattgt gagcggataa caattcccct gtagaaataa ttttgtttaa ctttaataag     60

gagatatacc atgacgcaat ttaatcccgt tgatcatcca catcgccgct acaacccgct    120

caccgggcaa tggattctgg tttcaccgca ccgcgctaag cgcccctggc agggggcgca    180

ggaaacgcca gccaaacagg tgttacctgc gcacgatcca gattgcttcc tctgcgcagg    240

taatgtgcgg gtgacaggcg ataaaaaccc cgattacacc gggacttacg ttttcactaa    300

tgactttgcg gctttgatgt ctgacacgcc agatgcgcca gaaagtcacg atccgctgat    360

gcgttgccag agcgcgcgcg gcaccagccg ggtgatctgc ttttcaccgg atcacagtaa    420

aacgctgcca gagctcagcg ttgcagcatt gacggaaatc gtcaaaacct ggcaggagca    480

aaccgcagaa ctggggaaaa cgtacccatg ggtgcaggtt tttgaaaaca aaggcgcggc    540

gatgggctgc tctaacccgc atccgcacgg tcagatttgg gcaaatagct tcctgcctaa    600
```

-continued

```
cgaagctgag cgcgaagacc gcctgcaaaa agaatatttt gccgaacaga aatcaccaat    660
gctggtggat tatgttcagc gcgagctggc agacggtagc cgtaccgttg tcgaaaccga    720
acactggtta gccgtcgtgc cttactgggc tgcctggccg ttcgaaacgc tactgctgcc    780
caaagcccac gttttacgga tcaccgattt gaccgacgcc cagcgcagcg atctggcgct    840
ggcgttgaaa aagctgacca gtcgttatga caacctcttc cagtgctcct tcccctactc    900
tatgggctgg cacggcgcgc catttaatgg cgaagagaat caacactggc agctgcacgc    960
gcacttttat ccgcctctgc tgcgctccgc caccgtacgt aaatttatgg ttggttatga   1020
aatgctggca gagacccagc gagacctgac cgcagaacag gcagcagagc gtttgcgcgc   1080
agtcagcgat atccattttc gcgaatccgg agtgtaaaag cttgcggccg cataatgctt   1140
aagtcgaaca gaaagtaatc gtattgtaca cggccgcata atcgaaatta atacgactca   1200
ctatagggga attgtgagcg gataacaatt ccccatctta gtatattagt taagtataag   1260
aaggagatat acagatcaca tatgagagtt ctggttaccg gtggtagcgg ttacattgga   1320
agtcatacct gtgtgcaatt actgcaaaac ggtcatgatg tcatcattct tgataacctc   1380
tgtaacagta agcgcagcgt actgcctgtt atcgagcgtt taggcggcaa acatccaacg   1440
tttgttgaag gcgatattcg taacgaagcg ttgatgaccg agatcctgca cgatcacgct   1500
atcgacaccg tgatccactt cgccgggctg aaagccgtgg gcgaatcggt acaaaaaccg   1560
ctggaatatt acgacaacaa tgtcaacggc actctgcgcc tgattagcgc catgcgcgcc   1620
gctaacgtca aaaactttat ttttagctcc tccgccaccg tttatggcga tcagcccaaa   1680
attccatacg ttgaaagctt cccgaccggc acaccgcaaa gcccttacgg caaaagcaag   1740
ctgatggtgg aacagatcct caccgatctg caaaaagccc agccggactg gagcattgcc   1800
ctgctgcgct acttcaaccc ggttggcgcg catccgtcgg gcgatatggg cgaagatccg   1860
caaggcattc cgaataacct gatgccatac atcgcccagg ttgctgtagg ccgtcgcgac   1920
tcgctggcga tttttggtaa cgattatccg accgaagatg gtactggcgt acgcgattac   1980
atccacgtaa tggatctggc ggacggtcac gtcgtggcga tggaaaaact ggcgaacaag   2040
ccaggcgtac acatctacaa cctcggcgct ggcgtaggca acagcgtgct ggacgtggtt   2100
aatgccttca gcaaagcctg cggcaaaccg gttaattatc attttgcacc gcgtcgcgag   2160
ggcgaccttc cggcctactg ggcggacgcc agcaaagccg accgtgaact gaactggcgc   2220
gtaacgcgca cactcgatga aatggcgcag gacacctggc actggcagtc acgccatcca   2280
cagggatatc ccgattaatg actcgagtga tctcgagtct ggtaaagaaa ccgctgctgc   2340
gaaatttgaa cgccagcaca tggactcgtc tactagcgca gcttaattaa cctaggctgc   2400
tgccaccgct gagcaataac tagcataacc ccttggggcc tctaaacggg tcttgagggg   2460
ttttttgctg aaacctcagg catttgagaa gcacacggtc acactgcttc cggtagtcaa   2520
taaaccggta aaccagcaat agacataagc ggctatttaa cgaccctgcc ctgaaccgac   2580
gaccgggtca tcgtggccgg atcttgcggc ccctcggctt gaacgaattg ttagacatta   2640
tttgccgact accttggtga tctcgccttt cacgtagtgg acaaattctt ccaactgatc   2700
tgcgcgcgag gccaagcgat cttcttcttg tccaagataa gcctgtctag cttcaagtat   2760
gacgggctga tactgggccg gcaggcgctc cattgcccag tcggcagcga catccttcgg   2820
cgcgattttg ccggttactg cgctgtacca aatgcgggac aacgtaagca ctacatttcg   2880
ctcatcgcca gcccagtcgg gcggcgagtt ccatagcgtt aaggtttcat ttagcgcctc   2940
```

-continued aaatagatcc tgttcaggaa ccggatcaaa gagttcctcc gccgctggac ctaccaaggc 3000
aacgctatgt tctcttgctt ttgtcagcaa gatagccaga tcaatgtcga tcgtggctgg 3060
ctcgaagata cctgcaagaa tgtcattgcg ctgccattct ccaaattgca gttcgcgctt 3120
agctggataa cgccacggaa tgatgtcgtc gtgcacaaca atggtgactt ctacagcgcg 3180
gagaatctcg ctctctccag gggaagccga agtttccaaa aggtcgttga tcaaagctcg 3240
ccgcgttgtt tcatcaagcc ttacggtcac cgtaaccagc aaatcaatat cactgtgtgg 3300
cttcaggccg ccatccactg cggagccgta caaatgtacg gccagcaacg tcggttcgag 3360
atggcgctcg atgacgccaa ctacctctga tagttgagtc gatacttcgg cgatcaccgc 3420
ttccctcata ctcttccttt ttcaatatta ttgaagcatt tatcagggtt attgtctcat 3480
gagcggatac atatttgaat gtatttagaa aaataaacaa atagctagct cactcggtcg 3540
ctacgctccg ggcgtgagac tgcggcgggc gctgcggaca catacaaagt tacccacaga 3600
ttccgtggat aagcagggga ctaacatgtg aggcaaaaca gcagggccgc gccggtggcg 3660
tttttccata ggctccgccc tcctgccaga gttcacataa acagacgctt ttccggtgca 3720
tctgtgggag ccgtgaggct caaccatgaa tctgacagta cgggcgaaac ccgacaggac 3780
ttaaagatcc ccaccgtttc cggcgggtcg ctccctcttg cgctctcctg ttccgaccct 3840
gccgtttacc ggatacctgt tccgcctttc tcccttacgg gaagtgtggc gctttctcat 3900
agctcacaca ctggtatctc ggctcggtgt aggtcgttcg ctccaagctg ggctgtaagc 3960
aagaactccc cgttcagccc gactgctgcg ccttatccgg taactgttca cttgagtcca 4020
acccggaaaa gcacggtaaa acgccactgg cagcagccat tggtaactgg gagttcgcag 4080
aggatttgtt tagctaaaca cgcggttgct cttgaagtgt gcgccaaagt ccggctacac 4140
tggaaggaca gatttggttg ctgtgctctg cgaaagccag ttaccacggt taagcagttc 4200
cccaactgac ttaaccttcg atcaaaccac ctccccaggt ggtttttttcg tttacagggc 4260 aaaagattac gcgcagaaaa aaaggatctc aagaagatcc tttgatcttt tctactgaac 4320
cgctctagat ttcagtgcaa tttatctctt caaatgtagc acctgaagtc agccccatac 4380
gatataagtt gtaattctca tgttagtcat gccccgcgcc caccggaagg agctgactgg 4440
gttgaaggct ctcaagggca tcggtcgaga tcccggtgcc taatgagtga gctaacttac 4500
attaattgcg ttgcgctcac tgcccgcttt ccagtcggga aacctgtcgt gccagctgca 4560
ttaatgaatc ggccaacgcg cggggagagg cggtttgcgt attgggcgcc agggtggttt 4620
ttcttttcac cagtgagacg ggcaacagct gattgccctt caccgcctgg ccctgagaga 4680
gttgcagcaa gcggtccacg ctggtttgcc ccagcaggcg aaaatcctgt ttgatggtgg 4740
ttaacggcgg gatataacat gagctgtctt cggtatcgtc gtatcccact accgagatgt 4800
ccgcaccaac gcgcagcccg gactcggtaa tggcgcgcat tgcgcccagc gccatctgat 4860
cgttggcaac cagcatcgca gtgggaacga tgccctcatt cagcatttgc atggtttgtt 4920
gaaaaccgga catggcactc cagtcgcctt cccgttccgc tatcggctga atttgattgc 4980
gagtgagata tttatgccag ccagccagac gcagacgcgc cgagacagaa cttaatgggc 5040
ccgctaacag cgcgatttgc tggtgaccca atgcgaccag atgctccacg cccagtcgcg 5100
taccgtcttc atgggagaaa ataatactgt tgatgggtgt ctggtcagag acatcaagaa 5160
ataacgccgg aacattagtg caggcagctt ccacagcaat ggcatcctgg tcatccagcg 5220
gatagttaat gatcagccca ctgacgcgtt gcgcgagaag attgtgcacc gccgctttac 5280
aggcttcgac gccgcttcgt tctaccatcg acaccaccac gctggcaccc agttgatcgg 5340
cgcgagattt aatcgccgcg acaatttgcg acggcgcgtg cagggccaga ctggaggtgg 5400
caacgccaat cagcaacgac tgtttgcccg ccagttgttg tgccacgcgg ttgggaatgt 5460
aattcagctc cgccatcgcc gcttccactt tttcccgcgt tttcgcagaa acgtggctgg 5520
cctggttcac cacgcgggaa acggtctgat aagagacacc ggcatactct gcgacatcgt 5580
ataacgttac tggtttcaca ttcaccaccc tgaattgact ctcttccggg cgctatcatg 5640
ccataccgcg aaaggttttg cgccattcga tggtgtccgg gatctcgacg ctctccctta 5700
tgcgactcct gcattaggaa attaatacga ctcactata 5739

<210> SEQ ID NO 9
<211> LENGTH: 8232
<212> TYPE: DNA
<213> ORGANISM: Artificial Sequence
<220> FEATURE:
<223> OTHER INFORMATION: construct pCOLA-glmUM-glmS

<400> SEQUENCE: 9
cagcccactg acgcgttgcg cgagaagatt gtgcaccgcc gctttacagg cttcgacgcc 60
gcttcgttct accatcgaca ccaccacgct ggcacccagt tgatcggcgc gagatttaat 120
cgccgcgaca atttgcgacg gcgcgtgcag ggccagactg gaggtggcaa cgccaatcag 180
caacgactgt ttgcccgcca gttgttgtgc cacgcggttg ggaatgtaat tcagctccgc 240
catcgccgct tccacttttt cccgcgtttt cgcagaaacg tggctggcct ggttcaccac 300
gcgggaaacg gtctgataag agacaccggc atactctgcg acatcgtata acgttactgg 360
tttcacattc accaccctga attgactctc ttccgggcgc tatcatgcca taccgcgaaa 420
ggttttgcgc cattcgatgg tgtccgggat ctcgacgctc tcccttatgc gactcctgca 480
ttaggaaatt aatacgactc actatagggg aattgtgagc ggataacaat tcccctgtag 540
aaataatttt gtttaacttt aataaggaga tataccatgc tgaacaacgc gatgtctgtt 600
gttatcctgg cggcgggtaa aggtacccgt atgtactctg acctgccgaa agttctgcac 660
accctggcgg gtaaagcgat ggttcagcac gttatcgacg cggcgaacga actgggtgcg 720
gcgcacgttc acctggttta cggtcacggt ggtgacctgc tgaaacaggc gctgaaagac 780
gacaacctga actgggttct gcaggcggaa cagctgggta ccggtcacgc gatgcagcag 840
gcggcgccgt tcttcgcgga cgacgaagac atcctgatgc tgtacggtga cgttccgctg 900
atctctgttg aaaccctgca gcgtctgcgt gacgcgaaac cgcagggtgg tatcggtctg 960
ctgaccgtta aactggacga cccgaccggt tacggtcgta tcacccgtga aaacggtaaa 1020
gtaaccggta tcgttgaaca caaagacgcg accgacgaac agcgtcagat ccaggagatc 1080
aacaccggta tcctgatcgc gaacggtgca gacatgaaac gttggctggc gaaactgacc 1140
aacaacaacg cgcagggtga atactacatc accgacatca tcgcgctggc gtaccaggaa 1200
ggtcgtgaaa tcgttgcggt tcacccgcag cgtctgtctg aagttgaagg tgttaacaac 1260
cgtctgcagc tgtctcgtct ggaacgtgtt taccagtctg aacaggcgga aaaactgctg 1320
ctggcgggtg ttatgctgcg tgacccggcg cgtttcgacc tgcgtggtac cctgacccac 1380
ggtcgtgacg ttgaaatcga caccaacgtt atcatcgaag gtaacgttac cctgggtcac 1440
cgtgtaaaaa tcggcaccgg ttgcgttatc aaaaactctg ttatcggtga cgactgcgaa 1500
atctctccgt acaccgttgt tgaagacgcg aacctggcgg cggcgtgcac catcggtccg 1560
ttcgcgcgtc tgcgtccggg tgcggaactg ctggaaggtg cgcacgttgg taacttcgtt 1620

-continued

```
gaaatgaaaa aagcgcgtct gggtaaaggt tctaaagcgg gtcacctgac ctacctgggt   1680
gacgcggaaa tcggtgacaa cgttaacatc ggtgcgggta ccatcacctg caactacgac   1740
ggtgcgaaca aattcaaaac catcatcggt gacgacgttt tcgttggttc tgacacccag   1800
ctggttgcgc cggttaccgt tggtaaaggt gcgaccatcg cggcgggtac caccgttacc   1860
cgtaacgttg gtgaaaacgc gctggcgatc tctcgtgttc cgcagaccca gaaagaaggt   1920
tggcgtcgtc cggttaaaaa aaaataacga aggagataga accatgtcca accgtaaata   1980
cttcggtacg gacggtatcc gtggtcgtgt aggtgatgct ccgattacgc cggatttcgt   2040
cctgaaactc ggttgggcag cgggtaaagt tctcgcacgt cacggctctc gtaaaatcat   2100
catcggtaaa gacacccgta tctctggtta catgctcgaa tctgcactgg aagcgggtct   2160
ggctgcagct ggtctgtctg cactgttcac gggtccgatg ccaaccccag ctgtagcgta   2220
cctgactcgc actttccgtg cagaagcagg tatcgtgatc tctgcctctc acaacccgtt   2280
ctacgacaac ggtatcaaat tcttcagcat cgatggtacc aaactcccag acgcggttga   2340
agaggctatc gaagcggaaa tggagaaaga aatctcttgt gtagactctg ccgaactcgg   2400
taaagcgtct cgtatcgttg atgcagcggg tcgttacatc gagttctgca aagccacctt   2460
tccgaacgaa ctgagcctgt ctgagctgaa aatcgtcgta gactgtgcca acggtgcgac   2520
ttaccacatt gccccaaacg tactgcgtga gctgggtgct aacgtcatcg cgatcggttg   2580
tgaaccgaac ggtgtcaaca tcaacgcgga agtaggtgcg accgatgttc gtgcactgca   2640
ggctcgtgta ctcgcggaga aagcggatct cggtatcgcc tttgacggtg atggtgaccg   2700
tgttatcatg gttgaccacg aaggtaacaa agtggatggt gaccagatca tgtacatcat   2760
tgcccgtgaa ggtctgcgtc agggtcagct gcgtggtggt gcagtaggta ccctcatgag   2820
caacatgggt ctggaactgg ccctgaaaca gctgggtatc ccattcgctc gtgctaaagt   2880
aggcgaccgt tacgttctgg agaaaatgca ggagaaaggt tggcgtatcg gtgccgaaaa   2940
ctctggtcac gtcatcctgc tggacaaaac cactaccggt gacggtatcg tagcaggtct   3000
gcaggtactc gccgctatgg cccgtaacca catgtccctc catgacctct gctctggtat   3060
gaaaatgttc ccgcagatcc tggttaacgt tcgttacacc gcaggttctg gtgatccgct   3120
ggaacacgag tctgtgaaag ccgttaccgc agaagtggaa gcggccctgg gtaaccgtgg   3180
tcgtgtactg ctgcgtaaat ccggtactga gccactgatc cgtgttatgg ttgagggcga   3240
agatgaagcc caggtcaccg aatttgcgca ccgtattgcc gacgcagtca aagcggttta   3300
aatgggcagc agccatcacc atcatcacca cagccaggat ccgaattcga gctcggcgcg   3360
cctgcaggtc gacaagcttg cggccgcata atgcttaagt cgaacagaaa gtaatcgtat   3420
tgtacacggc cgcataatcg aaattaatac gactcactat aggggaattg tgagcggata   3480
acaattcccc atcttagtat attagttaag tataagaagg agatatacat atgtgcggta   3540
tcgttggtgc tatcgcacag cgtgatgtag cggagatcct cctggaaggt ctgcgtcgtc   3600
tcgaataccg tggttacgac tctgccggtc tggcagtagt ggatgcagaa ggtcacatga   3660
ctcgtctgcg tcgtctgggt aaagtgcaga tgctcgcgca ggcggcggaa gaacacccac   3720
tccacggtgg tacgggtatc gcacacactc gttgggcaac ccacggtgaa ccgtctgagg   3780
tcaacgcaca cccgcatgtt agcgagcaca tcgtagtcgt tcacaacggt atcatcgaga   3840
accacgaacc actccgtgag gaactcaaag cccgtggtta caccttcgta agcgaaaccg   3900
acacggaagt tatcgcccac ctcgttaact gggaactcaa acagggtggt actctgcgtg   3960
aagcagttct gcgtgccatt ccacagctgc gtggtgcata cggtaccgtg atcatggact   4020
```

-continued ctcgtcatcc ggataccctg ctcgccgcac gttctggttc tccactcgtt atcggtctgg 4080
gtatgggtga gaacttcatc gcctctgatc agctggccct gctcccagtt acccgtcgct 4140
tcatcttcct ggaagagggt gacatcgccg aaatcacccg tcgttccgtt aacatcttcg 4200
acaaaaacggg tgcggaagtt aaacgtcagg acatcgagtc taacctgcag tatgacgctg 4260
gtgacaaagg catctaccgt cactacatgc agaaagagat ctacgaacag ccgaacgcga 4320
tcaaaaacac cctgaccggt cgtatctctc acggtcaggt tgacctgtct gagctgggtc 4380
caaacgcgga cgaactcctg tccaaagtcg agcacatcca gatcctggct tgtggtacct 4440
cttacaactc cggtatggtt tctcgttact ggttcgaatc tctggcaggt atcccatgcg 4500
acgttgaaat cgcctccgaa ttccgttatc gtaaatctgc ggtacgtcgt aactccctca 4560
tgatcaccct gtctcagtct ggtgaaaccg ctgatactct ggcaggtctg cgtctcagca 4620
aagaactggg ttacctgggt tctctggcca tctgcaacgt tccgggttct agcctggttc 4680
gtgagtctga cctggctctg atgaccaacg cgggtacgga gatcggtgtt gcctctacca 4740
aagcgttcac tacccagctc actgtcctgc tgatgctggt tgccaaactg tctcgtctca 4800
aaggcctcga cgctagcatc gaacacgaca tcgtacacgg tctgcaggcc ctcccatctc 4860
gtatcgagca gatgctgtct caggacaaac gtatcgaagc actggcagaa gacttcagcg 4920
acaaacacca cgcgctgttt ctgggtcgtg gtgaccagta cccaattgcg ctggaaggtg 4980
ccctgaaact gaaagagatc agctacatcc atgcagaggc atacgcagcg ggtgagctga 5040
aacatggtcc actggccctg atcgacgcag atatgccggt tattgtggtt gctccgaaca 5100
acgaactgct ggagaaactg aaatccaaca tcgaggaagt acgtgcgcgt ggtggtcagc 5160
tgtacgtgtt tgctgaccag gacgcgggtt tcgtttccag cgacaacatg cacatcatcg 5220
aaatgccgca tgttgaagag gtaatcgcgc caatcttcta caccgtaccg ctgcagctgc 5280
tggcgtacca tgtagccctg atcaaaggta cggacgttga ccagccgcgt aacctggcga 5340
aatccgtgac cgtggaataa gacgtcggta ccctcgagtc tggtaaagaa accgctgctg 5400
cgaaatttga acgccagcac atggactcgt ctactagcgc agcttaatta acctaggctg 5460
ctgccaccgc tgagcaataa ctagcataac cccttggggc ctctaaacgg gtcttgaggg 5520
gttttttgct gaaacctcag gcatttgaga agcacacggt cacactgctt ccggtagtca 5580
ataaaccggt aaaccagcaa tagacataag cggctattta acgaccctgc cctgaaccga 5640
cgacaagctg acgaccgggt ctccgcaagt ggcacttttc ggggaaatgt gcgcggaacc 5700
cctatttgtt tatttttcta aatacattca aatatgtatc cgctcatgaa ttaattctta 5760
gaaaaactca tcgagcatca aatgaaactg caatttattc atatcaggat tatcaatacc 5820
atatttttga aaaagccgtt tctgtaatga aggagaaaac tcaccgaggc agttccatag 5880
gatggcaaga tcctggtatc ggtctgcgat tccgactcgt ccaacatcaa tacaacctat 5940
taatttcccc tcgtcaaaaa taaggttatc aagtgagaaa tcaccatgag tgacgactga 6000
atccggtgag aatggcaaaa gtttatgcat ttctttccag acttgttcaa caggccagcc 6060
attacgctcg tcatcaaaat cactcgcatc aaccaaaccg ttattcattc gtgattgcgc 6120
ctgagcgaga cgaaatacgc ggtcgctgtt aaaaggacaa ttacaaacag gaatcgaatg 6180
caaccggcgc aggaacactg ccagcgcatc aacaatattt tcacctgaat caggatattc 6240
ttctaatacc tggaatgctg ttttcccggg gatcgcagtg gtgagtaacc atgcatcatc 6300
aggagtacgg ataaaatgct tgatggtcgg aagaggcata aattccgtca gccagtttag 6360

-continued tctgaccatc tcatctgtaa catcattggc aacgctacct ttgccatgtt tcagaaacaa 6420
ctctggcgca tcgggcttcc catacaatcg atagattgtc gcacctgatt gcccgacatt 6480
atcgcgagcc catttatacc catataaatc agcatccatg ttggaattta atcgcggcct 6540
agagcaagac gtttcccgtt gaatatggct catactcttc ctttttcaat attattgaag 6600
catttatcag ggttattgtc tcatgagcgg atacatattt gaatgtattt agaaaaataa 6660
acaaataggc atgctagcgc agaaacgtcc tagaagatgc caggaggata cttagcagag 6720
agacaataag gccggagcga agccgttttt ccataggctc cgcccccctg acgaacatca 6780
cgaaatctga cgctcaaatc agtggtggcg aaacccgaca ggactataaa gataccaggc 6840 gtttcccccct gatggctccc tcttgcgctc tcctgttccc gtcctgcggc gtccgtgttg 6900
tggtggaggc tttacccaaa tcaccacgtc ccgttccgtg tagacagttc gctccaagct 6960
gggctgtgtg caagaacccc ccgttcagcc cgactgctgc gccttatccg gtaactatca 7020
tcttgagtcc aacccggaaa gacacgacaa aacgccactg gcagcagcca ttggtaactg 7080
agaattagtg gatttagata tcgagagtct tgaagtggtg gcctaacaga ggctacactg 7140
aaaggacagt atttggtatc tgcgctccac taaagccagt taccaggtta agcagttccc 7200
caactgactt aaccttcgat caaaccgcct ccccaggcgg tttttcgtt tacagagcag 7260 gagattacga cgatcgtaaa aggatctcaa gaagatcctt tacggattcc cgacaccatc 7320
actctagatt tcagtgcaat ttatctcttc aaatgtagca cctgaagtca gccccatacg 7380
atataagttg taattctcat gttagtcatg ccccgcgccc accggaagga gctgactggg 7440
ttgaaggctc tcaagggcat cggtcgagat cccggtgcct aatgagtgag ctaacttaca 7500
ttaattgcgt tgcgctcact gcccgctttc cagtcgggaa acctgtcgtg ccagctgcat 7560
taatgaatcg gccaacgcgc ggggagaggc ggtttgcgta ttgggcgcca gggtggtttt 7620
tcttttcacc agtgagacgg gcaacagctg attgcccttc accgcctggc cctgagagag 7680
ttgcagcaag cggtccacgc tggtttgccc cagcaggcga aaatcctgtt tgatggtggt 7740
taacggcggg atataacatg agctgtcttc ggtatcgtcg tatcccacta ccgagatgtc 7800
cgcaccaacg cgcagcccgg actcggtaat ggcgcgcatt gcgcccagcg ccatctgatc 7860
gttggcaacc agcatcgcag tgggaacgat gccctcattc agcatttgca tggtttgttg 7920
aaaaccggac atggcactcc agtcgccttc ccgttccgct atcggctgaa tttgattgcg 7980
agtgagatat ttatgccagc cagccagacg cagacgcgcc gagacagaac ttaatgggcc 8040
cgctaacagc gcgatttgct ggtgacccaa tgcgaccaga tgctccacgc ccagtcgcgt 8100
accgtcttca tgggagaaaa taatactgtt gatgggtgtc tggtcagaga catcaagaaa 8160
taacgccgga acattagtgc aggcagcttc cacagcaatg gcatcctggt catccagcgg 8220
atagttaatg at 8232

<210> SEQ ID NO 10
<211> LENGTH: 6792
<212> TYPE: DNA
<213> ORGANISM: Artificial Sequence
<220> FEATURE:
<223> OTHER INFORMATION: construct pINT-malE-PmgalT7

<400> SEQUENCE: 10
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180

-continued

```
accatatgcg gtgtgaaata ccgcacagat gcgtaaggag aaaataccgc atcaggcgcc    240
attcgccatt caggctgcgc aactgttggg aagggcgatc ggtgcgggcc tcttcgctat    300
tacgccagct ggcgaaaggg ggatgtgctg caaggcgatt aagttgggta acgccagggt    360
tttcccagtc acgacgttgt aaaacgacgg ccagtgaatt cgaagatcct ttgatctttt    420
ctacggggtc tgacgctcag tggaacgaaa actcacgtta agggattttg gtcatgagat    480
tatcaaaaag gatcttcacc tagatccttt taaactagtg aagttaccat cacggaaaaa    540
ggttatgctg cttttaagac ccactttcac atttaagttg tttttctaat ccgcatatga    600
tcaattcaag gccgaataag aaggctggct ctgcaccttg gtgatcaaat aattcgatag    660
cttgtcgtaa taatggcggc atactatcag tagtaggtgt ttccctttct tctttagcga    720
cttgatgctc ttgatcttcc aatacgcaac ctaaagtaaa atgccccact gcgctgagtg    780
catataatgc attctctagt gaaaaacctt gttggcataa aaaggctaat tgattttcga    840
gagtttcata ctgtttttct gtaggccgtg tacctaaatg tacttttgct ccatcgcgat    900
gacttagtaa agcacatcta aaacttttag cgttattacg taaaaaatct tgccagcttt    960
ccccttctaa agggcaaaag tgagtatggt gcctatctaa catctcaatg gctaaggcgt   1020
cgagcaaagc ccgcttattt tttacatgcc aatacaatgt aggctgctct acacctagct   1080
tctgggcgag tttacgggtt gttaaacctt cgattccgac ctcattaagc agctctaatg   1140
cgctgttaat cactttactt ttatctaaac gagacatact cttccttttt caatattatt   1200
gaagcattta tcagggttat tgtctcatga gcggatacat atttgaatgt atttagaaaa   1260
ataaacaaat aggggttccg cgcacatttc cccgaaaagt gccacctgaa attggccaga   1320
tgattaattc ctaatttttg ttgacactct atcattgata gagttatttt accactccct   1380
atcagtgata gagaaaagtg aaatgaatag ttcgacaaaa atctagaaat aattttgttt   1440
aactttaaga aggagatata caaatgaaaa tcgaagaagg taaactggta atctggatta   1500
acggcgataa aggctataac ggtctcgctg aagtcggtaa gaaattcgag aaagataccg   1560
gaattaaagt caccgttgag catccggata aactggaaga gaaattccca caggttgcgg   1620
caactggcga tggccctgac attatcttct gggcacacga ccgctttggt ggctacgctc   1680
aatctggcct gttggctgaa atcaccccgg acaaagcgtt ccaggacaag ctgtatccgt   1740
ttacctggga tgccgtacgt tacaacggca agctgattgc ttacccgatc gctgttgaag   1800
cgttatcgct gatttataac aaagatctgc tgccgaaccc gccaaaaacc tgggaagaga   1860
tcccggcgct ggataaagaa ctgaaagcga aaggtaagag cgcgctgatg ttcaacctgc   1920
aagaaccgta cttcacctgg ccgctgattg ctgctgacgg gggttatgcg ttcaagtatg   1980
aaaacggcaa gtacgacatt aaagacgtgg gcgtggataa cgctggcgcg aaagcgggtc   2040
tgaccttcct ggttgacctg attaaaaaca aacacatgaa tgcagacacc gattactcca   2100
tcgcagaagc tgcctttaat aaaggcgaaa cagcgatgac catcaacggc ccgtgggcat   2160
ggtccaacat cgacaccagc aaagtgaatt atggtgtaac ggtactgccg accttcaagg   2220
gtcaaccatc caaaccgttc gttggcgtgc tgagcgcagg tattaacgcc gccagtccga   2280
acaaagagct ggcaaaagag ttcctcgaaa actatctgct gactgatgaa ggtctggaag   2340
cggttaataa agacaaaccg ctgggtgccg tagcgctgaa gtcttacgag gaagagttgg   2400
cgaaagatcc acgtattgcc gccaccatgg aaaacgccca gaaaggtgaa atcatgccga   2460
acatcccgca gatgtccgct ttctggtatg ccgtgcgtac tgcggtgatc aacgccgcca   2520
```

-continued

```
gcggtcgtca gactgtcgat gaagccctga aagacgcgca gactatgagc ggtgaacact   2580
atgtcattag cctgtcgtcg gcagttgaac gtcgccagca cattcgtaac cagttttcgc   2640
agaagaacat cccgtttcag tttttcgatg caatttcacc gtcgccgctg ctggaccagc   2700
tggtgctgca atttttcccg cgtctggcgg atagctctct gaccggcggt gaaaaagcct   2760
gctttatgag ccatctgtct ctgtggcaca aatgtgtgga agaaaacctg ccgtatattg   2820
tggtttttga agatgacatc gttctgggca aagatgcgga caagttcctg attggtgatg   2880
aatggctgtt ttctcgtttc gacccggaag aaatctttat tatccgcctg gaaaccttcc   2940
tgcagaaagt cgtgtgcgaa agcacccata ttgccccgta tacgcaccgc gattttctga   3000
gtctgaaatc cgcacatttc ggcacggctg gttacgtcat cagtcagggc gcggccaaat   3060
ttctgctgga tattttcaag aacatctcca atgaacacat tgcgccgatc gacgaactga   3120
tttttaacca gttcctggtt aagaactcat tcaacgtcta ccaactgtcg ccggcaatct   3180
gtgttcagga actgcaactg aacaatgaaa gttccgctct gcagagccaa ctggaactgg   3240
aacgtaacaa attccgcaat aaaaagtctg aagaactgaa gcgtaaccgc aagaacttca   3300
tcgaaaagtt catctacatc ctgaaaaagc cgaagcgtat gctggataac aataagcgta   3360
agcgcgaaga gagtaagatc gaaaacgaca agatgatcat cgaatttaaa tgagcggccg   3420
cgtcgacacg caaaaaggcc atccgtcagg atggccttct gcttaattat ctagatgcct   3480
ggcagtttat ggcgggcgtc ctgcccgcca ccctccgggc cgttgcttcg caacgttcaa   3540
atccgctccc ggcggatttg tcctactcag gagagcgttc accgacaaac aacagataaa   3600
acgaaaggcc cagtctttcg actgagcctt tcgttttatt tgatgcctgg cagttcccta   3660
ctctcgcatg gggagacccc acactaccat catgtatgaa tatcctcctt agttcctatt   3720
ccgaagggta atggcatcag ggaatggcga acgcgctccc cacactacca tcatgtatga   3780
atatcctcct tagttcctat tccgaagttc ctattctcta gaaagtatag gaacttcggt   3840
ggaacgacgc gtaactcacg ttaagggatt ttggtcatga tcagcacgtg ttgacaatta   3900
atcatcggca tagtatatcg gcatagtata atacgacaag gtgaggaact aaaccatggc   3960
caagttgacc agtgccgttc cggtgctcac cgcgcgcgac gtcgccggag cggtcgagtt   4020
ctggaccgac cggctcgggt tctcccggga cttcgtggag gacgacttcg ccggtgtggt   4080
ccgggacgac gtgaccctgt tcatcagcgc ggtccaggac caggtggtgc cggacaacac   4140
cctggcctgg gtgtgggtgc gcggcctgga cgagctgtac gccgagtggt cggaggtcgt   4200
gtccacgaac ttccgggacg cctccgggcc ggccatgacc gagatcggcg agcagccgtg   4260
gggcgggag ttcgccctgc gcgacccggc cggcaactgc gtgcacttcg tggccgagga   4320
gcaggactga gtggcagggc ggggcgtaag gcgcgccatt taaatgaagt tcctattccg   4380
aagttcctat tctctagaaa gtataggaac ttcgaagcag ctccagccta cacaatcgct   4440
caagacggaa cccgcgcttg gcaggaaagt aatagggata gcagctccag cctacacaat   4500
cgctcaagac gtgtaatgct gcacaataac cctgctgcag aggcctgcat gcaagcttgg   4560
cgtaatcatg gtcatagctg tttcctgtgt gaaattgtta tccgctcaca attccacaca   4620
acatacgagc cggaagcata aagtgtaaag cctggggtgc ctaatgagtg agctaactca   4680
cattaattgc gttgcgctca ctgcccgctt tccagtcggg aaacctgtcg tgccagctgc   4740
attaatgaat cggccaacgc gcggggagag gcggtttgcg tattgggcgc tcttccgctt   4800
cctcgctcac tgactcgctg cgctcggtcg ttcggctgcg gcgagcggta tcagctcact   4860
caaaggcggt aatacggtta tccacagaat caggggataa cgcaggaaag aacatgtgag   4920
```

caaaaggcca gcaaaaggcc aggaaccgta aaaaggccgc gttgctggcg tttttccata 4980
ggctccgccc ccctgacgag catcacaaaa atcgacgctc aagtcagagg tggcgaaacc 5040
cgacaggact ataaagatac caggcgtttc cccctggaag ctccctcgtg cgctctcctg 5100
ttccgaccct gccgcttacc ggatacctgt ccgcctttct cccttcggga agcgtggcgc 5160
tttctcatag ctcacgctgt aggtatctca gttcggtgta ggtcgttcgc tccaagctgg 5220
gctgtgtgca cgaacccccc gttcagcccg accgctgcgc cttatccggt aactatcgtc 5280
ttgagtccaa cccggtaaga cacgacttat cgccactggc agcagccact ggtaacagga 5340
ttagcagagc gaggtatgta ggcggtgcta cagagttctt gaagtggtgg cctaactacg 5400
gctacactag aagaacagta tttggtatct gcgctctgct gaagccagtt accttcggaa 5460
aaagagttgg tagctcttga tccggcaaac aaaccaccgc tggtagcggt ggtttttttg 5520
tttgcaagca gcagattacg cgcagaaaaa aaggatctca agaagatcct ttgatctttt 5580
ctacggggtc tgacgctcag tggaacgaaa actcacgtta agggattttg gtcatgagat 5640
tatcaaaaag gatcttcacc tagatccttt taaattaaaa atgaagtttt aaatcaatct 5700
aaagtatata tgagtaaact tggtctgaca gttaccaatg cttaatcagt gaggcaccta 5760
tctcagcgat ctgtctattt cgttcatcca tagttgcctg actccccgtc gtgtagataa 5820
ctacgatacg ggagggctta ccatctggcc ccagtgctgc aatgataccg cgagacccac 5880
gctcaccggc tccagattta tcagcaataa accagccagc cggaagggcc gagcgcagaa 5940
gtggtcctgc aactttatcc gcctccatcc agtctattaa ttgttgccgg gaagctagag 6000
taagtagttc gccagttaat agtttgcgca acgttgttgc cattgctaca ggcatcgtgg 6060
tgtcacgctc gtcgtttggt atggcttcat tcagctccgg ttcccaacga tcaaggcgag 6120
ttacatgatc ccccatgttg tgcaaaaaag cggttagctc cttcggtcct ccgatcgttg 6180
tcagaagtaa gttggccgca gtgttatcac tcatggttat ggcagcactg cataattctc 6240
ttactgtcat gccatccgta agatgctttt ctgtgactgg tgagtactca accaagtcat 6300
tctgagaata gtgtatgcgg cgaccgagtt gctcttgccc ggcgtcaata cgggataata 6360
ccgcgccaca tagcagaact ttaaaagtgc tcatcattgg aaaacgttct tcggggcgaa 6420
aactctcaag gatcttaccg ctgttgagat ccagttcgat gtaacccact cgtgcaccca 6480
actgatcttc agcatctttt actttcacca gcgtttctgg gtgagcaaaa acaggaaggc 6540
aaaatgccgc aaaaaaggga ataagggcga cacggaaatg ttgaatactc atactcttcc 6600
tttttcaata ttattgaagc atttatcagg gttattgtct catgagcgga tacatatttg 6660
aatgtattta gaaaaataaa caaatagggg ttccgcgcac atttccccga aaagtgccac 6720
ctgacgtcta agaaaccatt attatcatga cattaaccta taaaaatagg cgtatcacga 6780
ggccctttcg tc 6792

<210> SEQ ID NO 11
<211> LENGTH: 6702
<212> TYPE: DNA
<213> ORGANISM: Artificial Sequence
<220> FEATURE:
<223> OTHER INFORMATION: construct pINT-malE-MsgalT8

<400> SEQUENCE: 11
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120

-continued

```
ttggcgggtg tcggggctgg cttaactatg cggcatcaga gcagattgta ctgagagtgc    180
accatatgcg gtgtgaaata ccgcacagat gcgtaaggag aaaataccgc atcaggcgcc    240
attcgccatt caggctgcgc aactgttggg aagggcgatc ggtgcgggcc tcttcgctat    300
tacgccagct ggcgaaaggg ggatgtgctg caaggcgatt aagttgggta acgccagggt    360
tttcccagtc acgacgttgt aaaacgacgg ccagtgaatt cgaagatcct ttgatctttt    420
ctacggggtc tgacgctcag tggaacgaaa actcacgtta agggattttg gtcatgagat    480
tatcaaaaag gatcttcacc tagatccttt taaactagtg aagttaccat cacggaaaaa    540
ggttatgctg cttttaagac ccactttcac atttaagttg tttttctaat ccgcatatga    600
tcaattcaag gccgaataag aaggctggct ctgcaccttg gtgatcaaat aattcgatag    660
cttgtcgtaa taatggcggc atactatcag tagtaggtgt ttccctttct tctttagcga    720
cttgatgctc ttgatcttcc aatacgcaac ctaaagtaaa atgccccact gcgctgagtg    780
catataatgc attctctagt gaaaaacctt gttggcataa aaaggctaat tgattttcga    840
gagtttcata ctgtttttct gtaggccgtg tacctaaatg tacttttgct ccatcgcgat    900
gacttagtaa agcacatcta aaacttttag cgttattacg taaaaaatct tgccagcttt    960
ccccttctaa agggcaaaag tgagtatggt gcctatctaa catctcaatg gctaaggcgt   1020
cgagcaaagc ccgcttattt tttacatgcc aatacaatgt aggctgctct acacctagct   1080
tctgggcgag tttacgggtt gttaaacctt cgattccgac ctcattaagc agctctaatg   1140
cgctgttaat cactttactt ttatctaaac gagacatact cttccttttt caatattatt   1200
gaagcattta tcagggttat tgtctcatga gcggatacat atttgaatgt atttagaaaa   1260
ataaacaaat aggggttccg cgcacatttc cccgaaaagt gccacctgaa attggccaga   1320
tgattaattc ctaatttttg ttgacactct atcattgata gagttatttt accactccct   1380
atcagtgata gagaaaagtg aaatgaatag ttcgacaaaa atctagaaat aattttgttt   1440
aactttaaga aggagatata caaatgaaaa tcgaagaagg taaactggta atctggatta   1500
acggcgataa aggctataac ggtctcgctg aagtcggtaa gaaattcgag aaagataccg   1560
gaattaaagt caccgttgag catccggata aactggaaga gaaattccca caggttgcgg   1620
caactggcga tggccctgac attatcttct gggcacacga ccgctttggt ggctacgctc   1680
aatctggcct gttggctgaa atcaccccgg acaaagcgtt ccaggacaag ctgtatccgt   1740
ttacctggga tgccgtacgt tacaacggca agctgattgc ttacccgatc gctgttgaag   1800
cgttatcgct gatttataac aaagatctgc tgccgaaccc gccaaaaacc tgggaagaga   1860
tcccggcgct ggataaagaa ctgaaagcga aaggtaagag cgcgctgatg ttcaacctgc   1920
aagaaccgta cttcacctgg ccgctgattg ctgctgacgg gggttatgcg ttcaagtatg   1980
aaaacggcaa gtacgacatt aaagacgtgg gcgtggataa cgctggcgcg aaagcgggtc   2040
tgaccttcct ggttgacctg attaaaaaca aacacatgaa tgcagacacc gattactcca   2100
tcgcagaagc tgcctttaat aaaggcgaaa cagcgatgac catcaacggc ccgtgggcat   2160
ggtccaacat cgacaccagc aaagtgaatt atggtgtaac ggtactgccg accttcaagg   2220
gtcaaccatc caaaccgttc gttggcgtgc tgagcgcagg tattaacgcc gccagtccga   2280
acaaagagct ggcaaaagag ttcctcgaaa actatctgct gactgatgaa ggtctggaag   2340
cggttaataa agacaaaccg ctgggtgccg tagcgctgaa gtcttacgag gaagagttgg   2400
cgaaagatcc acgtattgcc gccaccatgg aaaacgccca gaaaggtgaa atcatgccga   2460
acatcccgca gatgtccgct ttctggtatg ccgtgcgtac tgcggtgatc aacgccgcca   2520
```

-continued

```
gcggtcgtca gactgtcgat gaagccctga aagacgcgca gactatggat gaaatcaaac   2580
tgtcggtggt tatgccgtat tacaaacgtc tgcgtgaatt tatgcgtgtc ctgccgctga   2640
atgcccgctt ctttagccgt catgaatatg aagtggttct gagtctggac gaaccgtccg   2700
aagaagccga tctgctgcgt gtcctgcgcg acttcccgtc tattcgttgg cgcgttctgg   2760
tcaatgacct ggatcacccg tggcgtccgc cgtgccgtgc actgaacgtt ggcatccgta   2820
atgctctggg tgaaaacgtc ctggtcgtga gcccggaatc tgcgtttgtg accgatgttc   2880
cggcacgcgc tctggatcat attgcagcaa acccgggtac cgcagctctg ggtcacgttt   2940
gttttgcaac gttcgatgcg ctggaagccc gtcagggcag cctggaaaaa acgtgcgctc   3000
cgccgtggaa tctgtatggt tctatctgtg tcccgcgtga acgtctggca cgtgtgcatg   3060
gctacgacga aagcttcgat cgctggggcg gtgatgacga taacctgcgt attcgcctga   3120
tgcagaccga aacgtatctg catccgctgg acgatatgcg catcctgcac ctgagttttg   3180
aagcccgtaa agtgcgtcaa gcagcagaac cgccgtcccc ggaatacgca gaacgtattt   3240
tccagccggt gtcaccgcaa gcaaatccgg gcggttgggg tgaatcgttt cagcgcgttg   3300
cgttcgattg gcgtcgccaa tgagcggccg cgtcgacacg caaaaaggcc atccgtcagg   3360
atggccttct gcttaattat ctagatgcct ggcagtttat ggcgggcgtc ctgcccgcca   3420
ccctccgggc cgttgcttcg caacgttcaa atccgctccc ggcggatttg tcctactcag   3480
gagagcgttc accgacaaac aacagataaa acgaaaggcc cagtctttcg actgagcctt   3540
tcgttttatt tgatgcctgg cagttcccta ctctcgcatg gggagacccc acactaccat   3600
catgtatgaa tatcctcctt agttcctatt ccgaagggta atggcatcag ggaatggcga   3660
acgcgctccc cacactacca tcatgtatga atatcctcct tagttcctat tccgaagttc   3720
ctattctcta gaaagtatag gaacttcggt ggaacgacgc gtaactcacg ttaagggatt   3780
ttggtcatga tcagcacgtg ttgacaatta atcatcggca tagtatatcg gcatagtata   3840
atacgacaag gtgaggaact aaaccatggc caagttgacc agtgccgttc cggtgctcac   3900
cgcgcgcgac gtcgccggag cggtcgagtt ctggaccgac cggctcgggt tctcccggga   3960
cttcgtggag gacgacttcg ccggtgtggt ccgggacgac gtgaccctgt tcatcagcgc   4020
ggtccaggac caggtggtgc cggacaacac cctggcctgg gtgtgggtgc gcggcctgga   4080
cgagctgtac gccgagtggt cggaggtcgt gtccacgaac ttccgggacg cctccgggcc   4140
ggccatgacc gagatcggcg agcagccgtg ggggcgggag ttcgccctgc gcgacccggc   4200
cggcaactgc gtgcacttcg tggccgagga gcaggactga gtggcagggc ggggcgtaag   4260
gcgcgccatt taaatgaagt tcctattccg aagttcctat tctctagaaa gtataggaac   4320
ttcgaagcag ctccagccta cacaatcgct caagacggaa cccgcgcttg gcaggaaagt   4380
aatagggata gcagctccag cctacacaat cgctcaagac gtgtaatgct gcacaataac   4440
cctgctgcag aggcctgcat gcaagcttgg cgtaatcatg gtcatagctg tttcctgtgt   4500
gaaattgtta tccgctcaca attccacaca acatacgagc cggaagcata aagtgtaaag   4560
cctggggtgc ctaatgagtg agctaactca cattaattgc gttgcgctca ctgcccgctt   4620
tccagtcggg aaacctgtcg tgccagctgc attaatgaat cggccaacgc gcggggagag   4680
gcggtttgcg tattgggcgc tcttccgctt cctcgctcac tgactcgctg cgctcggtcg   4740
ttcggctgcg gcgagcggta tcagctcact caaaggcggt aatacggtta tccacagaat   4800
caggggataa cgcaggaaag aacatgtgag caaaaggcca gcaaaaggcc aggaaccgta   4860
```

-continued aaaaggccgc gttgctggcg tttttccata ggctccgccc ccctgacgag catcacaaaa 4920
atcgacgctc aagtcagagg tggcgaaacc cgacaggact ataaagatac caggcgtttc 4980
cccctggaag ctccctcgtg cgctctcctg ttccgaccct gccgcttacc ggatacctgt 5040
ccgcctttct cccttcggga agcgtggcgc tttctcatag ctcacgctgt aggtatctca 5100
gttcggtgta ggtcgttcgc tccaagctgg gctgtgtgca cgaacccccc gttcagcccg 5160
accgctgcgc cttatccggt aactatcgtc ttgagtccaa cccggtaaga cacgacttat 5220
cgccactggc agcagccact ggtaacagga ttagcagagc gaggtatgta ggcggtgcta 5280
cagagttctt gaagtggtgg cctaactacg gctacactag aagaacagta tttggtatct 5340
gcgctctgct gaagccagtt accttcggaa aaagagttgg tagctcttga tccggcaaac 5400
aaaccaccgc tggtagcggt ggtttttttg tttgcaagca gcagattacg cgcagaaaaa 5460
aaggatctca agaagatcct ttgatctttt ctacggggtc tgacgctcag tggaacgaaa 5520
actcacgtta agggattttg gtcatgagat tatcaaaaag gatcttcacc tagatccttt 5580
taaattaaaa atgaagtttt aaatcaatct aaagtatata tgagtaaact tggtctgaca 5640
gttaccaatg cttaatcagt gaggcaccta tctcagcgat ctgtctattt cgttcatcca 5700
tagttgcctg actccccgtc gtgtagataa ctacgatacg ggagggctta ccatctggcc 5760
ccagtgctgc aatgataccg cgagacccac gctcaccggc tccagattta tcagcaataa 5820
accagccagc cggaagggcc gagcgcagaa gtggtcctgc aactttatcc gcctccatcc 5880
agtctattaa ttgttgccgg gaagctagag taagtagttc gccagttaat agtttgcgca 5940
acgttgttgc cattgctaca ggcatcgtgg tgtcacgctc gtcgtttggt atggcttcat 6000
tcagctccgg ttcccaacga tcaaggcgag ttacatgatc ccccatgttg tgcaaaaaag 6060
cggttagctc cttcggtcct ccgatcgttg tcagaagtaa gttggccgca gtgttatcac 6120
tcatggttat ggcagcactg cataattctc ttactgtcat gccatccgta agatgctttt 6180
ctgtgactgg tgagtactca accaagtcat tctgagaata gtgtatgcgg cgaccgagtt 6240
gctcttgccc ggcgtcaata cgggataata ccgcgccaca tagcagaact ttaaaagtgc 6300
tcatcattgg aaaacgttct tcggggcgaa aactctcaag gatcttaccg ctgttgagat 6360
ccagttcgat gtaacccact cgtgcaccca actgatcttc agcatctttt actttcacca 6420
gcgtttctgg gtgagcaaaa acaggaaggc aaaatgccgc aaaaaaggga ataagggcga 6480
cacggaaatg ttgaatactc atactcttcc tttttcaata ttattgaagc atttatcagg 6540
gttattgtct catgagcgga tacatatttg aatgtattta gaaaaataaa caaatagggg 6600
ttccgcgcac atttccccga aaagtgccac ctgacgtcta agaaaccatt attatcatga 6660
cattaaccta taaaaatagg cgtatcacga ggccctttcg tc 6702

<210> SEQ ID NO 12
<211> LENGTH: 6777
<212> TYPE: DNA
<213> ORGANISM: Artificial Sequence
<220> FEATURE:
<223> OTHER INFORMATION: construct pINT-malE-KdgalT10

<400> SEQUENCE: 12
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accatatgcg gtgtgaaata ccgcacagat gcgtaaggag aaaataccgc atcaggcgcc 240

-continued

```
attcgccatt caggctgcgc aactgttggg aagggcgatc ggtgcgggcc tcttcgctat    300
tacgccagct ggcgaaaggg ggatgtgctg caaggcgatt aagttgggta acgccagggt    360
tttcccagtc acgacgttgt aaaacgacgg ccagtgaatt cgaagatcct ttgatctttt    420
ctacggggtc tgacgctcag tggaacgaaa actcacgtta agggattttg gtcatgagat    480
tatcaaaaag gatcttcacc tagatccttt taaactagtg aagttaccat cacggaaaaa    540
ggttatgctg cttttaagac ccactttcac atttaagttg tttttctaat ccgcatatga    600
tcaattcaag gccgaataag aaggctggct ctgcaccttg gtgatcaaat aattcgatag    660
cttgtcgtaa taatggcggc atactatcag tagtaggtgt ttccctttct tctttagcga    720
cttgatgctc ttgatcttcc aatacgcaac ctaaagtaaa atgccccact gcgctgagtg    780
catataatgc attctctagt gaaaaacctt gttggcataa aaaggctaat tgattttcga    840
gagtttcata ctgtttttct gtaggccgtg tacctaaatg tacttttgct ccatcgcgat    900
gacttagtaa agcacatcta aaacttttag cgttattacg taaaaaatct tgccagcttt    960
ccccttctaa agggcaaaag tgagtatggt gcctatctaa catctcaatg gctaaggcgt   1020
cgagcaaagc ccgcttattt tttacatgcc aatacaatgt aggctgctct acacctagct   1080
tctgggcgag tttacgggtt gttaaacctt cgattccgac ctcattaagc agctctaatg   1140
cgctgttaat cactttactt ttatctaaac gagacatact cttccttttt caatattatt   1200
gaagcattta tcagggttat tgtctcatga gcggatacat atttgaatgt atttagaaaa   1260
ataaacaaat aggggttccg cgcacatttc cccgaaaagt gccacctgaa attggccaga   1320
tgattaattc ctaattttg ttgacactct atcattgata gagttatttt accactccct   1380
atcagtgata gagaaaagtg aaatgaatag ttcgacaaaa atctagaaat aattttgttt   1440
aactttaaga aggagatata caaatgaaaa tcgaagaagg taaactggta atctggatta   1500
acggcgataa aggctataac ggtctcgctg aagtcggtaa gaaattcgag aaagataccg   1560
gaattaaagt caccgttgag catccggata aactggaaga gaaattccca caggttgcgg   1620
caactggcga tggccctgac attatcttct gggcacacga ccgctttggt ggctacgctc   1680
aatctggcct gttggctgaa atcaccccgg acaaagcgtt ccaggacaag ctgtatccgt   1740
ttacctggga tgccgtacgt tacaacggca agctgattgc ttacccgatc gctgttgaag   1800
cgttatcgct gatttataac aaagatctgc tgccgaaccc gccaaaaacc tgggaagaga   1860
tcccggcgct ggataaagaa ctgaaagcga aaggtaagag cgcgctgatg ttcaacctgc   1920
aagaaccgta cttcacctgg ccgctgattg ctgctgacgg gggttatgcg ttcaagtatg   1980
aaaacggcaa gtacgacatt aaagacgtgg gcgtggataa cgctggcgcg aaagcgggtc   2040
tgaccttcct ggttgacctg attaaaaaca aacacatgaa tgcagacacc gattactcca   2100
tcgcagaagc tgcctttaat aaaggcgaaa cagcgatgac catcaacggc ccgtgggcat   2160
ggtccaacat cgacaccagc aaagtgaatt atggtgtaac ggtactgccg accttcaagg   2220
gtcaaccatc caaaccgttc gttggcgtgc tgagcgcagg tattaacgcc gccagtccga   2280
acaaagagct ggcaaaagag ttcctcgaaa actatctgct gactgatgaa ggtctggaag   2340
cggttaataa agacaaaccg ctgggtgccg tagcgctgaa gtcttacgag gaagagttgg   2400
cgaaagatcc acgtattgcc gccaccatgg aaaacgccca gaaaggtgaa atcatgccga   2460
acatcccgca gatgtccgct ttctggtatg ccgtgcgtac tgcggtgatc aacgccgcca   2520
gcggtcgtca gactgtcgat gaagccctga aagacgcgca gactatggaa aactatgtcg   2580
```

-continued

```
tctctatccg caccgcagcc caacgccgcc agcatgtcgc cgccgaattc aataagcacc   2640
aaatcgcctt tcatttcttt gatgcggtga ccccggaaac gctggcggaa agcatcgcag   2700
aacactgccc gaacctggca gacgcctttc tgaccggcgg tgaaaagggc tgtttcatgt   2760
ctcatgtctg cctgtgggca aaatgtgtgg ctgatgacct gccgtatatt ggcatctttg   2820
aagatgacgt tattttcggt cagaacagct ctcgttttct gaatgatacc aaatggctgg   2880
acgaacgttt tcagaaccaa tcattcatta tccgcatgga aacgtttctg aaggcgaacc   2940
cggttgccct gagcaaatct ggcgtccgtc cgttcaatgg tcgtaagatc ctgcgcctgc   3000
agagttttgg cttcggtacc gcggcctatc tgatttccca gcaaaccgca atcacgctgc   3060
tgaattggat tcgcgaagtc gctccggaaa aactggaacc gattgataac atgctgttta   3120
atgcagcttc agaaattccg gaaatccaga tgtaccaaat ctcgccggcc ctgtgcattc   3180
aggaactgca actgaaccgc gcagatagtt ccctgtcatc gaccctggaa gacggtcgtc   3240
tggcacgtca ccagcaactg gatggcggta aaacccagcc ggaacagacg caagaaaacc   3300
gtaacatctt cgcatgggct aagaacaaga tcgtgaagga atacaagcgc gttaaacgtc   3360
gctggacgga tgacaaaaag attgttccgt tcaaatgagc ggccgcgtcg acacgcaaaa   3420
aggccatccg tcaggatggc cttctgctta attatctaga tgcctggcag tttatggcgg   3480
gcgtcctgcc cgccaccctc cgggccgttg cttcgcaacg ttcaaatccg ctcccggcgg   3540
atttgtccta ctcaggagag cgttcaccga caaacaacag ataaaacgaa aggcccagtc   3600
tttcgactga gcctttcgtt ttatttgatg cctggcagtt ccctactctc gcatggggag   3660
accccacact accatcatgt atgaatatcc tccttagttc ctattccgaa gggtaatggc   3720
atcagggaat ggcgaacgcg ctccccacac taccatcatg tatgaatatc ctccttagtt   3780
cctattccga agttcctatt ctctagaaag tataggaact tcggtggaac gacgcgtaac   3840
tcacgttaag ggattttggt catgatcagc acgtgttgac aattaatcat cggcatagta   3900
tatcggcata gtataatacg acaaggtgag gaactaaacc atggccaagt tgaccagtgc   3960
cgttccggtg ctcaccgcgc gcgacgtcgc cggagcggtc gagttctgga ccgaccggct   4020
cgggttctcc cgggacttcg tggaggacga cttcgccggt gtggtccggg acgacgtgac   4080
cctgttcatc agcgcggtcc aggaccaggt ggtgccggac aacaccctgg cctgggtgtg   4140
ggtgcgcggc ctggacgagc tgtacgccga gtggtcggag gtcgtgtcca cgaacttccg   4200
ggacgcctcc gggccggcca tgaccgagat cggcgagcag ccgtgggggc gggagttcgc   4260
cctgcgcgac ccggccggca actgcgtgca cttcgtggcc gaggagcagg actgagtggc   4320
agggcggggc gtaaggcgcg ccatttaaat gaagttccta ttccgaagtt cctattctct   4380
agaaagtata ggaacttcga agcagctcca gcctacacaa tcgctcaaga cggaacccgc   4440
gcttggcagg aaagtaatag ggatagcagc tccagcctac acaatcgctc aagacgtgta   4500
atgctgcaca ataaccctgc tgcagaggcc tgcatgcaag cttggcgtaa tcatggtcat   4560
agctgtttcc tgtgtgaaat tgttatccgc tcacaattcc acacaacata cgagccggaa   4620
gcataaagtg taaagcctgg ggtgcctaat gagtgagcta actcacatta attgcgttgc   4680
gctcactgcc cgctttccag tcgggaaacc tgtcgtgcca gctgcattaa tgaatcggcc   4740
aacgcgcggg gagaggcggt ttgcgtattg ggcgctcttc cgcttcctcg ctcactgact   4800
cgctgcgctc ggtcgttcgg ctgcggcgag cggtatcagc tcactcaaag gcggtaatac   4860
ggttatccac agaatcaggg gataacgcag gaaagaacat gtgagcaaaa ggccagcaaa   4920
aggccaggaa ccgtaaaaag gccgcgttgc tggcgttttt ccataggctc cgcccccctg   4980
```

-continued acgagcatca caaaaatcga cgctcaagtc agaggtggcg aaacccgaca ggactataaa 5040
gataccaggc gtttccccct ggaagctccc tcgtgcgctc tcctgttccg accctgccgc 5100
ttaccggata cctgtccgcc tttctccctt cgggaagcgt ggcgctttct catagctcac 5160
gctgtaggta tctcagttcg gtgtaggtcg ttcgctccaa gctgggctgt gtgcacgaac 5220
cccccgttca gcccgaccgc tgcgccttat ccggtaacta tcgtcttgag tccaacccgg 5280
taagacacga cttatcgcca ctggcagcag ccactggtaa caggattagc agagcgaggt 5340
atgtaggcgg tgctacagag ttcttgaagt ggtggcctaa ctacggctac actagaagaa 5400
cagtatttgg tatctgcgct ctgctgaagc cagttacctt cggaaaaaga gttggtagct 5460
cttgatccgg caaacaaacc accgctggta gcggtggttt ttttgtttgc aagcagcaga 5520
ttacgcgcag aaaaaaagga tctcaagaag atcctttgat cttttctacg gggtctgacg 5580
ctcagtggaa cgaaaactca cgttaaggga ttttggtcat gagattatca aaaaggatct 5640
tcacctagat ccttttaaat taaaaatgaa gttttaaatc aatctaaagt atatatgagt 5700
aaacttggtc tgacagttac caatgcttaa tcagtgaggc acctatctca gcgatctgtc 5760
tatttcgttc atccatagtt gcctgactcc ccgtcgtgta gataactacg atacgggagg 5820
gcttaccatc tggccccagt gctgcaatga taccgcgaga cccacgctca ccggctccag 5880
atttatcagc aataaaccag ccagccggaa gggccgagcg cagaagtggt cctgcaactt 5940
tatccgcctc catccagtct attaattgtt gccgggaagc tagagtaagt agttcgccag 6000
ttaatagttt gcgcaacgtt gttgccattg ctacaggcat cgtggtgtca cgctcgtcgt 6060
ttggtatggc ttcattcagc tccggttccc aacgatcaag gcgagttaca tgatccccca 6120
tgttgtgcaa aaaagcggtt agctccttcg gtcctccgat cgttgtcaga agtaagttgg 6180
ccgcagtgtt atcactcatg gttatggcag cactgcataa ttctcttact gtcatgccat 6240
ccgtaagatg cttttctgtg actggtgagt actcaaccaa gtcattctga gaatagtgta 6300
tgcggcgacc gagttgctct tgcccggcgt caatacggga taataccgcg ccacatagca 6360
gaactttaaa agtgctcatc attggaaaac gttcttcggg gcgaaaactc tcaaggatct 6420
taccgctgtt gagatccagt tcgatgtaac ccactcgtgc acccaactga tcttcagcat 6480
cttttacttt caccagcgtt tctgggtgag caaaaacagg aaggcaaaat gccgcaaaaa 6540
agggaataag ggcgacacgg aaatgttgaa tactcatact cttccttttt caatattatt 6600
gaagcattta tcagggttat tgtctcatga gcggatacat atttgaatgt atttagaaaa 6660
ataaacaaat aggggttccg cgcacatttc cccgaaaagt gccacctgac gtctaagaaa 6720
ccattattat catgacatta acctataaaa ataggcgtat cacgaggccc tttcgtc 6777

<210> SEQ ID NO 13
<211> LENGTH: 6786
<212> TYPE: DNA
<213> ORGANISM: Artificial Sequence
<220> FEATURE:
<223> OTHER INFORMATION: construct pINT-malE-gatD

<400> SEQUENCE: 13
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accatatgcg gtgtgaaata ccgcacagat gcgtaaggag aaaataccgc atcaggcgcc 240

-continued

```
attcgccatt caggctgcgc aactgttggg aagggcgatc ggtgcgggcc tcttcgctat    300
tacgccagct ggcgaaaggg ggatgtgctg caaggcgatt aagttgggta acgccagggt    360
tttcccagtc acgacgttgt aaaacgacgg ccagtgaatt cgaagatcct ttgatctttt    420
ctacggggtc tgacgctcag tggaacgaaa actcacgtta agggattttg gtcatgagat    480
tatcaaaaag gatcttcacc tagatccttt taaactagtg aagttaccat cacggaaaaa    540
ggttatgctg cttttaagac ccactttcac atttaagttg tttttctaat ccgcatatga    600
tcaattcaag gccgaataag aaggctggct ctgcaccttg gtgatcaaat aattcgatag    660
cttgtcgtaa taatggcggc atactatcag tagtaggtgt ttccctttct tctttagcga    720
cttgatgctc ttgatcttcc aatacgcaac ctaaagtaaa atgccccact gcgctgagtg    780
catataatgc attctctagt gaaaaacctt gttggcataa aaaggctaat tgattttcga    840
gagtttcata ctgtttttct gtaggccgtg tacctaaatg tacttttgct ccatcgcgat    900
gacttagtaa agcacatcta aaacttttag cgttattacg taaaaaatct tgccagcttt    960
ccccttctaa agggcaaaag tgagtatggt gcctatctaa catctcaatg gctaaggcgt   1020
cgagcaaagc ccgcttattt tttacatgcc aatacaatgt aggctgctct acacctagct   1080
tctgggcgag tttacgggtt gttaaacctt cgattccgac ctcattaagc agctctaatg   1140
cgctgttaat cactttactt ttatctaaac gagacatact cttccttttt caatattatt   1200
gaagcattta tcagggttat tgtctcatga gcggatacat atttgaatgt atttagaaaa   1260
ataaacaaat aggggttccg cgcacatttc cccgaaaagt gccacctgaa attggccaga   1320
tgattaattc ctaatttttg ttgacactct atcattgata gagttatttt accactccct   1380
atcagtgata gagaaaagtg aaatgaatag ttcgacaaaa atctagaaat aattttgttt   1440
aactttaaga aggagatata caaatgaaaa tcgaagaagg taaactggta atctggatta   1500
acggcgataa aggctataac ggtctcgctg aagtcggtaa gaaattcgag aaagataccg   1560
gaattaaagt caccgttgag catccggata aactggaaga gaaattccca caggttgcgg   1620
caactggcga tggccctgac attatcttct gggcacacga ccgctttggt ggctacgctc   1680
aatctggcct gttggctgaa atcaccccgg acaaagcgtt ccaggacaag ctgtatccgt   1740
ttacctggga tgccgtacgt tacaacggca agctgattgc ttacccgatc gctgttgaag   1800
cgttatcgct gatttataac aaagatctgc tgccgaaccc gccaaaaacc tgggaagaga   1860
tcccggcgct ggataaagaa ctgaaagcga aaggtaagag cgcgctgatg ttcaacctgc   1920
aagaaccgta cttcacctgg ccgctgattg ctgctgacgg gggttatgcg ttcaagtatg   1980
aaaacggcaa gtacgacatt aaagacgtgg gcgtggataa cgctggcgcg aaagcgggtc   2040
tgaccttcct ggttgacctg attaaaaaca aacacatgaa tgcagacacc gattactcca   2100
tcgcagaagc tgcctttaat aaaggcgaaa cagcgatgac catcaacggc ccgtgggcat   2160
ggtccaacat cgacaccagc aaagtgaatt atggtgtaac ggtactgccg accttcaagg   2220
gtcaaccatc caaaccgttc gttggcgtgc tgagcgcagg tattaacgcc gccagtccga   2280
acaaagagct ggcaaaagag ttcctcgaaa actatctgct gactgatgaa ggtctggaag   2340
cggttaataa agacaaaccg ctgggtgccg tagcgctgaa gtcttacgag gaagagttgg   2400
cgaaagatcc acgtattgcc gccaccatgg aaaacgccca gaaaggtgaa atcatgccga   2460
acatcccgca gatgtccgct ttctggtatg ccgtgcgtac tgcggtgatc aacgccgcca   2520
gcggtcgtca gactgtcgat gaagccctga aagacgcgca gactatgtcc tcagctttcc   2580
attacgtcat tagcctggca tcggcagttg aacgccgtca gcacattagc gaacagtttt   2640
```

-continued cccaatacga cattccgttt cagtttttcg atgcgatcag tccgtccccg ctgctgaacc 2700
agctggtgtc tcaatttttc ccgtccctgg ccgatagctc tctgaccgac ggcgaaaaag 2760
gttgctttat ttcacatctg tcgctgtggc acaagtgtgt tgaaaagaac ctgccgtata 2820
ttgtggtttt tgaagatgac atcctgctgg gcaagaatgc agataaattc ctgattgaag 2880
acgaatggtt tttctctcgt tttaacacga atgatgtctt catcgtgcgc ctggaaacct 2940
ttctgcagaa agtgtattgc caaccgagct acatcaagtc ttactacaac cgtgaactgc 3000
tgaccctgaa aagcacgcat ttcggcaccg caggttatat tatcagtctg ggtgcggcca 3060
agtttctgct gtccctgttc aacaaaatgc acattgaaga agttgctccg atcgatgaac 3120
tgctgtttaa taagttcctg gaacgcaaag actttacggt ctaccagttc agtccggcac 3180
tgtgcattca ggaactgcaa ctgaacaaat cagatgctgt cctgctgtcg caactggaac 3240
tggaacgtag caaatgtcgc attatgaccg aatctcgtat cggccgcgaa aagaaaaaac 3300
tgaaggataa gatcatccat gttctgacga agccgaaacg tatgctggaa aagaaacgtc 3360
agcgcaatga agacaagaaa atcaccatga ttatcgaatt tgaatgagcg gccgcgtcga 3420
cacgcaaaaa ggccatccgt caggatggcc ttctgcttaa ttatctagat gcctggcagt 3480
ttatggcggg cgtcctgccc gccaccctcc gggccgttgc ttcgcaacgt tcaaatccgc 3540
tcccggcgga tttgtcctac tcaggagagc gttcaccgac aaacaacaga taaaacgaaa 3600
ggcccagtct ttcgactgag cctttcgttt tatttgatgc ctggcagttc cctactctcg 3660
catggggaga ccccacacta ccatcatgta tgaatatcct ccttagttcc tattccgaag 3720
ggtaatggca tcagggaatg gcgaacgcgc tccccacact accatcatgt atgaatatcc 3780
tccttagttc ctattccgaa gttcctattc tctagaaagt ataggaactt cggtggaacg 3840
acgcgtaact cacgttaagg gattttggtc atgatcagca cgtgttgaca attaatcatc 3900
ggcatagtat atcggcatag tataatacga caaggtgagg aactaaacca tggccaagtt 3960
gaccagtgcc gttccggtgc tcaccgcgcg cgacgtcgcc ggagcggtcg agttctggac 4020
cgaccggctc gggttctccc gggacttcgt ggaggacgac ttcgccggtg tggtccggga 4080
cgacgtgacc ctgttcatca gcgcggtcca ggaccaggtg gtgccggaca acaccctggc 4140
ctgggtgtgg gtgcgcggcc tggacgagct gtacgccgag tggtcggagg tcgtgtccac 4200
gaacttccgg gacgcctccg ggccggccat gaccgagatc ggcgagcagc cgtgggggcg 4260
ggagttcgcc ctgcgcgacc cggccggcaa ctgcgtgcac ttcgtggccg aggagcagga 4320
ctgagtggca gggcggggcg taaggcgcgc catttaaatg aagttcctat tccgaagttc 4380
ctattctcta gaaagtatag gaacttcgaa gcagctccag cctacacaat cgctcaagac 4440
ggaacccgcg cttggcagga aagtaatagg gatagcagct ccagcctaca caatcgctca 4500
agacgtgtaa tgctgcacaa taaccctgct gcagaggcct gcatgcaagc ttggcgtaat 4560
catggtcata gctgtttcct gtgtgaaatt gttatccgct cacaattcca cacaacatac 4620
gagccggaag cataaagtgt aaagcctggg gtgcctaatg agtgagctaa ctcacattaa 4680
ttgcgttgcg ctcactgccc gctttccagt cgggaaacct gtcgtgccag ctgcattaat 4740
gaatcggcca acgcgcgggg agaggcggtt tgcgtattgg gcgctcttcc gcttcctcgc 4800
tcactgactc gctgcgctcg gtcgttcggc tgcggcgagc ggtatcagct cactcaaagg 4860
cggtaatacg gttatccaca gaatcagggg ataacgcagg aaagaacatg tgagcaaaag 4920
gccagcaaaa ggccaggaac cgtaaaaagg ccgcgttgct ggcgtttttc cataggctcc 4980

-continued

```
gccccccctga cgagcatcac aaaaatcgac gctcaagtca gaggtggcga aacccgacag   5040

gactataaag ataccaggcg tttccccctg gaagctccct cgtgcgctct cctgttccga   5100

ccctgccgct taccggatac ctgtccgcct ttctcccttc gggaagcgtg gcgctttctc   5160

atagctcacg ctgtaggtat ctcagttcgg tgtaggtcgt tcgctccaag ctgggctgtg   5220

tgcacgaacc ccccgttcag cccgaccgct gcgccttatc cggtaactat cgtcttgagt   5280

ccaacccggt aagacacgac ttatcgccac tggcagcagc cactggtaac aggattagca   5340

gagcgaggta tgtaggcggt gctacagagt tcttgaagtg gtggcctaac tacggctaca   5400

ctagaagaac agtatttggt atctgcgctc tgctgaagcc agttaccttc ggaaaaagag   5460

ttggtagctc ttgatccggc aaacaaacca ccgctggtag cggtggtttt tttgtttgca   5520

agcagcagat tacgcgcaga aaaaaaggat ctcaagaaga tcctttgatc ttttctacgg   5580

ggtctgacgc tcagtggaac gaaaactcac gttaagggat tttggtcatg agattatcaa   5640

aaaggatctt cacctagatc cttttaaatt aaaaatgaag ttttaaatca atctaaagta   5700

tatatgagta aacttggtct gacagttacc aatgcttaat cagtgaggca cctatctcag   5760

cgatctgtct atttcgttca tccatagttg cctgactccc cgtcgtgtag ataactacga   5820

tacgggaggg cttaccatct ggccccagtg ctgcaatgat accgcgagac ccacgctcac   5880

cggctccaga tttatcagca ataaaccagc cagccggaag ggccgagcgc agaagtggtc   5940

ctgcaacttt atccgcctcc atccagtcta ttaattgttg ccgggaagct agagtaagta   6000

gttcgccagt taatagtttg cgcaacgttg ttgccattgc tacaggcatc gtggtgtcac   6060

gctcgtcgtt tggtatggct tcattcagct ccggttccca acgatcaagg cgagttacat   6120

gatcccccat gttgtgcaaa aaagcggtta gctccttcgg tcctccgatc gttgtcagaa   6180

gtaagttggc cgcagtgtta tcactcatgg ttatggcagc actgcataat tctcttactg   6240

tcatgccatc cgtaagatgc ttttctgtga ctggtgagta ctcaaccaag tcattctgag   6300

aatagtgtat gcggcgaccg agttgctctt gcccggcgtc aatacgggat aataccgcgc   6360

cacatagcag aactttaaaa gtgctcatca ttggaaaacg ttcttcgggg cgaaaactct   6420

caaggatctt accgctgttg agatccagtt cgatgtaacc cactcgtgca cccaactgat   6480

cttcagcatc ttttactttc accagcgttt ctgggtgagc aaaaacagga aggcaaaatg   6540

ccgcaaaaaa gggaataagg gcgacacgga aatgttgaat actcatactc ttcctttttc   6600

aatattattg aagcatttat cagggttatt gtctcatgag cggatacata tttgaatgta   6660

tttagaaaaa taaacaaata ggggttccgc gcacatttcc ccgaaaagtg ccacctgacg   6720

tctaagaaac cattattatc atgacattaa cctataaaaa taggcgtatc acgaggccct   6780

ttcgtc                                                              6786
```

<210> SEQ ID NO 14
<211> LENGTH: 7506
<212> TYPE: DNA
<213> ORGANISM: Artificial Sequence
<220> FEATURE:
<223> OTHER INFORMATION: construct pINT-malE-BFgalT2

<400> SEQUENCE: 14

```
tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120

ttggcgggtg tcggggctgg cttaactatg cggcatcaga gcagattgta ctgagagtgc    180

accatatgcg gtgtgaaata ccgcacagat gcgtaaggag aaaataccgc atcaggcgcc    240
```

-continued

```
attcgccatt caggctgcgc aactgttggg aagggcgatc ggtgcgggcc tcttcgctat    300
tacgccagct ggcgaaaggg ggatgtgctg caaggcgatt aagttgggta acgccagggt    360
tttcccagtc acgacgttgt aaaacgacgg ccagtgaatt cgaagatcct ttgatctttt    420
ctacggggtc tgacgctcag tggaacgaaa actcacgtta agggattttg gtcatgagat    480
tatcaaaaag gatcttcacc tagatccttt taaactagtg aagttaccat cacggaaaaa    540
ggttatgctg cttttaagac ccactttcac atttaagttg tttttctaat ccgcatatga    600
tcaattcaag gccgaataag aaggctggct ctgcaccttg gtgatcaaat aattcgatag    660
cttgtcgtaa taatggcggc atactatcag tagtaggtgt ttccctttct tctttagcga    720
cttgatgctc ttgatcttcc aatacgcaac ctaaagtaaa atgccccact gcgctgagtg    780
catataatgc attctctagt gaaaaacctt gttggcataa aaaggctaat tgattttcga    840
gagtttcata ctgtttttct gtaggccgtg tacctaaatg tacttttgct ccatcgcgat    900
gacttagtaa agcacatcta aaacttttag cgttattacg taaaaaatct tgccagcttt    960
ccccttctaa agggcaaaag tgagtatggt gcctatctaa catctcaatg gctaaggcgt   1020
cgagcaaagc ccgcttattt tttacatgcc aatacaatgt aggctgctct acacctagct   1080
tctgggcgag tttacgggtt gttaaacctt cgattccgac ctcattaagc agctctaatg   1140
cgctgttaat cactttactt ttatctaaac gagacatact cttccttttt caatattatt   1200
gaagcattta tcagggttat tgtctcatga gcggatacat atttgaatgt atttagaaaa   1260
ataaacaaat aggggttccg cgcacatttc cccgaaaagt gccacctgaa attggccaga   1320
tgattaattc ctaattttg ttgacactct atcattgata gagttatttt accactccct    1380
atcagtgata gagaaaagtg aaatgaatag ttcgacaaaa atctagaaat aattttgttt   1440
aactttaaga aggagatata caaatgaaaa tcgaagaagg taaactggta atctggatta   1500
acggcgataa aggctataac ggtctcgctg aagtcggtaa gaaattcgag aaagataccg   1560
gaattaaagt caccgttgag catccggata aactggaaga gaaattccca caggttgcgg   1620
caactggcga tggccctgac attatcttct gggcacacga ccgctttggt ggctacgctc   1680
aatctggcct gttggctgaa atcaccccgg acaaagcgtt ccaggacaag ctgtatccgt   1740
ttacctggga tgccgtacgt tacaacggca agctgattgc ttacccgatc gctgttgaag   1800
cgttatcgct gatttataac aaagatctgc tgccgaaccc gccaaaaacc tgggaagaga   1860
tcccggcgct ggataaagaa ctgaaagcga aaggtaagag cgcgctgatg ttcaacctgc   1920
aagaaccgta cttcacctgg ccgctgattg ctgctgacgg gggttatgcg ttcaagtatg   1980
aaaacggcaa gtacgacatt aaagacgtgg gcgtggataa cgctggcgcg aaagcgggtc   2040
tgaccttcct ggttgacctg attaaaaaca aacacatgaa tgcagacacc gattactcca   2100
tcgcagaagc tgcctttaat aaaggcgaaa cagcgatgac catcaacggc ccgtgggcat   2160
ggtccaacat cgacaccagc aaagtgaatt atggtgtaac ggtactgccg accttcaagg   2220
gtcaaccatc caaaccgttc gttggcgtgc tgagcgcagg tattaacgcc gccagtccga   2280
acaaagagct ggcaaaagag ttcctcgaaa actatctgct gactgatgaa ggtctggaag   2340
cggttaataa agacaaaccg ctgggtgccg tagcgctgaa gtcttacgag gaagagttgg   2400
cgaaagatcc acgtattgcc gccaccatgg aaaacgccca gaaaggtgaa atcatgccga   2460
acatcccgca gatgtccgct ttctggtatg ccgtgcgtac tgcggtgatc aacgccgcca   2520
gcggtcgtca gactgtcgat gaagccctga aagacgcgca gactatgaac gtgaataagc   2580
```

-continued

```
cgaccaccga aaagaaactg attgacctga acaacgacat tatccataac tttgatgtga   2640
gcattgtgat gagcttctat aagcgttaca ccgaatttcg caaagtgctg ccgcataacg   2700
cgccgtatct gcagcgtaat ggcattgaag tcattatcgt gctggatgac ccggatgaaa   2760
aaagcgaact gctgatgctg ctgcaaaact atccgttcat caattggaag ctgattatca   2820
acgaacgtaa acatgcaccg cgcaaccacg cttctgttct gaatgtcggt ctgaaacatg   2880
cgaccaaaaa gtatattctg cagatcgatc cggaagttga atttctgacg gatattatct   2940
ggcaaatgcg tgacgccatt gaaaaatatc cgatgcacta catcctggcg atgatggcct   3000
atgtcccgta cgaacaggaa ctgaccgaaa acaacatcaa ggaactggat ttcatcccgt   3060
ggggcaacct gatggtggaa cgcaatcatc tgtataaact gcacggttac gatgaaacct   3120
tcattacgtg gggcggtgaa gataacaata tgcgtgcgcg cctggacatg tcaggcatta   3180
aaaagtttat cctgccggaa gccaagacca tccatcgtga aaagaactat gatccgaatg   3240
aacgttcgaa gcgcattaat aaacacagta tctccgactg gcgcaaaatg aactacccgt   3300
cagaagcaat tgctaataag gatatctggg gctcggaatt caacaaagtt atttatgatt   3360
ggcaggacaa tcaatacgcc aaagatctgt gctataccta cctgcagcaa tttattggtt   3420
tcgaaatccg tcatccggcg gcctttcgta aacgccacaa aaagattgtc ctgtgtcagg   3480
catataacga agaaaaactg atcgaaggct tcctgacgaa catggctaat tactttgatg   3540
gtattatcct gctggatgac gaaagtaccg atcgcacgtg ggacctggca atccatgata   3600
agatcatcct gaaggtgaaa aagaaacgtt ccggttttaa tgatctggaa aaccgcaata   3660
ttctgctgga cctgtcagcg tttttccagt cggaatggtt ttgcttcatg gatatcgacg   3720
aacgtttcga tgaacgcttt accaacttca gcgaattcga aaacaacaag gaaatccacg   3780
tggtttcttt tcgtggcgtg tatctgtgga atgatgaaca gagctacaag ggcgacattc   3840
cgaactctaa taaaggtatc ctgaccgttt atcgtatgtt ccgcccgatt ggtcataccc   3900
acatcaacac gcataagaaa ctgcacttca ttgcgacgcc gtattttacc aacacgtggc   3960
agagtaatat cctgtttaag gattacggct ccatgaaaga aaatgaccgt attcgcaagt   4020
atgaacgcta catccaggaa gatcagcaaa aagacatgag ctctggttat gattacctgc   4080
tgaacagcga aaatctgtat caactggaca aaattgaaga atactgagcg gccgcgtcga   4140
cacgcaaaaa ggccatccgt caggatggcc ttctgcttaa ttatctagat gcctggcagt   4200
ttatggcggg cgtcctgccc gccaccctcc gggccgttgc ttcgcaacgt tcaaatccgc   4260
tcccggcgga tttgtcctac tcaggagagc gttcaccgac aaacaacaga taaaacgaaa   4320
ggcccagtct ttcgactgag cctttcgttt tatttgatgc ctggcagttc cctactctcg   4380
catggggaga ccccacacta ccatcatgta tgaatatcct ccttagttcc tattccgaag   4440
ggtaatggca tcagggaatg gcgaacgcgc tccccacact accatcatgt atgaatatcc   4500
tccttagttc ctattccgaa gttcctattc tctagaaagt ataggaactt cggtggaacg   4560
acgcgtaact cacgttaagg gattttggtc atgatcagca cgtgttgaca attaatcatc   4620
ggcatagtat atcggcatag tataatacga caaggtgagg aactaaacca tggccaagtt   4680
gaccagtgcc gttccggtgc tcaccgcgcg cgacgtcgcc ggagcggtcg agttctggac   4740
cgaccggctc gggttctccc gggacttcgt ggaggacgac ttcgccggtg tggtccggga   4800
cgacgtgacc ctgttcatca gcgcggtcca ggaccaggtg gtgccggaca acaccctggc   4860
ctgggtgtgg gtgcgcggcc tggacgagct gtacgccgag tggtcggagg tcgtgtccac   4920
gaacttccgg gacgcctccg ggccggccat gaccgagatc ggcgagcagc cgtgggggcg   4980
```

```
ggagttcgcc ctgcgcgacc cggccggcaa ctgcgtgcac ttcgtggccg aggagcagga   5040
ctgagtggca gggcggggcg taaggcgcgc catttaaatg aagttcctat tccgaagttc   5100
ctattctcta gaaagtatag gaacttcgaa gcagctccag cctacacaat cgctcaagac   5160
ggaacccgcg cttggcagga aagtaatagg gatagcagct ccagcctaca caatcgctca   5220
agacgtgtaa tgctgcacaa taaccctgct gcagaggcct gcatgcaagc ttggcgtaat   5280
catggtcata gctgtttcct gtgtgaaatt gttatccgct cacaattcca cacaacatac   5340
gagccggaag cataaagtgt aaagcctggg gtgcctaatg agtgagctaa ctcacattaa   5400
ttgcgttgcg ctcactgccc gctttccagt cgggaaacct gtcgtgccag ctgcattaat   5460
gaatcggcca acgcgcgggg agaggcggtt tgcgtattgg gcgctcttcc gcttcctcgc   5520
tcactgactc gctgcgctcg gtcgttcggc tgcggcgagc ggtatcagct cactcaaagg   5580
cggtaatacg gttatccaca gaatcagggg ataacgcagg aaagaacatg tgagcaaaag   5640
gccagcaaaa ggccaggaac cgtaaaaagg ccgcgttgct ggcgtttttc cataggctcc   5700
gcccccctga cgagcatcac aaaaatcgac gctcaagtca gaggtggcga aacccgacag   5760
gactataaag ataccaggcg tttccccctg gaagctccct cgtgcgctct cctgttccga   5820
ccctgccgct taccggatac ctgtccgcct ttctcccttc gggaagcgtg gcgctttctc   5880
atagctcacg ctgtaggtat ctcagttcgg tgtaggtcgt tcgctccaag ctgggctgtg   5940
tgcacgaacc ccccgttcag cccgaccgct gcgccttatc cggtaactat cgtcttgagt   6000
ccaacccggt aagacacgac ttatcgccac tggcagcagc cactggtaac aggattagca   6060
gagcgaggta tgtaggcggt gctacagagt tcttgaagtg gtggcctaac tacggctaca   6120
ctagaagaac agtatttggt atctgcgctc tgctgaagcc agttaccttc ggaaaaagag   6180
ttggtagctc ttgatccggc aaacaaacca ccgctggtag cggtggtttt tttgtttgca   6240
agcagcagat tacgcgcaga aaaaaaggat ctcaagaaga tcctttgatc ttttctacgg   6300
ggtctgacgc tcagtggaac gaaaactcac gttaagggat tttggtcatg agattatcaa   6360
aaaggatctt cacctagatc cttttaaatt aaaaatgaag ttttaaatca atctaaagta   6420
tatatgagta aacttggtct gacagttacc aatgcttaat cagtgaggca cctatctcag   6480
cgatctgtct atttcgttca tccatagttg cctgactccc cgtcgtgtag ataactacga   6540
tacgggaggg cttaccatct ggccccagtg ctgcaatgat accgcgagac ccacgctcac   6600
cggctccaga tttatcagca ataaaccagc cagccggaag ggccgagcgc agaagtggtc   6660
ctgcaacttt atccgcctcc atccagtcta ttaattgttg ccgggaagct agagtaagta   6720
gttcgccagt taatagtttg cgcaacgttg ttgccattgc tacaggcatc gtggtgtcac   6780
gctcgtcgtt tggtatggct tcattcagct ccggttccca acgatcaagg cgagttacat   6840
gatcccccat gttgtgcaaa aaagcggtta gctccttcgg tcctccgatc gttgtcagaa   6900
gtaagttggc cgcagtgtta tcactcatgg ttatggcagc actgcataat tctcttactg   6960
tcatgccatc cgtaagatgc ttttctgtga ctggtgagta ctcaaccaag tcattctgag   7020
aatagtgtat gcggcgaccg agttgctctt gcccggcgtc aatacgggat aataccgcgc   7080
cacatagcag aactttaaaa gtgctcatca ttggaaaacg ttcttcgggg cgaaaactct   7140
caaggatctt accgctgttg agatccagtt cgatgtaacc cactcgtgca cccaactgat   7200
cttcagcatc ttttactttc accagcgttt ctgggtgagc aaaaacagga aggcaaaatg   7260
ccgcaaaaaa gggaataagg gcgacacgga aatgttgaat actcatactc ttcctttttc   7320
```

aatattattg aagcatttat cagggttatt gtctcatgag cggatacata tttgaatgta 7380
tttagaaaaa taaacaaata ggggttccgc gcacatttcc ccgaaaagtg ccacctgacg 7440
tctaagaaac cattattatc atgacattaa cctataaaaa taggcgtatc acgaggccct 7500
ttcgtc 7506

<210> SEQ ID NO 15
<211> LENGTH: 6717
<212> TYPE: DNA
<213> ORGANISM: Artificial Sequence
<220> FEATURE:
<223> OTHER INFORMATION: construct pINT-malE-lsgD

<400> SEQUENCE: 15
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accatatgcg gtgtgaaata ccgcacagat gcgtaaggag aaaataccgc atcaggcgcc 240
attcgccatt caggctgcgc aactgttggg aagggcgatc ggtgcgggcc tcttcgctat 300
tacgccagct ggcgaaaggg ggatgtgctg caaggcgatt aagttgggta acgccagggt 360
tttcccagtc acgacgttgt aaaacgacgg ccagtgaatt cgaagatcct ttgatctttt 420
ctacggggtc tgacgctcag tggaacgaaa actcacgtta agggattttg gtcatgagat 480
tatcaaaaag gatcttcacc tagatccttt taaactagtg aagttaccat cacggaaaaa 540
ggttatgctg cttttaagac ccactttcac atttaagttg tttttctaat ccgcatatga 600
tcaattcaag gccgaataag aaggctggct ctgcaccttg gtgatcaaat aattcgatag 660
cttgtcgtaa taatggcggc atactatcag tagtaggtgt ttccctttct tctttagcga 720
cttgatgctc ttgatcttcc aatacgcaac ctaaagtaaa atgccccact gcgctgagtg 780
catataatgc attctctagt gaaaaacctt gttggcataa aaaggctaat tgattttcga 840
gagtttcata ctgtttttct gtaggccgtg tacctaaatg tacttttgct ccatcgcgat 900
gacttagtaa agcacatcta aaacttttag cgttattacg taaaaaatct tgccagcttt 960
ccccttctaa agggcaaaag tgagtatggt gcctatctaa catctcaatg gctaaggcgt 1020
cgagcaaagc ccgcttattt tttacatgcc aatacaatgt aggctgctct acacctagct 1080
tctgggcgag tttacgggtt gttaaacctt cgattccgac ctcattaagc agctctaatg 1140
cgctgttaat cactttactt ttatctaaac gagacatact cttccttttt caatattatt 1200
gaagcattta tcagggttat tgtctcatga gcggatacat atttgaatgt atttagaaaa 1260
ataaacaaat aggggttccg cgcacatttc cccgaaaagt gccacctgaa attggccaga 1320
tgattaattc ctaatttttg ttgacactct atcattgata gagttatttt accactccct 1380
atcagtgata gagaaaagtg aaatgaatag ttcgacaaaa atctagaaat aattttgttt 1440
aactttaaga aggagatata caaatgaaaa tcgaagaagg taaactggta atctggatta 1500
acggcgataa aggctataac ggtctcgctg aagtcggtaa gaaattcgag aaagataccg 1560
gaattaaagt caccgttgag catccggata aactggaaga gaaattccca caggttgcgg 1620
caactggcga tggccctgac attatcttct gggcacacga ccgctttggt ggctacgctc 1680
aatctggcct gttggctgaa atcacccgg acaaagcgtt ccaggacaag ctgtatccgt 1740
ttacctggga tgccgtacgt tacaacggca agctgattgc ttacccgatc gctgttgaag 1800
cgttatcgct gatttataac aaagatctgc tgccgaaccc gccaaaaacc tgggaagaga 1860

-continued

```
tcccggcgct ggataaagaa ctgaaagcga aaggtaagag cgcgctgatg ttcaacctgc   1920
aagaaccgta cttcacctgg ccgctgattg ctgctgacgg gggttatgcg ttcaagtatg   1980
aaaacggcaa gtacgacatt aaagacgtgg gcgtggataa cgctggcgcg aaagcgggtc   2040
tgaccttcct ggttgacctg attaaaaaca aacacatgaa tgcagacacc gattactcca   2100
tcgcagaagc tgcctttaat aaaggcgaaa cagcgatgac catcaacggc ccgtgggcat   2160
ggtccaacat cgacaccagc aaagtgaatt atggtgtaac ggtactgccg accttcaagg   2220
gtcaaccatc caaaccgttc gttggcgtgc tgagcgcagg tattaacgcc gccagtccga   2280
acaaagagct ggcaaaagag ttcctcgaaa actatctgct gactgatgaa ggtctggaag   2340
cggttaataa agacaaaccg ctgggtgccg tagcgctgaa gtcttacgag gaagagttgg   2400
cgaaagatcc acgtattgcc gccaccatgg aaaacgccca gaaaggtgaa atcatgccga   2460
acatcccgca gatgtccgct ttctggtatg ccgtgcgtac tgcggtgatc aacgccgcca   2520
gcggtcgtca gactgtcgat gaagccctga aagacgcgca gactatgctg aagaagtacc   2580
tgattagcct ggataaggac attcaacgcc gcaagctgtt tttctcgcag aagaacacgg   2640
aagattttca aatttttctca gcgatcaaca ccatgcagaa agattgggac gaactggcat   2700
cgatcttcaa catcgaacaa ttcaaggctc attacttccg taacgtcacc aagggcgaaa   2760
ttggttgcac gctgagtcac ctgtccgtct atcagaaaat tgtggaagat aacgacatcg   2820
cagaagattc atacgctctg gtttgtgaag atgacgccct gtttcatctg gatttccagc   2880
aaaatctgac cgcactgctg agtgaaaaac tggaagctga aattatcctg ctgggccagt   2940
ccaacattaa caattttaat gatacggacc tggaaatcaa ttacccgacc acgtttagct   3000
tcctgtgcaa aaagaccggt aacgtgaatt atgcgttccc gtataaatct tactttgccg   3060
gcacggttgg ttacctgatt aaaaagagcg cggcccgtcg cttcattcag caaatctctc   3120
agaacaaacc gttttggctg gcggatgact ttctgctgtt cgaacaaaac ttcaatatcc   3180
gtaataaggt ggttcgcccg ctgatggtta ttgaaaaccc ggtcctgatc tcaaatctgg   3240
aatcggtgcg cggcagcctg tctaacaatc tgctgaaaaa gctgatgaaa tatccgctga   3300
aaaagatttt tgcgatcaaa aagaacctgg ccaattaagc ggccgcgtcg acacgcaaaa   3360
aggccatccg tcaggatggc cttctgctta attatctaga tgcctggcag tttatggcgg   3420
gcgtcctgcc cgccaccctc cgggccgttg cttcgcaacg ttcaaatccg ctcccggcgg   3480
atttgtccta ctcaggagag cgttcaccga caaacaacag ataaaacgaa aggcccagtc   3540
tttcgactga gcctttcgtt ttatttgatg cctggcagtt ccctactctc gcatggggag   3600
accccacact accatcatgt atgaatatcc tccttagttc ctattccgaa gggtaatggc   3660
atcagggaat ggcgaacgcg ctccccacac taccatcatg tatgaatatc ctccttagtt   3720
cctattccga agttcctatt ctctagaaag tataggaact tcggtggaac gacgcgtaac   3780
tcacgttaag ggattttggt catgatcagc acgtgttgac aattaatcat cggcatagta   3840
tatcggcata gtataatacg acaaggtgag gaactaaacc atggccaagt tgaccagtgc   3900
cgttccggtg ctcaccgcgc gcgacgtcgc cggagcggtc gagttctgga ccgaccggct   3960
cgggttctcc cgggacttcg tggaggacga cttcgccggt gtggtccggg acgacgtgac   4020
cctgttcatc agcgcggtcc aggaccaggt ggtgccggac aacaccctgg cctgggtgtg   4080
ggtgcgcggc ctggacgagc tgtacgccga gtggtcggag gtcgtgtcca cgaacttccg   4140
ggacgcctcc gggccggcca tgaccgagat cggcgagcag ccgtgggggc gggagttcgc   4200
```

-continued

```
cctgcgcgac ccggccggca actgcgtgca cttcgtggcc gaggagcagg actgagtggc   4260
agggcggggc gtaaggcgcg ccatttaaat gaagttccta ttccgaagtt cctattctct   4320
agaaagtata ggaacttcga agcagctcca gcctacacaa tcgctcaaga cggaacccgc   4380
gcttggcagg aaagtaatag ggatagcagc tccagcctac acaatcgctc aagacgtgta   4440
atgctgcaca ataaccctgc tgcagaggcc tgcatgcaag cttggcgtaa tcatggtcat   4500
agctgtttcc tgtgtgaaat tgttatccgc tcacaattcc acacaacata cgagccggaa   4560
gcataaagtg taaagcctgg ggtgcctaat gagtgagcta actcacatta attgcgttgc   4620
gctcactgcc cgctttccag tcgggaaacc tgtcgtgcca gctgcattaa tgaatcggcc   4680
aacgcgcggg gagaggcggt ttgcgtattg ggcgctcttc cgcttcctcg ctcactgact   4740
cgctgcgctc ggtcgttcgg ctgcggcgag cggtatcagc tcactcaaag gcggtaatac   4800
ggttatccac agaatcaggg gataacgcag gaaagaacat gtgagcaaaa ggccagcaaa   4860
aggccaggaa ccgtaaaaag gccgcgttgc tggcgttttt ccataggctc cgcccccctg   4920
acgagcatca caaaaatcga cgctcaagtc agaggtggcg aaacccgaca ggactataaa   4980
gataccaggc gtttccccct ggaagctccc tcgtgcgctc tcctgttccg accctgccgc   5040
ttaccggata cctgtccgcc tttctccctt cgggaagcgt ggcgctttct catagctcac   5100
gctgtaggta tctcagttcg gtgtaggtcg ttcgctccaa gctgggctgt gtgcacgaac   5160
cccccgttca gcccgaccgc tgcgccttat ccggtaacta tcgtcttgag tccaacccgg   5220
taagacacga cttatcgcca ctggcagcag ccactggtaa caggattagc agagcgaggt   5280
atgtaggcgg tgctacagag ttcttgaagt ggtggcctaa ctacggctac actagaagaa   5340
cagtatttgg tatctgcgct ctgctgaagc cagttacctt cggaaaaaga gttggtagct   5400
cttgatccgg caaacaaacc accgctggta gcggtggttt ttttgtttgc aagcagcaga   5460
ttacgcgcag aaaaaaagga tctcaagaag atcctttgat cttttctacg gggtctgacg   5520
ctcagtggaa cgaaaactca cgttaaggga ttttggtcat gagattatca aaaaggatct   5580
tcacctagat ccttttaaat taaaaatgaa gttttaaatc aatctaaagt atatatgagt   5640
aaacttggtc tgacagttac caatgcttaa tcagtgaggc acctatctca gcgatctgtc   5700
tatttcgttc atccatagtt gcctgactcc ccgtcgtgta gataactacg atacgggagg   5760
gcttaccatc tggccccagt gctgcaatga taccgcgaga cccacgctca ccggctccag   5820
atttatcagc aataaaccag ccagccggaa gggccgagcg cagaagtggt cctgcaactt   5880
tatccgcctc catccagtct attaattgtt gccgggaagc tagagtaagt agttcgccag   5940
ttaatagttt gcgcaacgtt gttgccattg ctacaggcat cgtggtgtca cgctcgtcgt   6000
ttggtatggc ttcattcagc tccggttccc aacgatcaag gcgagttaca tgatccccca   6060
tgttgtgcaa aaaagcggtt agctccttcg gtcctccgat cgttgtcaga agtaagttgg   6120
ccgcagtgtt atcactcatg gttatggcag cactgcataa ttctcttact gtcatgccat   6180
ccgtaagatg cttttctgtg actggtgagt actcaaccaa gtcattctga gaatagtgta   6240
tgcggcgacc gagttgctct tgcccggcgt caatacggga taataccgcg ccacatagca   6300
gaactttaaa agtgctcatc attggaaaac gttcttcggg gcgaaaactc tcaaggatct   6360
taccgctgtt gagatccagt tcgatgtaac ccactcgtgc acccaactga tcttcagcat   6420
cttttacttt caccagcgtt tctgggtgag caaaaacagg aaggcaaaat gccgcaaaaa   6480
agggaataag ggcgacacgg aaatgttgaa tactcatact cttccttttt caatattatt   6540
gaagcattta tcagggttat tgtctcatga gcggatacat atttgaatgt atttagaaaa   6600
```

ataaacaaat aggggttccg cgcacatttc cccgaaaagt gccacctgac gtctaagaaa 6660
ccattattat catgacatta acctataaaa ataggcgtat cacgaggccc tttcgtc 6717

<210> SEQ ID NO 16
<211> LENGTH: 6769
<212> TYPE: DNA
<213> ORGANISM: Artificial Sequence
<220> FEATURE:
<223> OTHER INFORMATION: construct pINT-malE-HPgalT

<400> SEQUENCE: 16
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accatatgcg gtgtgaaata ccgcacagat gcgtaaggag aaaataccgc atcaggcgcc 240
attcgccatt caggctgcgc aactgttggg aagggcgatc ggtgcgggcc tcttcgctat 300
tacgccagct ggcgaaaggg ggatgtgctg caaggcgatt aagttgggta acgccagggt 360
tttcccagtc acgacgttgt aaaacgacgg ccagtgaatt cgaagatcct ttgatctttt 420
ctacggggtc tgacgctcag tggaacgaaa actcacgtta agggattttg gtcatgagat 480
tatcaaaaag gatcttcacc tagatccttt taaactagtg aagttaccat cacggaaaaa 540
ggttatgctg cttttaagac ccactttcac atttaagttg tttttctaat ccgcatatga 600
tcaattcaag gccgaataag aaggctggct ctgcaccttg gtgatcaaat aattcgatag 660
cttgtcgtaa taatggcggc atactatcag tagtaggtgt ttccctttct tctttagcga 720
cttgatgctc ttgatcttcc aatacgcaac ctaaagtaaa atgccccact gcgctgagtg 780
catataatgc attctctagt gaaaaacctt gttggcataa aaaggctaat tgattttcga 840
gagtttcata ctgtttttct gtaggccgtg tacctaaatg tacttttgct ccatcgcgat 900
gacttagtaa agcacatcta aaacttttag cgttattacg taaaaaatct tgccagcttt 960
ccccttctaa agggcaaaag tgagtatggt gcctatctaa catctcaatg gctaaggcgt 1020
cgagcaaagc ccgcttattt tttacatgcc aatacaatgt aggctgctct acacctagct 1080
tctgggcgag tttacgggtt gttaaacctt cgattccgac ctcattaagc agctctaatg 1140
cgctgttaat cactttactt ttatctaaac gagacatact cttccttttt caatattatt 1200
gaagcattta tcagggttat tgtctcatga gcggatacat atttgaatgt atttagaaaa 1260
ataaacaaat aggggttccg cgcacatttc cccgaaaagt gccacctgaa attggccaga 1320
tgattaattc ctaatttttg ttgacactct atcattgata gagttatttt accactccct 1380
atcagtgata gagaaaagtg aaatgaatag ttcgacaaaa atctagaaat aattttgttt 1440
aactttaaga aggagatata caaatgaaaa tcgaagaagg taaactggta atctggatta 1500
acggcgataa aggctataac ggtctcgctg aagtcggtaa gaaattcgag aaagataccg 1560
gaattaaagt caccgttgag catccggata aactggaaga gaaattccca caggttgcgg 1620
caactggcga tggccctgac attatcttct gggcacacga ccgctttggt ggctacgctc 1680
aatctggcct gttggctgaa atcaccccgg acaaagcgtt ccaggacaag ctgtatccgt 1740
ttacctggga tgccgtacgt tacaacggca agctgattgc ttacccgatc gctgttgaag 1800
cgttatcgct gatttataac aaagatctgc tgccgaaccc gccaaaaacc tgggaagaga 1860
tcccggcgct ggataaagaa ctgaaagcga aaggtaagag cgcgctgatg ttcaacctgc 1920

-continued

```
aagaaccgta cttcacctgg ccgctgattg ctgctgacgg gggttatgcg ttcaagtatg   1980
aaaacggcaa gtacgacatt aaagacgtgg gcgtggataa cgctggcgcg aaagcgggtc   2040
tgaccttcct ggttgacctg attaaaaaca aacacatgaa tgcagacacc gattactcca   2100
tcgcagaagc tgcctttaat aaaggcgaaa cagcgatgac catcaacggc ccgtgggcat   2160
ggtccaacat cgacaccagc aaagtgaatt atggtgtaac ggtactgccg accttcaagg   2220
gtcaaccatc caaaccgttc gttggcgtgc tgagcgcagg tattaacgcc gccagtccga   2280
acaaagagct ggcaaaagag ttcctcgaaa actatctgct gactgatgaa ggtctggaag   2340
cggttaataa agacaaaccg ctgggtgccg tagcgctgaa gtcttacgag gaagagttgg   2400
cgaaagatcc acgtattgcc gccaccatgg aaaacgccca gaaaggtgaa atcatgccga   2460
acatcccgca gatgtccgct ttctggtatg ccgtgcgtac tgcggtgatc aacgccgcca   2520
gcggtcgtca gactgtcgat gaagccctga aagacgcgca gactatgcgt gtgtttatta   2580
tttccctgaa tcaaaaagtg tgtgatacct tcggtctggt gttccgtgat acgacgaccc   2640
tgctgaacaa cattaacgcg acccatcacc aggcccaaat ttttgatgca atctactcca   2700
aaacgttcga aggcggtctg catccgctgg ttaaaaaaca tctgcacccg tactttatta   2760
cccagaacat caaagacatg ggcattacca cgaatctgat cagcgaagtc tctaaattct   2820
actacgctct gaaataccat gcgaaattca tgagcctggg cgaactgggt tgctatgcta   2880
gtcactactc cctgtgggaa aaatgcattg aactgaacga agcgatttgt atcctggaag   2940
atgacatcac gctgaaagaa gattttaaag aaggcctgga cttcctggaa aaacatattc   3000
aggaactggg ttatgtgcgt ctgatgcacc tgctgtacga tccgaatgtt aaaagcgaac   3060
cgctgaacca taaaaatcac gaaatccagg aacgcgtggg cattatcaaa gcctattctc   3120
atggcgttgg cacccaaggt tacgtcatta cgccgaaaat cgcaaaagtc ttcaaaaaac   3180
atagtcgtaa atgggtggtt ccggtggata ccattatgga cgcgacgttt atccacggtg   3240
tcaaaaatct ggtgctgcaa ccgttcgtta ttgccgatga cgaacaaatt tcaaccatcg   3300
cacgcaaaga agaaccgtat tcgccgaaaa tcgccctgat gcgtgaactg cacttcaaat   3360
acctgaaata ctggcaattc gtctaagcgg ccgcgtcgac acgcaaaaag gccatccatc   3420
cgtcaggatg gccttctgct taattatcta gatgcctggc agtttatggc gggcgtcctg   3480
cccgccaccc tccgggccgt tgcttcgcaa cgttcaaatc cgctcccggc ggatttgtcc   3540
tactcaggag agcgttcacc gacaaacaac agataaaacg aaaggcccag tctttcgact   3600
gagcctttcg ttttatttga tgcctggcag ttccctactc tcgcatgggg agaccccaca   3660
ctaccatcat gtatgaatat cctccttagt tcctattccg aagggtaatg gcatcaggga   3720
atggcgaacg cgctccccac actaccatca tgtatgaata tcctccttag ttcctattcc   3780
gaagttccta ttctctagaa agtataggaa cttcggtgga acgacgcgta actcacgtta   3840
agggattttg gtcatgatca gcacgtgttg acaattaatc atcggcatag tatatcggca   3900
tagtataata cgacaaggtg aggaactaaa ccatggccaa gttgaccagt gccgttccgg   3960
tgctcaccgc gcgcgacgtc gccggagcgg tcgagttctg gaccgaccgg ctcgggttct   4020
cccgggactt cgtggaggac gacttcgccg gtgtggtccg ggacgacgtg accctgttca   4080
tcagcgcggt ccaggaccag gtggtgccgg acaacaccct ggcctgggtg tgggtgcgcg   4140
gcctggacga gctgtacgcc gagtggtcgg aggtcgtgtc cacgaacttc cgggacgcct   4200
ccgggccggc catgaccgag atcggcgagc agccgtgggg gcgggagttc gccctgcgcg   4260
acccggccgg caactgcgtg cacttcgtgg ccgaggagca ggactgagtg gcagggcggg   4320
```

-continued

```
gcgtaaggcg cgccatttaa atgaagttcc tattccgaag ttcctattct ctagaaagta   4380
taggaacttc gaagcagctc cagcctacac aatcgctcaa gacggaaccc gcgcttggca   4440
ggaaagtaat agggatagca gctccagcct acacaatcgc tcaagacgtg taatgctgca   4500
caataaccct gctgcagagg cctgcatgca agcttggcgt aatcatggtc atagctgttt   4560
cctgtgtgaa attgttatcc gctcacaatt ccacacaaca tacgagccgg aagcataaag   4620
tgtaaagcct ggggtgccta atgagtgagc taactcacat taattgcgtt gcgctcactg   4680
cccgctttcc agtcgggaaa cctgtcgtgc cagctgcatt aatgaatcgg ccaacgcgcg   4740
gggagaggcg gtttgcgtat tgggcgctct tccgcttcct cgctcactga ctcgctgcgc   4800
tcggtcgttc ggctgcggcg agcggtatca gctcactcaa aggcggtaat acggttatcc   4860
acagaatcag gggataacgc aggaaagaac atgtgagcaa aaggccagca aaaggccagg   4920
aaccgtaaaa aggccgcgtt gctggcgttt ttccataggc tccgcccccc tgacgagcat   4980
cacaaaaatc gacgctcaag tcagaggtgg cgaaacccga caggactata aagataccag   5040
gcgtttcccc ctggaagctc cctcgtgcgc tctcctgttc cgaccctgcc gcttaccgga   5100
tacctgtccg cctttctccc ttcgggaagc gtggcgcttt ctcatagctc acgctgtagg   5160
tatctcagtt cggtgtaggt cgttcgctcc aagctgggct gtgtgcacga accccccgtt   5220
cagcccgacc gctgcgcctt atccggtaac tatcgtcttg agtccaaccc ggtaagacac   5280
gacttatcgc cactggcagc agccactggt aacaggatta gcagagcgag gtatgtaggc   5340
ggtgctacag agttcttgaa gtggtggcct aactacggct acactagaag aacagtattt   5400
ggtatctgcg ctctgctgaa gccagttacc ttcggaaaaa gagttggtag ctcttgatcc   5460
ggcaaacaaa ccaccgctgg tagcggtggt ttttttgttt gcaagcagca gattacgcgc   5520
agaaaaaaag gatctcaaga agatcctttg atcttttcta cggggtctga cgctcagtgg   5580
aacgaaaact cacgttaagg gattttggtc atgagattat caaaaaggat cttcacctag   5640
atccttttaa attaaaaatg aagttttaaa tcaatctaaa gtatatatga gtaaacttgg   5700
tctgacagtt accaatgctt aatcagtgag gcacctatct cagcgatctg tctatttcgt   5760
tcatccatag ttgcctgact ccccgtcgtg tagataacta cgatacggga gggcttacca   5820
tctggcccca gtgctgcaat gataccgcga gacccacgct caccggctcc agatttatca   5880
gcaataaacc agccagccgg aagggccgag cgcagaagtg gtcctgcaac tttatccgcc   5940
tccatccagt ctattaattg ttgccgggaa gctagagtaa gtagttcgcc agttaatagt   6000
ttgcgcaacg ttgttgccat tgctacaggc atcgtggtgt cacgctcgtc gtttggtatg   6060
gcttcattca gctccggttc ccaacgatca aggcgagtta catgatcccc catgttgtgc   6120
aaaaaagcgg ttagctcctt cggtcctccg atcgttgtca gaagtaagtt ggccgcagtg   6180
ttatcactca tggttatggc agcactgcat aattctctta ctgtcatgcc atccgtaaga   6240
tgcttttctg tgactggtga gtactcaacc aagtcattct gagaatagtg tatgcggcga   6300
ccgagttgct cttgcccggc gtcaatacgg gataataccg cgccacatag cagaacttta   6360
aaagtgctca tcattggaaa acgttcttcg gggcgaaaac tctcaaggat cttaccgctg   6420
ttgagatcca gttcgatgta acccactcgt gcacccaact gatcttcagc atcttttact   6480
ttcaccagcg tttctgggtg agcaaaaaca ggaaggcaaa atgccgcaaa aaagggaata   6540
agggcgacac ggaaatgttg aatactcata ctcttccttt ttcaatatta ttgaagcatt   6600
tatcagggtt attgtctcat gagcggatac atatttgaat gtatttagaa aaataaacaa   6660
```

-continued atagggggttc cgcgcacatt tccccgaaaa gtgccacctg acgtctaaga aaccattatt 6720
atcatgacat taacctataa aaataggcgt atcacgaggc cctttcgtc 6769

<210> SEQ ID NO 17
<211> LENGTH: 4714
<212> TYPE: DNA
<213> ORGANISM: Artificial Sequence
<220> FEATURE:
<223> OTHER INFORMATION: construct pACYC-waaX

<400> SEQUENCE: 17
ggggaattgt gagcggataa caattcccct gtagaaataa ttttgtttaa ctttaataag 60
gagatatacc atgaaagtgt ttgtggtcaa cctggataag gataaggata aaaaagaaaa 120
aatcaagaat gaatgccgca acgcagaact ggactatgaa attatctcag cagttgatgg 180
ccgtgaactg agctacaacg aactgaaatc taaggtccat ccggtgtcac tgaattatct 240
gtcgaaaggc gaaattggtt gcgtcctgtc ccaccagcgt atttacaaac gcatcctgga 300
tgacgatatt gactatgctc tgatcctgga agacgatgtg gaactgagtc aagatatcaa 360
ggtttttctg aaggaattcc tgtccgtcaa agacaagaac aaaggcgatg tgtttctgct 420
gtacccgtca ggtctgcgtt tcctgaaccg tcgcatcaac gtgtcgcatg attatttctt 480
ttatgaagcg tacaacagct cttgtgccca cggttatatt atcagcaaca aagcggccaa 540
aaagctgatt cgcatcaata ccccgattat cctggttgca gatgcttggc tgtggtttta 600
ccagatttct ctgctgaaag tgtatgttct gaacaaagaa ctggttcgtg catatgacgt 660
cgataaaagt ctgtccacca tcgaaacgga acgcagcctg ctgctggacg aaaaggaaaa 720
gcatcagatg caaatcatca aaaagcaacc gctgtactac ctgatcaagt actaccacaa 780
gtacatccgt cgcctgttca tcaataagga taaataagaa ttcgagctcg gcgcgcctgc 840
aggtcgacaa gcttgcggcc gcataatgct taagtcgaac agaaagtaat cgtattgtac 900
acggccgcat aatcgaaatt aatacgactc actatagggg aattgtgagc ggataacaat 960
tccccatctt agtatattag ttaagtataa gaaggagata tacatatggc agatctcaat 1020
tggatatcgg ccggccacgc gatcgctgac gtcggtaccc tcgagtctgg taaagaaacc 1080
gctgctgcga aatttgaacg ccagcacatg gactcgtcta ctagcgcagc ttaattaacc 1140
taggctgctg ccaccgctga gcaataacta gcataacccc ttggggcctc taaacgggtc 1200
ttgaggggtt ttttgctgaa acctcaggca tttgagaagc acacggtcac actgcttccg 1260
gtagtcaata aaccggtaaa ccagcaatag acataagcgg ctatttaacg accctgccct 1320
gaaccgacga ccgggtcgaa tttgctttcg aatttctgcc attcatccgc ttattatcac 1380
ttattcaggc gtagcaccag gcgtttaagg gcaccaataa ctgccttaaa aaaattacgc 1440
cccgccctgc cactcatcgc agtactgttg taattcatta agcattctgc cgacatggaa 1500
gccatcacag acggcatgat gaacctgaat cgccagcggc atcagcacct tgtcgccttg 1560
cgtataatat ttgcccatag tgaaaacggg ggcgaagaag ttgtccatat tggccacgtt 1620
taaatcaaaa ctggtgaaac tcacccaggg attggctgag acgaaaaaca tattctcaat 1680
aaacccttta gggaaatagg ccaggttttc accgtaacac gccacatctt gcgaatatat 1740
gtgtagaaac tgccggaaat cgtcgtggta ttcactccag agcgatgaaa acgtttcagt 1800
ttgctcatgg aaaacggtgt aacaagggtg aacactatcc catatcacca gctcaccgtc 1860
tttcattgcc atacggaact ccggatgagc attcatcagg cgggcaagaa tgtgaataaa 1920
ggccggataa aacttgtgct tatttttctt tacggtcttt aaaaaggccg taatatccag 1980

-continued

```
ctgaacggtc tggttatagg tacattgagc aactgactga aatgcctcaa aatgttcttt   2040
acgatgccat tgggatatat caacggtggt atatccagtg atttttttct ccattttagc   2100
ttccttagct cctgaaaatc tcgataactc aaaaaatacg cccggtagtg atcttatttc   2160
attatggtga aagttggaac ctcttacgtg ccgatcaacg tctcattttc gccaaaagtt   2220
ggcccagggc ttcccggtat caacagggac accaggattt atttattctg cgaagtgatc   2280
ttccgtcaca ggtatttatt cggcgcaaag tgcgtcgggt gatgctgcca acttactgat   2340
ttagtgtatg atggtgtttt tgaggtgctc cagtggcttc tgtttctatc agctgtccct   2400
cctgttcagc tactgacggg gtggtgcgta acggcaaaag caccgccgga catcagcgct   2460
agcggagtgt atactggctt actatgttgg cactgatgag ggtgtcagtg aagtgcttca   2520
tgtggcagga gaaaaaaggc tgcaccggtg cgtcagcaga atatgtgata caggatatat   2580
tccgcttcct cgctcactga ctcgctacgc tcggtcgttc gactgcggcg agcggaaatg   2640
gcttacgaac ggggcggaga tttcctggaa gatgccagga agatacttaa cagggaagtg   2700
agagggccgc ggcaaagccg tttttccata ggctccgccc ccctgacaag catcacgaaa   2760
tctgacgctc aaatcagtgg tggcgaaacc cgacaggact ataaagatac caggcgtttc   2820
ccctggcggc tccctcgtgc gctctcctgt tcctgccttt cggtttaccg gtgtcattcc   2880
gctgttatgg ccgcgtttgt ctcattccac gcctgacact cagttccggg taggcagttc   2940
gctccaagct ggactgtatg cacgaacccc ccgttcagtc cgaccgctgc gccttatccg   3000
gtaactatcg tcttgagtcc aacccggaaa gacatgcaaa agcaccactg gcagcagcca   3060
ctggtaattg atttagagga gttagtcttg aagtcatgcg ccggttaagg ctaaactgaa   3120
aggacaagtt ttggtgactg cgctcctcca agccagttac ctcggttcaa agagttggta   3180
gctcagagaa ccttcgaaaa accgccctgc aaggcggttt tttcgttttc agagcaagag   3240
attacgcgca gaccaaaacg atctcaagaa gatcatctta ttaatcagat aaaatatttc   3300
tagatttcag tgcaatttat ctcttcaaat gtagcacctg aagtcagccc catacgatat   3360
aagttgtaat tctcatgtta gtcatgcccc gcgcccaccg gaaggagctg actgggttga   3420
aggctctcaa gggcatcggt cgagatcccg gtgcctaatg agtgagctaa cttacattaa   3480
ttgcgttgcg ctcactgccc gctttccagt cgggaaacct gtcgtgccag ctgcattaat   3540
gaatcggcca acgcgcgggg agaggcggtt tgcgtattgg gcgccagggt ggtttttctt   3600
ttcaccagtg agacgggcaa cagctgattg cccttcaccg cctggccctg agagagttgc   3660
agcaagcggt ccacgctggt ttgccccagc aggcgaaaat cctgtttgat ggtggttaac   3720
ggcgggatat aacatgagct gtcttcggta tcgtcgtatc ccactaccga gatgtccgca   3780
ccaacgcgca gcccggactc ggtaatggcg cgcattgcgc ccagcgccat ctgatcgttg   3840
gcaaccagca tcgcagtggg aacgatgccc tcattcagca tttgcatggt ttgttgaaaa   3900
ccggacatgg cactccagtc gccttcccgt tccgctatcg gctgaatttg attgcgagtg   3960
agatatttat gccagccagc cagacgcaga cgcgccgaga cagaacttaa tgggcccgct   4020
aacagcgcga tttgctggtg acccaatgcg accagatgct ccacgcccag tcgcgtaccg   4080
tcttcatggg agaaaataat actgttgatg ggtgtctggt cagagacatc aagaaataac   4140
gccggaacat tagtgcaggc agcttccaca gcaatggcat cctggtcatc cagcggatag   4200
ttaatgatca gcccactgac gcgttgcgcg agaagattgt gcaccgccgc tttacaggct   4260
tcgacgccgc ttcgttctac catcgacacc accacgctgg cacccagttg atcggcgcga   4320
```

-continued

```
gatttaatcg ccgcgacaat ttgcgacggc gcgtgcaggg ccagactgga ggtggcaacg   4380

ccaatcagca acgactgttt gcccgccagt tgttgtgcca cgcggttggg aatgtaattc   4440

agctccgcca tcgccgcttc cactttttcc cgcgttttcg cagaaacgtg gctggcctgg   4500

ttcaccacgc gggaaacggt ctgataagag acaccggcat actctgcgac atcgtataac   4560

gttactggtt tcacattcac caccctgaat tgactctctt ccgggcgcta tcatgccata   4620

ccgcgaaagg ttttgcgcca ttcgatggtg tccgggatct cgacgctctc ccttatgcga   4680

ctcctgcatt aggaaattaa tacgactcac tata                               4714
```

```
<210> SEQ ID NO 18
<211> LENGTH: 4760
<212> TYPE: DNA
<213> ORGANISM: Artificial Sequence
<220> FEATURE:
<223> OTHER INFORMATION: construct pACYC-wbdO

<400> SEQUENCE: 18

ggggaattgt gagcggataa caattcccct gtagaaataa ttttgtttaa ctttaataag     60

gagatatacc atgctgacgg aagtgcgccc ggtctctacg acgaaaccgc tggtgtctgt    120

gattctgccg gtgaacaaat tcaacccgta tctggatcgt gcaattcatt caatcctgag    180

tcagtcctat ccgtcgattg aactgattat cattgcaaac aattgcacca atgacttttt    240

cgatgctctg aaaaaacgtg aatgtgaaac cattaaagtg ctgcgcacga acatcgcgta    300

tctgccgtac tgcctgaata aaggcctgga tctgtgtaac ggtgactttg ttgcccgcat    360

ggattcagat gacatttcgc acccggaacg tatcgatcgc caggtcgact tcctgattaa    420

caatccggac atcgatgtgg ttggcaccaa tgcagtctat attgatgaag atgacatcga    480

actggaaaaa agcaacctgc cggtgaacaa taacgctatt cgtaaaatgc tgccgtataa    540

atgctgtctg gtgcatccgt ctgttatgtt tcgcaaaaat gtcgtgatca ccagcggcgg    600

ttacatgttc gcgaattatt ctgaagatta cgaactgtgg aaccgtctgg ccgttgaagg    660

ccgcaatttt tataacctga gcgaatacct gctgtattac cgtctgcaca ataaccaatc    720

aacgtcgaaa aataacctgt ttatggtgat ggcgaacgat gtcgccatta aagtgaaata    780

tttcctgctg accaagaaaa ttagctacct gctgggtatc attcgcacgg tcttttctgt    840

gttctattgc aaatacatca aatgaattcg agctcggcgc gcctgcaggt cgacaagctt    900

gcggccgcat aatgcttaag tcgaacagaa agtaatcgta ttgtacacgg ccgcataatc    960

gaaattaata cgactcacta taggggaatt gtgagcggat aacaattccc catcttagta   1020

tattagttaa gtataagaag gagatataca tatggcagat ctcaattgga tatcggccgg   1080

ccacgcgatc gctgacgtcg gtaccctcga gtctggtaaa gaaaccgctg ctgcgaaatt   1140

tgaacgccag cacatggact cgtctactag cgcagcttaa ttaacctagg ctgctgccac   1200

cgctgagcaa taactagcat aaccccttgg ggcctctaaa cgggtcttga ggggtttttt   1260

gctgaaacct caggcatttg agaagcacac ggtcacactg cttccggtag tcaataaacc   1320

ggtaaaccag caatagacat aagcggctat ttaacgaccc tgccctgaac cgacgaccgg   1380

gtcgaatttg ctttcgaatt tctgccattc atccgcttat tatcacttat tcaggcgtag   1440

caccaggcgt ttaagggcac caataactgc cttaaaaaaa ttacgccccg ccctgccact   1500

catcgcagta ctgttgtaat tcattaagca ttctgccgac atggaagcca tcacagacgg   1560

catgatgaac ctgaatcgcc agcggcatca gcaccttgtc gccttgcgta taatatttgc   1620

ccatagtgaa aacgggggcg aagaagttgt ccatattggc cacgtttaaa tcaaaactgg   1680
```

-continued

```
tgaaactcac ccagggattg gctgagacga aaaacatatt ctcaataaac cctttaggga   1740
aataggccag gttttcaccg taacacgcca catcttgcga atatatgtgt agaaactgcc   1800
ggaaatcgtc gtggtattca ctccagagcg atgaaaacgt ttcagtttgc tcatggaaaa   1860
cggtgtaaca agggtgaaca ctatcccata tcaccagctc accgtctttc attgccatac   1920
ggaactccgg atgagcattc atcaggcggg caagaatgtg aataaaggcc ggataaaact   1980
tgtgcttatt tttctttacg gtctttaaaa aggccgtaat atccagctga acggtctggt   2040
tataggtaca ttgagcaact gactgaaatg cctcaaaatg ttctttacga tgccattggg   2100
atatatcaac ggtggtatat ccagtgattt ttttctccat tttagcttcc ttagctcctg   2160
aaaatctcga taactcaaaa aatacgcccg gtagtgatct tatttcatta tggtgaaagt   2220
tggaacctct tacgtgccga tcaacgtctc attttcgcca aaagttggcc cagggcttcc   2280
cggtatcaac agggacacca ggatttattt attctgcgaa gtgatcttcc gtcacaggta   2340
tttattcggc gcaaagtgcg tcgggtgatg ctgccaactt actgatttag tgtatgatgg   2400
tgtttttgag gtgctccagt ggcttctgtt tctatcagct gtccctcctg ttcagctact   2460
gacggggtgg tgcgtaacgg caaaagcacc gccggacatc agcgctagcg gagtgtatac   2520
tggcttacta tgttggcact gatgagggtg tcagtgaagt gcttcatgtg gcaggagaaa   2580
aaaggctgca ccggtgcgtc agcagaatat gtgatacagg atatattccg cttcctcgct   2640
cactgactcg ctacgctcgg tcgttcgact gcggcgagcg gaaatggctt acgaacgggg   2700
cggagatttc ctggaagatg ccaggaagat acttaacagg gaagtgagag ggccgcggca   2760
aagccgtttt tccataggct ccgcccccct gacaagcatc acgaaatctg acgctcaaat   2820
cagtggtggc gaaacccgac aggactataa agataccagg cgtttcccct ggcggctccc   2880
tcgtgcgctc tcctgttcct gcctttcggt ttaccggtgt cattccgctg ttatggccgc   2940
gtttgtctca ttccacgcct gacactcagt tccgggtagg cagttcgctc caagctggac   3000
tgtatgcacg aaccccccgt tcagtccgac cgctgcgcct tatccggtaa ctatcgtctt   3060
gagtccaacc cggaaagaca tgcaaaagca ccactggcag cagccactgg taattgattt   3120
agaggagtta gtcttgaagt catgcgccgg ttaaggctaa actgaaagga caagttttgg   3180
tgactgcgct cctccaagcc agttacctcg gttcaaagag ttggtagctc agagaacctt   3240
cgaaaaaccg ccctgcaagg cggttttttc gttttcagag caagagatta cgcgcagacc   3300
aaaacgatct caagaagatc atcttattaa tcagataaaa tatttctaga tttcagtgca   3360
atttatctct tcaaatgtag cacctgaagt cagccccata cgatataagt tgtaattctc   3420
atgttagtca tgccccgcgc ccaccggaag gagctgactg ggttgaaggc tctcaagggc   3480
atcggtcgag atcccggtgc ctaatgagtg agctaactta cattaattgc gttgcgctca   3540
ctgcccgctt tccagtcggg aaacctgtcg tgccagctgc attaatgaat cggccaacgc   3600
gcggggagag gcggtttgcg tattgggcgc cagggtggtt tttcttttca ccagtgagac   3660
gggcaacagc tgattgccct tcaccgcctg gccctgagag agttgcagca agcggtccac   3720
gctggtttgc cccagcaggc gaaaatcctg tttgatggtg gttaacggcg ggatataaca   3780
tgagctgtct tcggtatcgt cgtatcccac taccgagatg tccgcaccaa cgcgcagccc   3840
ggactcggta atggcgcgca ttgcgcccag cgccatctga tcgttggcaa ccagcatcgc   3900
agtgggaacg atgccctcat tcagcatttg catggtttgt tgaaaaccgg acatggcact   3960
ccagtcgcct tcccgttccg ctatcggctg aatttgattg cgagtgagat atttatgcca   4020
```

gccagccaga cgcagacgcg ccgagacaga acttaatggg cccgctaaca gcgcgatttg 4080
ctggtgaccc aatgcgacca gatgctccac gcccagtcgc gtaccgtctt catgggagaa 4140
aataatactg ttgatgggtg tctggtcaga gacatcaaga aataacgccg gaacattagt 4200
gcaggcagct tccacagcaa tggcatcctg gtcatccagc ggatagttaa tgatcagccc 4260
actgacgcgt tgcgcgagaa gattgtgcac cgccgcttta caggcttcga cgccgcttcg 4320
ttctaccatc gacaccacca cgctggcacc cagttgatcg gcgcgagatt taatcgccgc 4380
gacaatttgc gacggcgcgt gcagggccag actggaggtg gcaacgccaa tcagcaacga 4440
ctgtttgccc gccagttgtt gtgccacgcg gttgggaatg taattcagct ccgccatcgc 4500
cgcttccact ttttcccgcg ttttcgcaga aacgtggctg gcctggttca ccacgcggga 4560
aacggtctga taagagacac cggcatactc tgcgacatcg tataacgtta ctggtttcac 4620
attcaccacc ctgaattgac tctcttccgg gcgctatcat gccataccgc gaaaggtttt 4680
gcgccattcg atggtgtccg ggatctcgac gctctccctt atgcgactcc tgcattagga 4740
aattaatacg actcactata 4760

<210> SEQ ID NO 19
<211> LENGTH: 4795
<212> TYPE: DNA
<213> ORGANISM: Artificial Sequence
<220> FEATURE:
<223> OTHER INFORMATION: construct pACYC-furA

<400> SEQUENCE: 19
ggggaattgt gagcggataa caattcccct gtagaaataa ttttgtttaa ctttaataag 60
gagatatacc atggataaaa tcaaacaggg cagcgcctct ctggttgtcg gtgaccagca 120
agaaaaacat ccggtggttt cagtgctgct gccggttaat cgtgtcgatc gctttttcat 180
tccggcagtt gaatcgatcc tgacccaaac gctgcaggat tttgaactga tcattatcgc 240
taatggctgt agcaccgaac atctgaacaa aattcgtctg acgtatggtg atcacaatcg 300
tgttcgcatt ctgaacaccg aaatcaaagg cctgccgttt gcgctgaatc tgggcgtgca 360
caacgcccgt ggtctgtata ttgcacgcat ggatgctgat gacatttcta tcccggaacg 420
cctggaaaaa caactgaata cgctggaaca gaacaagaaa attggcgtcg tgagctctgg 480
tgtggacttt attgatgaaa atgaccaggc gatccgtgag ggtaaattcc cggaactgac 540
cgacaaagat catcgtcgcc tgctgccgct gatttgctgt atcgcccacc cgacggttat 600
ggtccgcaaa gaaattatca acaaactggg cggttatagt tttggtagtt tctccgaaga 660
ctacgatctg tggctgcgta ttatgcgcga actgccggaa gttgaatttt atcgtatccc 720
ggaatccctg ctgaaatacc gtcgccatgg caatcaggcc accagttcca aaaacattaa 780
gaaaattcgc gcgtacaact cagccctgaa aattcgtgaa ctgtttctgt cgcgcaaact 840
gaaattcatt atcggtatta tcctgccggc acgtatggtg accctgtggc gcaaatgaga 900
attcgagctc ggcgcgcctg caggtcgaca agcttgcggc cgcataatgc ttaagtcgaa 960
cagaaagtaa tcgtattgta cacggccgca taatcgaaat taatacgact cactataggg 1020
gaattgtgag cggataacaa ttccccatct tagtatatta gttaagtata agaaggagat 1080
atacatatgg cagatctcaa ttggatatcg gccggccacg cgatcgctga cgtcggtacc 1140
ctcgagtctg gtaaagaaac cgctgctgcg aaatttgaac gccagcacat ggactcgtct 1200
actagcgcag cttaattaac ctaggctgct gccaccgctg agcaataact agcataaccc 1260
cttggggcct ctaaacgggt cttgaggggt tttttgctga aacctcaggc atttgagaag 1320
cacacggtca cactgcttcc ggtagtcaat aaaccggtaa accagcaata gacataagcg 1380
gctatttaac gaccctgccc tgaaccgacg accgggtcga atttgctttc gaatttctgc 1440
cattcatccg cttattatca cttattcagg cgtagcacca ggcgtttaag ggcaccaata 1500
actgccttaa aaaaattacg ccccgccctg ccactcatcg cagtactgtt gtaattcatt 1560
aagcattctg ccgacatgga agccatcaca gacggcatga tgaacctgaa tcgccagcgg 1620
catcagcacc ttgtcgcctt gcgtataata tttgcccata gtgaaaacgg gggcgaagaa 1680
gttgtccata ttggccacgt ttaaatcaaa actggtgaaa ctcacccagg gattggctga 1740
gacgaaaaac atattctcaa taaacccttt agggaaatag gccaggtttt caccgtaaca 1800
cgccacatct tgcgaatata tgtgtagaaa ctgccggaaa tcgtcgtggt attcactcca 1860
gagcgatgaa aacgtttcag tttgctcatg gaaaacggtg taacaagggt gaacactatc 1920
ccatatcacc agctcaccgt ctttcattgc catacggaac tccggatgag cattcatcag 1980
gcgggcaaga atgtgaataa aggccggata aaacttgtgc ttatttttct ttacggtctt 2040
taaaaaggcc gtaatatcca gctgaacggt ctggttatag gtacattgag caactgactg 2100
aaatgcctca aaatgttctt tacgatgcca ttgggatata tcaacggtgg tatatccagt 2160
gatttttttc tccattttag cttccttagc tcctgaaaat ctcgataact caaaaaatac 2220
gcccggtagt gatcttattt cattatggtg aaagttggaa cctcttacgt gccgatcaac 2280
gtctcatttt cgccaaaagt tggcccaggg cttcccggta tcaacaggga caccaggatt 2340
tatttattct gcgaagtgat cttccgtcac aggtatttat tcggcgcaaa gtgcgtcggg 2400
tgatgctgcc aacttactga tttagtgtat gatggtgttt ttgaggtgct ccagtggctt 2460
ctgtttctat cagctgtccc tcctgttcag ctactgacgg ggtggtgcgt aacggcaaaa 2520
gcaccgccgg acatcagcgc tagcggagtg tatactggct tactatgttg gcactgatga 2580
gggtgtcagt gaagtgcttc atgtggcagg agaaaaaagg ctgcaccggt gcgtcagcag 2640
aatatgtgat acaggatata ttccgcttcc tcgctcactg actcgctacg ctcggtcgtt 2700
cgactgcggc gagcggaaat ggcttacgaa cggggcggag atttcctgga agatgccagg 2760
aagatactta acagggaagt gagagggccg cggcaaagcc gtttttccat aggctccgcc 2820
cccctgacaa gcatcacgaa atctgacgct caaatcagtg gtggcgaaac ccgacaggac 2880
tataaagata ccaggcgttt ccccctggcgg ctccctcgtg cgctctcctg ttcctgcctt 2940
tcggtttacc ggtgtcattc cgctgttatg gccgcgtttg tctcattcca cgcctgacac 3000
tcagttccgg gtaggcagtt cgctccaagc tggactgtat gcacgaaccc cccgttcagt 3060
ccgaccgctg cgccttatcc ggtaactatc gtcttgagtc caacccggaa agacatgcaa 3120
aagcaccact ggcagcagcc actggtaatt gatttagagg agttagtctt gaagtcatgc 3180
gccggttaag gctaaactga aaggacaagt tttggtgact gcgctcctcc aagccagtta 3240
cctcggttca aagagttggt agctcagaga accttcgaaa aaccgccctg caaggcggtt 3300
ttttcgtttt cagagcaaga gattacgcgc agaccaaaac gatctcaaga agatcatctt 3360
attaatcaga taaaatattt ctagatttca gtgcaattta tctcttcaaa tgtagcacct 3420
gaagtcagcc ccatacgata taagttgtaa ttctcatgtt agtcatgccc cgcgcccacc 3480
ggaaggagct gactgggttg aaggctctca agggcatcgg tcgagatccc ggtgcctaat 3540
gagtgagcta acttacatta attgcgttgc gctcactgcc cgctttccag tcgggaaacc 3600
tgtcgtgcca gctgcattaa tgaatcggcc aacgcgcggg gagaggcggt ttgcgtattg 3660

-continued ggcgccaggg tggtttttct tttcaccagt gagacgggca acagctgatt gcccttcacc 3720
gcctggccct gagagagttg cagcaagcgg tccacgctgg tttgccccag caggcgaaaa 3780
tcctgtttga tggtggttaa cggcgggata taacatgagc tgtcttcggt atcgtcgtat 3840
cccactaccg agatgtccgc accaacgcgc agcccggact cggtaatggc gcgcattgcg 3900
cccagcgcca tctgatcgtt ggcaaccagc atcgcagtgg gaacgatgcc ctcattcagc 3960
atttgcatgg tttgttgaaa accggacatg gcactccagt cgccttcccg ttccgctatc 4020
ggctgaattt gattgcgagt gagatattta tgccagccag ccagacgcag acgcgccgag 4080
acagaactta atgggcccgc taacagcgcg atttgctggt gacccaatgc gaccagatgc 4140
tccacgccca gtcgcgtacc gtcttcatgg gagaaaataa tactgttgat gggtgtctgg 4200
tcagagacat caagaaataa cgccggaaca ttagtgcagg cagcttccac agcaatggca 4260
tcctggtcat ccagcggata gttaatgatc agcccactga cgcgttgcgc gagaagattg 4320
tgcaccgccg ctttacaggc ttcgacgccg cttcgttcta ccatcgacac caccacgctg 4380
gcacccagtt gatcggcgcg agatttaatc gccgcgacaa tttgcgacgg cgcgtgcagg 4440
gccagactgg aggtggcaac gccaatcagc aacgactgtt tgcccgccag ttgttgtgcc 4500
acgcggttgg gaatgtaatt cagctccgcc atcgccgctt ccactttttc ccgcgttttc 4560
gcagaaacgt ggctggcctg gttcaccacg cgggaaacgg tctgataaga gacaccggca 4620
tactctgcga catcgtataa cgttactggt ttcacattca ccaccctgaa ttgactctct 4680
tccgggcgct atcatgccat accgcgaaag gttttgcgcc attcgatggt gtccgggatc 4740
tcgacgctct cccttatgcg actcctgcat taggaaatta atacgactca ctata 4795

<210> SEQ ID NO 20
<211> LENGTH: 6383
<212> TYPE: DNA
<213> ORGANISM: Artificial Sequence
<220> FEATURE:
<223> OTHER INFORMATION: construct pET-PmnagT

<400> SEQUENCE: 20
ggggaattgt gagcggataa caattcccct ctagaaataa ttttgtttaa ctttaagaag 60
gagatatacc atgggcagca gccatcacca tcatcaccac agccaggatc cgaattcgag 120
ctcggcgcgc ctgcaggtcg acaagcttgc ggccgcataa tgcttaagtc gaacagaaag 180
taatcgtatt gtacacggcc gcataatcga aattaatacg actcactata ggggaattgt 240
gagcggataa caattcccca tcttagtata ttagttaagt ataagaagga gatatacata 300
tggaaaataa acctttagtt tcagttttga tttgtgctta taatgtcgag aaatatattg 360
aagaatgtat taatgcagtg attaatcaga catataagaa cttagaaatt attattgtga 420
atgatggttc ttctgataat acttattttc ttttaaaaaa gttagctgaa aaagataatc 480
gtataaaaat attaaatttc aataatcata ttggaataat ttctgcttta aatgaaggtt 540
taaaagagat agctggagaa tatattgctc gaacagattc tgatgatata actaagccag 600
attggattga gaaaatatta acttgtatgc aaaatgatcc taaaatcatc gctatgggat 660
cttatcttac tgtcttgtca gaagaaaata atggtagtgt gcttgctaat catcataaaa 720
ataaagttga atggaaaaat ccattagagc acaaagatat tgttgagaaa atgttatttg 780
gtaatcctat tcataataat tcaatggtta tgagaagtga gatatataca aagtatcact 840
taatttatga tccagattat cattatgctg aagattataa attttggctg gaagttagtc 900
gaattgggaa attagcaaat tatcctgagt cactcgtata ttatagactt caccgaaatc 960

-continued aaacatcttc tattcataat agccaacaag aaataaatgg taaaaaatta cgtttacaag 1020
ctcttaatta ttatttaaaa gatcttggta ttgattatca gttacctgaa aaatttttat 1080
tcaaagatat agcgttattg caagaaatat tttatgaacg aggtatgttt agagaaaata 1140
taataaggcg tatcatctac gaatgttatc tttccttggg agagtataat tataaagata 1200
tttattattt tttaataaat aaaaataact ttctttctat aaaagacaaa tttaaaataa 1260
taaaaaaata tcttcgtcct gataaatatt catctactta ttaggacgtc ggtaccctcg 1320
agtctggtaa agaaaccgct gctgcgaaat ttgaacgcca gcacatggac tcgtctacta 1380
gcgcagctta attaacctag gctgctgcca ccgctgagca ataactagca taaccccttg 1440
gggcctctaa acgggtcttg aggggttttt tgctgaaagg aggaactata tccggattgg 1500
cgaatgggac gcgccctgta gcggcgcatt aagcgcggcg ggtgtggtgg ttacgcgcag 1560
cgtgaccgct acacttgcca gcgccctagc gcccgctcct ttcgctttct tcccttcctt 1620
tctcgccacg ttcgccggct ttccccgtca agctctaaat cgggggctcc ctttagggtt 1680
ccgatttagt gctttacggc acctcgaccc caaaaaactt gattagggtg atggttcacg 1740
tagtgggcca tcgccctgat agacggtttt tcgccctttg acgttggagt ccacgttctt 1800
taatagtgga ctcttgttcc aaactggaac aacactcaac cctatctcgg tctattcttt 1860
tgatttataa gggattttgc cgatttcggc ctattggtta aaaaatgagc tgatttaaca 1920
aaaatttaac gcgaatttta acaaaatatt aacgtttaca atttctggcg gcacgatggc 1980
atgagattat caaaaaggat cttcacctag atccttttaa attaaaaatg aagttttaaa 2040
tcaatctaaa gtatatatga gtaaacttgg tctgacagtt accaatgctt aatcagtgag 2100
gcacctatct cagcgatctg tctatttcgt tcatccatag ttgcctgact ccccgtcgtg 2160
tagataacta cgatacggga gggcttacca tctggcccca gtgctgcaat gataccgcga 2220
gacccacgct caccggctcc agatttatca gcaataaacc agccagccgg aagggccgag 2280
cgcagaagtg gtcctgcaac tttatccgcc tccatccagt ctattaattg ttgccgggaa 2340
gctagagtaa gtagttcgcc agttaatagt ttgcgcaacg ttgttgccat tgctacaggc 2400
atcgtggtgt cacgctcgtc gtttggtatg gcttcattca gctccggttc ccaacgatca 2460
aggcgagtta catgatcccc catgttgtgc aaaaaagcgg ttagctcctt cggtcctccg 2520
atcgttgtca gaagtaagtt ggccgcagtg ttatcactca tggttatggc agcactgcat 2580
aattctctta ctgtcatgcc atccgtaaga tgcttttctg tgactggtga gtactcaacc 2640
aagtcattct gagaatagtg tatgcggcga ccgagttgct cttgcccggc gtcaatacgg 2700
gataataccg cgccacatag cagaacttta aaagtgctca tcattggaaa acgttcttcg 2760
gggcgaaaac tctcaaggat cttaccgctg ttgagatcca gttcgatgta acccactcgt 2820
gcacccaact gatcttcagc atcttttact ttcaccagcg tttctgggtg agcaaaaaca 2880
ggaaggcaaa atgccgcaaa aaagggaata agggcgacac ggaaatgttg aatactcata 2940
ctcttccttt ttcaatcatg attgaagcat ttatcagggt tattgtctca tgagcggata 3000
catatttgaa tgtatttaga aaaataaaca aataggtcat gaccaaaatc ccttaacgtg 3060
agttttcgtt ccactgagcg tcagaccccg tagaaaagat caaaggatct tcttgagatc 3120
ctttttttct gcgcgtaatc tgctgcttgc aaacaaaaaa accaccgcta ccagcggtgg 3180
tttgtttgcc ggatcaagag ctaccaactc tttttccgaa ggtaactggc ttcagcagag 3240
cgcagatacc aaatactgtc cttctagtgt agccgtagtt aggccaccac ttcaagaact 3300

-continued ctgtagcacc gcctacatac ctcgctctgc taatcctgtt accagtggct gctgccagtg 3360
gcgataagtc gtgtcttacc gggttggact caagacgata gttaccggat aaggcgcagc 3420
ggtcgggctg aacggggggt tcgtgcacac agcccagctt ggagcgaacg acctacaccg 3480
aactgagata cctacagcgt gagctatgag aaagcgccac gcttcccgaa gggagaaagg 3540
cggacaggta tccggtaagc ggcagggtcg gaacaggaga gcgcacgagg gagcttccag 3600
ggggaaacgc ctggtatctt tatagtcctg tcgggtttcg ccacctctga cttgagcgtc 3660
gatttttgtg atgctcgtca ggggggcgga gcctatggaa aaacgccagc aacgcggcct 3720
ttttacggtt cctggccttt tgctggcctt ttgctcacat gttctttcct gcgttatccc 3780
ctgattctgt ggataaccgt attaccgcct ttgagtgagc tgataccgct cgccgcagcc 3840
gaacgaccga gcgcagcgag tcagtgagcg aggaagcgga agagcgcctg atgcggtatt 3900
ttctccttac gcatctgtgc ggtatttcac accgcatata tggtgcactc tcagtacaat 3960
ctgctctgat gccgcatagt taagccagta tacactccgc tatcgctacg tgactgggtc 4020
atggctgcgc cccgacaccc gccaacaccc gctgacgcgc cctgacgggc ttgtctgctc 4080
ccggcatccg cttacagaca agctgtgacc gtctccggga gctgcatgtg tcagaggttt 4140
tcaccgtcat caccgaaacg cgcgaggcag ctgcggtaaa gctcatcagc gtggtcgtga 4200
agcgattcac agatgtctgc ctgttcatcc gcgtccagct cgttgagttt ctccagaagc 4260
gttaatgtct ggcttctgat aaagcgggcc atgttaaggg cggttttttc ctgtttggtc 4320
actgatgcct ccgtgtaagg gggatttctg ttcatggggg taatgatacc gatgaaacga 4380
gagaggatgc tcacgatacg ggttactgat gatgaacatg cccggttact ggaacgttgt 4440
gagggtaaac aactggcggt atggatgcgg cgggaccaga gaaaaatcac tcagggtcaa 4500
tgccagcgct tcgttaatac agatgtaggt gttccacagg gtagccagca gcatcctgcg 4560
atgcagatcc ggaacataat ggtgcagggc gctgacttcc gcgtttccag actttacgaa 4620
acacggaaac cgaagaccat tcatgttgtt gctcaggtcg cagacgtttt gcagcagcag 4680
tcgcttcacg ttcgctcgcg tatcggtgat tcattctgct aaccagtaag gcaaccccgc 4740
cagcctagcc gggtcctcaa cgacaggagc acgatcatgc tagtcatgcc ccgcgcccac 4800
cggaaggagc tgactgggtt gaaggctctc aagggcatcg gtcgagatcc cggtgcctaa 4860
tgagtgagct aacttacatt aattgcgttg cgctcactgc ccgctttcca gtcgggaaac 4920
ctgtcgtgcc agctgcatta atgaatcggc caacgcgcgg ggagaggcgg tttgcgtatt 4980
gggcgccagg gtggtttttc ttttcaccag tgagacgggc aacagctgat tgcccttcac 5040
cgcctggccc tgagagagtt gcagcaagcg gtccacgctg gtttgcccca gcaggcgaaa 5100
atcctgtttg atggtggtta acggcgggat ataacatgag ctgtcttcgg tatcgtcgta 5160
tcccactacc gagatgtccg caccaacgcg cagcccggac tcggtaatgg cgcgcattgc 5220
gcccagcgcc atctgatcgt tggcaaccag catcgcagtg ggaacgatgc cctcattcag 5280
catttgcatg gtttgttgaa aaccggacat ggcactccag tcgccttccc gttccgctat 5340
cggctgaatt tgattgcgag tgagatattt atgccagcca gccagacgca gacgcgccga 5400
gacagaactt aatgggcccg ctaacagcgc gatttgctgg tgacccaatg cgaccagatg 5460
ctccacgccc agtcgcgtac cgtcttcatg ggagaaaata atactgttga tgggtgtctg 5520
gtcagagaca tcaagaaata acgccggaac attagtgcag gcagcttcca cagcaatggc 5580
atcctggtca tccagcggat agttaatgat cagcccactg acgcgttgcg cgagaagatt 5640
gtgcaccgcc gctttacagg cttcgacgcc gcttcgttct accatcgaca ccaccacgct 5700
ggcacccagt tgatcggcgc gagatttaat cgccgcgaca atttgcgacg gcgcgtgcag 5760
ggccagactg gaggtggcaa cgccaatcag caacgactgt ttgcccgcca gttgttgtgc 5820
cacgcggttg ggaatgtaat tcagctccgc catcgccgct tccacttttt cccgcgtttt 5880
cgcagaaacg tggctggcct ggttcaccac gcgggaaacg gtctgataag agacaccggc 5940
atactctgcg acatcgtata acgttactgg tttcacattc accaccctga attgactctc 6000
ttccgggcgc tatcatgcca taccgcgaaa ggttttgcgc cattcgatgg tgtccgggat 6060
ctcgacgctc tcccttatgc gactcctgca ttaggaagca gcccagtagt aggttgaggc 6120
cgttgagcac cgccgccgca aggaatggtg catgcaagga gatggcgccc aacagtcccc 6180
cggccacggg gcctgccacc atacccacgc cgaaacaagc gctcatgagc ccgaagtggc 6240
gagcccgatc ttccccatcg gtgatgtcgg cgatataggc gccagcaacc gcacctgtgg 6300
cgccggtgat gccggccacg atgcgtccgg cgtagaggat cgagatcgat ctcgatcccg 6360
cgaaattaat acgactcact ata 6383

<210> SEQ ID NO 21
<211> LENGTH: 6711
<212> TYPE: DNA
<213> ORGANISM: Artificial Sequence
<220> FEATURE:
<223> OTHER INFORMATION: construct pINT-yjhB

<400> SEQUENCE: 21
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accatatgcg gtgtgaaata ccgcacagat gcgtaaggag aaaataccgc atcaggcgcc 240
attcgccatt caggctgcgc aactgttggg aagggcgatc ggtgcgggcc tcttcgctat 300
tacgccagct ggcgaaaggg ggatgtgctg caaggcgatt aagttgggta acgccagggt 360
tttcccagtc acgacgttgt aaaacgacgg ccagtgaatt cgaagatcct ttgatctttt 420
ctacggggtc tgacgctcag tggaacgaaa actcacgtta agggattttg gtcatgagat 480
tatcaaaaag gatcttcacc tagatccttt taaactagtg aagttaccat cacggaaaaa 540
ggttatgctg cttttaagac ccactttcac atttaagttg tttttctaat ccgcatatga 600
tcaattcaag gccgaataag aaggctggct ctgcaccttg gtgatcaaat aattcgatag 660
cttgtcgtaa taatggcggc atactatcag tagtaggtgt ttccctttct tctttagcga 720
cttgatgctc ttgatcttcc aatacgcaac ctaaagtaaa atgccccact gcgctgagtg 780
catataatgc attctctagt gaaaaacctt gttggcataa aaaggctaat tgattttcga 840
gagtttcata ctgtttttct gtaggccgtg tacctaaatg tacttttgct ccatcgcgat 900
gacttagtaa agcacatcta aaacttttag cgttattacg taaaaaatct tgccagcttt 960
ccccttctaa agggcaaaag tgagtatggt gcctatctaa catctcaatg gctaaggcgt 1020
cgagcaaagc ccgcttattt tttacatgcc aatacaatgt aggctgctct acacctagct 1080
tctgggcgag tttacgggtt gttaaacctt cgattccgac ctcattaagc agctctaatg 1140
cgctgttaat cactttactt ttatctaaac gagacatact cttccttttt caatattatt 1200
gaagcattta tcagggttat tgtctcatga gcggatacat atttgaatgt atttagaaaa 1260
ataaacaaat aggggttccg cgcacatttc cccgaaaagt gccacctgaa attggccaga 1320

-continued tgattaattc ctaattttg ttgacactct atcattgata gagttatttt accactccct 1380
atcagtgata gagaaaagtg aaatgaatag ttcgacaaaa atctagaaat aattttgttt 1440
aactttaaga aggagatata caagagctcg agtcgaagga gatagaacca tggcaacagc 1500
atggtataaa caagttaatc caccacaacg gaaagctctt ttttccgcat ggcttggata 1560
tgtatttgat ggctttgatt ttatgatgat attttacatt cttcatatta taaaagcaga 1620
tcttggcatt acggatattc aggctacttt aatagggaca gtggccttca tagccagacc 1680
tattggaggt ggtttttttg gtgccatggc tgataaatat ggtcgtaagc caatgatgat 1740
gtgggcaatt ttcatttact cagtcggaac aggccttagc ggtattgcta caaacttata 1800
tatgctcgca gtttgccgtt ttattgttgg cttagggatg tctggtgaat atgcatgtgc 1860
ttcaacttat gcggtagaaa gttggcctaa aaatcttcaa tctaaagcta gtgctttttt 1920
ggtaagtggt ttttctgttg gaaatattat tgcggcacaa ataatccctc agtttgctga 1980
agtatatgga tggagaaact ctttttttat aggcctgtta ccagttttac tagttctttg 2040
gatcagaaaa agtgctccag aaagtcagga gtggattgaa gataaatata aggataaatc 2100
aacatttttg tctgtcttca gaaaaccaca tctttcaatc tctatgatcg ttttcctcgt 2160
ctgtttttgt ctatttggtg caaactggcc gataaacgga ctacttcctt cctacctggc 2220
agataatgga gttaatacag tggtcatttc aactctgatg acaatagcag gtttaggaac 2280
actgacaggt acaatatttt ttggttttgt tggtgataag attggtgtaa aaaaagcctt 2340
tgtagtcggt ctaataactt catttatttt cctttgtcct cttttttta tttctgtgaa 2400
aaactcttct cttataggat tatgtctctt tggattaatg tttacaaatt taggtattgc 2460
agggttggtt ccaaaattta tatatgatta ctttccaaca aaattaagag gattagggac 2520
cggtcttatt tataacttag gggcaactgg aggaatggcc gcacctgtat tagctacata 2580
catttcagga tattatggct taggtgtttc attattcatt gttacggttg cattctctgc 2640
cttattaatt ttgttagttg gttttgatat tccaggtaaa atttataaac tatccgtggc 2700
taaatgataa atcgatacta gcataacccc ttggggcctc taaacgcgtc gacacgcaaa 2760
aaggccatcc gtcaggatgg ccttctgctt aatttgatgc ctggcagttt atggcgggcg 2820
tcctgcccgc caccctccgg gccgttgctt cgcaacgttc aaatccgctc ccggcggatt 2880
tgtcctactc aggagagcgt tcaccgacaa acaacagata aaacgaaagg cccagtcttt 2940
cgactgagcc tttcgtttta tttgatgcct ggcagttccc tactctcgca tggggagacc 3000
ccacactacc atcatgtatg aatatcctcc ttagttccta ttccgaagtt cctattctct 3060
agaaagtata ggaacttcgg cgcgtcctac ctgtgacgga agatcacttc gcagaataaa 3120
taaatcctgg tgtccctgtt gataccggga agccctgggc caacttttgg cgaaaatgag 3180
acgttgatcg gcacgtaaga ggttccaact ttcaccataa tgaaataaga tcactaccgg 3240
gcgtattttt tgagttgtcg agattttcag gagctaagga agctaaaatg gagaaaaaaa 3300
tcactggata taccaccgtt gatatatccc aatggcatcg taaagaacat tttgaggcat 3360
ttcagtcagt tgctcaatgt acctataacc agaccgttca gctggatatt acggcctttt 3420
taaagaccgt aaagaaaaat aagcacaagt tttatccggc ctttattcac attcttgccc 3480
gcctgatgaa tgctcatccg gaattacgta tggcaatgaa agacggtgag ctggtgatat 3540
gggatagtgt tcacccttgt tacaccgttt tccatgagca aactgaaacg ttttcatcgc 3600
tctggagtga ataccacgac gatttccggc agtttctaca catatattcg caagatgtgg 3660
cgtgttacgg tgaaaacctg gcctatttcc ctaaagggtt tattgagaat atgtttttcg 3720

-continued

```
tctcagccaa tccctgggtg agtttcacca gttttgattt aaacgtggcc aatatggaca   3780
acttcttcgc ccccgttttc accatgggca aatattatac gcaaggcgac aaggtgctga   3840
tgccgctggc gattcaggtt catcatgccg tttgtgatgg cttccatgtc ggcagatgct   3900
taatgaatac aacagtactg cgatgagtgg cagggcgggg cgtaaggcgc gccatttaaa   3960
tgaagttcct attccgaagt tcctattctc tagaaagtat aggaacttcg aagcagctcc   4020
agcctacaca atcgctcaag acgtgtaatg ctgcaatctg catgcaagct tggcactggc   4080
cacgcaaaaa ggccatccgt caggatggcc ttctgcttaa tttgatgcct ggcagtttat   4140
ggcgggcgtc ctgcccgcca ccctccgggc cgttgcttcg caacgttcaa atccgctccc   4200
ggcggatttg tcctactcag gagagcgttc accgacaaac aacagataaa acgaaaggcc   4260
cagtctttcg actgagcctt tcgttttatt tgatgcctgg cagttcccta ctctcgcatg   4320
gggagacccc acactaccat cggggggcca tcgatgcagg tggcactttt cggggaaatg   4380
tgcgcggaac ccctatttgt ttatttttct aaatacattc aaatatgtat ccgctcatga   4440
gacaataacc ctgctgcaga ggcctgcatg caagcttggc gtaatcatgg tcatagctgt   4500
ttcctgtgtg aaattgttat ccgctcacaa ttccacacaa catacgagcc ggaagcataa   4560
agtgtaaagc ctggggtgcc taatgagtga gctaactcac attaattgcg ttgcgctcac   4620
tgcccgcttt ccagtcggga aacctgtcgt gccagctgca ttaatgaatc ggccaacgcg   4680
cggggagagg cggtttgcgt attgggcgct cttccgcttc ctcgctcact gactcgctgc   4740
gctcggtcgt tcggctgcgg cgagcggtat cagctcactc aaaggcggta atacggttat   4800
ccacagaatc aggggataac gcaggaaaga acatgtgagc aaaaggccag caaaaggcca   4860
ggaaccgtaa aaaggccgcg ttgctggcgt ttttccatag gctccgcccc cctgacgagc   4920
atcacaaaaa tcgacgctca agtcagaggt ggcgaaaccc gacaggacta taaagatacc   4980
aggcgtttcc ccctggaagc tccctcgtgc gctctcctgt tccgaccctg ccgcttaccg   5040
gatacctgtc cgcctttctc ccttcgggaa gcgtggcgct ttctcatagc tcacgctgta   5100
ggtatctcag ttcggtgtag gtcgttcgct ccaagctggg ctgtgtgcac gaaccccccg   5160
ttcagcccga ccgctgcgcc ttatccggta actatcgtct tgagtccaac ccggtaagac   5220
acgacttatc gccactggca gcagccactg gtaacaggat tagcagagcg aggtatgtag   5280
gcggtgctac agagttcttg aagtggtggc ctaactacgg ctacactaga agaacagtat   5340
ttggtatctg cgctctgctg aagccagtta ccttcggaaa aagagttggt agctcttgat   5400
ccggcaaaca aaccaccgct ggtagcggtg gtttttttgt ttgcaagcag cagattacgc   5460
gcagaaaaaa aggatctcaa gaagatcctt tgatcttttc tacggggtct gacgctcagt   5520
ggaacgaaaa ctcacgttaa gggattttgg tcatgagatt atcaaaaagg atcttcacct   5580
agatcctttt aaattaaaaa tgaagtttta aatcaatcta aagtatatat gagtaaactt   5640
ggtctgacag ttaccaatgc ttaatcagtg aggcacctat ctcagcgatc tgtctatttc   5700
gttcatccat agttgcctga ctccccgtcg tgtagataac tacgatacgg gagggcttac   5760
catctggccc cagtgctgca atgataccgc gagacccacg ctcaccggct ccagatttat   5820
cagcaataaa ccagccagcc ggaagggccg agcgcagaag tggtcctgca actttatccg   5880
cctccatcca gtctattaat tgttgccggg aagctagagt aagtagttcg ccagttaata   5940
gtttgcgcaa cgttgttgcc attgctacag gcatcgtggt gtcacgctcg tcgtttggta   6000
tggcttcatt cagctccggt tcccaacgat caaggcgagt tacatgatcc cccatgttgt   6060
```

gcaaaaaagc ggttagctcc ttcggtcctc cgatcgttgt cagaagtaag ttggccgcag 6120
tgttatcact catggttatg gcagcactgc ataattctct tactgtcatg ccatccgtaa 6180
gatgcttttc tgtgactggt gagtactcaa ccaagtcatt ctgagaatag tgtatgcggc 6240
gaccgagttg ctcttgcccg gcgtcaatac gggataatac cgcgccacat agcagaactt 6300
taaaagtgct catcattgga aaacgttctt cggggcgaaa actctcaagg atcttaccgc 6360
tgttgagatc cagttcgatg taacccactc gtgcacccaa ctgatcttca gcatctttta 6420
ctttcaccag cgtttctggg tgagcaaaaa caggaaggca aaatgccgca aaaaagggaa 6480
taagggcgac acggaaatgt tgaatactca tactcttcct ttttcaatat tattgaagca 6540
tttatcaggg ttattgtctc atgagcggat acatatttga atgtatttag aaaaataaac 6600
aaataggggt tccgcgcaca tttccccgaa aagtgccacc tgacgtctaa gaaaccatta 6660
ttatcatgac attaacctat aaaaataggc gtatcacgag gccctttcgt c 6711

<210> SEQ ID NO 22
<211> LENGTH: 6867
<212> TYPE: DNA
<213> ORGANISM: Artificial Sequence
<220> FEATURE:
<223> OTHER INFORMATION: construct pINT-yebQ

<400> SEQUENCE: 22
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accatatgcg gtgtgaaata ccgcacagat gcgtaaggag aaaataccgc atcaggcgcc 240
attcgccatt caggctgcgc aactgttggg aagggcgatc ggtgcgggcc tcttcgctat 300
tacgccagct ggcgaaaggg ggatgtgctg caaggcgatt aagttgggta acgccagggt 360
tttcccagtc acgacgttgt aaaacgacgg ccagtgaatt cgaagatcct ttgatctttt 420
ctacggggtc tgacgctcag tggaacgaaa actcacgtta agggattttg gtcatgagat 480
tatcaaaaag gatcttcacc tagatccttt taaactagtg aagttaccat cacggaaaaa 540
ggttatgctg cttttaagac ccactttcac atttaagttg tttttctaat ccgcatatga 600
tcaattcaag gccgaataag aaggctggct ctgcaccttg gtgatcaaat aattcgatag 660
cttgtcgtaa taatggcggc atactatcag tagtaggtgt ttccctttct tctttagcga 720
cttgatgctc ttgatcttcc aatacgcaac ctaaagtaaa atgccccact gcgctgagtg 780
catataatgc attctctagt gaaaaacctt gttggcataa aaaggctaat tgattttcga 840
gagtttcata ctgtttttct gtaggccgtg tacctaaatg tacttttgct ccatcgcgat 900
gacttagtaa agcacatcta aaacttttag cgttattacg taaaaaatct tgccagcttt 960
ccccttctaa agggcaaaag tgagtatggt gcctatctaa catctcaatg gctaaggcgt 1020
cgagcaaagc ccgcttattt tttacatgcc aatacaatgt aggctgctct acacctagct 1080
tctgggcgag tttacgggtt gttaaacctt cgattccgac ctcattaagc agctctaatg 1140
cgctgttaat cactttactt ttatctaaac gagacatact cttccttttt caatattatt 1200
gaagcattta tcagggttat tgtctcatga gcggatacat atttgaatgt atttagaaaa 1260
ataaacaaat aggggttccg cgcacatttc cccgaaaagt gccacctgaa attggccaga 1320
tgattaattc ctaatttttg ttgacactct atcattgata gagttatttt accactccct 1380
atcagtgata gagaaaagtg aaatgaatag ttcgacaaaa atctagaaat aattttgttt 1440

-continued aactttaaga aggagatata caagagctcg agtcgaagga gatagaacca tgccaaaagt 1500
tcaggccgac ggcctgccat tgccccagcg atacggtgcg atattaacca ttgtgattgg 1560
tatttcgatg gccgtccttg acggcgcaat cgccaacgtc gccctgccaa caatcgccac 1620
ggaccttcat gccacgccag ccagttccat ctgggtagtg aacgcctatc aaatcgccat 1680
tgtcatctcc ctgctctcgt tttcgtttct gggcgatatg tttggctatc gacgtattta 1740
taaatgcggt ctggtcgttt ttctgttgtc ttcactgttc tgcgcccttt ctgattcgct 1800
gcaaatgctc acccttgcgc gtgtcataca aggtttcggc ggtgcagcgt tgatgagcgt 1860
taataccgca cttatccgcc tgatctatcc acaacgtttt ctgggtagag ggatgggcat 1920
aaactcgttt attgttgccg tctcttctgc tgccgggccg acaattgctg cagcaatcct 1980
ctccatcgca tcctggaaat ggttattttt aatcaacgta ccgttaggta ttatcgccct 2040
gcttctggcg atgcgttttc tgccacccaa tggttctcgc gccagtaaac cccgtttcga 2100
cctgcccagc gccgtgatga acgcgttaac cttcggcctg cttatcactg cgttgagtgg 2160
tttcgctcag gggcaatcgc tgacgttaat tgctgcggaa ctggtggtaa tggttgttgt 2220
tggtattttc tttattcgcc gccagctttc tcttcccgta ccgctgctac cggtggattt 2280
actgcgtatc ccgctgtttt cactttctat ttgcacatct gtttgctctt tctgcgcaca 2340
aatgctggca atggtttccc tgccctttta cctgcaaacc gtgctcgggc gtagtgaagt 2400
cgaaacaggt ttacttctga caccgtggcc gttagcaacg atggtgatgg ctccgctggc 2460
aggctatttg attgaacgcg tacatgcagg attgctgggg gctttagggt tgttcatcat 2520
ggctgcgggg ctttttttccc tggttctgct gcccgcgtca cctgcggata tcaatattat 2580
ctggccgatg atcttatgtg gtgctggatt tggcttattc cagtcaccca ataaccacac 2640
cattattacc tccgcgcctc gcgaacgtag cggtggagcc agtggcatgt taggaacggc 2700
tcgtctactg ggtcagagta gcggcgcggc gctggtggcg ctgatgctaa atcagtttgg 2760
agataatggt acacacgtct cgctgatggc tgcggctatt ctggcagtga ttgctgcctg 2820
tgtcagtggt ttacgtatca ctcagccacg atccagggca taataaatcg atactagcat 2880
aaccccttgg ggcctctaaa cgcgtcgaca cgcaaaaagg ccatccgtca ggatggcctt 2940
ctgcttaatt tgatgcctgg cagtttatgg cgggcgtcct gcccgccacc ctccgggccg 3000
ttgcttcgca acgttcaaat ccgctcccgg cggatttgtc ctactcagga gagcgttcac 3060
cgacaaacaa cagataaaac gaaaggccca gtctttcgac tgagcctttc gttttatttg 3120
atgcctggca gttccctact ctcgcatggg gagaccccac actaccatca tgtatgaata 3180
tcctccttag ttcctattcc gaagttccta ttctctagaa agtataggaa cttcggcgcg 3240
tcctacctgt gacggaagat cacttcgcag aataaataaa tcctggtgtc cctgttgata 3300
ccgggaagcc ctgggccaac ttttggcgaa aatgagacgt tgatcggcac gtaagaggtt 3360
ccaactttca ccataatgaa ataagatcac taccgggcgt atttttttgag ttgtcgagat 3420 tttcaggagc taaggaagct aaaatggaga aaaaaatcac tggatatacc accgttgata 3480
tatcccaatg gcatcgtaaa gaacattttg aggcatttca gtcagttgct caatgtacct 3540
ataaccagac cgttcagctg gatattacgg cctttttaaa gaccgtaaag aaaaataagc 3600
acaagtttta tccggccttt attcacattc ttgcccgcct gatgaatgct catccggaat 3660
tacgtatggc aatgaaagac ggtgagctgg tgatatggga tagtgttcac ccttgttaca 3720
ccgttttcca tgagcaaact gaaacgtttt catcgctctg gagtgaatac cacgacgatt 3780

-continued tccggcagtt tctacacata tattcgcaag atgtggcgtg ttacggtgaa aacctggcct 3840
atttccctaa agggtttatt gagaatatgt ttttcgtctc agccaatccc tgggtgagtt 3900
tcaccagttt tgatttaaac gtggccaata tggacaactt cttcgccccc gttttcacca 3960
tgggcaaata ttatacgcaa ggcgacaagg tgctgatgcc gctggcgatt caggttcatc 4020
atgccgtttg tgatggcttc catgtcggca gatgcttaat gaatacaaca gtactgcgat 4080
gagtggcagg gcggggcgta aggcgcgcca tttaaatgaa gttcctattc cgaagttcct 4140
attctctaga aagtatagga acttcgaagc agctccagcc tacacaatcg ctcaagacgt 4200
gtaatgctgc aatctgcatg caagcttggc actggccacg caaaaaggcc atccgtcagg 4260
atggccttct gcttaatttg atgcctggca gtttatggcg ggcgtcctgc ccgccaccct 4320
ccgggccgtt gcttcgcaac gttcaaatcc gctcccggcg gatttgtcct actcaggaga 4380
gcgttcaccg acaaacaaca gataaaacga aaggcccagt ctttcgactg agcctttcgt 4440
tttatttgat gcctggcagt tccctactct cgcatgggga gaccccacac taccatcggg 4500
gggccatcga tgcaggtggc acttttcggg gaaatgtgcg cggaacccct atttgtttat 4560
ttttctaaat acattcaaat atgtatccgc tcatgagaca ataaccctgc tgcagaggcc 4620
tgcatgcaag cttggcgtaa tcatggtcat agctgtttcc tgtgtgaaat tgttatccgc 4680
tcacaattcc acacaacata cgagccggaa gcataaagtg taaagcctgg ggtgcctaat 4740
gagtgagcta actcacatta attgcgttgc gctcactgcc cgctttccag tcgggaaacc 4800
tgtcgtgcca gctgcattaa tgaatcggcc aacgcgcggg gagaggcggt ttgcgtattg 4860
ggcgctcttc cgcttcctcg ctcactgact cgctgcgctc ggtcgttcgg ctgcggcgag 4920
cggtatcagc tcactcaaag gcggtaatac ggttatccac agaatcaggg gataacgcag 4980
gaaagaacat gtgagcaaaa ggccagcaaa aggccaggaa ccgtaaaaag gccgcgttgc 5040
tggcgttttt ccataggctc cgcccccctg acgagcatca caaaaatcga cgctcaagtc 5100
agaggtggcg aaacccgaca ggactataaa gataccaggc gtttccccct ggaagctccc 5160
tcgtgcgctc tcctgttccg accctgccgc ttaccggata cctgtccgcc tttctccctt 5220
cgggaagcgt ggcgctttct catagctcac gctgtaggta tctcagttcg gtgtaggtcg 5280
ttcgctccaa gctgggctgt gtgcacgaac cccccgttca gcccgaccgc tgcgccttat 5340
ccggtaacta tcgtcttgag tccaacccgg taagacacga cttatcgcca ctggcagcag 5400
ccactggtaa caggattagc agagcgaggt atgtaggcgg tgctacagag ttcttgaagt 5460
ggtggcctaa ctacggctac actagaagaa cagtatttgg tatctgcgct ctgctgaagc 5520
cagttacctt cggaaaaaga gttggtagct cttgatccgg caaacaaacc accgctggta 5580
gcggtggttt ttttgtttgc aagcagcaga ttacgcgcag aaaaaaagga tctcaagaag 5640
atcctttgat cttttctacg gggtctgacg ctcagtggaa cgaaaactca cgttaaggga 5700
ttttggtcat gagattatca aaaaggatct tcacctagat ccttttaaat taaaaatgaa 5760
gttttaaatc aatctaaagt atatatgagt aaacttggtc tgacagttac caatgcttaa 5820
tcagtgaggc acctatctca gcgatctgtc tatttcgttc atccatagtt gcctgactcc 5880
ccgtcgtgta gataactacg atacgggagg gcttaccatc tggccccagt gctgcaatga 5940
taccgcgaga cccacgctca ccggctccag atttatcagc aataaaccag ccagccggaa 6000
gggccgagcg cagaagtggt cctgcaactt tatccgcctc catccagtct attaattgtt 6060
gccgggaagc tagagtaagt agttcgccag ttaatagttt gcgcaacgtt gttgccattg 6120
ctacaggcat cgtggtgtca cgctcgtcgt ttggtatggc ttcattcagc tccggttccc 6180
aacgatcaag gcgagttaca tgatccccca tgttgtgcaa aaaagcggtt agctccttcg 6240
gtcctccgat cgttgtcaga agtaagttgg ccgcagtgtt atcactcatg gttatggcag 6300
cactgcataa ttctcttact gtcatgccat ccgtaagatg cttttctgtg actggtgagt 6360
actcaaccaa gtcattctga gaatagtgta tgcggcgacc gagttgctct tgcccggcgt 6420
caatacggga taataccgcg ccacatagca gaactttaaa agtgctcatc attggaaaac 6480
gttcttcggg gcgaaaactc tcaaggatct taccgctgtt gagatccagt tcgatgtaac 6540
ccactcgtgc acccaactga tcttcagcat cttttacttt caccagcgtt tctgggtgag 6600
caaaaacagg aaggcaaaat gccgcaaaaa agggaataag ggcgacacgg aaatgttgaa 6660
tactcatact cttccttttt caatattatt gaagcattta tcagggttat tgtctcatga 6720
gcggatacat atttgaatgt atttagaaaa ataaacaaat aggggttccg cgcacatttc 6780
cccgaaaagt gccacctgac gtctaagaaa ccattattat catgacatta acctataaaa 6840
ataggcgtat cacgaggccc tttcgtc 6867

<210> SEQ ID NO 23
<211> LENGTH: 6768
<212> TYPE: DNA
<213> ORGANISM: Artificial Sequence
<220> FEATURE:
<223> OTHER INFORMATION: construct pINT-proP

<400> SEQUENCE: 23
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accatatgcg gtgtgaaata ccgcacagat gcgtaaggag aaaataccgc atcaggcgcc 240
attcgccatt caggctgcgc aactgttggg aagggcgatc ggtgcgggcc tcttcgctat 300
tacgccagct ggcgaaaggg ggatgtgctg caaggcgatt aagttgggta acgccagggt 360
tttcccagtc acgacgttgt aaaacgacgg ccagtgaatt cgaagatcct ttgatctttt 420
ctacggggtc tgacgctcag tggaacgaaa actcacgtta agggattttg gtcatgagat 480
tatcaaaaag gatcttcacc tagatccttt taaactagtg aagttaccat cacggaaaaa 540
ggttatgctg cttttaagac ccactttcac atttaagttg tttttctaat ccgcatatga 600
tcaattcaag gccgaataag aaggctggct ctgcaccttg gtgatcaaat aattcgatag 660
cttgtcgtaa taatggcggc atactatcag tagtaggtgt ttccctttct tctttagcga 720
cttgatgctc ttgatcttcc aatacgcaac ctaaagtaaa atgccccact gcgctgagtg 780
catataatgc attctctagt gaaaaacctt gttggcataa aaaggctaat tgattttcga 840
gagtttcata ctgtttttct gtaggccgtg tacctaaatg tacttttgct ccatcgcgat 900
gacttagtaa agcacatcta aaacttttag cgttattacg taaaaaatct tgccagcttt 960
ccccttctaa agggcaaaag tgagtatggt gcctatctaa catctcaatg gctaaggcgt 1020
cgagcaaagc ccgcttattt tttacatgcc aatacaatgt aggctgctct acacctagct 1080
tctgggcgag tttacgggtt gttaaacctt cgattccgac ctcattaagc agctctaatg 1140
cgctgttaat cactttactt ttatctaaac gagacatact cttccttttt caatattatt 1200
gaagcattta tcagggttat tgtctcatga gcggatacat atttgaatgt atttagaaaa 1260
ataaacaaat aggggttccg cgcacatttc cccgaaaagt gccacctgaa attggccaga 1320

-continued

```
tgattaattc ctaattttttg ttgacactct atcattgata gagttatttt accactccct   1380
atcagtgata gagaaaagtg aaatgaatag ttcgacaaaa atctagaaat aattttgttt   1440
aactttaaga aggagatata caagagctcg agtcgaagga gatagaacca tgccgaacaa   1500
agctgaaacc tccccggcga aactgcgtct gaaagccttc ctgaaacgta tcaagattat   1560
gaacaccacc gaaaacagca aacagaagcc ggttaacgtg gttgcatttg ctttcctgct   1620
gaccgcgttt ctgacgggta tcgccagctc tttccaaacc ccgacgctga gcctgtttct   1680
ggcgcaggaa attcaagtct ctccgtttat ggtgggcatg ttctatacct caaatgcagt   1740
gctgggcatc gttctgtcgc agattctggc taaatacagt gattcccaag atgaccgtcg   1800
caagattatc attttctgca gtctgctggc gatcggcggt tgtatcacct tcgcctacaa   1860
ccgtaactac tacgtgctga tgttttttcgc gacgttcctg ctgtccctgg gtagttccgc   1920
aaacccgcag gcatttgcac tggcacgtga atatgcagac tacaccaaac gcgaagctat   1980
catgtttacc acgattatgc gcacgcagat cagcctggca tggattgttg gcccgccgct   2040
gtcattctcg attgcgctgg gctggggttt tgaatatatg tacatggtcg cggcctcagc   2100
atttctgctg tgcgctatca ttgctaaagc gctgctgccg tatgtgccgc gtaaagccgt   2160
cgtgccgctg accaagccgg atgaagttgc gggtctgccg gccaaaaata aaaagcagag   2220
tgacaagcaa tccatccgcc tgctgtttat tacgtgcttc ctgatgtgga gttgtaacgg   2280
catgtatctg atctccatgc cgctgcatgt tattaatgaa ctgcacctga gtgaacgtct   2340
ggcgggcatt ctgatgggta ccgcagctgg cctggaaatc ccggtgatgc tgattgccgg   2400
ctatctgacc aaatacctga cgaaaaagtc tctgatcctg accgccctgt tcatgggtct   2460
gtttttctat attggcatgc tgtttgcaga acagacgtgg caactggtcg ccctgcaggc   2520
atttaacgct atcttcattg gtatcattgc gaccctgggc atggtgtact ttcaagatct   2580
gatgccgggc aaaatgggtt cagccaccac gctgttctcg aacgcggcca aatcatcgtg   2640
gatcgttgca ggtccgtttg tcggcatcat tgctcagatt tggaattata gctctgtgtt   2700
ctacatcagc attgttctgg tcgcggtgtc tctgtttagc atgtctaaag ttaagagcgt   2760
ctaataaatc gatactagca taaccccttg gggcctctaa acgcgtcgac acgcaaaaag   2820
gccatccgtc aggatggcct tctgcttaat ttgatgcctg gcagtttatg gcgggcgtcc   2880
tgcccgccac cctccgggcc gttgcttcgc aacgttcaaa tccgctcccg gcggatttgt   2940
cctactcagg agagcgttca ccgacaaaca acagataaaa cgaaaggccc agtctttcga   3000
ctgagccttt cgttttattt gatgcctggc agttccctac tctcgcatgg ggagacccca   3060
cactaccatc atgtatgaat atcctcctta gttcctattc cgaagttcct attctctaga   3120
aagtatagga acttcggcgc gtcctacctg tgacggaaga tcacttcgca gaataaataa   3180
atcctggtgt ccctgttgat accgggaagc cctgggccaa cttttggcga aaatgagacg   3240
ttgatcggca cgtaagaggt tccaactttc accataatga aataagatca ctaccgggcg   3300
tattttttga gttgtcgaga ttttcaggag ctaaggaagc taaaatggag aaaaaaatca   3360
ctggatatac caccgttgat atatcccaat ggcatcgtaa agaacatttt gaggcatttc   3420
agtcagttgc tcaatgtacc tataaccaga ccgttcagct ggatattacg gcctttttaa   3480
agaccgtaaa gaaaaataag cacaagtttt atccggcctt tattcacatt cttgcccgcc   3540
tgatgaatgc tcatccggaa ttacgtatgg caatgaaaga cggtgagctg gtgatatggg   3600
atagtgttca cccttgttac accgttttcc atgagcaaac tgaaacgttt tcatcgctct   3660
ggagtgaata ccacgacgat ttccggcagt ttctacacat atattcgcaa gatgtggcgt   3720
```

-continued gttacggtga aaacctggcc tatttcccta aagggtttat tgagaatatg tttttcgtct 3780
cagccaatcc ctgggtgagt ttcaccagtt ttgatttaaa cgtggccaat atggacaact 3840
tcttcgcccc cgttttcacc atgggcaaat attatacgca aggcgacaag gtgctgatgc 3900
cgctggcgat tcaggttcat catgccgttt gtgatggctt ccatgtcggc agatgcttaa 3960
tgaatacaac agtactgcga tgagtggcag ggcggggcgt aaggcgcgcc atttaaatga 4020
agttcctatt ccgaagttcc tattctctag aaagtatagg aacttcgaag cagctccagc 4080
ctacacaatc gctcaagacg tgtaatgctg caatctgcat gcaagcttgg cactggccac 4140
gcaaaaaggc catccgtcag gatggccttc tgcttaattt gatgcctggc agtttatggc 4200
gggcgtcctg cccgccaccc tccgggccgt tgcttcgcaa cgttcaaatc cgctcccggc 4260
ggatttgtcc tactcaggag agcgttcacc gacaaacaac agataaaacg aaaggcccag 4320
tctttcgact gagcctttcg ttttatttga tgcctggcag ttccctactc tcgcatgggg 4380
agaccccaca ctaccatcgg ggggccatcg atgcaggtgg cacttttcgg ggaaatgtgc 4440
gcggaacccc tatttgttta tttttctaaa tacattcaaa tatgtatccg ctcatgagac 4500
aataaccctg ctgcagaggc ctgcatgcaa gcttggcgta atcatggtca tagctgtttc 4560
ctgtgtgaaa ttgttatccg ctcacaattc cacacaacat acgagccgga agcataaagt 4620
gtaaagcctg gggtgcctaa tgagtgagct aactcacatt aattgcgttg cgctcactgc 4680
ccgctttcca gtcgggaaac ctgtcgtgcc agctgcatta atgaatcggc caacgcgcgg 4740
ggagaggcgg tttgcgtatt gggcgctctt ccgcttcctc gctcactgac tcgctgcgct 4800
cggtcgttcg gctgcggcga gcggtatcag ctcactcaaa ggcggtaata cggttatcca 4860
cagaatcagg ggataacgca ggaaagaaca tgtgagcaaa aggccagcaa aaggccagga 4920
accgtaaaaa ggccgcgttg ctggcgtttt tccataggct ccgcccccct gacgagcatc 4980
acaaaaatcg acgctcaagt cagaggtggc gaaacccgac aggactataa agataccagg 5040
cgtttccccc tggaagctcc ctcgtgcgct ctcctgttcc gaccctgccg cttaccggat 5100
acctgtccgc ctttctccct tcgggaagcg tggcgctttc tcatagctca cgctgtaggt 5160
atctcagttc ggtgtaggtc gttcgctcca agctgggctg tgtgcacgaa ccccccgttc 5220
agcccgaccg ctgcgcctta tccggtaact atcgtcttga gtccaacccg gtaagacacg 5280
acttatcgcc actggcagca gccactggta acaggattag cagagcgagg tatgtaggcg 5340
gtgctacaga gttcttgaag tggtggccta actacggcta cactagaaga acagtatttg 5400
gtatctgcgc tctgctgaag ccagttacct tcggaaaaag agttggtagc tcttgatccg 5460
gcaaacaaac caccgctggt agcggtggtt tttttgtttg caagcagcag attacgcgca 5520
gaaaaaaagg atctcaagaa gatcctttga tcttttctac ggggtctgac gctcagtgga 5580
acgaaaactc acgttaaggg attttggtca tgagattatc aaaaaggatc ttcacctaga 5640
tccttttaaa ttaaaaatga agttttaaat caatctaaag tatatatgag taaacttggt 5700
ctgacagtta ccaatgctta atcagtgagg cacctatctc agcgatctgt ctatttcgtt 5760
catccatagt tgcctgactc cccgtcgtgt agataactac gatacgggag ggcttaccat 5820
ctggccccag tgctgcaatg ataccgcgag acccacgctc accggctcca gatttatcag 5880
caataaacca gccagccgga agggccgagc gcagaagtgg tcctgcaact ttatccgcct 5940
ccatccagtc tattaattgt tgccgggaag ctagagtaag tagttcgcca gttaatagtt 6000
tgcgcaacgt tgttgccatt gctacaggca tcgtggtgtc acgctcgtcg tttggtatgg 6060

```
cttcattcag ctccggttcc caacgatcaa ggcgagttac atgatccccc atgttgtgca   6120

aaaaagcggt tagctccttc ggtcctccga tcgttgtcag aagtaagttg gccgcagtgt   6180

tatcactcat ggttatggca gcactgcata attctcttac tgtcatgcca tccgtaagat   6240

gcttttctgt gactggtgag tactcaacca agtcattctg agaatagtgt atgcggcgac   6300

cgagttgctc ttgcccggcg tcaatacggg ataataccgc gccacatagc agaactttaa   6360

aagtgctcat cattggaaaa cgttcttcgg ggcgaaaact ctcaaggatc ttaccgctgt   6420

tgagatccag ttcgatgtaa cccactcgtg cacccaactg atcttcagca tcttttactt   6480

tcaccagcgt ttctgggtga gcaaaaacag gaaggcaaaa tgccgcaaaa aagggaataa   6540

gggcgacacg gaaatgttga atactcatac tcttcctttt tcaatattat tgaagcattt   6600

atcagggtta ttgtctcatg agcggataca tatttgaatg tatttagaaa aataaacaaa   6660

taggggttcc gcgcacattt ccccgaaaag tgccacctga cgtctaagaa accattatta   6720

tcatgacatt aacctataaa aataggcgta tcacgaggcc ctttcgtc                6768
```

<210> SEQ ID NO 24
<211> LENGTH: 6672
<212> TYPE: DNA
<213> ORGANISM: Artificial Sequence
<220> FEATURE:
<223> OTHER INFORMATION: construct pINT-Cn-setA

<400> SEQUENCE: 24

```
tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120

ttggcgggtg tcggggctgg cttaactatg cggcatcaga gcagattgta ctgagagtgc    180

accatatgcg gtgtgaaata ccgcacagat gcgtaaggag aaaataccgc atcaggcgcc    240

attcgccatt caggctgcgc aactgttggg aagggcgatc ggtgcgggcc tcttcgctat    300

tacgccagct ggcgaaaggg ggatgtgctg caaggcgatt aagttgggta acgccagggt    360

tttcccagtc acgacgttgt aaaacgacgg ccagtgaatt cgaagatcct ttgatctttt    420

ctacggggtc tgacgctcag tggaacgaaa actcacgtta agggattttg gtcatgagat    480

tatcaaaaag gatcttcacc tagatccttt taaactagtg aagttaccat cacggaaaaa    540

ggttatgctg cttttaagac ccactttcac atttaagttg tttttctaat ccgcatatga    600

tcaattcaag gccgaataag aaggctggct ctgcaccttg gtgatcaaat aattcgatag    660

cttgtcgtaa taatggcggc atactatcag tagtaggtgt ttccctttct tctttagcga    720

cttgatgctc ttgatcttcc aatacgcaac ctaaagtaaa atgccccact gcgctgagtg    780

catataatgc attctctagt gaaaaacctt gttggcataa aaaggctaat tgattttcga    840

gagtttcata ctgtttttct gtaggccgtg tacctaaatg tacttttgct ccatcgcgat    900

gacttagtaa agcacatcta aaacttttag cgttattacg taaaaaatct tgccagcttt    960

ccccttctaa agggcaaaag tgagtatggt gcctatctaa catctcaatg gctaaggcgt   1020

cgagcaaagc ccgcttattt tttacatgcc aatacaatgt aggctgctct acacctagct   1080

tctgggcgag tttacgggtt gttaaacctt cgattccgac ctcattaagc agctctaatg   1140

cgctgttaat cactttactt ttatctaaac gagacatact cttccttttt caatattatt   1200

gaagcattta tcagggttat tgtctcatga gcggatacat atttgaatgt atttagaaaa   1260

ataaacaaat aggggttccg cgcacatttc cccgaaaagt gccacctgaa attggccaga   1320

tgattaattc ctaatttttg ttgacactct atcattgata gagttatttt accactccct   1380
```

-continued atcagtgata gagaaaagtg aaatgaatag ttcgacaaaa atctagaaat aattttgttt 1440
aactttaaga aggagatata caagagctcg agtcgaagga gatagaacca tgctgtggtt 1500
tctgacccgt gctcgtcgct tcaatccggt ttatgcggcc tttatggccg tcagcttcat 1560
gattggtgtg gccggtgcac tgcaggcacc gaccctgtct ctgtttctga cgcgtgaagt 1620
tgaagtccgc ccgttttggg ttggtctgtt ctacacggtc aacgcaattg ctggcatcgg 1680
tgtgagtctg ctgctggcca aacgtagtga ttcccaaggc gaccgtcgca aactgattat 1740
ggtgtgctgt gttatggcgg tcgccaactg cgtcctgttt gcattcaatc gccattatct 1800
gaccctgatc acgctgggtg tgatgtttgc aagcattgct aataccgcga tgccgcagat 1860
cttcgcactg gctcgtgaat acgccgatcg ttctgcacgc gaagtggtta tgtttagctc 1920
tattatgcgc gcccaactga gtctggcatg ggttattggc ccgccgctgt ccttcatgct 1980
ggccctgaaa tatggtttta ccacgatgtt cctgattgca gctggcattt ttgtgatctc 2040
actggctctg attatcttcg cgctgccgtc ggtgccgcgt gttgaacagc cggccgaagt 2100
ggcaattacc caagttagcg gttggaaaga ttctaacgtt cgcatgctgt ttatcgcctc 2160
aatgctgatg tggacctgta atacgatgta tattatcgac atgccgctgt ggatttcgca 2220
ggatctgggt ctgccggatg aactggccgg tctgctgatg ggtaccgccg caggcattga 2280
aatcccggct atgatcctgg cgggttatta cgtgaaacgt tttggcaaac gcaacatgat 2340
ggtcgcagct gtggcggccg gtattctgtt ttacgttggc ctgatcctgt tccatagcaa 2400
aacggcgctg gtcgtgctgc agctgtttaa tgccgtcttc attggtatta tcgcaggcat 2460
cggtatgctg tggtttcaag atctgatgcc gggtcgtccg ggtagcgcaa ccaccctgtt 2520
caccaactca atttcgacgg gcgtgattct ggccggtatt ctgcagggtg ccctggcaga 2580
aggttttggt cactatagtg tgtactggct gatggcagct ctggctgtta tcgcgctgtt 2640
cctgaccagc cgcgttaaaa acgtctaata aatcgatact agcataaccc cttggggcct 2700
ctaaacgcgt cgacacgcaa aaaggccatc cgtcaggatg gccttctgct taatttgatg 2760
cctggcagtt tatggcgggc gtcctgcccg ccaccctccg ggccgttgct tcgcaacgtt 2820
caaatccgct cccggcggat ttgtcctact caggagagcg ttcaccgaca aacaacagat 2880
aaaacgaaag gcccagtctt tcgactgagc ctttcgtttt atttgatgcc tggcagttcc 2940
ctactctcgc atggggagac cccacactac catcatgtat gaatatcctc cttagttcct 3000
attccgaagt tcctattctc tagaaagtat aggaacttcg gcgcgtccta cctgtgacgg 3060
aagatcactt cgcagaataa ataaatcctg gtgtccctgt tgataccggg aagccctggg 3120
ccaacttttg gcgaaaatga gacgttgatc ggcacgtaag aggttccaac tttcaccata 3180
atgaaataag atcactaccg ggcgtatttt ttgagttgtc gagattttca ggagctaagg 3240
aagctaaaat ggagaaaaaa atcactggat ataccaccgt tgatatatcc caatggcatc 3300
gtaaagaaca ttttgaggca tttcagtcag ttgctcaatg tacctataac cagaccgttc 3360
agctggatat tacggccttt ttaaagaccg taaagaaaaa taagcacaag ttttatccgg 3420
cctttattca cattcttgcc cgcctgatga atgctcatcc ggaattacgt atggcaatga 3480
aagacggtga gctggtgata tgggatagtg ttcacccttg ttacaccgtt ttccatgagc 3540
aaactgaaac gttttcatcg ctctggagtg aataccacga cgatttccgg cagtttctac 3600
acatatattc gcaagatgtg gcgtgttacg gtgaaaacct ggcctatttc cctaaagggt 3660
ttattgagaa tatgtttttc gtctcagcca atccctgggt gagtttcacc agttttgatt 3720

-continued

```
taaacgtggc caatatggac aacttcttcg cccccgtttt caccatgggc aaatattata   3780
cgcaaggcga caaggtgctg atgccgctgg cgattcaggt tcatcatgcc gtttgtgatg   3840
gcttccatgt cggcagatgc ttaatgaata caacagtact gcgatgagtg gcagggcggg   3900
gcgtaaggcg cgccatttaa atgaagttcc tattccgaag ttcctattct ctagaaagta   3960
taggaacttc gaagcagctc cagcctacac aatcgctcaa gacgtgtaat gctgcaatct   4020
gcatgcaagc ttggcactgg ccacgcaaaa aggccatccg tcaggatggc cttctgctta   4080
atttgatgcc tggcagttta tggcgggcgt cctgcccgcc accctccggg ccgttgcttc   4140
gcaacgttca aatccgctcc cggcggattt gtcctactca ggagagcgtt caccgacaaa   4200
caacagataa aacgaaaggc ccagtctttc gactgagcct ttcgttttat ttgatgcctg   4260
gcagttccct actctcgcat ggggagaccc cacactacca tcgggggcc atcgatgcag   4320
gtggcacttt tcggggaaat gtgcgcggaa cccctatttg tttatttttc taaatacatt   4380
caaatatgta tccgctcatg agacaataac cctgctgcag aggcctgcat gcaagcttgg   4440
cgtaatcatg gtcatagctg tttcctgtgt gaaattgtta tccgctcaca attccacaca   4500
acatacgagc cggaagcata aagtgtaaag cctggggtgc ctaatgagtg agctaactca   4560
cattaattgc gttgcgctca ctgcccgctt tccagtcggg aaacctgtcg tgccagctgc   4620
attaatgaat cggccaacgc gcggggagag gcggtttgcg tattgggcgc tcttccgctt   4680
cctcgctcac tgactcgctg cgctcggtcg ttcggctgcg gcgagcggta tcagctcact   4740
caaaggcggt aatacggtta tccacagaat caggggataa cgcaggaaag aacatgtgag   4800
caaaaggcca gcaaaaggcc aggaaccgta aaaaggccgc gttgctggcg tttttccata   4860
ggctccgccc ccctgacgag catcacaaaa atcgacgctc aagtcagagg tggcgaaacc   4920
cgacaggact ataaagatac caggcgtttc cccctggaag ctccctcgtg cgctctcctg   4980
ttccgaccct gccgcttacc ggatacctgt ccgcctttct cccttcggga agcgtggcgc   5040
tttctcatag ctcacgctgt aggtatctca gttcggtgta ggtcgttcgc tccaagctgg   5100
gctgtgtgca cgaacccccc gttcagcccg accgctgcgc cttatccggt aactatcgtc   5160
ttgagtccaa cccggtaaga cacgacttat cgccactggc agcagccact ggtaacagga   5220
ttagcagagc gaggtatgta ggcggtgcta cagagttctt gaagtggtgg cctaactacg   5280
gctacactag aagaacagta tttggtatct gcgctctgct gaagccagtt accttcggaa   5340
aaagagttgg tagctcttga tccggcaaac aaaccaccgc tggtagcggt ggtttttttg   5400
tttgcaagca gcagattacg cgcagaaaaa aaggatctca agaagatcct ttgatctttt   5460
ctacggggtc tgacgctcag tggaacgaaa actcacgtta agggattttg gtcatgagat   5520
tatcaaaaag gatcttcacc tagatccttt taaattaaaa atgaagtttt aaatcaatct   5580
aaagtatata tgagtaaact tggtctgaca gttaccaatg cttaatcagt gaggcaccta   5640
tctcagcgat ctgtctattt cgttcatcca tagttgcctg actccccgtc gtgtagataa   5700
ctacgatacg ggagggctta ccatctggcc ccagtgctgc aatgataccg cgagacccac   5760
gctcaccggc tccagattta tcagcaataa accagccagc cggaagggcc gagcgcagaa   5820
gtggtcctgc aactttatcc gcctccatcc agtctattaa ttgttgccgg gaagctagag   5880
taagtagttc gccagttaat agtttgcgca acgttgttgc cattgctaca ggcatcgtgg   5940
tgtcacgctc gtcgtttggt atggcttcat tcagctccgg ttcccaacga tcaaggcgag   6000
ttacatgatc ccccatgttg tgcaaaaaag cggttagctc cttcggtcct ccgatcgttg   6060
tcagaagtaa gttggccgca gtgttatcac tcatggttat ggcagcactg cataattctc   6120
```

-continued ttactgtcat gccatccgta agatgctttt ctgtgactgg tgagtactca accaagtcat 6180
tctgagaata gtgtatgcgg cgaccgagtt gctcttgccc ggcgtcaata cgggataata 6240
ccgcgccaca tagcagaact ttaaaagtgc tcatcattgg aaaacgttct tcggggcgaa 6300
aactctcaag gatcttaccg ctgttgagat ccagttcgat gtaacccact cgtgcaccca 6360
actgatcttc agcatctttt actttcacca gcgtttctgg gtgagcaaaa acaggaaggc 6420
aaaatgccgc aaaaaaggga ataagggcga cacggaaatg ttgaatactc atactcttcc 6480
tttttcaata ttattgaagc atttatcagg gttattgtct catgagcgga tacatatttg 6540
aatgtattta gaaaaataaa caaatagggg ttccgcgcac atttccccga aaagtgccac 6600
ctgacgtcta agaaaccatt attatcatga cattaaccta taaaaatagg cgtatcacga 6660
ggccctttcg tc 6672

<210> SEQ ID NO 25
<211> LENGTH: 7074
<212> TYPE: DNA
<213> ORGANISM: Artificial Sequence
<220> FEATURE:
<223> OTHER INFORMATION: construct pINT-spoVB

<400> SEQUENCE: 25
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accatatgcg gtgtgaaata ccgcacagat gcgtaaggag aaaataccgc atcaggcgcc 240
attcgccatt caggctgcgc aactgttggg aagggcgatc ggtgcgggcc tcttcgctat 300
tacgccagct ggcgaaaggg ggatgtgctg caaggcgatt aagttgggta acgccagggt 360
tttcccagtc acgacgttgt aaaacgacgg ccagtgaatt cgaagatcct ttgatctttt 420
ctacggggtc tgacgctcag tggaacgaaa actcacgtta agggattttg gtcatgagat 480
tatcaaaaag gatcttcacc tagatccttt taaactagtg aagttaccat cacggaaaaa 540
ggttatgctg cttttaagac ccactttcac atttaagttg tttttctaat ccgcatatga 600
tcaattcaag gccgaataag aaggctggct ctgcaccttg gtgatcaaat aattcgatag 660
cttgtcgtaa taatggcggc atactatcag tagtaggtgt ttccctttct tctttagcga 720
cttgatgctc ttgatcttcc aatacgcaac ctaaagtaaa atgccccact gcgctgagtg 780
catataatgc attctctagt gaaaaacctt gttggcataa aaaggctaat tgattttcga 840
gagtttcata ctgtttttct gtaggccgtg tacctaaatg tacttttgct ccatcgcgat 900
gacttagtaa agcacatcta aaacttttag cgttattacg taaaaaatct tgccagcttt 960
ccccttctaa agggcaaaag tgagtatggt gcctatctaa catctcaatg gctaaggcgt 1020
cgagcaaagc ccgcttattt tttacatgcc aatacaatgt aggctgctct acacctagct 1080
tctgggcgag tttacgggtt gttaaacctt cgattccgac ctcattaagc agctctaatg 1140
cgctgttaat cactttactt ttatctaaac gagacatact cttccttttt caatattatt 1200
gaagcattta tcagggttat tgtctcatga gcggatacat atttgaatgt atttagaaaa 1260
ataaacaaat aggggttccg cgcacatttc cccgaaaagt gccacctgaa attggccaga 1320
tgattaattc ctaatttttg ttgacactct atcattgata gagttatttt accactccct 1380
atcagtgata gagaaaagtg aaatgaatag ttcgacaaaa atctagaaat aattttgttt 1440

-continued

```
aactttaaga aggagatata caagagctcg agtcgaagga gatagaacca tgaatgactc   1500
ggtcggtgct aagcgtcaaa gtgcgtggaa gggtgcgttc gtcctggtcg ttgcgggcat   1560
cgttaccaag atcctgtctg ccgtgtatcg tgttccgttt cagaacattg tcggcgatgt   1620
gggtttctat atctaccagc aagtttaccc gtttctgggc attgcggtca tgctgagtac   1680
ctccggtttt ccggtgatca tctcgaagct gatgaacgat tacagcgacc ataaacagaa   1740
gattatgaag atcagtgcac tgtatgtgac ggcagcaggt ctggttctgt ttgccctgat   1800
gtacgcaggt gcagctccgc tggcgggctt catgggtgat gaccgtctgg tcatgctgat   1860
tcgcgtggcg gcctttgctt tcatcctgtt tccgttcacc gcggtttttc gcggctattt   1920
ccagggtgtg cacgacatga tgccgtctgc tctgagtcag attacggaac aactgctgcg   1980
tgtggcagtt ctgctgggcc tgtctttttg gctgctgaaa tccggtcgtt cactgtacgc   2040
agctggtgca ggtgcagcat caggttcgat tgcaggtagt ctggcagctc tgtgcgttct   2100
ggcagtcttc tggtataaac gtgaagaaac caaaaaggat ggcggtcata tcgaaacggc   2160
ggttattatc aaaaagctgc tgctgtactc cgtgaccatt tgtatcagct ctgttctgat   2220
gctgctgctg cagctggttg atgcgctgaa cctgtattcg ctgctgagcg acggcaccga   2280
atcacatgcg gccaaacaac tgaagggcat ttacgaccgt ggtcagccgc tgctgcaact   2340
gggtacggtg tttgcggttt ccattgcagc ttcactggtc ccgagcatct ctaaagccgt   2400
gcacgaaaat aagccgttca ttatcaaaga aaaggctacc tctgcggtca aactgtgcct   2460
ggcggtgggc attggtgcta gtgcgggcct gttttgtatt ctggaaccgg ttaacatcat   2520
gctgttccag aattccgaag gtacccagac gctgcaaatc tttagtctgt ccatttttct   2580
tgcctcaatc gcactgaccg cagcagcaat cctgcaaggt gcaggtcata cggtgttccc   2640
ggcagtcagc gtgctggctg gcggtgcgct gaaatgggtc ctgaacgtgt ggctggttcc   2700
gggttggggt attaccggtg ctgcactggc tacggttctg gcatttgcag cagtcgcatg   2760
cctgaacctg cgtcgcatct ggtcgaaagg ttggctgacc aatattggcg gtgtgatcgc   2820
acgtctgtgc tggtgtagcc tgctgatggt gtttttcctg ctggtctata tgaaactgtg   2880
gcagctgttt gttccggtca gccgtgccgg cgcagtttgc gaatcactgt cggccagcgt   2940
gattggcggt ctgctgttca tctactgtat gatccgcatg aagatcttca ccgatgaaga   3000
actgagcggc ctgccgttcg gttctgcgct gagtaaactg aaaaagcgtc gcgaaaagca   3060
cggtcgctaa taaatcgata ctagcataac cccttggggc ctctaaacgc gtcgacacgc   3120
aaaaaggcca tccgtcagga tggccttctg cttaatttga tgcctggcag tttatggcgg   3180
gcgtcctgcc cgccaccctc cgggccgttg cttcgcaacg ttcaaatccg ctcccggcgg   3240
atttgtccta ctcaggagag cgttcaccga caaacaacag ataaaacgaa aggcccagtc   3300
tttcgactga gcctttcgtt ttatttgatg cctggcagtt ccctactctc gcatggggag   3360
accccacact accatcatgt atgaatatcc tccttagttc ctattccgaa gttcctattc   3420
tctagaaagt ataggaactt cggcgcgtcc tacctgtgac ggaagatcac ttcgcagaat   3480
aaataaatcc tggtgtccct gttgataccg ggaagccctg ggccaacttt tggcgaaaat   3540
gagacgttga tcggcacgta agaggttcca actttcacca taatgaaata agatcactac   3600
cgggcgtatt ttttgagttg tcgagatttt caggagctaa ggaagctaaa atggagaaaa   3660
aaatcactgg atataccacc gttgatatat cccaatggca tcgtaaagaa cattttgagg   3720
catttcagtc agttgctcaa tgtacctata accagaccgt tcagctggat attacggcct   3780
ttttaaagac cgtaaagaaa aataagcaca agttttatcc ggcctttatt cacattcttg   3840
```

-continued

```
cccgcctgat gaatgctcat ccggaattac gtatggcaat gaaagacggt gagctggtga   3900
tatgggatag tgttcaccct tgttacaccg ttttccatga gcaaactgaa acgttttcat   3960
cgctctggag tgaataccac gacgatttcc ggcagtttct acacatatat tcgcaagatg   4020
tggcgtgtta cggtgaaaac ctggcctatt tccctaaagg gtttattgag aatatgtttt   4080
tcgtctcagc caatccctgg gtgagtttca ccagttttga tttaaacgtg gccaatatgg   4140
acaacttctt cgcccccgtt ttcaccatgg gcaaatatta tacgcaaggc gacaaggtgc   4200
tgatgccgct ggcgattcag gttcatcatg ccgtttgtga tggcttccat gtcggcagat   4260
gcttaatgaa tacaacagta ctgcgatgag tggcagggcg gggcgtaagg cgcgccattt   4320
aaatgaagtt cctattccga agttcctatt ctctagaaag tataggaact tcgaagcagc   4380
tccagcctac acaatcgctc aagacgtgta atgctgcaat ctgcatgcaa gcttggcact   4440
ggccacgcaa aaaggccatc cgtcaggatg gccttctgct taatttgatg cctggcagtt   4500
tatggcgggc gtcctgcccg ccaccctccg ggccgttgct tcgcaacgtt caaatccgct   4560
cccggcggat ttgtcctact caggagagcg ttcaccgaca aacaacagat aaaacgaaag   4620
gcccagtctt tcgactgagc ctttcgtttt atttgatgcc tggcagttcc ctactctcgc   4680
atggggagac cccacactac catcgggggg ccatcgatgc aggtggcact tttcggggaa   4740
atgtgcgcgg aacccctatt tgtttatttt tctaaataca ttcaaatatg tatccgctca   4800
tgagacaata accctgctgc agaggcctgc atgcaagctt ggcgtaatca tggtcatagc   4860
tgtttcctgt gtgaaattgt tatccgctca caattccaca caacatacga gccggaagca   4920
taaagtgtaa agcctggggt gcctaatgag tgagctaact cacattaatt gcgttgcgct   4980
cactgcccgc tttccagtcg ggaaacctgt cgtgccagct gcattaatga atcggccaac   5040
gcgcggggag aggcggtttg cgtattgggc gctcttccgc ttcctcgctc actgactcgc   5100
tgcgctcggt cgttcggctg cggcgagcgg tatcagctca ctcaaaggcg gtaatacggt   5160
tatccacaga atcaggggat aacgcaggaa agaacatgtg agcaaaaggc cagcaaaagg   5220
ccaggaaccg taaaaaggcc gcgttgctgg cgtttttcca taggctccgc ccccctgacg   5280
agcatcacaa aaatcgacgc tcaagtcaga ggtggcgaaa cccgacagga ctataaagat   5340
accaggcgtt tccccctgga agctccctcg tgcgctctcc tgttccgacc ctgccgctta   5400
ccggatacct gtccgccttt ctcccttcgg gaagcgtggc gctttctcat agctcacgct   5460
gtaggtatct cagttcggtg taggtcgttc gctccaagct gggctgtgtg cacgaacccc   5520
ccgttcagcc cgaccgctgc gccttatccg gtaactatcg tcttgagtcc aacccggtaa   5580
gacacgactt atcgccactg gcagcagcca ctggtaacag gattagcaga gcgaggtatg   5640
taggcggtgc tacagagttc ttgaagtggt ggcctaacta cggctacact agaagaacag   5700
tatttggtat ctgcgctctg ctgaagccag ttaccttcgg aaaaagagtt ggtagctctt   5760
gatccggcaa acaaaccacc gctggtagcg gtggtttttt tgtttgcaag cagcagatta   5820
cgcgcagaaa aaaaggatct caagaagatc ctttgatctt ttctacgggg tctgacgctc   5880
agtggaacga aaactcacgt taagggattt tggtcatgag attatcaaaa aggatcttca   5940
cctagatcct tttaaattaa aaatgaagtt ttaaatcaat ctaaagtata tatgagtaaa   6000
cttggtctga cagttaccaa tgcttaatca gtgaggcacc tatctcagcg atctgtctat   6060
ttcgttcatc catagttgcc tgactccccg tcgtgtagat aactacgata cgggagggct   6120
taccatctgg ccccagtgct gcaatgatac cgcgagaccc acgctcaccg gctccagatt   6180
```

```
tatcagcaat aaaccagcca gccggaaggg ccgagcgcag aagtggtcct gcaactttat   6240

ccgcctccat ccagtctatt aattgttgcc gggaagctag agtaagtagt tcgccagtta   6300

atagtttgcg caacgttgtt gccattgcta caggcatcgt ggtgtcacgc tcgtcgtttg   6360

gtatggcttc attcagctcc ggttcccaac gatcaaggcg agttacatga tcccccatgt   6420

tgtgcaaaaa agcggttagc tccttcggtc ctccgatcgt tgtcagaagt aagttggccg   6480

cagtgttatc actcatggtt atggcagcac tgcataattc tcttactgtc atgccatccg   6540

taagatgctt ttctgtgact ggtgagtact caaccaagtc attctgagaa tagtgtatgc   6600

ggcgaccgag ttgctcttgc ccggcgtcaa tacgggataa taccgcgcca catagcagaa   6660

ctttaaaagt gctcatcatt ggaaaacgtt cttcggggcg aaaactctca aggatcttac   6720

cgctgttgag atccagttcg atgtaaccca ctcgtgcacc caactgatct tcagcatctt   6780

ttactttcac cagcgtttct gggtgagcaa aaacaggaag gcaaaatgcc gcaaaaaagg   6840

gaataagggc gacacggaaa tgttgaatac tcatactctt cctttttcaa tattattgaa   6900

gcatttatca gggttattgt ctcatgagcg gatacatatt tgaatgtatt tagaaaaata   6960

aacaaatagg ggttccgcgc acatttcccc gaaaagtgcc acctgacgtc taagaaacca   7020

ttattatcat gacattaacc tataaaaata ggcgtatcac gaggcccttt cgtc         7074
```

<210> SEQ ID NO 26
<211> LENGTH: 6699
<212> TYPE: DNA
<213> ORGANISM: Artificial Sequence
<220> FEATURE:
<223> OTHER INFORMATION: construct pINT-yabM

<400> SEQUENCE: 26

```
tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120

ttggcgggtg tcggggctgg cttaactatg cggcatcaga gcagattgta ctgagagtgc    180

accatatgcg gtgtgaaata ccgcacagat gcgtaaggag aaaataccgc atcaggcgcc    240

attcgccatt caggctgcgc aactgttggg aagggcgatc ggtgcgggcc tcttcgctat    300

tacgccagct ggcgaaaggg ggatgtgctg caaggcgatt aagttgggta acgccagggt    360

tttcccagtc acgacgttgt aaaacgacgg ccagtgaatt cgaagatcct ttgatctttt    420

ctacggggtc tgacgctcag tggaacgaaa actcacgtta agggattttg gtcatgagat    480

tatcaaaaag gatcttcacc tagatccttt taaactagtg aagttaccat cacggaaaaa    540

ggttatgctg cttttaagac ccactttcac atttaagttg tttttctaat ccgcatatga    600

tcaattcaag gccgaataag aaggctggct ctgcaccttg gtgatcaaat aattcgatag    660

cttgtcgtaa taatggcggc atactatcag tagtaggtgt ttccctttct tctttagcga    720

cttgatgctc ttgatcttcc aatacgcaac ctaaagtaaa atgccccact gcgctgagtg    780

catataatgc attctctagt gaaaaacctt gttggcataa aaaggctaat tgattttcga    840

gagtttcata ctgtttttct gtaggccgtg tacctaaatg tacttttgct ccatcgcgat    900

gacttagtaa agcacatcta aaacttttag cgttattacg taaaaaatct tgccagcttt    960

ccccttctaa agggcaaaag tgagtatggt gcctatctaa catctcaatg gctaaggcgt   1020

cgagcaaagc ccgcttattt tttacatgcc aatacaatgt aggctgctct acacctagct   1080

tctgggcgag tttacgggtt gttaaacctt cgattccgac ctcattaagc agctctaatg   1140

cgctgttaat cactttactt ttatctaaac gagacatact cttccttttt caatattatt   1200
```

-continued

```
gaagcattta tcagggttat tgtctcatga gcggatacat atttgaatgt atttagaaaa   1260
ataaacaaat aggggttccg cgcacatttc cccgaaaagt gccacctgaa attggccaga   1320
tgattaattc ctaatttttg ttgacactct atcattgata gagttatttt accactccct   1380
atcagtgata gagaaaagtg aaatgaatag ttcgacaaaa atctagaaat aattttgttt   1440
aactttaaga aggagatata caagagctcg agtcgaagga gatagaacca tgaaggctct   1500
gtggtcgcgt cgccgtcgta tccacccggt ctatctggct tttatggcag tttcgtttat   1560
ggttggcatc gcaggtgcgc tgcagtcacc gaccctgtcg ctgtttctga gccgtgaagt   1620
gggtgttcgc ccgttttggg tgggcctgtt ctatacggtt aacgcagtcg ctggtattat   1680
cgtttccctg ctgctggcca aacgttcaga taatcagggc gaccgtcgca tgctgattct   1740
gttctgctgt gttatggcga tcgccaacgc agtcctgttt gccttcaatc gccattatct   1800
gaccctggtc attgcaggtg tgctgctgag ctctatcgct agcgtggcga tgccgcagat   1860
ttttgctctg gcgcgtgaat acgcagatag ttccgcccgc gaagcagtca tgttctcatc   1920
ggtgatgcgt gcccaactgt cgctggcatg ggttatcggt ccgccgctga gctttgccat   1980
tgcactgaac tacggcttta ccgcgatgtt cctggtggcg gccctgctgt ttttcgtctg   2040
cgtggctctg atttggttca ccctgccgag cgttccgcgt gcagaaaaca cggcagctga   2100
accgctgagt gatatctccg gttggaaaca ccgtgacgtg cgcatgctgt ttattgcctc   2160
tgttttcatg tggacctgta atacgatgta tgttatcgat atgccgctgt acattagtat   2220
cgtcctgggt ctgccggaca agctggcagg tctgctgatg ggtaccgcag caggcctgga   2280
aattccggtc atgctgctgg ctggtcatta tgtgaaacgt tttggcaagc gcccgatgat   2340
gctgctggcg gttggctgcg gtgtcctgtt ttacctgggt ctggtgctgt tccacggccg   2400
tacggaactg atgctgctgc agctgctgaa cgctctgttt atcggcatta tcgcgggcat   2460
tggtatgatc tggttccaag atctgatgcc gggtcgtccg ggttctgcaa ccacgctgtt   2520
taccaatagc atttctacgg gtgtgatcct ggcaggtgtg ctgcagggcg ttatggccga   2580
aacctttggc catcacgcag tctattggct ggcttccctg ctggcgctga tttctttcgc   2640
tctgagttgg caagttcgtg aagcgcgcac ggtgaagagt gttccgctgg cctaataaat   2700
cgatactagc ataacccctt ggggcctcta aacgcgtcga cacgcaaaaa ggccatccgt   2760
caggatggcc ttctgcttaa tttgatgcct ggcagtttat ggcgggcgtc ctgcccgcca   2820
ccctccgggc cgttgcttcg caacgttcaa atccgctccc ggcggatttg tcctactcag   2880
gagagcgttc accgacaaac aacagataaa acgaaaggcc cagtctttcg actgagcctt   2940
tcgttttatt tgatgcctgg cagttcccta ctctcgcatg gggagacccc acactaccat   3000
catgtatgaa tatcctcctt agttcctatt ccgaagttcc tattctctag aaagtatagg   3060
aacttcggcg cgtcctacct gtgacggaag atcacttcgc agaataaata aatcctggtg   3120
tccctgttga taccgggaag ccctgggcca acttttggcg aaaatgagac gttgatcggc   3180
acgtaagagg ttccaacttt caccataatg aaataagatc actaccgggc gtattttttg   3240
agttgtcgag attttcagga gctaaggaag ctaaaatgga gaaaaaaatc actggatata   3300
ccaccgttga tatatcccaa tggcatcgta aagaacattt tgaggcattt cagtcagttg   3360
ctcaatgtac ctataaccag accgttcagc tggatattac ggccttttta aagaccgtaa   3420
agaaaaataa gcacaagttt tatccggcct ttattcacat tcttgcccgc ctgatgaatg   3480
ctcatccgga attacgtatg gcaatgaaag acggtgagct ggtgatatgg gatagtgttc   3540
```

-continued

```
acccttgtta caccgttttc catgagcaaa ctgaaacgtt ttcatcgctc tggagtgaat   3600

accacgacga tttccggcag tttctacaca tatattcgca agatgtggcg tgttacggtg   3660

aaaacctggc ctatttccct aaagggttta ttgagaatat gtttttcgtc tcagccaatc   3720

cctgggtgag tttcaccagt tttgatttaa acgtggccaa tatggacaac ttcttcgccc   3780

ccgttttcac catgggcaaa tattatacgc aaggcgacaa ggtgctgatg ccgctggcga   3840

ttcaggttca tcatgccgtt tgtgatggct tccatgtcgg cagatgctta atgaatacaa   3900

cagtactgcg atgagtggca gggcggggcg taaggcgcgc catttaaatg aagttcctat   3960

tccgaagttc ctattctcta gaaagtatag gaacttcgaa gcagctccag cctacacaat   4020

cgctcaagac gtgtaatgct gcaatctgca tgcaagcttg gcactggcca cgcaaaaagg   4080

ccatccgtca ggatggcctt ctgcttaatt tgatgcctgg cagtttatgg cgggcgtcct   4140

gcccgccacc ctccgggccg ttgcttcgca acgttcaaat ccgctcccgg cggatttgtc   4200

ctactcagga gagcgttcac cgacaaacaa cagataaaac gaaaggccca gtctttcgac   4260

tgagcctttc gttttatttg atgcctggca gttccctact ctcgcatggg gagaccccac   4320

actaccatcg gggggccatc gatgcaggtg gcacttttcg gggaaatgtg cgcggaaccc   4380

ctatttgttt atttttctaa atacattcaa atatgtatcc gctcatgaga caataaccct   4440

gctgcagagg cctgcatgca agcttggcgt aatcatggtc atagctgttt cctgtgtgaa   4500

attgttatcc gctcacaatt ccacacaaca tacgagccgg aagcataaag tgtaaagcct   4560

ggggtgccta atgagtgagc taactcacat taattgcgtt gcgctcactg cccgctttcc   4620

agtcgggaaa cctgtcgtgc cagctgcatt aatgaatcgg ccaacgcgcg gggagaggcg   4680

gtttgcgtat tgggcgctct tccgcttcct cgctcactga ctcgctgcgc tcggtcgttc   4740

ggctgcggcg agcggtatca gctcactcaa aggcggtaat acggttatcc acagaatcag   4800

gggataacgc aggaaagaac atgtgagcaa aaggccagca aaaggccagg aaccgtaaaa   4860

aggccgcgtt gctggcgttt ttccataggc tccgcccccc tgacgagcat cacaaaaatc   4920

gacgctcaag tcagaggtgg cgaaacccga caggactata aagataccag gcgtttcccc   4980

ctggaagctc cctcgtgcgc tctcctgttc cgaccctgcc gcttaccgga tacctgtccg   5040

cctttctccc ttcgggaagc gtggcgcttt ctcatagctc acgctgtagg tatctcagtt   5100

cggtgtaggt cgttcgctcc aagctgggct gtgtgcacga accccccgtt cagcccgacc   5160

gctgcgcctt atccggtaac tatcgtcttg agtccaaccc ggtaagacac gacttatcgc   5220

cactggcagc agccactggt aacaggatta gcagagcgag gtatgtaggc ggtgctacag   5280

agttcttgaa gtggtggcct aactacggct acactagaag aacagtattt ggtatctgcg   5340

ctctgctgaa gccagttacc ttcggaaaaa gagttggtag ctcttgatcc ggcaaacaaa   5400

ccaccgctgg tagcggtggt ttttttgttt gcaagcagca gattacgcgc agaaaaaaag   5460

gatctcaaga agatcctttg atcttttcta cggggtctga cgctcagtgg aacgaaaact   5520

cacgttaagg gattttggtc atgagattat caaaaaggat cttcacctag atccttttaa   5580

attaaaaatg aagttttaaa tcaatctaaa gtatatatga gtaaacttgg tctgacagtt   5640

accaatgctt aatcagtgag gcacctatct cagcgatctg tctatttcgt tcatccatag   5700

ttgcctgact ccccgtcgtg tagataacta cgatacggga gggcttacca tctggcccca   5760

gtgctgcaat gataccgcga gacccacgct caccggctcc agatttatca gcaataaacc   5820

agccagccgg aagggccgag cgcagaagtg gtcctgcaac tttatccgcc tccatccagt   5880

ctattaattg ttgccgggaa gctagagtaa gtagttcgcc agttaatagt ttgcgcaacg   5940
```

```
ttgttgccat tgctacaggc atcgtggtgt cacgctcgtc gtttggtatg gcttcattca   6000

gctccggttc ccaacgatca aggcgagtta catgatcccc catgttgtgc aaaaaagcgg   6060

ttagctcctt cggtcctccg atcgttgtca gaagtaagtt ggccgcagtg ttatcactca   6120

tggttatggc agcactgcat aattctctta ctgtcatgcc atccgtaaga tgcttttctg   6180

tgactggtga gtactcaacc aagtcattct gagaatagtg tatgcggcga ccgagttgct   6240

cttgcccggc gtcaatacgg gataataccg cgccacatag cagaacttta aaagtgctca   6300

tcattggaaa acgttcttcg gggcgaaaac tctcaaggat cttaccgctg ttgagatcca   6360

gttcgatgta acccactcgt gcacccaact gatcttcagc atcttttact ttcaccagcg   6420

tttctgggtg agcaaaaaca ggaaggcaaa atgccgcaaa aaagggaata agggcgacac   6480

ggaaatgttg aatactcata ctcttccttt ttcaatatta ttgaagcatt tatcagggtt   6540

attgtctcat gagcggatac atatttgaat gtatttagaa aaataaacaa ataggggttc   6600

cgcgcacatt tccccgaaaa gtgccacctg acgtctaaga aaccattatt atcatgacat   6660

taacctataa aaataggcgt atcacgaggc cctttcgtc                          6699
```

<210> SEQ ID NO 27
<211> LENGTH: 6684
<212> TYPE: DNA
<213> ORGANISM: Artificial Sequence
<220> FEATURE:
<223> OTHER INFORMATION: construct pINT-ydeA

<400> SEQUENCE: 27

```
tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120

ttggcgggtg tcggggctgg cttaactatg cggcatcaga gcagattgta ctgagagtgc    180

accatatgcg gtgtgaaata ccgcacagat gcgtaaggag aaaataccgc atcaggcgcc    240

attcgccatt caggctgcgc aactgttggg aagggcgatc ggtgcgggcc tcttcgctat    300

tacgccagct ggcgaaaggg ggatgtgctg caaggcgatt aagttgggta acgccagggt    360

tttcccagtc acgacgttgt aaaacgacgg ccagtgaatt cgaagatcct ttgatctttt    420

ctacggggtc tgacgctcag tggaacgaaa actcacgtta agggattttg gtcatgagat    480

tatcaaaaag gatcttcacc tagatccttt taaactagtg aagttaccat cacggaaaaa    540

ggttatgctg cttttaagac ccactttcac atttaagttg tttttctaat ccgcatatga    600

tcaattcaag gccgaataag aaggctggct ctgcaccttg gtgatcaaat aattcgatag    660

cttgtcgtaa taatggcggc atactatcag tagtaggtgt ttccctttct tctttagcga    720

cttgatgctc ttgatcttcc aatacgcaac ctaaagtaaa atgccccact gcgctgagtg    780

catataatgc attctctagt gaaaaacctt gttggcataa aaaggctaat tgattttcga    840

gagtttcata ctgtttttct gtaggccgtg tacctaaatg tacttttgct ccatcgcgat    900

gacttagtaa agcacatcta aaacttttag cgttattacg taaaaaatct tgccagcttt    960

ccccttctaa agggcaaaag tgagtatggt gcctatctaa catctcaatg gctaaggcgt   1020

cgagcaaagc ccgcttattt tttacatgcc aatacaatgt aggctgctct acacctagct   1080

tctgggcgag tttacgggtt gttaaacctt cgattccgac ctcattaagc agctctaatg   1140

cgctgttaat cactttactt ttatctaaac gagacatact cttccttttt caatattatt   1200

gaagcattta tcagggttat tgtctcatga gcggatacat atttgaatgt atttagaaaa   1260
```

-continued

```
ataaacaaat aggggttccg cgcacatttc cccgaaaagt gccacctgaa attggccaga   1320
tgattaattc ctaatttttg ttgacactct atcattgata gagttatttt accactccct   1380
atcagtgata gagaaaagtg aaatgaatag ttcgacaaaa atctagaaat aattttgttt   1440
aactttaaga aggagatata caagagctcg agtcgaagga gatagaacca tgacaacaaa   1500
cactgtttcc cgcaaagtgg cgtggctacg ggtcgttacg ctggcagtcg ccgccttcat   1560
cttcaacacc accgaatttg tccctgttgg cctgctctct gacattgcgc aaagttttca   1620
catgcaaacc gctcaggtcg gcatcatgtt gaccatttac gcatgggtag tagcgctaat   1680
gtcattgcct tttatgttaa tgaccagtca ggttgaacgg cgcaaattac tgatctgcct   1740
gtttgtggtg tttattgcca gccacgtact gtcgtttttg tcgtggagct ttaccgttct   1800
ggtgatcagt cgcattggtg tggcttttgc acatgcgatt ttctggtcga ttacggcgtc   1860
tctggcgatc cgtatggctc cggccgggaa gcgagcacag gcattgagtt taattgccac   1920
cggtacagca ctggcgatgg tcttaggttt acctctcggg cgcattgtgg gccagtattt   1980
cggttggcga atgaccttct tcgcgattgg tattggggcg cttatcaccc ttttgtgcct   2040
gattaagtta cttcccttac tgcccagtga gcattccggt tcactgaaaa gcctcccgct   2100
attgttccgc cgcccggcat tgatgagcat ttatttgtta actgtggtgg ttgtcaccgc   2160
ccattacacg gcatacagct atatcgagcc ttttgtacaa aacattgcgg gattcagcgc   2220
caactttgcc acggcattac tgttattact cggtggtgcg ggcattattg gcagcgtgat   2280
tttcggtaaa ctgggtaatc agtatgcgtc tgcgttggtg agtacggcga ttgcgctgtt   2340
gctggtgtgc ctggcattgc tgttacctgc ggcgaacagt gaaatacacc tcggggtgct   2400
gagtattttc tgggggatcg cgatgatgat catcgggctt ggtatgcagg ttaaagtgct   2460
ggcgctggca ccagatgcta ccgacgtcgc gatggcgcta ttctccggca tatttaatat   2520
tggaatcggg gcgggtgcgt tggtaggtaa tcaggtgagt ttgcactggt caatgtcgat   2580
gattggttat gtgggcgcgg tgcctgcttt tgccgcgtta atttggtcaa tcattatatt   2640
tcgccgctgg ccagtgacac tcgaagaaca gacgcaatag taaatcgata ctagcataac   2700
cccttggggc ctctaaacgc gtcgacacgc aaaaaggcca tccgtcagga tggccttctg   2760
cttaatttga tgcctggcag tttatggcgg gcgtcctgcc cgccaccctc cgggccgttg   2820
cttcgcaacg ttcaaatccg ctcccggcgg atttgtccta ctcaggagag cgttcaccga   2880
caaacaacag ataaaacgaa aggcccagtc tttcgactga gcctttcgtt ttatttgatg   2940
cctggcagtt ccctactctc gcatggggag accccacact accatcatgt atgaatatcc   3000
tccttagttc ctattccgaa gttcctattc tctagaaagt ataggaactt cggcgcgtcc   3060
tacctgtgac ggaagatcac ttcgcagaat aaataaatcc tggtgtccct gttgataccg   3120
ggaagccctg ggccaacttt tggcgaaaat gagacgttga tcggcacgta agaggttcca   3180
actttcacca taatgaaata agatcactac cgggcgtatt ttttgagttg tcgagatttt   3240
caggagctaa ggaagctaaa atggagaaaa aaatcactgg atataccacc gttgatatat   3300
cccaatggca tcgtaaagaa cattttgagg catttcagtc agttgctcaa tgtacctata   3360
accagaccgt tcagctggat attacggcct ttttaaagac cgtaaagaaa aataagcaca   3420
agttttatcc ggcctttatt cacattcttg cccgcctgat gaatgctcat ccggaattac   3480
gtatggcaat gaaagacggt gagctggtga tatgggatag tgttcaccct tgttacaccg   3540
ttttccatga gcaaactgaa acgttttcat cgctctggag tgaataccac gacgatttcc   3600
ggcagtttct acacatatat tcgcaagatg tggcgtgtta cggtgaaaac ctggcctatt   3660
```

```
tccctaaagg gtttattgag aatatgtttt tcgtctcagc caatccctgg gtgagtttca   3720
ccagttttga tttaaacgtg gccaatatgg acaacttctt cgcccccgtt ttcaccatgg   3780
gcaaatatta tacgcaaggc gacaaggtgc tgatgccgct ggcgattcag gttcatcatg   3840
ccgtttgtga tggcttccat gtcggcagat gcttaatgaa tacaacagta ctgcgatgag   3900
tggcagggcg gggcgtaagg cgcgccattt aaatgaagtt cctattccga agttcctatt   3960
ctctagaaag tataggaact tcgaagcagc tccagcctac acaatcgctc aagacgtgta   4020
atgctgcaat ctgcatgcaa gcttggcact ggccacgcaa aaaggccatc cgtcaggatg   4080
gccttctgct taatttgatg cctggcagtt tatggcgggc gtcctgcccg ccaccctccg   4140
ggccgttgct tcgcaacgtt caaatccgct cccggcggat ttgtcctact caggagagcg   4200
ttcaccgaca aacaacagat aaaacgaaag gcccagtctt tcgactgagc ctttcgtttt   4260
atttgatgcc tggcagttcc ctactctcgc atggggagac cccacactac catcgggggg   4320
ccatcgatgc aggtggcact tttcggggaa atgtgcgcgg aacccctatt tgtttatttt   4380
tctaaataca ttcaaatatg tatccgctca tgagacaata accctgctgc agaggcctgc   4440
atgcaagctt ggcgtaatca tggtcatagc tgtttcctgt gtgaaattgt tatccgctca   4500
caattccaca caacatacga gccggaagca taaagtgtaa agcctggggt gcctaatgag   4560
tgagctaact cacattaatt gcgttgcgct cactgcccgc tttccagtcg ggaaacctgt   4620
cgtgccagct gcattaatga atcggccaac gcgcggggag aggcggtttg cgtattgggc   4680
gctcttccgc ttcctcgctc actgactcgc tgcgctcggt cgttcggctg cggcgagcgg   4740
tatcagctca ctcaaaggcg gtaatacggt tatccacaga atcaggggat aacgcaggaa   4800
agaacatgtg agcaaaaggc cagcaaaagg ccaggaaccg taaaaaggcc gcgttgctgg   4860
cgtttttcca taggctccgc ccccctgacg agcatcacaa aaatcgacgc tcaagtcaga   4920
ggtggcgaaa cccgacagga ctataaagat accaggcgtt tccccctgga agctccctcg   4980
tgcgctctcc tgttccgacc ctgccgctta ccggatacct gtccgccttt ctcccttcgg   5040
gaagcgtggc gctttctcat agctcacgct gtaggtatct cagttcggtg taggtcgttc   5100
gctccaagct gggctgtgtg cacgaacccc ccgttcagcc cgaccgctgc gccttatccg   5160
gtaactatcg tcttgagtcc aacccggtaa gacacgactt atcgccactg gcagcagcca   5220
ctggtaacag gattagcaga gcgaggtatg taggcggtgc tacagagttc ttgaagtggt   5280
ggcctaacta cggctacact agaagaacag tatttggtat ctgcgctctg ctgaagccag   5340
ttaccttcgg aaaaagagtt ggtagctctt gatccggcaa acaaaccacc gctggtagcg   5400
gtggtttttt tgtttgcaag cagcagatta cgcgcagaaa aaaaggatct caagaagatc   5460
ctttgatctt ttctacgggg tctgacgctc agtggaacga aaactcacgt taagggattt   5520
tggtcatgag attatcaaaa aggatcttca cctagatcct tttaaattaa aaatgaagtt   5580
ttaaatcaat ctaaagtata tatgagtaaa cttggtctga cagttaccaa tgcttaatca   5640
gtgaggcacc tatctcagcg atctgtctat ttcgttcatc catagttgcc tgactccccg   5700
tcgtgtagat aactacgata cgggagggct taccatctgg ccccagtgct gcaatgatac   5760
cgcgagaccc acgctcaccg gctccagatt tatcagcaat aaaccagcca gccggaaggg   5820
ccgagcgcag aagtggtcct gcaactttat ccgcctccat ccagtctatt aattgttgcc   5880
gggaagctag agtaagtagt tcgccagtta atagtttgcg caacgttgtt gccattgcta   5940
caggcatcgt ggtgtcacgc tcgtcgtttg gtatggcttc attcagctcc ggttcccaac   6000
```

-continued

```
gatcaaggcg agttacatga tcccccatgt tgtgcaaaaa agcggttagc tccttcggtc   6060

ctccgatcgt tgtcagaagt aagttggccg cagtgttatc actcatggtt atggcagcac   6120

tgcataattc tcttactgtc atgccatccg taagatgctt ttctgtgact ggtgagtact   6180

caaccaagtc attctgagaa tagtgtatgc ggcgaccgag ttgctcttgc ccggcgtcaa   6240

tacgggataa taccgcgcca catagcagaa ctttaaaagt gctcatcatt ggaaaacgtt   6300

cttcggggcg aaaactctca aggatcttac cgctgttgag atccagttcg atgtaaccca   6360

ctcgtgcacc caactgatct tcagcatctt ttactttcac cagcgtttct gggtgagcaa   6420

aaacaggaag gcaaaatgcc gcaaaaaagg gaataagggc gacacggaaa tgttgaatac   6480

tcatactctt cctttttcaa tattattgaa gcatttatca gggttattgt ctcatgagcg   6540

gatacatatt tgaatgtatt tagaaaaata aacaaatagg ggttccgcgc acatttcccc   6600

gaaaagtgcc acctgacgtc taagaaacca ttattatcat gacattaacc tataaaaata   6660

ggcgtatcac gaggcccttt cgtc                                          6684
```

<210> SEQ ID NO 28
<211> LENGTH: 6738
<212> TYPE: DNA
<213> ORGANISM: Artificial Sequence
<220> FEATURE:
<223> OTHER INFORMATION: construct pINT-propP2

<400> SEQUENCE: 28

```
tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120

ttggcgggtg tcggggctgg cttaactatg cggcatcaga gcagattgta ctgagagtgc    180

accatatgcg gtgtgaaata ccgcacagat gcgtaaggag aaaataccgc atcaggcgcc    240

attcgccatt caggctgcgc aactgttggg aagggcgatc ggtgcgggcc tcttcgctat    300

tacgccagct ggcgaaaggg ggatgtgctg caaggcgatt aagttgggta acgccagggt    360

tttcccagtc acgacgttgt aaaacgacgg ccagtgaatt cgaagatcct ttgatctttt    420

ctacggggtc tgacgctcag tggaacgaaa actcacgtta agggattttg gtcatgagat    480

tatcaaaaag gatcttcacc tagatccttt taaactagtg aagttaccat cacggaaaaa    540

ggttatgctg cttttaagac ccactttcac atttaagttg tttttctaat ccgcatatga    600

tcaattcaag gccgaataag aaggctggct ctgcaccttg gtgatcaaat aattcgatag    660

cttgtcgtaa taatggcggc atactatcag tagtaggtgt ttccctttct tctttagcga    720

cttgatgctc ttgatcttcc aatacgcaac ctaaagtaaa atgccccact gcgctgagtg    780

catataatgc attctctagt gaaaaacctt gttggcataa aaaggctaat tgattttcga    840

gagtttcata ctgtttttct gtaggccgtg tacctaaatg tacttttgct ccatcgcgat    900

gacttagtaa agcacatcta aaacttttag cgttattacg taaaaaatct tgccagcttt    960

ccccttctaa agggcaaaag tgagtatggt gcctatctaa catctcaatg gctaaggcgt   1020

cgagcaaagc ccgcttattt tttacatgcc aatacaatgt aggctgctct acacctagct   1080

tctgggcgag tttacgggtt gttaaacctt cgattccgac ctcattaagc agctctaatg   1140

cgctgttaat cactttactt ttatctaaac gagacatact cttccttttt caatattatt   1200

gaagcattta tcagggttat tgtctcatga gcggatacat atttgaatgt atttagaaaa   1260

ataaacaaat aggggttccg cgcacatttc cccgaaaagt gccacctgaa attggccaga   1320

tgattaattc ctaatttttg ttgacactct atcattgata gagttatttt accactccct   1380
```

-continued atcagtgata gagaaaagtg aaatgaatag ttcgacaaaa atctagaaat aattttgttt 1440
aactttaaga aggagatata caagagctcg agtcgaagga gatagaacca tgaatgaatc 1500
cgccgtgaaa atcaaccgca cctttatctc ccactatgct ctgctgctga aactgatgac 1560
catgttcgtc caacaacaga acagtacccc gtccaatatt gtggcgttta acttcctgct 1620
gatcgccttt ctgacgggta ttgcgagcgc cttccagacc ccgacgctgt cactgtatct 1680
gtcgcaagaa atcaatgtta gtccgttttt cgttggtctg ttttactccg ttaacgcgat 1740
tatcggcatt atcctgagcc agattctggc caaatattct gataagcaag atgaccgtcg 1800
caaagtcatg attgtgtgct gtctgatcgc agtgctgggt tgcctgatct ttgcttacag 1860
ccgtaattat tacgttctga ttatcattgg caccacgctg ctgggcctgg gtagctctgc 1920
aaacccgcag tcatttgcac tggctcgtga atatgcagaa agttcccatc gcgaagctgt 1980
tatgttcacc acgattatgc gcacccagat cagtctggca tggattgtcg gtccgccgct 2040
gtcctttttc attgctctga attggggctt tgattatatg tacctggtcg caggttcagc 2100
tttcctgctg tgcgccggcg tgtcgaaact gctgccgaag atcccgcgtc agtctgcagt 2160
caaaaatcaa gaaattctgg acaacacccc gccgcgtcgc agtgtgattt acctgtttat 2220
cgccaatctg ctgctgtgga cgtgtaattc catgtacctg atcaacatgc cgctgttcgt 2280
gattaacgaa ctgcacctgg gtaaagaact ggcaggtacc ctgatgggta cggcagcagg 2340
cctggaaatt ccggtgatga tctttgccgg ctatctgacc aaatacttct caaaaaagcg 2400
cctgatgatg attgcactgg tttcgggtct ggctttttat tcatcgctgc tgttcagcga 2460
tcagacctgg caactgatcg gcctgcagat gctgaacgcg atctttattg gtatcaccgc 2520
cacgattggc atggtttatt tccaagacct gatgccgacc aaaatgggta cggcgaccac 2580
gctgtttagt aatgcagcta agagctcttg gatcattggc ggtccgatcg cgggcatcat 2640
tgccgaaatc tggcattaca actctgtgtt ttatgtggcg gttgccctga ttttcatcag 2700
cgtcggctgt atgtggaagg ttaagtctgt ctaataaatc gatactagca taaccccttg 2760
gggcctctaa acgcgtcgac acgcaaaaag gccatccgtc aggatggcct tctgcttaat 2820
ttgatgcctg gcagtttatg gcgggcgtcc tgcccgccac cctccgggcc gttgcttcgc 2880
aacgttcaaa tccgctcccg gcggatttgt cctactcagg agagcgttca ccgacaaaca 2940
acagataaaa cgaaaggccc agtctttcga ctgagccttt cgttttattt gatgcctggc 3000
agttccctac tctcgcatgg ggagacccca cactaccatc atgtatgaat atcctcctta 3060
gttcctattc cgaagttcct attctctaga aagtatagga acttcggcgc gtcctacctg 3120
tgacggaaga tcacttcgca gaataaataa atcctggtgt ccctgttgat accgggaagc 3180
cctgggccaa cttttggcga aaatgagacg ttgatcggca cgtaagaggt tccaactttc 3240
accataatga aataagatca ctaccgggcg tattttttga gttgtcgaga ttttcaggag 3300
ctaaggaagc taaaatggag aaaaaaatca ctggatatac caccgttgat atatcccaat 3360
ggcatcgtaa agaacatttt gaggcatttc agtcagttgc tcaatgtacc tataaccaga 3420
ccgttcagct ggatattacg gcctttttaa agaccgtaaa gaaaaataag cacaagtttt 3480
atccggcctt tattcacatt cttgcccgcc tgatgaatgc tcatccggaa ttacgtatgg 3540
caatgaaaga cggtgagctg gtgatatggg atagtgttca cccttgttac accgttttcc 3600
atgagcaaac tgaaacgttt tcatcgctct ggagtgaata ccacgacgat ttccggcagt 3660
ttctacacat atattcgcaa gatgtggcgt gttacggtga aaacctggcc tatttcccta 3720

-continued

```
aagggtttat tgagaatatg tttttcgtct cagccaatcc ctgggtgagt ttcaccagtt   3780
ttgatttaaa cgtggccaat atggacaact tcttcgcccc cgttttcacc atgggcaaat   3840
attatacgca aggcgacaag gtgctgatgc cgctggcgat tcaggttcat catgccgttt   3900
gtgatggctt ccatgtcggc agatgcttaa tgaatacaac agtactgcga tgagtggcag   3960
ggcggggcgt aaggcgcgcc atttaaatga agttcctatt ccgaagttcc tattctctag   4020
aaagtatagg aacttcgaag cagctccagc ctacacaatc gctcaagacg tgtaatgctg   4080
caatctgcat gcaagcttgg cactggccac gcaaaaaggc catccgtcag gatggccttc   4140
tgcttaattt gatgcctggc agtttatggc gggcgtcctg cccgccaccc tccgggccgt   4200
tgcttcgcaa cgttcaaatc cgctcccggc ggatttgtcc tactcaggag agcgttcacc   4260
gacaaacaac agataaaacg aaaggcccag tctttcgact gagcctttcg ttttatttga   4320
tgcctggcag ttccctactc tcgcatgggg agaccccaca ctaccatcgg ggggccatcg   4380
atgcaggtgg cacttttcgg ggaaatgtgc gcggaacccc tatttgttta tttttctaaa   4440
tacattcaaa tatgtatccg ctcatgagac aataaccctg ctgcagaggc ctgcatgcaa   4500
gcttggcgta atcatggtca tagctgtttc ctgtgtgaaa ttgttatccg ctcacaattc   4560
cacacaacat acgagccgga agcataaagt gtaaagcctg gggtgcctaa tgagtgagct   4620
aactcacatt aattgcgttg cgctcactgc ccgctttcca gtcgggaaac ctgtcgtgcc   4680
agctgcatta atgaatcggc caacgcgcgg ggagaggcgg tttgcgtatt gggcgctctt   4740
ccgcttcctc gctcactgac tcgctgcgct cggtcgttcg gctgcggcga gcggtatcag   4800
ctcactcaaa ggcggtaata cggttatcca cagaatcagg ggataacgca ggaaagaaca   4860
tgtgagcaaa aggccagcaa aaggccagga accgtaaaaa ggccgcgttg ctggcgtttt   4920
tccataggct ccgcccccct gacgagcatc acaaaaatcg acgctcaagt cagaggtggc   4980
gaaacccgac aggactataa agataccagg cgtttccccc tggaagctcc ctcgtgcgct   5040
ctcctgttcc gaccctgccg cttaccggat acctgtccgc ctttctccct tcgggaagcg   5100
tggcgctttc tcatagctca cgctgtaggt atctcagttc ggtgtaggtc gttcgctcca   5160
agctgggctg tgtgcacgaa ccccccgttc agcccgaccg ctgcgcctta tccggtaact   5220
atcgtcttga gtccaacccg gtaagacacg acttatcgcc actggcagca gccactggta   5280
acaggattag cagagcgagg tatgtaggcg gtgctacaga gttcttgaag tggtggccta   5340
actacggcta cactagaaga acagtatttg gtatctgcgc tctgctgaag ccagttacct   5400
tcggaaaaag agttggtagc tcttgatccg gcaaacaaac caccgctggt agcggtggtt   5460
tttttgtttg caagcagcag attacgcgca gaaaaaaagg atctcaagaa gatcctttga   5520
tcttttctac ggggtctgac gctcagtgga acgaaaactc acgttaaggg attttggtca   5580
tgagattatc aaaaaggatc ttcacctaga tccttttaaa ttaaaaatga agttttaaat   5640
caatctaaag tatatatgag taaacttggt ctgacagtta ccaatgctta atcagtgagg   5700
cacctatctc agcgatctgt ctatttcgtt catccatagt tgcctgactc cccgtcgtgt   5760
agataactac gatacgggag ggcttaccat ctggccccag tgctgcaatg ataccgcgag   5820
acccacgctc accggctcca gatttatcag caataaacca gccagccgga agggccgagc   5880
gcagaagtgg tcctgcaact ttatccgcct ccatccagtc tattaattgt tgccgggaag   5940
ctagagtaag tagttcgcca gttaatagtt tgcgcaacgt tgttgccatt gctacaggca   6000
tcgtggtgtc acgctcgtcg tttggtatgg cttcattcag ctccggttcc caacgatcaa   6060
ggcgagttac atgatccccc atgttgtgca aaaaagcggt tagctccttc ggtcctccga   6120
```

tcgttgtcag aagtaagttg gccgcagtgt tatcactcat ggttatggca gcactgcata 6180
attctcttac tgtcatgcca tccgtaagat gcttttctgt gactggtgag tactcaacca 6240
agtcattctg agaatagtgt atgcggcgac cgagttgctc ttgcccggcg tcaatacggg 6300
ataataccgc gccacatagc agaactttaa aagtgctcat cattggaaaa cgttcttcgg 6360
ggcgaaaact ctcaaggatc ttaccgctgt tgagatccag ttcgatgtaa cccactcgtg 6420
cacccaactg atcttcagca tcttttactt tcaccagcgt ttctgggtga gcaaaaacag 6480
gaaggcaaaa tgccgcaaaa aagggaataa gggcgacacg gaaatgttga atactcatac 6540
tcttcctttt tcaatattat tgaagcattt atcagggtta ttgtctcatg agcggataca 6600
tatttgaatg tatttagaaa aataaacaaa taggggttcc gcgcacattt ccccgaaaag 6660
tgccacctga cgtctaagaa accattatta tcatgacatt aacctataaa aataggcgta 6720
tcacgaggcc ctttcgtc 6738

<210> SEQ ID NO 29
<211> LENGTH: 6513
<212> TYPE: DNA
<213> ORGANISM: Artificial Sequence
<220> FEATURE:
<223> OTHER INFORMATION: construct pINT-Pc-setA

<400> SEQUENCE: 29
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accatatgcg gtgtgaaata ccgcacagat gcgtaaggag aaaataccgc atcaggcgcc 240
attcgccatt caggctgcgc aactgttggg aagggcgatc ggtgcgggcc tcttcgctat 300
tacgccagct ggcgaaaggg ggatgtgctg caaggcgatt aagttgggta acgccagggt 360
tttcccagtc acgacgttgt aaaacgacgg ccagtgaatt cgaagatcct ttgatctttt 420
ctacggggtc tgacgctcag tggaacgaaa actcacgtta agggattttg gtcatgagat 480
tatcaaaaag gatcttcacc tagatccttt taaactagtg aagttaccat cacggaaaaa 540
ggttatgctg cttttaagac ccactttcac atttaagttg tttttctaat ccgcatatga 600
tcaattcaag gccgaataag aaggctggct ctgcaccttg gtgatcaaat aattcgatag 660
cttgtcgtaa taatggcggc atactatcag tagtaggtgt ttccctttct tctttagcga 720
cttgatgctc ttgatcttcc aatacgcaac ctaaagtaaa atgccccact gcgctgagtg 780
catataatgc attctctagt gaaaaacctt gttggcataa aaaggctaat tgattttcga 840
gagtttcata ctgtttttct gtaggccgtg tacctaaatg tacttttgct ccatcgcgat 900
gacttagtaa agcacatcta aaacttttag cgttattacg taaaaaatct tgccagcttt 960
ccccttctaa agggcaaaag tgagtatggt gcctatctaa catctcaatg gctaaggcgt 1020
cgagcaaagc ccgcttattt tttacatgcc aatacaatgt aggctgctct acacctagct 1080
tctgggcgag tttacgggtt gttaaacctt cgattccgac ctcattaagc agctctaatg 1140
cgctgttaat cactttactt ttatctaaac gagacatact cttccttttt caatattatt 1200
gaagcattta tcagggttat tgtctcatga gcggatacat atttgaatgt atttagaaaa 1260
ataaacaaat aggggttccg cgcacatttc cccgaaaagt gccacctgaa attggccaga 1320
tgattaattc ctaatttttg ttgacactct atcattgata gagttatttt accactccct 1380

-continued

```
atcagtgata gagaaaagtg aaatgaatag ttcgacaaaa atctagaaat aattttgttt   1440
aactttaaga aggagatata caagagctcg agtcgaagga gatagaacca tgttctacac   1500
gggctcggca gttattggta tcgtcgtctc gcagatgctg gctacgcgct cggatcgtca   1560
gggtgaccgc aagtcgctga tcttcgtttg ctgtctgctg ggtgcgctgg cctgcatgct   1620
gtttgcgtgg aaccgcaatt atttcatcct gctgtttatt ggtgtgctgc tgagctcttt   1680
cggcagtacc gccaacccgc agctgtttgc actggctcgc gaacatgcag ataaaacggg   1740
tcgtgaagcg gccatgttca gttccatcct gcgtgcccaa atttccctgg catgggtggt   1800
tggtccgccg attgcgtttg ccctggcact gggcttcggt tttaccacga tgtacctgac   1860
cgcagctgtc gtgttcatcc tgtgtggtat tctggtgaag ctgtttctgc cgagcatgcc   1920
gaaagccgtt gaaaagacca cgagcaccct ggaatctccg cgtcgcaatc gtcgcgacac   1980
gctgctgctg tttgttgcgt gcaccctgat gtggacgtgt aacggcatct atctgattaa   2040
tatgccgctg tacctggttc atgaactgca cctgccggaa aaactggcag gtatcatgat   2100
gggtgtcgca gcaggtctgg aaatcccggt tatgctgatt gccggttatg tcgcaaaacg   2160
tttcggcaag cgctttctga tgcgtctggc tgtcgcgagc ggtctgctgt ttttcggcgg   2220
tctgctggtg ctggatggcg aaatcgccct gctggcactg caggctctga acgcgatttt   2280
catcggcatt ctggctggca ttggtatgct gtactttcag gacctgatgc cgggccaagc   2340
aggtgcagct accacgctgt ttaccaacac cacgcgcgtg ggttggatta tctcaggttc   2400
gctggctggc atcgtggcgg aaatttggaa ttatcacgct gtgtttttct ttgcgctgct   2460
gatgatcgtc ggctctattt actgcatgtg gcgtattaaa gatgcgtaat aaatcgatac   2520
tagcataacc ccttggggcc tctaaacgcg tcgacacgca aaaaggccat ccgtcaggat   2580
ggccttctgc ttaatttgat gcctggcagt ttatggcggg cgtcctgccc gccaccctcc   2640
gggccgttgc ttcgcaacgt tcaaatccgc tcccggcgga tttgtcctac tcaggagagc   2700
gttcaccgac aaacaacaga taaaacgaaa ggcccagtct ttcgactgag cctttcgttt   2760
tatttgatgc ctggcagttc cctactctcg catggggaga ccccacacta ccatcatgta   2820
tgaatatcct ccttagttcc tattccgaag ttcctattct ctagaaagta taggaacttc   2880
ggcgcgtcct acctgtgacg gaagatcact tcgcagaata aataaatcct ggtgtccctg   2940
ttgataccgg gaagccctgg gccaactttt ggcgaaaatg agacgttgat cggcacgtaa   3000
gaggttccaa ctttcaccat aatgaaataa gatcactacc gggcgtattt tttgagttgt   3060
cgagattttc aggagctaag gaagctaaaa tggagaaaaa aatcactgga tataccaccg   3120
ttgatatatc ccaatggcat cgtaaagaac attttgaggc atttcagtca gttgctcaat   3180
gtacctataa ccagaccgtt cagctggata ttacggcctt tttaaagacc gtaaagaaaa   3240
ataagcacaa gttttatccg gcctttattc acattcttgc ccgcctgatg aatgctcatc   3300
cggaattacg tatggcaatg aaagacggtg agctggtgat atgggatagt gttcaccctt   3360
gttacaccgt tttccatgag caaactgaaa cgttttcatc gctctggagt gaataccacg   3420
acgatttccg gcagtttcta cacatatatt cgcaagatgt ggcgtgttac ggtgaaaacc   3480
tggcctattt ccctaaaggg tttattgaga atatgttttt cgtctcagcc aatccctggg   3540
tgagtttcac cagttttgat ttaaacgtgg ccaatatgga caacttcttc gcccccgttt   3600
tcaccatggg caaatattat acgcaaggcg acaaggtgct gatgccgctg gcgattcagg   3660
ttcatcatgc cgtttgtgat ggcttccatg tcggcagatg cttaatgaat acaacagtac   3720
tgcgatgagt ggcagggcgg ggcgtaaggc gcgccattta aatgaagttc ctattccgaa   3780
```

```
gttcctattc tctagaaagt ataggaactt cgaagcagct ccagcctaca caatcgctca   3840
agacgtgtaa tgctgcaatc tgcatgcaag cttggcactg gccacgcaaa aaggccatcc   3900
gtcaggatgg ccttctgctt aatttgatgc ctggcagttt atggcgggcg tcctgcccgc   3960
caccctccgg gccgttgctt cgcaacgttc aaatccgctc ccggcggatt tgtcctactc   4020
aggagagcgt tcaccgacaa acaacagata aaacgaaagg cccagtcttt cgactgagcc   4080
tttcgtttta tttgatgcct ggcagttccc tactctcgca tggggagacc ccacactacc   4140
atcggggggc catcgatgca ggtggcactt ttcggggaaa tgtgcgcgga acccctattt   4200
gtttattttt ctaaatacat tcaaatatgt atccgctcat gagacaataa ccctgctgca   4260
gaggcctgca tgcaagcttg gcgtaatcat ggtcatagct gtttcctgtg tgaaattgtt   4320
atccgctcac aattccacac aacatacgag ccggaagcat aaagtgtaaa gcctggggtg   4380
cctaatgagt gagctaactc acattaattg cgttgcgctc actgcccgct ttccagtcgg   4440
gaaacctgtc gtgccagctg cattaatgaa tcggccaacg cgcggggaga ggcggtttgc   4500
gtattgggcg ctcttccgct tcctcgctca ctgactcgct gcgctcggtc gttcggctgc   4560
ggcgagcggt atcagctcac tcaaaggcgg taatacggtt atccacagaa tcaggggata   4620
acgcaggaaa gaacatgtga gcaaaaggcc agcaaaaggc caggaaccgt aaaaaggccg   4680
cgttgctggc gtttttccat aggctccgcc cccctgacga gcatcacaaa aatcgacgct   4740
caagtcagag gtggcgaaac ccgacaggac tataaagata ccaggcgttt ccccctggaa   4800
gctccctcgt gcgctctcct gttccgaccc tgccgcttac cggatacctg tccgcctttc   4860
tcccttcggg aagcgtggcg ctttctcata gctcacgctg taggtatctc agttcggtgt   4920
aggtcgttcg ctccaagctg ggctgtgtgc acgaaccccc cgttcagccc gaccgctgcg   4980
ccttatccgg taactatcgt cttgagtcca acccggtaag acacgactta tcgccactgg   5040
cagcagccac tggtaacagg attagcagag cgaggtatgt aggcggtgct acagagttct   5100
tgaagtggtg gcctaactac ggctacacta gaagaacagt atttggtatc tgcgctctgc   5160
tgaagccagt taccttcgga aaaagagttg gtagctcttg atccggcaaa caaaccaccg   5220
ctggtagcgg tggttttttt gtttgcaagc agcagattac gcgcagaaaa aaaggatctc   5280
aagaagatcc tttgatcttt tctacggggt ctgacgctca gtggaacgaa aactcacgtt   5340
aagggatttt ggtcatgaga ttatcaaaaa ggatcttcac ctagatcctt ttaaattaaa   5400
aatgaagttt taaatcaatc taaagtatat atgagtaaac ttggtctgac agttaccaat   5460
gcttaatcag tgaggcacct atctcagcga tctgtctatt tcgttcatcc atagttgcct   5520
gactccccgt cgtgtagata actacgatac gggagggctt accatctggc cccagtgctg   5580
caatgatacc gcgagaccca cgctcaccgg ctccagattt atcagcaata aaccagccag   5640
ccggaagggc cgagcgcaga agtggtcctg caactttatc cgcctccatc cagtctatta   5700
attgttgccg ggaagctaga gtaagtagtt cgccagttaa tagtttgcgc aacgttgttg   5760
ccattgctac aggcatcgtg gtgtcacgct cgtcgtttgg tatggcttca ttcagctccg   5820
gttcccaacg atcaaggcga gttacatgat cccccatgtt gtgcaaaaaa gcggttagct   5880
ccttcggtcc tccgatcgtt gtcagaagta agttggccgc agtgttatca ctcatggtta   5940
tggcagcact gcataattct cttactgtca tgccatccgt aagatgcttt tctgtgactg   6000
gtgagtactc aaccaagtca ttctgagaat agtgtatgcg gcgaccgagt tgctcttgcc   6060
cggcgtcaat acgggataat accgcgccac atagcagaac tttaaaagtg ctcatcattg   6120
```

-continued

```
gaaaacgttc ttcggggcga aaactctcaa ggatcttacc gctgttgaga tccagttcga   6180

tgtaacccac tcgtgcaccc aactgatctt cagcatcttt tactttcacc agcgtttctg   6240

ggtgagcaaa aacaggaagg caaaatgccg caaaaaaggg aataagggcg acacggaaat   6300

gttgaatact catactcttc ctttttcaat attattgaag catttatcag ggttattgtc   6360

tcatgagcgg atacatattt gaatgtattt agaaaaataa acaaataggg gttccgcgca   6420

catttccccg aaaagtgcca cctgacgtct aagaaaccat tattatcatg acattaacct   6480

ataaaaatag gcgtatcacg aggccctttc gtc                                6513
```

<210> SEQ ID NO 30
<211> LENGTH: 6810
<212> TYPE: DNA
<213> ORGANISM: Artificial Sequence
<220> FEATURE:
<223> OTHER INFORMATION: construct pINT-fucP

<400> SEQUENCE: 30

```
tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120

ttggcgggtg tcggggctgg cttaactatg cggcatcaga gcagattgta ctgagagtgc    180

accatatgcg gtgtgaaata ccgcacagat gcgtaaggag aaaataccgc atcaggcgcc    240

attcgccatt caggctgcgc aactgttggg aagggcgatc ggtgcgggcc tcttcgctat    300

tacgccagct ggcgaaaggg ggatgtgctg caaggcgatt aagttgggta acgccagggt    360

tttcccagtc acgacgttgt aaaacgacgg ccagtgaatt cgaagatcct ttgatctttt    420

ctacggggtc tgacgctcag tggaacgaaa actcacgtta agggattttg gtcatgagat    480

tatcaaaaag gatcttcacc tagatccttt taaactagtg aagttaccat cacggaaaaa    540

ggttatgctg cttttaagac ccactttcac atttaagttg tttttctaat ccgcatatga    600

tcaattcaag gccgaataag aaggctggct ctgcaccttg gtgatcaaat aattcgatag    660

cttgtcgtaa taatggcggc atactatcag tagtaggtgt ttccctttct tctttagcga    720

cttgatgctc ttgatcttcc aatacgcaac ctaaagtaaa atgccccact gcgctgagtg    780

catataatgc attctctagt gaaaaacctt gttggcataa aaaggctaat tgattttcga    840

gagtttcata ctgtttttct gtaggccgtg tacctaaatg tacttttgct ccatcgcgat    900

gacttagtaa agcacatcta aaacttttag cgttattacg taaaaaatct tgccagcttt    960

ccccttctaa agggcaaaag tgagtatggt gcctatctaa catctcaatg gctaaggcgt   1020

cgagcaaagc ccgcttattt tttacatgcc aatacaatgt aggctgctct acacctagct   1080

tctgggcgag tttacgggtt gttaaacctt cgattccgac ctcattaagc agctctaatg   1140

cgctgttaat cactttactt ttatctaaac gagacatact cttccttttt caatattatt   1200

gaagcattta tcagggttat tgtctcatga gcggatacat atttgaatgt atttagaaaa   1260

ataaacaaat aggggttccg cgcacatttc cccgaaaagt gccacctgaa attggccaga   1320

tgattaattc ctaatttttg ttgacactct atcattgata gagttatttt accactccct   1380

atcagtgata gagaaaagtg aaatgaatag ttcgacaaaa atctagaaat aattttgttt   1440

aactttaaga aggagatata caagagctcg agtcgaagga gatagaacca tgggaaacac   1500

atcaatacaa acgcagagtt accgtgcggt agataaagat gcagggcaaa gcagaagtta   1560

cattattcca ttcgcgctgc tgtgctcact gttttttctt tgggcggtag ccaataacct   1620

taacgacatt ttattacctc aattccagca ggcttttacg ctgacaaatt tccaggctgg   1680
```

-continued

```
cctgatccaa tcggcctttt actttggtta tttcattatc ccaatccctg ctgggatatt   1740
gatgaaaaaa ctcagttata aagcagggat tattaccggg ttatttttat atgccttggg   1800
tgctgcatta ttctggcccg ccgcagaaat aatgaactac accttgtttt tagttggcct   1860
atttattatt gcagccggat taggttgtct ggaaactgcc gcaaaccctt ttgttacggt   1920
attagggccg gaaagtagtg gtcacttccg cttaaatctt gcgcaaacat ttaactcgtt   1980
tggcgcaatt atcgcggttg tctttgggca aagtcttatt ttgtctaacg tgccacatca   2040
atcgcaagac gttctcgata aaatgtctcc agagcaattg agtgcgtata aacacagcct   2100
ggtattatcg gtacagacac cttatatgat catcgtggct atcgtgttac tggtcgccct   2160
gctgatcatg ctgacgaaat tcccggcatt gcagagtgat aatcacagtg acgccaaaca   2220
aggatcgttc tccgcatcgc tttctcgcct ggcgcgtatt cgccactggc gctgggcggt   2280
attagcgcaa ttctgctatg tcggcgcaca aacggcctgc tggagctatt tgattcgcta   2340
cgctgtagaa gaaattccag gtatgactgc aggctttgcc gctaactatt taaccggaac   2400
catggtgtgc ttctttattg gtcgtttcac cggtacctgg ctcatcagtc gcttcgcacc   2460
acacaaagtc ctggccgcct acgcattaat cgctatggca ctgtgcctga tctcagcctt   2520
cgctggcggt catgtgggct taatagccct gactttatgc agcgccttta tgtcgattca   2580
gtacccaaca atcttctcgc tgggcattaa gaatctcggc caggacacca aatatggttc   2640
gtccttcatc gttatgacca ttattggcgg cggtattgtc actccggtca tgggttttgt   2700
cagtgacgcg gcgggcaaca tccccactgc tgaactgatc cccgcactct gcttcgcggt   2760
catctttatc tttgcccgtt tccgttctca aacggcaact aactgataaa tcgatactag   2820
cataacccct tggggcctct aaacgcgtcg acacgcaaaa aggccatccg tcaggatggc   2880
cttctgctta atttgatgcc tggcagttta tggcgggcgt cctgcccgcc accctccggg   2940
ccgttgcttc gcaacgttca aatccgctcc cggcggattt gtcctactca ggagagcgtt   3000
caccgacaaa caacagataa aacgaaaggc ccagtctttc gactgagcct ttcgttttat   3060
ttgatgcctg gcagttccct actctcgcat ggggagaccc cacactacca tcatgtatga   3120
atatcctcct tagttcctat tccgaagttc ctattctcta gaaagtatag gaacttcggc   3180
gcgtcctacc tgtgacggaa gatcacttcg cagaataaat aaatcctggt gtccctgttg   3240
ataccgggaa gccctgggcc aacttttggc gaaaatgaga cgttgatcgg cacgtaagag   3300
gttccaactt tcaccataat gaaataagat cactaccggg cgtatttttt gagttgtcga   3360
gattttcagg agctaaggaa gctaaaatgg agaaaaaaat cactggatat accaccgttg   3420
atatatccca atggcatcgt aaagaacatt ttgaggcatt tcagtcagtt gctcaatgta   3480
cctataacca gaccgttcag ctggatatta cggccttttt aaagaccgta aagaaaaata   3540
agcacaagtt ttatccggcc tttattcaca ttcttgcccg cctgatgaat gctcatccgg   3600
aattacgtat ggcaatgaaa gacggtgagc tggtgatatg ggatagtgtt cacccttgtt   3660
acaccgtttt ccatgagcaa actgaaacgt tttcatcgct ctggagtgaa taccacgacg   3720
atttccggca gtttctacac atatattcgc aagatgtggc gtgttacggt gaaaacctgg   3780
cctatttccc taaagggttt attgagaata tgtttttcgt ctcagccaat ccctgggtga   3840
gtttcaccag ttttgattta aacgtggcca atatggacaa cttcttcgcc cccgttttca   3900
ccatgggcaa atattatacg caaggcgaca aggtgctgat gccgctggcg attcaggttc   3960
atcatgccgt ttgtgatggc ttccatgtcg gcagatgctt aatgaataca acagtactgc   4020
```

-continued

```
gatgagtggc agggcggggc gtaaggcgcg ccatttaaat gaagttccta ttccgaagtt   4080
cctattctct agaaagtata ggaacttcga agcagctcca gcctacacaa tcgctcaaga   4140
cgtgtaatgc tgcaatctgc atgcaagctt ggcactggcc acgcaaaaag gccatccgtc   4200
aggatggcct tctgcttaat ttgatgcctg gcagtttatg gcgggcgtcc tgcccgccac   4260
cctccgggcc gttgcttcgc aacgttcaaa tccgctcccg gcggatttgt cctactcagg   4320
agagcgttca ccgacaaaca acagataaaa cgaaaggccc agtctttcga ctgagccttt   4380
cgttttattt gatgcctggc agttccctac tctcgcatgg ggagacccca cactaccatc   4440
ggggggccat cgatgcaggt ggcacttttc ggggaaatgt gcgcggaacc cctatttgtt   4500
tatttttcta aatacattca aatatgtatc cgctcatgag acaataaccc tgctgcagag   4560
gcctgcatgc aagcttggcg taatcatggt catagctgtt tcctgtgtga aattgttatc   4620
cgctcacaat tccacacaac atacgagccg gaagcataaa gtgtaaagcc tggggtgcct   4680
aatgagtgag ctaactcaca ttaattgcgt tgcgctcact gcccgctttc cagtcgggaa   4740
acctgtcgtg ccagctgcat taatgaatcg gccaacgcgc ggggagaggc ggtttgcgta   4800
ttgggcgctc ttccgcttcc tcgctcactg actcgctgcg ctcggtcgtt cggctgcggc   4860
gagcggtatc agctcactca aaggcggtaa tacggttatc cacagaatca ggggataacg   4920
caggaaagaa catgtgagca aaaggccagc aaaaggccag gaaccgtaaa aaggccgcgt   4980
tgctggcgtt tttccatagg ctccgccccc ctgacgagca tcacaaaaat cgacgctcaa   5040
gtcagaggtg gcgaaacccg acaggactat aaagatacca ggcgtttccc cctggaagct   5100
ccctcgtgcg ctctcctgtt ccgaccctgc cgcttaccgg atacctgtcc gcctttctcc   5160
cttcgggaag cgtggcgctt tctcatagct cacgctgtag gtatctcagt tcggtgtagg   5220
tcgttcgctc caagctgggc tgtgtgcacg aaccccccgt tcagcccgac cgctgcgcct   5280
tatccggtaa ctatcgtctt gagtccaacc cggtaagaca cgacttatcg ccactggcag   5340
cagccactgg taacaggatt agcagagcga ggtatgtagg cggtgctaca gagttcttga   5400
agtggtggcc taactacggc tacactagaa gaacagtatt tggtatctgc gctctgctga   5460
agccagttac cttcggaaaa agagttggta gctcttgatc cggcaaacaa accaccgctg   5520
gtagcggtgg tttttttgtt tgcaagcagc agattacgcg cagaaaaaaa ggatctcaag   5580
aagatccttt gatcttttct acggggtctg acgctcagtg gaacgaaaac tcacgttaag   5640
ggattttggt catgagatta tcaaaaagga tcttcaccta gatcctttta aattaaaaat   5700
gaagttttaa atcaatctaa agtatatatg agtaaacttg gtctgacagt taccaatgct   5760
taatcagtga ggcacctatc tcagcgatct gtctatttcg ttcatccata gttgcctgac   5820
tccccgtcgt gtagataact acgatacggg agggcttacc atctggcccc agtgctgcaa   5880
tgataccgcg agacccacgc tcaccggctc cagatttatc agcaataaac cagccagccg   5940
gaagggccga gcgcagaagt ggtcctgcaa ctttatccgc ctccatccag tctattaatt   6000
gttgccggga agctagagta agtagttcgc cagttaatag tttgcgcaac gttgttgcca   6060
ttgctacagg catcgtggtg tcacgctcgt cgtttggtat ggcttcattc agctccggtt   6120
cccaacgatc aaggcgagtt acatgatccc ccatgttgtg caaaaaagcg gttagctcct   6180
tcggtcctcc gatcgttgtc agaagtaagt tggccgcagt gttatcactc atggttatgg   6240
cagcactgca taattctctt actgtcatgc catccgtaag atgcttttct gtgactggtg   6300
agtactcaac caagtcattc tgagaatagt gtatgcggcg accgagttgc tcttgcccgg   6360
cgtcaatacg ggataatacc gcgccacata gcagaacttt aaaagtgctc atcattggaa   6420
```

aacgttcttc ggggcgaaaa ctctcaagga tcttaccgct gttgagatcc agttcgatgt 6480
aacccactcg tgcacccaac tgatcttcag catcttttac tttcaccagc gtttctgggt 6540
gagcaaaaac aggaaggcaa aatgccgcaa aaaagggaat aagggcgaca cggaaatgtt 6600
gaatactcat actcttcctt tttcaatatt attgaagcat ttatcagggt tattgtctca 6660
tgagcggata catatttgaa tgtatttaga aaaataaaca aataggggtt ccgcgcacat 6720
ttccccgaaa agtgccacct gacgtctaag aaaccattat tatcatgaca ttaacctata 6780
aaaataggcg tatcacgagg ccctttcgtc 6810

<210> SEQ ID NO 31
<211> LENGTH: 6933
<212> TYPE: DNA
<213> ORGANISM: Artificial Sequence
<220> FEATURE:
<223> OTHER INFORMATION: construct pINT-mdeA

<400> SEQUENCE: 31
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accatatgcg gtgtgaaata ccgcacagat gcgtaaggag aaaataccgc atcaggcgcc 240
attcgccatt caggctgcgc aactgttggg aagggcgatc ggtgcgggcc tcttcgctat 300
tacgccagct ggcgaaaggg ggatgtgctg caaggcgatt aagttgggta acgccagggt 360
tttcccagtc acgacgttgt aaaacgacgg ccagtgaatt cgaagatcct ttgatctttt 420
ctacggggtc tgacgctcag tggaacgaaa actcacgtta agggattttg gtcatgagat 480
tatcaaaaag gatcttcacc tagatccttt taaactagtg aagttaccat cacggaaaaa 540
ggttatgctg cttttaagac ccactttcac atttaagttg tttttctaat ccgcatatga 600
tcaattcaag gccgaataag aaggctggct ctgcaccttg gtgatcaaat aattcgatag 660
cttgtcgtaa taatggcggc atactatcag tagtaggtgt ttccctttct tctttagcga 720
cttgatgctc ttgatcttcc aatacgcaac ctaaagtaaa atgccccact gcgctgagtg 780
catataatgc attctctagt gaaaaacctt gttggcataa aaaggctaat tgattttcga 840
gagtttcata ctgtttttct gtaggccgtg tacctaaatg tacttttgct ccatcgcgat 900
gacttagtaa agcacatcta aaacttttag cgttattacg taaaaaatct tgccagcttt 960
ccccttctaa agggcaaaag tgagtatggt gcctatctaa catctcaatg gctaaggcgt 1020
cgagcaaagc ccgcttattt tttacatgcc aatacaatgt aggctgctct acacctagct 1080
tctgggcgag tttacgggtt gttaaacctt cgattccgac ctcattaagc agctctaatg 1140
cgctgttaat cactttactt ttatctaaac gagacatact cttccttttt caatattatt 1200
gaagcattta tcagggttat tgtctcatga gcggatacat atttgaatgt atttagaaaa 1260
ataaacaaat aggggttccg cgcacatttc cccgaaaagt gccacctgaa attggccaga 1320
tgattaattc ctaatttttg ttgacactct atcattgata gagttatttt accactccct 1380
atcagtgata gagaaaagtg aaatgaatag ttcgacaaaa atctagaaat aattttgttt 1440
aactttaaga aggagatata caagagctcg agtcgaagga gatagaacca tgtccaaaaa 1500
acaaaaactg acgatgatta ttacgatgct gatgggtggc ttcttcggtc tgctgaatga 1560
aacgctgctg gtgacggcac tgccgagcat catgaaagac ttcgaaattt cttatacgca 1620

-continued

```
ggttcaatgg ctgaccacgg catttctgct gaccaacggc atcgttattc cgctgtcagc   1680
tctggtcatt cagcgttaca ccacgcgcca agttttcctg gtcggtatct ctattttctt   1740
tctgggcacg ctgctgtcag gtctgtcgcc gcattttgcg accctgctgg ttgcgcgtat   1800
tatccaggca ctgggcgctg gtatcatgat gccgctgatg atgaccacga ttctggatgt   1860
cttccaaccg cacgaacgcg gcaaatatat gggcattttt ggtctggtga tcggtctggc   1920
accggcaatc ggtccgaccc tgagtggtta tctggttgaa tacttcaact ggcgttccct   1980
gtttcatgtg gttgcgccga tcgcggccgt tacctttctg attggcttca aaacgatcaa   2040
aaatgtgggt accacgatta aagttccgat cgactttatt tcagtcatct tctcggtgct   2100
gggctttggc ggtctgctgt atggtaccag ctctatttca gaaaaaggct tcgataatcc   2160
gatcgtcctg gtgtcgatga ttggcggtgt cgtgctggtt gcactgtttg tcctgcgtca   2220
gtaccgcctg agcaccccgc tgctgaactt cgctgtgttc aaaaaacaaac aattcaccgt   2280
tggcattatc attatgggtg tgacgatggt tagcatgatc ggctctgaaa ccattctgcc   2340
gatctttgtt cagaacctgc tgcatcgtag tgcactggac tccggtctga cgctgctgcc   2400
gggtgcaatt gtgatggcct tcatgagcat gacctctggc gccctgtatg aaaaatttgg   2460
tccgcgcaat ctggcactgg tgggtatggc tattgttgtc atcaccacgg catattttgt   2520
ggttatggat gaacagacca gtacgattat gctggcaacc gtctacgcta ttcgcatggt   2580
gggcatcgcg ctgggtctga ttccggttat gacccatacg atgaaccagc tgaaaccgga   2640
aatgaatgcg cacggcagtt ccatgaccaa cacggtgcag caaattgccg gcagcatcgg   2700
taccgcagct ctgatcacga ttctgagtca cgcctccaaa aacttttcac cgaccatgtc   2760
ggattacaac ggtatgaaca aaatcgacat gatgaaccag atcaaagtcg ataccatgct   2820
gcatggctac cacgcgggtt ttctgttcgc cctgctgatt accgtggtgt cgttcttctg   2880
ttcatttatg ctgcaaggca aaaagaaaga agtggattcc cgccagtaat aaatcgatac   2940
tagcataacc ccttggggcc tctaaacgcg tcgacacgca aaaaggccat ccgtcaggat   3000
ggccttctgc ttaatttgat gcctggcagt ttatggcggg cgtcctgccc gccaccctcc   3060
gggccgttgc ttcgcaacgt tcaaatccgc tcccggcgga tttgtcctac tcaggagagc   3120
gttcaccgac aaacaacaga taaaacgaaa ggcccagtct ttcgactgag cctttcgttt   3180
tatttgatgc ctggcagttc cctactctcg catggggaga ccccacacta ccatcatgta   3240
tgaatatcct ccttagttcc tattccgaag ttcctattct ctagaaagta taggaacttc   3300
ggcgcgtcct acctgtgacg gaagatcact tcgcagaata aataaatcct ggtgtccctg   3360
ttgataccgg gaagccctgg gccaactttt ggcgaaaatg agacgttgat cggcacgtaa   3420
gaggttccaa ctttcaccat aatgaaataa gatcactacc gggcgtattt tttgagttgt   3480
cgagattttc aggagctaag gaagctaaaa tggagaaaaa aatcactgga tataccaccg   3540
ttgatatatc ccaatggcat cgtaaagaac attttgaggc atttcagtca gttgctcaat   3600
gtacctataa ccagaccgtt cagctggata ttacggcctt tttaaagacc gtaaagaaaa   3660
ataagcacaa gttttatccg gcctttattc acattcttgc ccgcctgatg aatgctcatc   3720
cggaattacg tatggcaatg aaagacggtg agctggtgat atgggatagt gttcaccctt   3780
gttacaccgt tttccatgag caaactgaaa cgttttcatc gctctggagt gaataccacg   3840
acgatttccg gcagtttcta cacatatatt cgcaagatgt ggcgtgttac ggtgaaaacc   3900
tggcctattt ccctaaaggg tttattgaga atatgttttt cgtctcagcc aatccctggg   3960
tgagtttcac cagttttgat ttaaacgtgg ccaatatgga caacttcttc gcccccgttt   4020
```

-continued

```
tcaccatggg caaatattat acgcaaggcg acaaggtgct gatgccgctg gcgattcagg   4080
ttcatcatgc cgtttgtgat ggcttccatg tcggcagatg cttaatgaat acaacagtac   4140
tgcgatgagt ggcagggcgg ggcgtaaggc gcgccattta aatgaagttc ctattccgaa   4200
gttcctattc tctagaaagt ataggaactt cgaagcagct ccagcctaca caatcgctca   4260
agacgtgtaa tgctgcaatc tgcatgcaag cttggcactg gccacgcaaa aaggccatcc   4320
gtcaggatgg ccttctgctt aatttgatgc ctggcagttt atggcgggcg tcctgcccgc   4380
caccctccgg gccgttgctt cgcaacgttc aaatccgctc ccggcggatt tgtcctactc   4440
aggagagcgt tcaccgacaa acaacagata aaacgaaagg cccagtcttt cgactgagcc   4500
tttcgtttta tttgatgcct ggcagttccc tactctcgca tggggagacc ccacactacc   4560
atcgggggc catcgatgca ggtggcactt ttcggggaaa tgtgcgcgga acccctattt   4620
gtttattttt ctaaatacat tcaaatatgt atccgctcat gagacaataa ccctgctgca   4680
gaggcctgca tgcaagcttg gcgtaatcat ggtcatagct gtttcctgtg tgaaattgtt   4740
atccgctcac aattccacac aacatacgag ccggaagcat aaagtgtaaa gcctggggtg   4800
cctaatgagt gagctaactc acattaattg cgttgcgctc actgcccgct ttccagtcgg   4860
gaaacctgtc gtgccagctg cattaatgaa tcggccaacg cgcggggaga ggcggtttgc   4920
gtattgggcg ctcttccgct tcctcgctca ctgactcgct gcgctcggtc gttcggctgc   4980
ggcgagcggt atcagctcac tcaaaggcgg taatacggtt atccacagaa tcaggggata   5040
acgcaggaaa gaacatgtga gcaaaaggcc agcaaaaggc caggaaccgt aaaaaggccg   5100
cgttgctggc gtttttccat aggctccgcc cccctgacga gcatcacaaa aatcgacgct   5160
caagtcagag gtggcgaaac ccgacaggac tataaagata ccaggcgttt ccccctggaa   5220
gctccctcgt gcgctctcct gttccgaccc tgccgcttac cggatacctg tccgcctttc   5280
tcccttcggg aagcgtggcg ctttctcata gctcacgctg taggtatctc agttcggtgt   5340
aggtcgttcg ctccaagctg ggctgtgtgc acgaaccccc cgttcagccc gaccgctgcg   5400
ccttatccgg taactatcgt cttgagtcca acccggtaag acacgactta tcgccactgg   5460
cagcagccac tggtaacagg attagcagag cgaggtatgt aggcggtgct acagagttct   5520
tgaagtggtg gcctaactac ggctacacta gaagaacagt atttggtatc tgcgctctgc   5580
tgaagccagt taccttcgga aaaagagttg gtagctcttg atccggcaaa caaaccaccg   5640
ctggtagcgg tggttttttt gtttgcaagc agcagattac gcgcagaaaa aaaggatctc   5700
aagaagatcc tttgatcttt tctacggggt ctgacgctca gtggaacgaa aactcacgtt   5760
aagggatttt ggtcatgaga ttatcaaaaa ggatcttcac ctagatcctt ttaaattaaa   5820
aatgaagttt taaatcaatc taaagtatat atgagtaaac ttggtctgac agttaccaat   5880
gcttaatcag tgaggcacct atctcagcga tctgtctatt tcgttcatcc atagttgcct   5940
gactccccgt cgtgtagata actacgatac gggagggctt accatctggc cccagtgctg   6000
caatgatacc gcgagaccca cgctcaccgg ctccagattt atcagcaata aaccagccag   6060
ccggaagggc cgagcgcaga agtggtcctg caactttatc cgcctccatc cagtctatta   6120
attgttgccg ggaagctaga gtaagtagtt cgccagttaa tagtttgcgc aacgttgttg   6180
ccattgctac aggcatcgtg gtgtcacgct cgtcgtttgg tatggcttca ttcagctccg   6240
gttcccaacg atcaaggcga gttacatgat cccccatgtt gtgcaaaaaa gcggttagct   6300
ccttcggtcc tccgatcgtt gtcagaagta agttggccgc agtgttatca ctcatggtta   6360
```

-continued

```
tggcagcact gcataattct cttactgtca tgccatccgt aagatgcttt tctgtgactg   6420

gtgagtactc aaccaagtca ttctgagaat agtgtatgcg gcgaccgagt tgctcttgcc   6480

cggcgtcaat acgggataat accgcgccac atagcagaac tttaaaagtg ctcatcattg   6540

gaaaacgttc ttcggggcga aaactctcaa ggatcttacc gctgttgaga tccagttcga   6600

tgtaacccac tcgtgcaccc aactgatctt cagcatcttt tactttcacc agcgtttctg   6660

ggtgagcaaa aacaggaagg caaaatgccg caaaaaaggg aataagggcg acacggaaat   6720

gttgaatact catactcttc ctttttcaat attattgaag catttatcag ggttattgtc   6780

tcatgagcgg atacatattt gaatgtattt agaaaaataa acaaataggg gttccgcgca   6840

catttccccg aaaagtgcca cctgacgtct aagaaaccat tattatcatg acattaacct   6900

ataaaaatag gcgtatcacg aggccctttc gtc                                6933
```

<210> SEQ ID NO 32
<211> LENGTH: 7248
<212> TYPE: DNA
<213> ORGANISM: Artificial Sequence
<220> FEATURE:
<223> OTHER INFORMATION: construct pINT-lmrA

<400> SEQUENCE: 32

```
tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120

ttggcgggtg tcggggctgg cttaactatg cggcatcaga gcagattgta ctgagagtgc    180

accatatgcg gtgtgaaata ccgcacagat gcgtaaggag aaaataccgc atcaggcgcc    240

attcgccatt caggctgcgc aactgttggg aagggcgatc ggtgcgggcc tcttcgctat    300

tacgccagct ggcgaaaggg ggatgtgctg caaggcgatt aagttgggta acgccagggt    360

tttcccagtc acgacgttgt aaaacgacgg ccagtgaatt cgaagatcct ttgatctttt    420

ctacggggtc tgacgctcag tggaacgaaa actcacgtta agggattttg gtcatgagat    480

tatcaaaaag gatcttcacc tagatccttt taaactagtg aagttaccat cacggaaaaa    540

ggttatgctg cttttaagac ccactttcac atttaagttg tttttctaat ccgcatatga    600

tcaattcaag gccgaataag aaggctggct ctgcaccttg gtgatcaaat aattcgatag    660

cttgtcgtaa taatggcggc atactatcag tagtaggtgt ttccctttct tctttagcga    720

cttgatgctc ttgatcttcc aatacgcaac ctaaagtaaa atgccccact gcgctgagtg    780

catataatgc attctctagt gaaaaacctt gttggcataa aaaggctaat tgattttcga    840

gagtttcata ctgtttttct gtaggccgtg tacctaaatg tacttttgct ccatcgcgat    900

gacttagtaa agcacatcta aaacttttag cgttattacg taaaaaatct tgccagcttt    960

ccccttctaa agggcaaaag tgagtatggt gcctatctaa catctcaatg gctaaggcgt   1020

cgagcaaagc ccgcttattt tttacatgcc aatacaatgt aggctgctct acacctagct   1080

tctgggcgag tttacgggtt gttaaacctt cgattccgac ctcattaagc agctctaatg   1140

cgctgttaat cactttactt ttatctaaac gagacatact cttccttttt caatattatt   1200

gaagcattta tcagggttat tgtctcatga gcggatacat atttgaatgt atttagaaaa   1260

ataaacaaat aggggttccg cgcacatttc cccgaaaagt gccacctgaa attggccaga   1320

tgattaattc ctaatttttg ttgacactct atcattgata gagttatttt accactccct   1380

atcagtgata gagaaaagtg aaatgaatag ttcgacaaaa atctagaaat aattttgttt   1440

aactttaaga aggagatata caagagctcg agtcgaagga gatagaacca tggcgaaccg   1500
```

-continued

```
tatcgaaggc aaagctgtgg acaaaacctc aatcaaacat ttcattaaac tgatccgtgc   1560
cgcaaaaccg cgttacctgt ttttcattat cggtattctg gcgggtatcg tgggcaccct   1620
gattcagctg caagtcccga aaatggtgca gccgctggtt aactcttttg gtcatggcgt   1680
taatggcggt aaagttgccc tggtcattgc actgtatatc ggtagtgcag cagtctccgc   1740
aattgcagct atcgtgctgg gtatctttgg cgaaagcgtg gttaaaaacc tgcgtacgcg   1800
cgtttgggat aaaatgattc acctgccggt gaaatacttc gacgaagtta aaaccggtga   1860
aatgagctct cgtctggcga atgataccac gcaagtgaaa aacctgattg caaatagcat   1920
cccgcaggct tttacgtcta ttctgctgct ggtcggcagt atcgtgttca tgctgcagat   1980
gcaatggcgc ctgaccctgg ctatgattat cgcggttccg gtcgtgatgc tgattatgtt   2040
tccgatcatg acgttcggtc agaaaattgg ccgtacccgc caagatagcc tggcgaactt   2100
tcagggtatt gcctcagaat cgctgagcga aatccgtctg gtgaaaagtt ccaatgccga   2160
aaaacaggca tccaaaaaag ctgaaaacga cgttaatgca ctgtataaaa ttggtgtcaa   2220
agaagcgatc tttgatggcc tgatgagtcc ggtcatgatg ctgtccatga tgctgatgat   2280
cttcggtctg ctggcctatg gcatttacct gatcagcacg ggtgtgatgt ctctgggtac   2340
cctgctgggc atgatgatgt acctgatgaa cctgattggc gcggtgccga ccgttgccac   2400
gtttttcacc gaactggcga aagcctctgg tagtacgggc cgtctgaccg aactgctgga   2460
tgaagaacag gaagttctgc atcagggtga atcgctggat ctggaaggca aaaccctgag   2520
cgcacgtcac gtcgactttg cttatgatga ctctgaacaa attctgcgcg atatctcctt   2580
tgaagcgcag ccgaattcaa ttatcgcatt cgctggcccg agtggcggtg gcaaatcaac   2640
catcttttcg ctgctggaac gcttctacca accgacggcc ggtgaaatta ccatcgatgg   2700
ccagccgatt gacaacatct cactggaaaa ttggcgttcg cagattggtt tcgttagcca   2760
agactctgct attatggcgg gcacgatccg cgaaaacctg acctatggtc tggaaggcga   2820
ttacacggat gaagacctgt ggcaggtcct ggacctggcg tttgcccgtt cattcgtgga   2880
aaacatgccg gatcagctga ataccgaagt tggtgaacgc ggcgtcaaaa tttcgggtgg   2940
ccagcgtcaa cgcctggcaa tcgctcgtgc gtttctgcgc aatccgaaaa ttctgatgct   3000
ggatgaagcc accgcatctc tggactccga atcagaatcg atggtgcaga aagcgctgga   3060
tagtctgatg aaaggtcgta ccacgctggt gattgcccat cgcctgtcca cgatcgttga   3120
tgcagacaaa atctacttca tcgaaaaagg ccagatcacc ggtagcggca aacacaacga   3180
actggtcgca acccacccgc tgtacgcaaa atatgtctcg gaacaactga cggtcggcca   3240
ataataaatc gatactagca taaccccttg gggcctctaa acgcgtcgac acgcaaaaag   3300
gccatccgtc aggatggcct tctgcttaat ttgatgcctg gcagtttatg gcgggcgtcc   3360
tgcccgccac cctccgggcc gttgcttcgc aacgttcaaa tccgctcccg gcggatttgt   3420
cctactcagg agagcgttca ccgacaaaca acagataaaa cgaaaggccc agtctttcga   3480
ctgagccttt cgttttattt gatgcctggc agttccctac tctcgcatgg ggagacccca   3540
cactaccatc atgtatgaat atcctcctta gttcctattc cgaagttcct attctctaga   3600
aagtatagga acttcggcgc gtcctacctg tgacggaaga tcacttcgca gaataaataa   3660
atcctggtgt ccctgttgat accgggaagc cctgggccaa cttttggcga aaatgagacg   3720
ttgatcggca cgtaagaggt tccaactttc accataatga aataagatca ctaccgggcg   3780
tattttttga gttgtcgaga ttttcaggag ctaaggaagc taaaatggag aaaaaaatca   3840
```

-continued

```
ctggatatac caccgttgat atatcccaat ggcatcgtaa agaacatttt gaggcatttc   3900
agtcagttgc tcaatgtacc tataaccaga ccgttcagct ggatattacg gcctttttaa   3960
agaccgtaaa gaaaaataag cacaagtttt atccggcctt tattcacatt cttgcccgcc   4020
tgatgaatgc tcatccggaa ttacgtatgg caatgaaaga cggtgagctg gtgatatggg   4080
atagtgttca cccttgttac accgttttcc atgagcaaac tgaaacgttt tcatcgctct   4140
ggagtgaata ccacgacgat ttccggcagt ttctacacat atattcgcaa gatgtggcgt   4200
gttacggtga aaacctggcc tatttcccta aagggtttat tgagaatatg tttttcgtct   4260
cagccaatcc ctgggtgagt ttcaccagtt ttgatttaaa cgtggccaat atggacaact   4320
tcttcgcccc cgttttcacc atgggcaaat attatacgca aggcgacaag gtgctgatgc   4380
cgctggcgat tcaggttcat catgccgttt gtgatggctt ccatgtcggc agatgcttaa   4440
tgaatacaac agtactgcga tgagtggcag ggcggggcgt aaggcgcgcc atttaaatga   4500
agttcctatt ccgaagttcc tattctctag aaagtatagg aacttcgaag cagctccagc   4560
ctacacaatc gctcaagacg tgtaatgctg caatctgcat gcaagcttgg cactggccac   4620
gcaaaaaggc catccgtcag gatggccttc tgcttaattt gatgcctggc agtttatggc   4680
gggcgtcctg cccgccaccc tccgggccgt tgcttcgcaa cgttcaaatc cgctcccggc   4740
ggatttgtcc tactcaggag agcgttcacc gacaaacaac agataaaacg aaaggcccag   4800
tctttcgact gagcctttcg ttttatttga tgcctggcag ttccctactc tcgcatgggg   4860
agaccccaca ctaccatcgg ggggccatcg atgcaggtgg cacttttcgg ggaaatgtgc   4920
gcggaacccc tatttgttta tttttctaaa tacattcaaa tatgtatccg ctcatgagac   4980
aataaccctg ctgcagaggc ctgcatgcaa gcttggcgta atcatggtca tagctgtttc   5040
ctgtgtgaaa ttgttatccg ctcacaattc cacacaacat acgagccgga agcataaagt   5100
gtaaagcctg gggtgcctaa tgagtgagct aactcacatt aattgcgttg cgctcactgc   5160
ccgctttcca gtcgggaaac ctgtcgtgcc agctgcatta atgaatcggc caacgcgcgg   5220
ggagaggcgg tttgcgtatt gggcgctctt ccgcttcctc gctcactgac tcgctgcgct   5280
cggtcgttcg gctgcggcga gcggtatcag ctcactcaaa ggcggtaata cggttatcca   5340
cagaatcagg ggataacgca ggaaagaaca tgtgagcaaa aggccagcaa aaggccagga   5400
accgtaaaaa ggccgcgttg ctggcgtttt tccataggct ccgcccccct gacgagcatc   5460
acaaaaatcg acgctcaagt cagaggtggc gaaacccgac aggactataa agataccagg   5520
cgtttccccc tggaagctcc ctcgtgcgct ctcctgttcc gaccctgccg cttaccggat   5580
acctgtccgc ctttctccct tcgggaagcg tggcgctttc tcatagctca cgctgtaggt   5640
atctcagttc ggtgtaggtc gttcgctcca agctgggctg tgtgcacgaa ccccccgttc   5700
agcccgaccg ctgcgcctta tccggtaact atcgtcttga gtccaacccg gtaagacacg   5760
acttatcgcc actggcagca gccactggta acaggattag cagagcgagg tatgtaggcg   5820
gtgctacaga gttcttgaag tggtggccta actacggcta cactagaaga acagtatttg   5880
gtatctgcgc tctgctgaag ccagttacct tcggaaaaag agttggtagc tcttgatccg   5940
gcaaacaaac caccgctggt agcggtggtt tttttgtttg caagcagcag attacgcgca   6000
gaaaaaaagg atctcaagaa gatcctttga tcttttctac ggggtctgac gctcagtgga   6060
acgaaaactc acgttaaggg attttggtca tgagattatc aaaaaggatc ttcacctaga   6120
tccttttaaa ttaaaaatga agttttaaat caatctaaag tatatatgag taaacttggt   6180
ctgacagtta ccaatgctta atcagtgagg cacctatctc agcgatctgt ctatttcgtt   6240
```

catccatagt tgcctgactc cccgtcgtgt agataactac gatacgggag ggcttaccat 6300
ctggccccag tgctgcaatg ataccgcgag acccacgctc accggctcca gatttatcag 6360
caataaacca gccagccgga agggccgagc gcagaagtgg tcctgcaact ttatccgcct 6420
ccatccagtc tattaattgt tgccgggaag ctagagtaag tagttcgcca gttaatagtt 6480
tgcgcaacgt tgttgccatt gctacaggca tcgtggtgtc acgctcgtcg tttggtatgg 6540
cttcattcag ctccggttcc caacgatcaa ggcgagttac atgatccccc atgttgtgca 6600
aaaaagcggt tagctccttc ggtcctccga tcgttgtcag aagtaagttg gccgcagtgt 6660
tatcactcat ggttatggca gcactgcata attctcttac tgtcatgcca tccgtaagat 6720
gcttttctgt gactggtgag tactcaacca agtcattctg agaatagtgt atgcggcgac 6780
cgagttgctc ttgcccggcg tcaatacggg ataataccgc gccacatagc agaactttaa 6840
aagtgctcat cattggaaaa cgttcttcgg ggcgaaaact ctcaaggatc ttaccgctgt 6900
tgagatccag ttcgatgtaa cccactcgtg cacccaactg atcttcagca tcttttactt 6960
tcaccagcgt ttctgggtga gcaaaaacag gaaggcaaaa tgccgcaaaa aagggaataa 7020
gggcgacacg gaaatgttga atactcatac tcttcctttt tcaatattat tgaagcattt 7080
atcagggtta ttgtctcatg agcggataca tatttgaatg tatttagaaa aataaacaaa 7140
taggggttcc gcgcacattt ccccgaaaag tgccacctga cgtctaagaa accattatta 7200
tcatgacatt aacctataaa aataggcgta tcacgaggcc ctttcgtc 7248

<210> SEQ ID NO 33
<211> LENGTH: 6684
<212> TYPE: DNA
<213> ORGANISM: Artificial Sequence
<220> FEATURE:
<223> OTHER INFORMATION: construct pINT-Ps-setA

<400> SEQUENCE: 33
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accatatgcg gtgtgaaata ccgcacagat gcgtaaggag aaaataccgc atcaggcgcc 240
attcgccatt caggctgcgc aactgttggg aagggcgatc ggtgcgggcc tcttcgctat 300
tacgccagct ggcgaaaggg ggatgtgctg caaggcgatt aagttgggta acgccagggt 360
tttcccagtc acgacgttgt aaaacgacgg ccagtgaatt cgaagatcct ttgatctttt 420
ctacggggtc tgacgctcag tggaacgaaa actcacgtta agggattttg gtcatgagat 480
tatcaaaaag gatcttcacc tagatccttt taaactagtg aagttaccat cacggaaaaa 540
ggttatgctg cttttaagac ccactttcac atttaagttg tttttctaat ccgcatatga 600
tcaattcaag gccgaataag aaggctggct ctgcaccttg gtgatcaaat aattcgatag 660
cttgtcgtaa taatggcggc atactatcag tagtaggtgt ttccctttct tctttagcga 720
cttgatgctc ttgatcttcc aatacgcaac ctaaagtaaa atgccccact gcgctgagtg 780
catataatgc attctctagt gaaaaacctt gttggcataa aaaggctaat tgattttcga 840
gagtttcata ctgtttttct gtaggccgtg tacctaaatg tacttttgct ccatcgcgat 900
gacttagtaa agcacatcta aaacttttag cgttattacg taaaaaatct tgccagcttt 960
ccccttctaa agggcaaaag tgagtatggt gcctatctaa catctcaatg gctaaggcgt 1020

-continued

```
cgagcaaagc ccgcttattt tttacatgcc aatacaatgt aggctgctct acacctagct   1080
tctgggcgag tttacgggtt gttaaacctt cgattccgac ctcattaagc agctctaatg   1140
cgctgttaat cactttactt ttatctaaac gagacatact cttccttttt caatattatt   1200
gaagcattta tcagggttat tgtctcatga gcggatacat atttgaatgt atttagaaaa   1260
ataaacaaat aggggttccg cgcacatttc cccgaaaagt gccacctgaa attggccaga   1320
tgattaattc ctaatttttg ttgacactct atcattgata gagttatttt accactccct   1380
atcagtgata gagaaaagtg aaatgaatag ttcgacaaaa atctagaaat aattttgttt   1440
aactttaaga aggagatata caagagctcg agtcgaagga gatagaacca tgaacgaaag   1500
ccagagctct catggcggtt catggctgtc ggttattgcg ctggccctgg cggcctttat   1560
cttcaatacc acggaattcg ttccggtcgc gctgctgtca gatattggcc gttcgtttga   1620
catgccgcca tcacaagtgg gtctgatgct gaccatctat gcgtgggtgg ttgccctgat   1680
gtcgctgccg atgatgctgc tgacccgcaa cgtcgaacgt cgcacgctgc tgatttttgt   1740
gttcgtcgtg ttcatcggca gtcatctggt gagttccgtg gcgtcatcgt ttagcatgct   1800
gatgatttct cgtattggta tcgcactgtc ccacgctgtg ttttggagta tcaccgcatc   1860
cctggctgtg cgtgttgcac cggctggtaa acaggcccag gcactgggtc tgctggcaac   1920
cggttcagca ctggctatgg tcctgggtat tccgctgggc cgtgttgtcg gtgaactgct   1980
ggattggcgc accacgttcc tgagcattgc catcgtggca gctctggtgg ttctgtgtct   2040
ggcacgtacc ctgccgctgc tgccgagtca gaatagtggt tccctgcgtt ccctgccgat   2100
gctgtttaaa cgtccggcgc tggttgcggc atatgttctg accgccctgg ttattacggc   2160
gcagtttacc gcctatacgt acattgaacc gttcgcacaa accatcgctc atctgtctgg   2220
caacatgacc acggcactgc tgctgctgtt tggcggtgct ggtattctgg gcacggtgct   2280
gttcagccgt tattctaatc gctacccgaa aggttttctg atcgcagcta ttagtatcat   2340
ggcaatgtgt ctgctgctgc tgctgccggc ctcccgcgat agctctctgc tggccgccct   2400
ggtcgtggtt tggggtattg cgggcatgtg tttcggcctg gcgctgcagg ccaaagttct   2460
gaacctggca agcgatgcta ccgacgtcgc gatggccctg ttttctggca tttataatgt   2520
tggtatcggc ggtggcgccc tgctgggttc actggttacg gcacacctgg gcctgtcgga   2580
cgttggtatt gtcggtggcc tgctggccct gagcggcgtc gtgctgtgct gttttgccac   2640
ctatcgcttt gcacgtccgg tgggttctgc agctctgtaa taaatcgata ctagcataac   2700
cccttggggc ctctaaacgc gtcgacacgc aaaaaggcca tccgtcagga tggccttctg   2760
cttaatttga tgcctggcag tttatggcgg gcgtcctgcc cgccaccctc cgggccgttg   2820
cttcgcaacg ttcaaatccg ctcccggcgg atttgtccta ctcaggagag cgttcaccga   2880
caaacaacag ataaaacgaa aggcccagtc tttcgactga gcctttcgtt ttatttgatg   2940
cctggcagtt ccctactctc gcatggggag accccacact accatcatgt atgaatatcc   3000
tccttagttc ctattccgaa gttcctattc tctagaaagt ataggaactt cggcgcgtcc   3060
tacctgtgac ggaagatcac ttcgcagaat aaataaatcc tggtgtccct gttgataccg   3120
ggaagccctg ggccaacttt tggcgaaaat gagacgttga tcggcacgta agaggttcca   3180
actttcacca taatgaaata agatcactac cgggcgtatt ttttgagttg tcgagatttt   3240
caggagctaa ggaagctaaa atggagaaaa aaatcactgg atataccacc gttgatatat   3300
cccaatggca tcgtaaagaa cattttgagg catttcagtc agttgctcaa tgtacctata   3360
accagaccgt tcagctggat attacggcct ttttaaagac cgtaaagaaa aataagcaca   3420
```

agttttatcc ggcctttatt cacattcttg cccgcctgat gaatgctcat ccggaattac 3480
gtatggcaat gaaagacggt gagctggtga tatgggatag tgttcaccct tgttacaccg 3540
ttttccatga gcaaactgaa acgttttcat cgctctggag tgaataccac gacgatttcc 3600
ggcagtttct acacatatat tcgcaagatg tggcgtgtta cggtgaaaac ctggcctatt 3660
tccctaaagg gtttattgag aatatgtttt tcgtctcagc caatccctgg gtgagtttca 3720
ccagttttga tttaaacgtg gccaatatgg acaacttctt cgcccccgtt ttcaccatgg 3780
gcaaatatta tacgcaaggc gacaaggtgc tgatgccgct ggcgattcag gttcatcatg 3840
ccgtttgtga tggcttccat gtcggcagat gcttaatgaa tacaacagta ctgcgatgag 3900
tggcagggcg gggcgtaagg cgcgccattt aaatgaagtt cctattccga agttcctatt 3960
ctctagaaag tataggaact tcgaagcagc tccagcctac acaatcgctc aagacgtgta 4020
atgctgcaat ctgcatgcaa gcttggcact ggccacgcaa aaaggccatc cgtcaggatg 4080
gccttctgct taatttgatg cctggcagtt tatggcgggc gtcctgcccg ccaccctccg 4140
ggccgttgct tcgcaacgtt caaatccgct cccggcggat ttgtcctact caggagagcg 4200
ttcaccgaca aacaacagat aaaacgaaag gcccagtctt tcgactgagc ctttcgtttt 4260
atttgatgcc tggcagttcc ctactctcgc atggggagac cccacactac catcgggggg 4320
ccatcgatgc aggtggcact tttcggggaa atgtgcgcgg aacccctatt tgtttatttt 4380
tctaaataca ttcaaatatg tatccgctca tgagacaata accctgctgc agaggcctgc 4440
atgcaagctt ggcgtaatca tggtcatagc tgtttcctgt gtgaaattgt tatccgctca 4500
caattccaca caacatacga gccggaagca taaagtgtaa agcctggggt gcctaatgag 4560
tgagctaact cacattaatt gcgttgcgct cactgcccgc tttccagtcg ggaaacctgt 4620
cgtgccagct gcattaatga atcggccaac gcgcggggag aggcggtttg cgtattgggc 4680
gctcttccgc ttcctcgctc actgactcgc tgcgctcggt cgttcggctg cggcgagcgg 4740
tatcagctca ctcaaaggcg gtaatacggt tatccacaga atcaggggat aacgcaggaa 4800
agaacatgtg agcaaaaggc cagcaaaagg ccaggaaccg taaaaaggcc gcgttgctgg 4860
cgtttttcca taggctccgc ccccctgacg agcatcacaa aaatcgacgc tcaagtcaga 4920
ggtggcgaaa cccgacagga ctataaagat accaggcgtt tccccctgga agctccctcg 4980
tgcgctctcc tgttccgacc ctgccgctta ccggatacct gtccgccttt ctcccttcgg 5040
gaagcgtggc gctttctcat agctcacgct gtaggtatct cagttcggtg taggtcgttc 5100
gctccaagct gggctgtgtg cacgaacccc ccgttcagcc cgaccgctgc gccttatccg 5160
gtaactatcg tcttgagtcc aacccggtaa gacacgactt atcgccactg gcagcagcca 5220
ctggtaacag gattagcaga gcgaggtatg taggcggtgc tacagagttc ttgaagtggt 5280
ggcctaacta cggctacact agaagaacag tatttggtat ctgcgctctg ctgaagccag 5340
ttaccttcgg aaaaagagtt ggtagctctt gatccggcaa acaaaccacc gctggtagcg 5400
gtggtttttt tgtttgcaag cagcagatta cgcgcagaaa aaaaggatct caagaagatc 5460
ctttgatctt ttctacgggg tctgacgctc agtggaacga aaactcacgt taagggattt 5520
tggtcatgag attatcaaaa aggatcttca cctagatcct tttaaattaa aaatgaagtt 5580
ttaaatcaat ctaaagtata tatgagtaaa cttggtctga cagttaccaa tgcttaatca 5640
gtgaggcacc tatctcagcg atctgtctat ttcgttcatc catagttgcc tgactccccg 5700
tcgtgtagat aactacgata cgggagggct taccatctgg ccccagtgct gcaatgatac 5760

-continued

```
cgcgagaccc acgctcaccg gctccagatt tatcagcaat aaaccagcca gccggaaggg   5820

ccgagcgcag aagtggtcct gcaactttat ccgcctccat ccagtctatt aattgttgcc   5880

gggaagctag agtaagtagt tcgccagtta atagtttgcg caacgttgtt gccattgcta   5940

caggcatcgt ggtgtcacgc tcgtcgtttg gtatggcttc attcagctcc ggttcccaac   6000

gatcaaggcg agttacatga tcccccatgt tgtgcaaaaa agcggttagc tccttcggtc   6060

ctccgatcgt tgtcagaagt aagttggccg cagtgttatc actcatggtt atggcagcac   6120

tgcataattc tcttactgtc atgccatccg taagatgctt ttctgtgact ggtgagtact   6180

caaccaagtc attctgagaa tagtgtatgc ggcgaccgag ttgctcttgc ccggcgtcaa   6240

tacgggataa taccgcgcca catagcagaa ctttaaaagt gctcatcatt ggaaaacgtt   6300

cttcggggcg aaaactctca aggatcttac cgctgttgag atccagttcg atgtaaccca   6360

ctcgtgcacc caactgatct tcagcatctt ttactttcac cagcgtttct gggtgagcaa   6420

aaacaggaag gcaaaatgcc gcaaaaaagg gaataagggc gacacggaaa tgttgaatac   6480

tcatactctt cctttttcaa tattattgaa gcatttatca gggttattgt ctcatgagcg   6540

gatacatatt tgaatgtatt tagaaaaata aacaaatagg ggttccgcgc acatttcccc   6600

gaaaagtgcc acctgacgtc taagaaacca ttattatcat gacattaacc tataaaaata   6660

ggcgtatcac gaggcccttt cgtc                                          6684
```

```
<210> SEQ ID NO 34
<211> LENGTH: 6692
<212> TYPE: DNA
<213> ORGANISM: Artificial Sequence
<220> FEATURE:
<223> OTHER INFORMATION: construct pINT-Bb-setA

<400> SEQUENCE: 34

tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120

ttggcgggtg tcggggctgg cttaactatg cggcatcaga gcagattgta ctgagagtgc    180

accatatgcg gtgtgaaata ccgcacagat gcgtaaggag aaaataccgc atcaggcgcc    240

attcgccatt caggctgcgc aactgttggg aagggcgatc ggtgcgggcc tcttcgctat    300

tacgccagct ggcgaaaggg ggatgtgctg caaggcgatt aagttgggta acgccagggt    360

tttcccagtc acgacgttgt aaaacgacgg ccagtgaatt cgaagatcct ttgatctttt    420

ctacggggtc tgacgctcag tggaacgaaa actcacgtta agggattttg gtcatgagat    480

tatcaaaaag gatcttcacc tagatccttt taaactagtg aagttaccat cacggaaaaa    540

ggttatgctg cttttaagac ccactttcac atttaagttg tttttctaat ccgcatatga    600

tcaattcaag gccgaataag aaggctggct ctgcaccttg gtgatcaaat aattcgatag    660

cttgtcgtaa taatggcggc atactatcag tagtaggtgt ttccctttct tctttagcga    720

cttgatgctc ttgatcttcc aatacgcaac ctaaagtaaa atgccccact gcgctgagtg    780

catataatgc attctctagt gaaaaacctt gttggcataa aaaggctaat tgattttcga    840

gagtttcata ctgtttttct gtaggccgtg tacctaaatg tacttttgct ccatcgcgat    900

gacttagtaa agcacatcta aaacttttag cgttattacg taaaaaatct tgccagcttt    960

ccccttctaa agggcaaaag tgagtatggt gcctatctaa catctcaatg gctaaggcgt   1020

cgagcaaagc ccgcttattt tttacatgcc aatacaatgt aggctgctct acacctagct   1080

tctgggcgag tttacgggtt gttaaacctt cgattccgac ctcattaagc agctctaatg   1140
```

-continued

```
cgctgttaat cactttactt ttatctaaac gagacatact cttccttttt caatattatt   1200
gaagcattta tcagggttat tgtctcatga gcggatacat atttgaatgt atttagaaaa   1260
ataaacaaat aggggttccg cgcacatttc cccgaaaagt gccacctgaa attggccaga   1320
tgattaattc ctaatttttg ttgacactct atcattgata gagttatttt accactccct   1380
atcagtgata gagaaaagtg aaatgaatag ttcgacaaaa atctagaaat aattttgttt   1440
aactttaaga aggagatata caagagctcg agtcgaagga gatagaacca tgaccattgc   1500
aacggtttcc cgcaaaaccg cttggctgcg tgtggttacc ctggccgttg ccgcctttat   1560
cttcaacacc acggaatttg tcccggtggg cctgctgagt gatattgcgc agtccttcgg   1620
catggaaacc gcccaagtgg gtattatgct gacgatctat gcctgggttg tggcactgat   1680
gagcctgccg tttatgctga tgacctctca ggtggaacgt cgccgtctgc tgattagcat   1740
ctttctgctg ttcatcgcaa gtcatgttct gtcctttctg gcgtggaatt tcaccgttct   1800
ggtcatttct cgcattggta tcgcgtttgc ccacgcaatt ttctggtcaa tcacggcttc   1860
gctggcgatt cgtatggctc cggcgggcaa gaaagcgcag gcactgagtc tgctggcgac   1920
cggtacggct ctggcgatgg ttctgggtct gccgatcggc cgcattgtcg gtcaatactt   1980
tggctggcgt accacgtttt tcgtgattgg cgttgtcgca gctatcaccc tgttctgcct   2040
gattaaactg ctgccgaaac tgccgagcga acatagtggt tccctgagct ctgtgccgaa   2100
actgtttcgc cgtccggcgc tggttaacat ctatgccctg attgcaatcg tggttaccgc   2160
acactacacg gcttatagtt acatcgaacc gttcgtgcag caaattgccg gcctgtccgc   2220
taactttgcg accctgctgc tgctgctgtt tggcggtgcg ggtattatcg gctctgttct   2280
gtttggtaaa tggggcaata aacatgccag cggtctggtc tctggcgcca ttgcactgat   2340
ggccgcatgt ctggtgctgc tgctgccggc agctcagggt gaactgaccc tggccggcct   2400
gtcactgttt tggggtattt cgatcatgat tgtcgcactg ggtatgcaag tgaaagttct   2460
ggctctggcc ccggatgcca ccgatgttgc catgagcctg ttttctggca tcttcaacat   2520
cggcattggt gccggcgcac tgctgggtaa tcaggtgtca ctgcacattt caatgtcgga   2580
catcggtttt attggcgcca tcccggcaat tatcgctctg gtctggtcga ttctggtgtc   2640
cgccgttggc cggttgccct ggaagaacat ccgcaggcaa cccactaata aatcgatact   2700
agcataaccc cttggggcct ctaaacgcgt cgacacgcaa aaaggccatc cgtcaggatg   2760
gccttctgct taatttgatg cctggcagtt tatggcgggc gtcctgcccg ccaccctccg   2820
ggccgttgct tcgcaacgtt caaatccgct cccggcggat ttgtcctact caggagagcg   2880
ttcaccgaca aacaacagat aaaacgaaag gcccagtctt tcgactgagc ctttcgtttt   2940
atttgatgcc tggcagttcc ctactctcgc atggggagac cccacactac catcatgtat   3000
gaatatcctc cttagttcct attccgaagt tcctattctc tagaaagtat aggaacttcg   3060
gcgcgtccta cctgtgacgg aagatcactt cgcagaataa ataaatcctg gtgtccctgt   3120
tgataccggg aagccctggg ccaacttttg gcgaaaatga gacgttgatc ggcacgtaag   3180
aggttccaac tttcaccata atgaaataag atcactaccg ggcgtatttt ttgagttgtc   3240
gagattttca ggagctaagg aagctaaaat ggagaaaaaa atcactggat ataccaccgt   3300
tgatatatcc caatggcatc gtaaagaaca ttttgaggca tttcagtcag ttgctcaatg   3360
tacctataac cagaccgttc agctggatat tacggccttt ttaaagaccg taaagaaaaa   3420
taagcacaag ttttatccgg cctttattca cattcttgcc cgcctgatga atgctcatcc   3480
```

-continued

```
ggaattacgt atggcaatga aagacggtga gctggtgata tgggatagtg ttcacccttg   3540
ttacaccgtt ttccatgagc aaactgaaac gttttcatcg ctctggagtg aataccacga   3600
cgatttccgg cagtttctac acatatattc gcaagatgtg gcgtgttacg gtgaaaacct   3660
ggcctatttc cctaaagggt ttattgagaa tatgtttttc gtctcagcca atccctgggt   3720
gagtttcacc agttttgatt taaacgtggc caatatggac aacttcttcg cccccgtttt   3780
caccatgggc aaatattata cgcaaggcga caaggtgctg atgccgctgg cgattcaggt   3840
tcatcatgcc gtttgtgatg gcttccatgt cggcagatgc ttaatgaata caacagtact   3900
gcgatgagtg gcagggcggg gcgtaaggcg cgccatttaa atgaagttcc tattccgaag   3960
ttcctattct ctagaaagta taggaacttc gaagcagctc cagcctacac aatcgctcaa   4020
gacgtgtaat gctgcaatct gcatgcaagc ttggcactgg ccacgcaaaa aggccatccg   4080
tcaggatggc cttctgctta atttgatgcc tggcagttta tggcgggcgt cctgcccgcc   4140
accctccggg ccgttgcttc gcaacgttca aatccgctcc cggcggattt gtcctactca   4200
ggagagcgtt caccgacaaa caacagataa aacgaaaggc ccagtctttc gactgagcct   4260
ttcgttttat ttgatgcctg gcagttccct actctcgcat ggggagaccc cacactacca   4320
tcgggggggc atcgatgcag gtggcacttt tcggggaaat gtgcgcggaa cccctatttg   4380
tttatttttc taaatacatt caaatatgta tccgctcatg agacaataac cctgctgcag   4440
aggcctgcat gcaagcttgg cgtaatcatg gtcatagctg tttcctgtgt gaaattgtta   4500
tccgctcaca attccacaca acatacgagc cggaagcata aagtgtaaag cctggggtgc   4560
ctaatgagtg agctaactca cattaattgc gttgcgctca ctgcccgctt tccagtcggg   4620
aaacctgtcg tgccagctgc attaatgaat cggccaacgc gcggggagag gcggtttgcg   4680
tattgggcgc tcttccgctt cctcgctcac tgactcgctg cgctcggtcg ttcggctgcg   4740
gcgagcggta tcagctcact caaaggcggt aatacggtta tccacagaat caggggataa   4800
cgcaggaaag aacatgtgag caaaaggcca gcaaaaggcc aggaaccgta aaaaggccgc   4860
gttgctggcg tttttccata ggctccgccc ccctgacgag catcacaaaa atcgacgctc   4920
aagtcagagg tggcgaaacc cgacaggact ataaagatac caggcgtttc cccctggaag   4980
ctccctcgtg cgctctcctg ttccgaccct gccgcttacc ggatacctgt ccgcctttct   5040
cccttcggga agcgtggcgc tttctcatag ctcacgctgt aggtatctca gttcggtgta   5100
ggtcgttcgc tccaagctgg gctgtgtgca cgaacccccc gttcagcccg accgctgcgc   5160
cttatccggt aactatcgtc ttgagtccaa cccggtaaga cacgacttat cgccactggc   5220
agcagccact ggtaacagga ttagcagagc gaggtatgta ggcggtgcta cagagttctt   5280
gaagtggtgg cctaactacg gctacactag aagaacagta tttggtatct gcgctctgct   5340
gaagccagtt accttcggaa aaagagttgg tagctcttga tccggcaaac aaaccaccgc   5400
tggtagcggt ggtttttttg tttgcaagca gcagattacg cgcagaaaaa aaggatctca   5460
agaagatcct ttgatctttt ctacggggtc tgacgctcag tggaacgaaa actcacgtta   5520
agggattttg gtcatgagat tatcaaaaag gatcttcacc tagatccttt taaattaaaa   5580
atgaagtttt aaatcaatct aaagtatata tgagtaaact tggtctgaca gttaccaatg   5640
cttaatcagt gaggcaccta tctcagcgat ctgtctattt cgttcatcca tagttgcctg   5700
actccccgtc gtgtagataa ctacgatacg ggagggctta ccatctggcc ccagtgctgc   5760
aatgataccg cgagacccac gctcaccggc tccagattta tcagcaataa accagccagc   5820
cggaagggcc gagcgcagaa gtggtcctgc aactttatcc gcctccatcc agtctattaa   5880
```

ttgttgccgg gaagctagag taagtagttc gccagttaat agtttgcgca acgttgttgc 5940
cattgctaca ggcatcgtgg tgtcacgctc gtcgtttggt atggcttcat tcagctccgg 6000
ttcccaacga tcaaggcgag ttacatgatc ccccatgttg tgcaaaaaag cggttagctc 6060
cttcggtcct ccgatcgttg tcagaagtaa gttggccgca gtgttatcac tcatggttat 6120
ggcagcactg cataattctc ttactgtcat gccatccgta agatgctttt ctgtgactgg 6180
tgagtactca accaagtcat tctgagaata gtgtatgcgg cgaccgagtt gctcttgccc 6240
ggcgtcaata cgggataata ccgcgccaca tagcagaact ttaaaagtgc tcatcattgg 6300
aaaacgttct tcggggcgaa aactctcaag gatcttaccg ctgttgagat ccagttcgat 6360
gtaacccact cgtgcaccca actgatcttc agcatctttt actttcacca gcgtttctgg 6420
gtgagcaaaa acaggaaggc aaaatgccgc aaaaaaggga ataagggcga cacggaaatg 6480
ttgaatactc atactcttcc tttttcaata ttattgaagc atttatcagg gttattgtct 6540
catgagcgga tacatatttg aatgtattta gaaaaataaa caaatagggg ttccgcgcac 6600
atttccccga aaagtgccac ctgacgtcta agaaaccatt attatcatga cattaaccta 6660
taaaaatagg cgtatcacga ggccctttcg tc 6692

<210> SEQ ID NO 35
<211> LENGTH: 35
<212> TYPE: DNA
<213> ORGANISM: Artificial Sequence
<220> FEATURE:
<223> OTHER INFORMATION: Primer

<400> SEQUENCE: 35
ttactcagca ataaactgat attccgtcag gctgg 35

<210> SEQ ID NO 36
<211> LENGTH: 83
<212> TYPE: DNA
<213> ORGANISM: Artificial Sequence
<220> FEATURE:
<223> OTHER INFORMATION: Primer

<400> SEQUENCE: 36
ttgtaatctc gcgctcttca catcagactt tccatataga gcgtaatttc cgttaacgtc 60
ggtagtgctg accttgccgg agg 83

<210> SEQ ID NO 37
<211> LENGTH: 53
<212> TYPE: DNA
<213> ORGANISM: Artificial Squence
<220> FEATURE:
<223> OTHER INFORMATION: Primer

<400> SEQUENCE: 37
ctgtctctta tcacatctcc tgaaatggcc agatgtaatt cctaattttt gtt 53

<210> SEQ ID NO 38
<211> LENGTH: 44
<212> TYPE: DNA
<213> ORGANISM: Artificial Sequence
<220> FEATURE:
<223> OTHER INFORMATION: Primer

<400> SEQUENCE: 38
ctgtctctta tcacatctca cattacatct gagcgattgt tagg 44

<210> SEQ ID NO 39
<211> LENGTH: 30
<212> TYPE: DNA
<213> ORGANISM: Artificial Sequence
<220> FEATURE:
<223> OTHER INFORMATION: Primer

<400> SEQUENCE: 39
gatcacatat gagagttctg gttaccggtg 30

<210> SEQ ID NO 40
<211> LENGTH: 40
<212> TYPE: DNA
<213> ORGANISM: Artificial Sequence
<220> FEATURE:
<223> OTHER INFORMATION: Primer

<400> SEQUENCE: 40
gatcactcga gtcattaatc gggatatccc tgtggatggc 40

<210> SEQ ID NO 41
<211> LENGTH: 60
<212> TYPE: DNA
<213> ORGANISM: Artificial Sequence
<220> FEATURE:
<223> OTHER INFORMATION: Primer

<400> SEQUENCE: 41
gtcgatgaag ccctgaaaga cgcgcagact atgcacttca ttgaaaacaa aaacttcgtc 60

<210> SEQ ID NO 42
<211> LENGTH: 60
<212> TYPE: DNA
<213> ORGANISM: Artificial Sequence
<220> FEATURE:
<223> OTHER INFORMATION: Primer

<400> SEQUENCE: 42
gatggccttt ttgcgtgtcg acgcggccgc ctagataaac aggatgatat ttttgccttg 60

<210> SEQ ID NO 43
<211> LENGTH: 60
<212> TYPE: DNA
<213> ORGANISM: Artificial Sequence
<220> FEATURE:
<223> OTHER INFORMATION: Primer

<400> SEQUENCE: 43
caaggcaaaa atatcatcct gtttatctag gcggccgcgt cgacacgcaa aaaggccatc 60

<210> SEQ ID NO 44
<211> LENGTH: 60
<212> TYPE: DNA
<213> ORGANISM: Artificial Sequence
<220> FEATURE:
<223> OTHER INFORMATION: Primer

<400> SEQUENCE: 44
gacgaagttt ttgttttcaa tgaagtgcat agtctgcgcg tctttcaggg cttcatcgac 60

<210> SEQ ID NO 45
<211> LENGTH: 60
<212> TYPE: DNA
<213> ORGANISM: Artificial Sequence
<220> FEATURE:
<223> OTHER INFORMATION: Primer

<400> SEQUENCE: 45
atggcctttt tgcgtgtcga cgcggccgct taattcgagc gggtaaagat cttcatcagg 60

<210> SEQ ID NO 46
<211> LENGTH: 60
<212> TYPE: DNA
<213> ORGANISM: Artificial Sequence
<220> FEATURE:
<223> OTHER INFORMATION: Primer

<400> SEQUENCE: 46
atggcctttt tgcgtgtcga cgcggccgct taattcgagc gggtaaagat cttcatcagg 60

<210> SEQ ID NO 47
<211> LENGTH: 60
<212> TYPE: DNA
<213> ORGANISM: Artificial Sequence
<220> FEATURE:
<223> OTHER INFORMATION: Primer

<400> SEQUENCE: 47
ctgatgaaga tctttacccg ctcgaattaa gcggccgcgt cgacacgcaa aaaggccatc 60

<210> SEQ ID NO 48
<211> LENGTH: 60
<212> TYPE: DNA
<213> ORGANISM: Artificial Sequence
<220> FEATURE:
<223> OTHER INFORMATION: Primer

<400> SEQUENCE: 48
cggggtacgc ttaatcaggt tatcaatcat agtctgcgcg tctttcaggg cttcatcgac 60

<210> SEQ ID NO 49
<211> LENGTH: 60
<212> TYPE: DNA
<213> ORGANISM: Artificial Sequence
<220> FEATURE:
<223> OTHER INFORMATION: Primer

<400> SEQUENCE: 49
gtcgatgaag ccctgaaaga cgcgcagact atgagcggtg aacactatgt cattagcctg 60

<210> SEQ ID NO 50
<211> LENGTH: 60
<212> TYPE: DNA
<213> ORGANISM: Artificial Sequence
<220> FEATURE:
<223> OTHER INFORMATION: Primer

<400> SEQUENCE: 50
gatggccttt ttgcgtgtcg acgcggccgc tcatttaaat tcgatgatca tcttgtcgtt 60

<210> SEQ ID NO 51
<211> LENGTH: 60
<212> TYPE: DNA
<213> ORGANISM: Artificial Sequence
<220> FEATURE:
<223> OTHER INFORMATION: Primer

<400> SEQUENCE: 51
aacgacaaga tgatcatcga atttaaatga gcggccgcgt cgacacgcaa aaaggccatc 60

<210> SEQ ID NO 52

<211> LENGTH: 60
<212> TYPE: DNA
<213> ORGANISM: Artificial Sequence
<220> FEATURE:
<223> OTHER INFORMATION: Primer

<400> SEQUENCE: 52
caggctaatg acatagtgtt caccgctcat agtctgcgcg tctttcaggg cttcatcgac 60

<210> SEQ ID NO 53
<211> LENGTH: 60
<212> TYPE: DNA
<213> ORGANISM: Artificial Sequence
<220> FEATURE:
<223> OTHER INFORMATION: Primer

<400> SEQUENCE: 53
gtcgatgaag ccctgaaaga cgcgcagact atggatgaaa tcaaactgtc ggtggttatg 60

<210> SEQ ID NO 54
<211> LENGTH: 60
<212> TYPE: DNA
<213> ORGANISM: Artificial Sequence
<220> FEATURE:
<223> OTHER INFORMATION: Primer

<400> SEQUENCE: 54
gatggccttt ttgcgtgtcg acgcggccgc tcattggcga cgccaatcga acgcaacgcg 60

<210> SEQ ID NO 55
<211> LENGTH: 60
<212> TYPE: DNA
<213> ORGANISM: Artificial Sequence
<220> FEATURE:
<223> OTHER INFORMATION: Primer

<400> SEQUENCE: 55
cgcgttgcgt tcgattggcg tcgccaatga gcggccgcgt cgacacgcaa aaaggccatc 60

<210> SEQ ID NO 56
<211> LENGTH: 60
<212> TYPE: DNA
<213> ORGANISM: Artificial Sequence
<220> FEATURE:
<223> OTHER INFORMATION: Primer

<400> SEQUENCE: 56
cataaccacc gacagtttga tttcatccat agtctgcgcg tctttcaggg cttcatcgac 60

<210> SEQ ID NO 57
<211> LENGTH: 60
<212> TYPE: DNA
<213> ORGANISM: Artificial Sequence
<220> FEATURE:
<223> OTHER INFORMATION: Primer

<400> SEQUENCE: 57
gtcgatgaag ccctgaaaga cgcgcagact atggaaaact atgtcgtctc tatccgcacc 60

<210> SEQ ID NO 58
<211> LENGTH: 60
<212> TYPE: DNA
<213> ORGANISM: Artificial Sequence
<220> FEATURE:
<223> OTHER INFORMATION: Primer

<400> SEQUENCE: 58
gatggccttt ttgcgtgtcg acgcggccgc tcatttgaac ggaacaatct ttttgtcatc 60

<210> SEQ ID NO 59
<211> LENGTH: 60
<212> TYPE: DNA
<213> ORGANISM: Artificial Sequence
<220> FEATURE:
<223> OTHER INFORMATION: Primer

<400> SEQUENCE: 59
gatgacaaaa agattgttcc gttcaaatga gcggccgcgt cgacacgcaa aaaggccatc 60

<210> SEQ ID NO 60
<211> LENGTH: 60
<212> TYPE: DNA
<213> ORGANISM: Artificial Sequence
<220> FEATURE:
<223> OTHER INFORMATION: Primer

<400> SEQUENCE: 60
ggtgcggata gagacgacat agttttccat agtctgcgcg tctttcaggg cttcatcgac 60

<210> SEQ ID NO 61
<211> LENGTH: 60
<212> TYPE: DNA
<213> ORGANISM: Artificial Sequence
<220> FEATURE:
<223> OTHER INFORMATION: Primer

<400> SEQUENCE: 61
gtcgatgaag ccctgaaaga cgcgcagact atgtcctcag ctttccatta cgtcattagc 60

<210> SEQ ID NO 62
<211> LENGTH: 60
<212> TYPE: DNA
<213> ORGANISM: Artificial Sequence
<220> FEATURE:
<223> OTHER INFORMATION: Primer

<400> SEQUENCE: 62
gatggccttt ttgcgtgtcg acgcggccgc tcattcaaat tcgataatca tggtgatttt 60

<210> SEQ ID NO 63
<211> LENGTH: 60
<212> TYPE: DNA
<213> ORGANISM: Artificial Sequence
<220> FEATURE:
<223> OTHER INFORMATION: Primer

<400> SEQUENCE: 63
aaaatcacca tgattatcga atttgaatga gcggccgcgt cgacacgcaa aaaggccatc 60

<210> SEQ ID NO 64
<211> LENGTH: 60
<212> TYPE: DNA
<213> ORGANISM: Artificial Sequence
<220> FEATURE:
<223> OTHER INFORMATION: Primer

<400> SEQUENCE: 64
gctaatgacg taatggaaag ctgaggacat agtctgcgcg tctttcaggg cttcatcgac 60

<210> SEQ ID NO 65
<211> LENGTH: 60
<212> TYPE: DNA

<213> ORGANISM: Artificial Sequence
<220> FEATURE:
<223> OTHER INFORMATION: Primer

<400> SEQUENCE: 65
gtcgatgaag ccctgaaaga cgcgcagact atgaacgtga ataagccgac caccgaaaag 60

<210> SEQ ID NO 66
<211> LENGTH: 60
<212> TYPE: DNA
<213> ORGANISM: Artificial Sequence
<220> FEATURE:
<223> OTHER INFORMATION: Primer

<400> SEQUENCE: 66
gatggccttt ttgcgtgtcg acgcggccgc tcagtattct tcaattttgt ccagttgata 60

<210> SEQ ID NO 67
<211> LENGTH: 60
<212> TYPE: DNA
<213> ORGANISM: Artificial Sequence
<220> FEATURE:
<223> OTHER INFORMATION: Primer

<400> SEQUENCE: 67
tatcaactgg acaaaattga agaatactga gcggccgcgt cgacacgcaa aaaggccatc 60

<210> SEQ ID NO 68
<211> LENGTH: 60
<212> TYPE: DNA
<213> ORGANISM: Artificial Sequence
<220> FEATURE:
<223> OTHER INFORMATION: Primer

<400> SEQUENCE: 68
cttttcggtg gtcggcttat tcacgttcat agtctgcgcg tctttcaggg cttcatcgac 60

<210> SEQ ID NO 69
<211> LENGTH: 60
<212> TYPE: DNA
<213> ORGANISM: Artificial Sequence
<220> FEATURE:
<223> OTHER INFORMATION: Primer

<400> SEQUENCE: 69
gtgatcaacg ccgccagcgg tcgtcagact gtcgatgaag ccctgaaaga cgcgcagact 60

<210> SEQ ID NO 70
<211> LENGTH: 60
<212> TYPE: DNA
<213> ORGANISM: Artificial Sequence
<220> FEATURE:
<223> OTHER INFORMATION: Primer

<400> SEQUENCE: 70
gcggccgcgt cgacacgcaa aaaggccatc catccgtcag gatggccttc tgcttaattt 60

<210> SEQ ID NO 71
<211> LENGTH: 60
<212> TYPE: DNA
<213> ORGANISM: Artificial Sequence
<220> FEATURE:
<223> OTHER INFORMATION: Primer

<400> SEQUENCE: 71
aaattaagca gaaggccatc ctgacggatg gatggccttt ttgcgtgtcg acgcggccgc 60

<210> SEQ ID NO 72
<211> LENGTH: 60
<212> TYPE: DNA
<213> ORGANISM: Artificial Sequence
<220> FEATURE:
<223> OTHER INFORMATION: Primer

<400> SEQUENCE: 72
agtctgcgcg tctttcaggg cttcatcgac agtctgacga ccgctggcgg cgttgatcac 60

<210> SEQ ID NO 73
<211> LENGTH: 66
<212> TYPE: DNA
<213> ORGANISM: Artificial Sequence
<220> FEATURE:
<223> OTHER INFORMATION: Primer

<400> SEQUENCE: 73
gtttaacttt aataaggaga tataccatgc tgacggaagt gcgcccggtc tctacgacga 60
aaccgc 66

<210> SEQ ID NO 74
<211> LENGTH: 66
<212> TYPE: DNA
<213> ORGANISM: Artificial Sequence
<220> FEATURE:
<223> OTHER INFORMATION: Primer

<400> SEQUENCE: 74
cgacctgcag gcgcgccgag ctcgaattca tttgatgtat ttgcaataga acacagaaaa 60
gaccgt 66

<210> SEQ ID NO 75
<211> LENGTH: 66
<212> TYPE: DNA
<213> ORGANISM: Artificial Sequence
<220> FEATURE:
<223> OTHER INFORMATION: Primer

<400> SEQUENCE: 75
gtgttctatt gcaaatacat caaatgaatt cgagctcggc gcgcctgcag gtcgacaagc 60
ttgcgg 66

<210> SEQ ID NO 76
<211> LENGTH: 69
<212> TYPE: DNA
<213> ORGANISM: Artificial Sequence
<220> FEATURE:
<223> OTHER INFORMATION: Primer

<400> SEQUENCE: 76
gagaccgggc gcacttccgt cagcatggta tatctcctta ttaaagttaa acaaaattat 60
ttctacagg 69

<210> SEQ ID NO 77
<211> LENGTH: 62
<212> TYPE: DNA
<213> ORGANISM: Artificial Sequence
<220> FEATURE:
<223> OTHER INFORMATION: Primer

<400> SEQUENCE: 77
gtatggtgac cctgtggcgc aaatgagaat tcgagctcgg cgcgcctgca ggtcgacaag 60
ct 62

<210> SEQ ID NO 78
<211> LENGTH: 64
<212> TYPE: DNA
<213> ORGANISM: Artificial Sequence
<220> FEATURE:
<223> OTHER INFORMATION: Primer

<400> SEQUENCE: 78
gcgctgccct gtttgatttt atccatggta tatctcctta ttaaagttaa acaaaattat 60
ttct 64

<210> SEQ ID NO 79
<211> LENGTH: 63
<212> TYPE: DNA
<213> ORGANISM: Artificial Sequence
<220> FEATURE:
<223> OTHER INFORMATION: Primer

<400> SEQUENCE: 79
cctgcaggcg cgccgagctc gaattctcat ttgcgccaca gggtcaccat acgtgccggc 60
agg 63

<210> SEQ ID NO 80
<211> LENGTH: 66
<212> TYPE: DNA
<213> ORGANISM: Artificial Sequence
<220> FEATURE:
<223> OTHER INFORMATION: Primer

<400> SEQUENCE: 80
gtttaacttt aataaggaga tataccatgg ataaaatcaa acagggcagc gcctctctgg 60
ttgtcg 66

<210> SEQ ID NO 81
<211> LENGTH: 57
<212> TYPE: DNA
<213> ORGANISM: Artificial Sequence
<220> FEATURE:
<223> OTHER INFORMATION: Primer

<400> SEQUENCE: 81
cagactcgag ggtaccgacg tcctaataag tagatgaata tttatcagga cgaagat 57

<210> SEQ ID NO 82
<211> LENGTH: 55
<212> TYPE: DNA
<213> ORGANISM: Artificial Sequence
<220> FEATURE:
<223> OTHER INFORMATION: Primer

<400> SEQUENCE: 82
aactaaaggt ttattttcca tatgtatatc tccttcttat acttaactaa tatac 55

<210> SEQ ID NO 83
<211> LENGTH: 64
<212> TYPE: DNA
<213> ORGANISM: Artificial Sequence
<220> FEATURE:
<223> OTHER INFORMATION: Primer

<400> SEQUENCE: 83
taaatattca tctacttatt aggacgtcgg taccctcgag tctggtaaag aaaccgctgc 60
tgcg 64

<210> SEQ ID NO 84
<211> LENGTH: 59
<212> TYPE: DNA
<213> ORGANISM: Artificial Sequence
<220> FEATURE:
<223> OTHER INFORMATION: Primer

<400> SEQUENCE: 84
gtataagaag gagatataca tatggaaaat aaacctttag tttcagtttt gatttgtgc 59

<210> SEQ ID NO 85
<211> LENGTH: 75
<212> TYPE: DNA
<213> ORGANISM: Artificial Sequence
<220> FEATURE:
<223> OTHER INFORMATION: Primer

<400> SEQUENCE: 85
taactttaag aaggagatat acaagagctc gagtcgaagg agatagaacc atggcaacag 60
catggtataa acaag 75

<210> SEQ ID NO 86
<211> LENGTH: 82
<212> TYPE: DNA
<213> ORGANISM: Artificial Sequence
<220> FEATURE:
<223> OTHER INFORMATION: Primer

<400> SEQUENCE: 86
gcgtgtcgac gcgtttagag gccccaaggg gttatgctag tatcgattta tcatttagcc 60
acggatagtt tataaatttt ac 82

<210> SEQ ID NO 87
<211> LENGTH: 80
<212> TYPE: DNA
<213> ORGANISM: Artificial Sequence
<220> FEATURE:
<223> OTHER INFORMATION: Primer

<400> SEQUENCE: 87
ggttctatct ccttcgactc gagctcttgt atatctcctt cttaaagtta aacaaaatta 60
tttctagatt tttgtcgaac 80

<210> SEQ ID NO 88
<211> LENGTH: 63
<212> TYPE: DNA
<213> ORGANISM: Artificial Sequence
<220> FEATURE:
<223> OTHER INFORMATION: Primer

<400> SEQUENCE: 88
taaatcgata ctagcataac cccttggggc ctctaaacgc gtcgacacgc aaaaaggcca 60
tcc 63

<210> SEQ ID NO 89
<211> LENGTH: 80
<212> TYPE: DNA
<213> ORGANISM: Artificial Sequence
<220> FEATURE:

<223> OTHER INFORMATION: Primer

<400> SEQUENCE: 89
gttcgacaaa aatctagaaa taattttgtt taactttaag aaggagatat acaagagctc 60
gagtcgaagg agatagaacc 80

<210> SEQ ID NO 90
<211> LENGTH: 63
<212> TYPE: DNA
<213> ORGANISM: Artificial Sequence
<220> FEATURE:
<223> OTHER INFORMATION: Primer

<400> SEQUENCE: 90
ggatggcctt tttgcgtgtc gacgcgttta gaggccccaa ggggttatgc tagtatcgat 60
tta 63

<210> SEQ ID NO 91
<211> LENGTH: 34
<212> TYPE: DNA
<213> ORGANISM: Artificial Sequence
<220> FEATURE:
<223> OTHER INFORMATION: Primer

<400> SEQUENCE: 91
atatgacgtc tcattagcgg tttttcagga gacg 34

<210> SEQ ID NO 92
<211> LENGTH: 35
<212> TYPE: DNA
<213> ORGANISM: Artificial Sequence
<220> FEATURE:
<223> OTHER INFORMATION: Primer

<400> SEQUENCE: 92
atatcatatg ccgtccgaag cattccgtcg tcacc 35

<210> SEQ ID NO 93
<211> LENGTH: 62
<212> TYPE: DNA
<213> ORGANISM: Artificial Sequence
<220> FEATURE:
<223> OTHER INFORMATION: Primer

<400> SEQUENCE: 93
taactttaat aaggagatat accatgacgc aatttaatcc cgttgatcat ccacatcgcc 60
gc 62

<210> SEQ ID NO 94
<211> LENGTH: 67
<212> TYPE: DNA
<213> ORGANISM: Artificial Sequence
<220> FEATURE:
<223> OTHER INFORMATION: Primer

<400> SEQUENCE: 94
attttcgcga atccggagtg taaaagcttg cggccgcata atgcttaagt cgaacagaaa 60
gtaatcg 67

<210> SEQ ID NO 95
<211> LENGTH: 72
<212> TYPE: DNA
<213> ORGANISM: Artificial Sequence
<220> FEATURE:
<223> OTHER INFORMATION: Primer

<400> SEQUENCE: 95
aagcattatg cggccgcaag cttttacact ccggattcgc gaaaatggat atcgctgact 60
gcgcgcaaac gc 72

<210> SEQ ID NO 96
<211> LENGTH: 68
<212> TYPE: DNA
<213> ORGANISM: Artificial Sequence
<220> FEATURE:
<223> OTHER INFORMATION: Primer

<400> SEQUENCE: 96
tcaacgggat taaattgcgt catggtatat ctccttatta aagttaaaca aaattatttc 60
tacagggg 68

<210> SEQ ID NO 97
<211> LENGTH: 57
<212> TYPE: DNA
<213> ORGANISM: Artificial Sequence
<220> FEATURE:
<223> OTHER INFORMATION: Primer

<400> SEQUENCE: 97
atggtgatgg ctgctgccca tttaaaccgc tttgactgcg tcggcaatac ggtgcgc 57

<210> SEQ ID NO 98
<211> LENGTH: 60
<212> TYPE: DNA
<213> ORGANISM: Artificial Sequence
<220> FEATURE:
<223> OTHER INFORMATION: Primer

<400> SEQUENCE: 98
gtttaacttt aataaggaga tataccatgc tgaacaacgc gatgtctgtt gttatcctgg 60

<210> SEQ ID NO 99
<211> LENGTH: 53
<212> TYPE: DNA
<213> ORGANISM: Artificial Sequence
<220> FEATURE:
<223> OTHER INFORMATION: Primer

<400> SEQUENCE: 99
cgcagtcaaa gcggtttaaa tgggcagcag ccatcaccat catcaccaca gcc 53

<210> SEQ ID NO 100
<211> LENGTH: 59
<212> TYPE: DNA
<213> ORGANISM: Artificial Sequence
<220> FEATURE:
<223> OTHER INFORMATION: Primer

<400> SEQUENCE: 100
tcgcgttgtt cagcatggta tatctcctta ttaaagttaa acaaaattat ttctacagg 59

<210> SEQ ID NO 101
<211> LENGTH: 35
<212> TYPE: DNA
<213> ORGANISM: Artificial Sequence
<220> FEATURE:
<223> OTHER INFORMATION: Primer -continued

```
<400> SEQUENCE: 101

atatatcata tgtgcggtat cgttggtgct atcgc                              35


<210> SEQ ID NO 102
<211> LENGTH: 36
<212> TYPE: DNA
<213> ORGANISM: Artificial Sequence
<220> FEATURE:
<223> OTHER INFORMATION: Primer

<400> SEQUENCE: 102

atatatgacg tcttattcca cggtcacgga tttcgc                             36
```